US009217150B2

(12) United States Patent
Jørgensen et al.

(10) Patent No.: US 9,217,150 B2
(45) Date of Patent: Dec. 22, 2015

(54) NRPS-PKS GENE CLUSTER AND ITS MANIPULATION AND UTILITY

(75) Inventors: Hanne Jørgensen, Trondheim (NO); Trond Erling Ellingsen, Trondheim (NO); Kristin Fløgstad Degnes, Trondheim (NO); Per Bruheim, Trondheim (NO); Håvard Sletta, Trondheim (NO); Espen Fjærvik, Trondheim (NO); Geir Klinkenberg, Heimdal (NO); Sergey Zotchev, Trondheim (NO)

(73) Assignee: SINTEF TTO AS, Trondheim (NO)

( * ) Notice: Subject to any disclaimer, the term of this patent is extended or adjusted under 35 U.S.C. 154(b) by 429 days.

(21) Appl. No.: 12/922,718

(22) PCT Filed: Mar. 20, 2009

(86) PCT No.: PCT/GB2009/000759
§ 371 (c)(1),
(2), (4) Date: Dec. 21, 2010

(87) PCT Pub. No.: WO2009/115822
PCT Pub. Date: Sep. 24, 2009

(65) Prior Publication Data

US 2011/0117606 A1 May 19, 2011

(30) Foreign Application Priority Data

Mar. 20, 2008 (GB) .................................. 0805363.9

(51) Int. Cl.

| | |
|---|---|
| ***C07H 21/04*** | (2006.01) |
| ***C12P 7/26*** | (2006.01) |
| ***C12N 9/00*** | (2006.01) |
| ***C12N 15/52*** | (2006.01) |
| ***C07K 14/36*** | (2006.01) |
| ***C12P 17/10*** | (2006.01) |
| ***C12R 1/465*** | (2006.01) |
| *C12P 19/62* | (2006.01) |

(52) U.S. Cl.
CPC ................ *C12N 15/52* (2013.01); *C07K 14/36* (2013.01); *C12P 17/10* (2013.01); *C12R 1/465* (2013.01); *C12P 19/62* (2013.01)

(58) Field of Classification Search
CPC .......... C12N 15/52; C12P 17/10; C07K 14/36
USPC ..................... 536/23.2; 435/121, 252.35, 183
See application file for complete search history.

(56) References Cited

U.S. PATENT DOCUMENTS

2004/0115762 A1* 6/2004 Zotchev et al. .............. 435/69.1
2005/0176653 A1* 8/2005 McAlpine et al. .............. 514/25

FOREIGN PATENT DOCUMENTS

JP 04-001179 A1 1/1992

OTHER PUBLICATIONS

Database EMBL, XP002531355, Accession No. AM238663 of Leblond et al, p. 1, Feb. 27, 2007.
Choulet et al, Molecular Biology and Evolution, The University of Chicago Press, 23(12):2361-2369 (Jan. 1, 2006).
Database EMBL, XP002531356, Accession No. L27466 of Butler et al, pp. 1-2, Jan. 11, 1994.
Butler et al, Applied and Environmental Microbiology, 61(8):3145-3150 (1995).
Database UniProt *Streptomyces coelicolor*, XP 002531357, Accession No. Q9FCD9 of Bentley et al, p. 1, Mar. 1, 2001.
Bentley et al, Nature, 417:141:-147 (Jan. 1, 2002).
Bredholdt et al, Environmental Microbiology, 9(11):2756-2764 (Nov. 2007).
Izumikawa et al, Bioorganic and Medicinal Chemistry, 11(16):3401-3405 (Aug. 5, 2003).
Katz, ACS Chemical Reviews, 97(7):2557-2575 (1997).
Kojiri et al, The Journal of Antibiotics, 45(6):868-874 (Jun. 1992).
Takahashi et al, The Journal of Antibiotics, 50(2):186-188 (Feb. 1997).
Atschul, et al, "Gapped BLAST and PSI BLAST, a new generation of protein database search programs," Nucleic Acids Research, 1997, vol. 25 (17), p. 3389-3402.

(Continued)

*Primary Examiner* — Tekchand Saidha
*Assistant Examiner* — Younus Meah
(74) *Attorney, Agent, or Firm* — Porter, Wright, Morris & Arthur LLP; Holly Kozlowski

(57) ABSTRACT

The present invention provides a nucleic acid molecule comprising: (a) a nucleotide sequence as shown in SEQ ID No. 1; or (b) a nucleotide sequence which is the complement of SEQ ID No. 1; or (c) a nucleotide sequence which is degenerate with SEQ ID No. 1; or (d) a nucleotide sequence having at least 85% sequence identity (preferably at least 87%, 90%, 91%, 92%, 93%, 94%, 95%, 96%, 97%, 98% or 99% sequence identity) with SEQ ID No. 1; or (e) a part of any one of (a) to (d), wherein said nucleic acid molecule encodes or is a complementary to a nucleic acid molecule encoding one or more polypeptides, or comprises or is complementary to a nucleic acid molecule comprising one or more genetic elements, having functional activity in the synthesis of a polyketide-based or macrolactam molecule. Particularly the invention contemplates the modification of the nucleic acid of the invention, encoding the biosynthetic machinery for the synthesis of the polyketide macrolactam BE-14106, including expressing in a microorganism the modified nucleic acid molecule. In certain aspects the modification includes introducing, mutating, deleting, replacing or inactivating a sequence encoding one or more activities or proteins encoded by said nucleic acid molecule. Other aspects of the invention include a microorganism containing the modified and unmodified nucleic acid and recovering the polyketide-based or macrolactam molecule from said microorganism.

26 Claims, 2 Drawing Sheets

(56) References Cited

OTHER PUBLICATIONS

Bassett, et al, "Cellular response and molecular mechanism of antitumor acitvity by leinamycin in MiaPaCa human pancreatic cancer cells," Anticancer Drugs, 2003, vol. 15(7), p. 689-96.
Bisang, et al, "A Chain Initiation Factor Common to Both Modular and Aromatic Polyketide Synthases," Letters to Nature, Sep. 30, 1999, V01 (6752), p. 502-505.
Borgos, et al, "Effect of glucose limitation and specific mutations in the module 5 enoyl reductast domains in the nystatin and amphotericin polyketide synthases on polyene macrolide biosynthesis," Arch Microbiol, Apr. 2006: 185 (3), p. 165-171.
Borgos, et al, "Probing the Structure—Function Relationship of Polyene Macrolides: Engineered Biosynthesis of Soluble Nystatin Analogues," J Med. Chem., Apr. 20, 2006, 49 (8), p. 2431-2439.
Bredholt, et al, "Actinomycetes from Sediments in the Trondheim Fjord, Norway: Diversity and Biological Activity," Mar. Drugs, Jan. 23, 2008; 6 (1), p. 12-14.
Bruheim, et al, "Chemical Diversity of Polyene Macrolides Produced by *Streptomyces noursei* ATCC 11455 and Recombinant Strain ERD44 with Genetically Altered Polyketide Synthase NysC," Antimicrobial Agents and Chemotherapy, Nov. 2004 48 (11), p. 4120-4129.
Chen, et al, "Aminoacyl-S-Enzyme Intermediates in beta-Hydroxylations and alpha, beta-Desaturations of Amino Acids in Peptide Antibiotics," Biochemistry, Oct. 2, 2001; 40 (39), p. 11651-11659.
Cheng, et al, "Identification and localization of the gene cluster encoding biosynthesis of the antitumor macrolactam leinamycin in *Streptomyces atroolivaceus* S-140," Journal of Bacteriology, Dec. 2002 184 (24), p. 7013-7024.
Cheng, et al, Type 1 polyketide synthase requiring a discrete acyltransferase for polyketide biosynthesis, Proc. National Academy of Science USA, Mar. 18, 2003, 100 (6), p. 3149-3154.
Du, et al, "The biosynthetic gene cluster for the antitumor drug bleomycin from *Streptomyces verticillus* ATCC15003 supporting functional interactions between nonribosomal peptide synthetases and a polyketide synthase," Chemistry & Biology, Aug. 7, 2000 (8), p. 623-642.
Flett, et al, "High efficiency intergeneric conjugal transfer of plasmid DNA from *Escherichia coli* to bethyl DNA-restricting *Streptomycetes*," FEMS Microbiology Letters, Oct. 1997, 155 (2), p. 223-229.
Futamura, et al, Discovery of Incednine as a Potent Modulator of the Anti-apoptotic Function of Bcl-xL from Microbial Origin, J. Am Chem Soc., Feb. 13, 2008, 130 (6), p. 1822-1823.
Hara, et al, "Leinamycin, a new antitumor antibiotic from *Streptomyces*: producing organism fermentation and isolation," The Journal of Antibiotics, Dec. 1989, 42 (12), p. 1768-1774.
Hara, et al, A Novel Antitumor Antibiotic Produced by a *Streptomyces* SP, The Journal of Antibiotics, Feb. 1989, 42 (2), p. 333-335.
He, et al, The LuxR family members GdmRl and GdmRll are positive regulators of geldanamycin biosynthesis in *Streptomyces hygroscopicus* 17997, Arch Microbiol, May 2008, 189 (5), p. 501-510.
Holm, et al, "Dali: a network tool for protein structure comparison," Trends Biochem Sci. Nov. 1995, 20(11), p. 478-480.
Holm, et al, "Touring protein fold space with Dali/FSSP," Nucleic Acids Res., Jan. 1, 1998, 26 (1), p. 316-319.
Ikeda, et al, "Organization of the biosynthetic gene cluster for the polyketide anthelmintic macrolide avermectin in *Streptomyces avermitilis*," Proc. Natl. Acad. Sci. USA, Aug. 17, 1999, 96 (17) p. 9509-9514.
Ishikawa, et al, "FramePlot: a new implementation of the Frame analysis for predicting protein-coding regions in bacterial DNA with a high G + C content," FEMS Microbiology Letters, May 15, 1999, 174 (2) p. 251-253.
Jakobi, et al, "Maltophilin: A new Antifungal Compound Produced by *Strenotrophomonas maltophilia* R3089," The Journal of Antibiotics, (Tokyo), Nov. 1996, 49 (11) p. 1101-1104.
Jomon, et al, "A New Antibiotic, Ikarugamycin," JAntibiot (Tokyo), 1972 Nat, 25 (5), p. 271-280.
Kakavas, et al, "Identification and Characterization of the Niddamycin Polyketide Synthase Genes from *Streptomyces caelestis*," J. Bacteriol., Dec. 1997, 179 (23), p. 7515-7522.
Kanda, et al, "Synthesis and Antitumor Activity of Novel Thioester Derivatives of Leinamycin," J. Med. Chem., Apr. 22, 1999, 42 (8), p. 1330-1332.
Kanda, et al, "Synthesis and Antitumor Activity of Leinamycin Derivatives: Modifications of C-8 Hydroxy and C-9 Keto Groups," Bioorganic & Medicinal Chemistry Letters, Apr. 21, 1998, 8 (8), p. 909-912.
Kanda, et al, "Synthesis and Antitumor Activity of Novel C-8 Ester Derivatives of Leinamycin." Bioorganic & Medicinal Chemistry Letters, Feb. 10, 2003, 13 (3), p. 455-458.
Kim, et al, "Biochemical Evidence for an Editing Role of Thioesterase II in the Biosynthesis of the Polyketide Pikromycin," The Journal of Biological Chemistry, Dec. 13, 2002, 277 (50), p. 48028-48034.
Komiyama, et al, "Antitumor Activity of a New AntitumorAntibiotic, Stubomycin," The Journal of Antibiotics (Tokyo), Jun. 1982, 35 (6), p. 703-706.
Kuhstoss, et al, "Production of a novel polyketide through the construction of a hybrid polyketide synthase," Gene, Dec. 12, 1996, 183 (1-2), p. 231-236.
Leskiw, et al,"TTA codons in some genes prevent their expression in a class of developmental, antibiotic-negative, *Streptomyces* mutants," Proc. Natl Acad Sci USA, Mar. 15, 1991, 88 (6), p. 2461-2465.
Long, et al, "Engineering specificity of starter unit selection by the erythromycin-producing polyketide synthase", Molecular Microbioloty, 2002, 43 (5), p. 1215-1225.
Marahiel, et al, "Modular Peptide Synthetases Involved in Nonribosomal Peptide Synthesis," Chem Rev. Nov. 10, 1997, 97 (7), p. 2651-2674.
McDaniel, et al, "Genetic Approaches to Polyketide Antibiotics. 1." Chem Rev. Feb. 2005, 105 (2), p. 543-58.
Mitchell, et al, "Aureoverticillactam, a Novel 22-Atom Macrocyclic Lactam from the Marine Actinomycete *Streptomyces aureoverticillatus*," J. Nat. Prod., Aug. 2004, 67 (8), p. 1400-1402.
Myers, et al, "Optimal alignments in linear space," Comput Appl Biosci., Mar. 1988, 4 (1), p. 11-17.
Naruse, et al, "Fluvirucins A1, A2, B1, B2, B3, B4 and B5, New Antibiotics Active Against Influenza A Virus. III. The Stereochemistry and Absolute Configuration of Fluvirucin A1," The Journal of Antibiotics (Tokyo), Jul. 1991, 44 (7), p. 756-761.
Nishida, et al, "Amino acid starter unit in the biosynthesis of macrolactam polyketide antitumor antibiotic vicenistatin," Tetrahedron, Sep. 2001, 57 (39), p. 8237-8242.
Nowakowski, et al, "A Phase I Trial of Twice-Weekly 17-Allylamino-Demethoxy-Geldanamycin in Patients with Advanced Cancer," Clinical Cancer Research, Oct. 15, 2006, 12 (20 Pt 1), p. 6087-6093.
Ogasawara, et al, "Involvement of Glutamate Mutase in the Biosynthesis of the Unique Starter Unit of the Macrolactam Polyketide Antibiotic Vicenistatin," The Journal of Antibiotics (Tokyo), Jul. 2005, 58 (7), p. 468-472.
Ogasawara, et al, "Cloning, Sequencing, and Functional Analysis of the Biosynthetic Gene Cluster of Macrolactam Antibiotic Vicenistatin in *Streptomyces halstedii*," Chemistry & Biology, Jan. 2004, 11 (1), p. 79-86.
Ortiz, et al, "The DNA-binding characteristics of the *Streptomyces reticuli* regulator FurS depend on the redox state of its cysteine residues," Mol Gen Genet, Oct. 2000, 264 (3), p. 341-353.
Otsuka, et al, "Non-Fatty Acyl Polyketide Starter in the Biosynthesis of Vicenistatin, an Antitumor Macrolactam Antibiotic," Tetrahedron Letters, May 1998, 39 (20), p. 3185-3188.
Otsuka, et al, "Biosynthetic Pathway of Macrolactam Polyketide Glycoside Antitumor Antibiotic Vicenistatins," Tetrahedron, Oct. 2000, 56 (42), p. 8281-8286.
Pearson, et al, "Improved tools for biological sequence comparison," Proc. Natl. Acad. Sci. USA, Apr. 1988, 85 (8), p. 2444-2448.
Pearson, "Rapid and Sensitive Sequence Comparison with FASTP and FASTA," Methods Enzymol., 1990, 183, p. 63-98.

(56) References Cited

OTHER PUBLICATIONS

Pulsawat, et al, "Characterization of biosynthetic gene cluster for the production of virginiamycin M, a streptogramin type A antibiotic, in *Streptomyces virginiae*," Gene, May 15, 2007, 393 (1-2), p. 31-42.
Ramos, et al, "The TetR Family of Transcriptional Repressors," Microbiology and Molecular Biology Reviews, Jun. 2005, 69 (2), p. 326-356.
Reeves, et al, "Aleration of the Substrate Specificity of a Modular Polyketide Synthase Acyltransferase Domain through Site-Specific Mutations," Biochemistry, Dec. 25, 2001, 40 (51), p. 15464-15470.
Reger, et al, "Biochemical and Crystallographic Analysis of Substrate Binding and Conformational Changes in Acetyl-CoA Synthetase," Biochemistry, Jun. 5, 2007, 46 (22), p. 6536-6546.
Schwarzer, et al, "Regeneration of misprimed nonribosomal peptide synthetases by type 11 thioesterases," Proc. Natl. Acad. Sci. USA, Oct. 29, 2002, 99 (22), p. 14083-14088.
Sekurova, et al, "In Vivo Analysis of the Regulatory Genes in the Nystatin Biosynthetic Gene Cluster of Streptomyces noursei ATCC 11455 Reveals Their Differential Control Over Antibiotic Biosynthesis," Journal of Bacteriology, Mar. 2004, 186 (5), p. 1345-1354.
Sekurova, et al, "Molecular cloning and analysis of a pleiotropic regulatory gene locus from the nystatin producer Streptomyces noursei ATCC11455," FEMS Microbiology Letters, Aug. 15, 1999, 177 (2), p. 297-304.
Shibata, et al, "Chemical Modification of Hitachimycin Synthesis, Antibacterial, Cytocidal and in Vivo Antitumor Activities of Hitachimycin Derivatives," The Journal of Antibiotics (Tokyo), May 1988, 41 (5), p. 614-623.
Shibata, et al, "Chemical Modification of Hitachimycin II. Synthesis and Antitumor Activities of Carbonate Derivatives," The Journal of Antibiotics (Tokyo), May 1989, 42 (5), p. 718-726.
Shibata, et al, "Chemical Modification of Hitachimycin III. Synthesis and Antitumor Activities of Amino Acyl Derivatives," The Journal of Antibiotics (Tokyo), Jul. 1989, 42 (7), p. 1114-1123.
Shindo, et al, "Vicenistatin, A Novel 20-Membered Macrocyclic Lactam Antitumor Antibiotic," The Journal of Antibiotics (Tokyo), Jul. 1993, 46 (7), p. 1076-1081.
Simunovic, et al., "Myxovirescin A Biosynthesis is Directed by Hybrid Polyketide Synthases/Nonribosomal Peptide Synthetase, 3-Hydroxy-3-Methylglutaryl-CoA Synthases, and trans-Acting Acyltransferases," Chembiochem, Aug. 2006, 7 (8), p. 1206-1220.
Sun, et al, "Organization of the biosynthetic gene cluster in *Streptomyces* sp. DSM 4137 for the novel neuroprotectant polyketide meridamycin," Microbiology, 2006, 152, p. 3507-3515.
Tang, et al, "Chain Initiation in the Leinamycin-producing Hybrid Nonribosomal Peptide/Polyketide Synthetase from *Streptomyces atroolivaceus* S-140. Discrete, Monofunctional Adenylation Enzyme and Peptidyl Carrier Protein that Directly Load d-Alanine," The Journal of Biological Chemistry, Jul. 13, 2007, 282 (28), p. 20273-20282.
Thompson, et al, "CLUSTAL W: improving the sensitivity of progressive multiple sequence alignment through sequence weighting, position-specific gap penalties and weight matrix choice," Nucleic Acid Research, Nov. 11, 1994, 22 (22), p. 4673-4680.
Udwary, et al, "Genome sequencing reveals complex secondary metabolome in the marine actinomycete *Salinispora tropica*," Proc. Natl. Acad. Sc. USA, Jun. 19, 2007, 104 (25), p. 10376-10381.
Umezawa, et al, "A New Antitumor Antibiotic, Stubomycin," J Antibiot (Tokyo), Mar. 1981, 34 (3), p. 259-265.
Uraji, et al, "Effect of sale on the activity of *Streptomyces prolyl* aminopeptidase," Biochima et Biophysica Acta, Nov. 2007, 1774 (11), p. 1462-1469.
Waldron, et al, "Cloning and analysis of the spinosad biosynthetic gene cluster of *Saccharapolyspora spinosa*," Chemistry & Biology, May 2001, 8 (5), p. 487-499.
Walker, et al, "Distantly related sequences in the alpha- and beta-subunits of ATP synthase, myosin, kinases and other ATP-requiring enzymes and a common nucleotide binding fold," The EMBO Journal, 1982, 1 (8), p. 945-951.
Weissman, et al, "Combinatorial Biosynthesis of Reduced Polyketides," Nat Rev Microbiol., Dec. 2005, 3 (12), p. 925-936.
Yamamoto, et al, "Bafilomycin A1 Prevents Maturation of Autophagic Vacuoles by Inhibiting Fusion between Autophagosomes and Lysosomes in Rat Hepatoma Cell Line, H-4-II-E Cells," Cell Structure and Function, Feb. 1998, 23 (1), p. 33-42.
Zafriri, et al, "Mode of Action of *Myxococcus xanthus* Antibiotic TA," Antimicrobial Agents and Chemotheraphy, Feb. 1981, 19 (2), p. 349-351.
Zotchev, et al, "Identification of a gene cluster for antibacterial polyketide-derived antibiotic biosynthesis in the nystatin producer *Streptomyces noursei* ATCC 11455," Microbiology, Mar. 2000, 146 (Pt 3), p. 611-619.

* cited by examiner

NRPS-PKS GENE CLUSTER AND ITS MANIPULATION AND UTILITY

The present application is a 371 of PCT/GB2009/000759 filed Mar. 20, 2009.

The present invention relates to the cloning and sequencing of the gene cluster encoding the biosynthetic machinery for the synthesis of the polyketide macrolactam BE-14106, which includes a both a non-ribosomal peptide synthetase (NRPS) adenylation domain and a modular polyketide biosynthetic enzyme or enzyme complex (PKS; polyketide synthase enzyme or enzyme complex). The biosynthesis machinery thus comprises a hybrid NRPS-PKS enzyme system. The invention accordingly relates to novel genes and nucleic acid molecules encoding the biosynthetic machinery for the synthesis of the macrolactam BE-14106, including a modular NRPS-polyketide biosynthetic enzyme or enzyme system involved in BE-14106 biosynthesis and the biosynthetic machinery including the modular NRPS-polyketide synthase enzyme system or complex itself (as well as components thereof). The invention further relates to the use of these genes, nucleic acid molecules, the machinery, enzymes and enzyme systems or complexes thereof both in facilitating BE-14106 biosynthesis and in the synthesis of BE-14106 derivatives and novel macrolactam structures.

Polyketides or polyketide-based or related structures are, or form the basis of, natural products synthesized by bacteria, fungi, plants, and animals, many of which have applied potential as pharmaceuticals or as agricultural or veterinary products, e.g. as antibiotics, antifungals, cytostatics, anticholesterolemics, antiparasitics, coccidiostatics, animal growth promoters and natural insecticides.

The Gram-positive bacteria *Streptomyces* are the main producers of polyketides and polyketide-based molecules, and the genetics and biochemistry of polyketide biosynthesis in these organisms are relatively well characterized (McDaniel R, et al; Chem Rev. 2005 February; 105(2):543-58.)

Other producers include other actinomycetes. A range of different polyketide-based (or polyketide-related) molecules are known, of which macrolactams represent one class. The biosynthetic gene clusters for synthesis of the macrolactams vicenistatin and salinilactam have been reported Ogasawara Y. et al; Chem Biol. 2004 January; 11(1):79-98, and Udwary et al; Proc Natl Acad Sci USA 2007 Jun. 19; 104(25):10376-81, respectively.

BE-14106 (alternative name GT-32A) is a macrolactam antibiotic having a chemical structure as set out in FIG. 1. It has been isolated from a strain of *Streptomyces spheroides* and has been shown to have cytotoxic effects on leukemia cell lines, as well as antimicrobial activity against a range of tested organisms, antiproliferative activity against a H-ras transformed BALB3T3 cell line and inhibitory activity against mixed lymphocyte reaction (JP4001179, Kojiri et al 1992 Journal of Antibiotics, 868-74, Takahashi et al 1997, Journal of Antibiotics 186-8). An 8-deoxy analogue (GT-32B) has also been isolated from an unspecified *Streptomyces* species and this was shown to share many of the activities of BE-14106 (Takahashi et al, supra).

Macrolactam compounds such as BE-14106 can be formed via activation and priming of the PKS system with an activated amino acid and extension of the amino acid residue (aminoacyl chain) by repeated condensations of simple carboxylic acids by polyketide synthases (PKS) in a manner similar to fatty acid biosynthesis. Thus, unlike the case with a simply polyketide chain where the "starter unit" is a carboxylic acid residue, in this case, the starter unit for the PKS is an aminoacyl intermediate synthesized from an amino acid and an acyl chain. PKSs can be organised as iterative PKSs which re-use domains in a cyclic fashion or as modular (Type I) PKSs which contain a sequence of separate modules (or repeated units) and do not re-use domains. Each module is responsible for one condensation cycle in the synthesis of the polyketide chain and contains various enzyme domains. In the case of BE-14106 the "polyketide" chain is strictly speaking a hybrid amino acid-polyketide chain, or an aminoacyl chain, but is referred to herein as a "polyketide chain". Thus, besides domains for the condensation of the next carboxylic acid onto the growing polyketide chain, catalysed by the β-ketoacyl synthase (KS) domain, modules of type I PKS may contain domains with β-ketoreductase (KR), dehydratase (DH) or enoyl reductase (ER) activities, which determine the reduced state of incorporated extender units. The acyltransferase (AT) and acyl carrier protein (ACP) domains present in each module are responsible for the choice of extender unit and retention of the growing polyketide chain on the PKS, respectively. Upon completion of synthesis, the polyketide chain is released from PKSs via action of a thioesterase (TE), that is probably also involved in cyclization of the final product. Thus, PKSs type I represent an assembly line for polyketide biosynthesis, that can be manipulated by changing the number of modules, their specificities towards carboxylic acids, and by inactivating or inserting domains with reductive activities (Weissman and Leadlay, Nat. Rev. Microbiol. 2005 December; 3(12):925-36.). After the polyketide moiety is synthesized and cyclized to form a macrolactone (or macrolactam) ring, it may be modified via hydroxylation, glycosylation, methylation and/or acylation. These modifications may be important for the biological activities of certain polyketide-based product. As will be described in more detail below, in work leading up to the present invention the genes encoding the BE-14106 NRPS-PKS enzyme system (the BE-14016 "gene cluster") have been cloned and sequenced and it has been determined that the BE-14106 NRPS-PKS enzyme system contains several type I PKSs, each of which is organized in the modular way, and is made up of repeated units (modules).

The genes for polyketide biosynthesis in *Streptomyces* are generally organized in clusters, and a number of such clusters have already been identified, responsible for the synthesis of various natural products. The molecular cloning and complete DNA sequencing of several macrolide antibiotic gene clusters of *Streptomyces* has been described, including those for avermectin, pikromycin and rapamycin (Ikeda H., Omura S. (2002). Biosynthesis, Regulation, and Genetics of Macrolide Production. In: Macrolide Antibiotics: Chemistry, Biology and Practice, 2nd Ed. (ed. S. Omura), pp. 286-326, Academic Press, New York.) As mentioned above, gene clusters for the biosystems of certain macrolactam antibiotics have also been reported.

As noted above and described below, the present invention is based on the identification, cloning and sequencing of a novel gene cluster for biosynthesis of BE-14106 which has not heretofore been available. Analysis of the cloned genes has further allowed the elucidation of the biosynthetic pathway for BE-14106. Accordingly it is now proposed that the normal process of synthesis of BE-14106 is initiated through the synthesis of a starter unit (C17-C25), where an acyl moiety is synthesised from 1 proprionate and 2 acetate units. Synthesis of the starter unit continues with the activation of a glycine molecule by an NRPS adenylation domain and loading of the activated glycine on to a peptidyl carrier protein. The oxidative deamination of glycine releases ammonium, which makes a nucleophilic attack on the C-17 carbonyl to form a C-17 imino group, which is subsequently reduced to an amino group. Release of the aminoacyl chain from the peptidyl carrier protein, results in the formation of a carboxylic acid, which is then adenylated and ligated to coenzyme A (CoA). The resultant activated aminoacyl-CoA is transferred to the ACP domain of a PKS by an acyltransferase and extended and modified by the sequential action of the enzymes in the PKS system as described in more detail below. The β-ketoacyl synthase (KS) enzyme domain in each module catalyses the condensation of the appropriate carboxylic acid (e.g. acetate or propionate) as determined by the acyltransferase (AT) module. Enzyme domains with β-ketoreductase (KR) or dehydratase (DH) activity determine the reduced state of incorporated extender units.

The C20-C25 hydrocarbon side chain of BE-14106 is comprised from part of the starter unit and results from the cyclisation of the macrolactam ring. Finally, further modification of the macrolactam ring occurs via hydroxylation.

The BE-14106 biosynthetic gene cluster also encodes or includes various regulatory elements and proteins for the transport of the synthesized molecules.

Since the chemical synthesis of compounds such as this is highly complex, a biosynthetic route in practice needs to be used and accordingly the isolation or purification of the compounds from appropriate hosts is desirable. As has been recognised in the art, this affords the opportunity of manipulating genes of the PKS gene cluster in order to change the biosynthesis and thereby result in the synthesis of new or modified polyketide or polyketide-based compounds. Whilst the modification of a number of PKS gene clusters has been described resulting in the synthesis of various new compounds, there remains a need and desire to increase the repertoire of available compounds, especially antibiotics, and/or to improve upon the properties (e.g. efficacy, toxicity, solubility in water etc.) of existing drugs. The present invention is directed to these aims, and is based on the cloning and DNA sequencing of the BE-14106 biosynthetic gene cluster. This provides the first sequence for these antibiotic biosynthetic genes, as well as a tool for genetic manipulation in order to modify the expression levels or properties of BE-14106 and/or the producing organism, or to obtain novel potentially useful compounds. In this respect, whilst the antibiotic BE-14106 is known, in the background of a plurality of polyketide-based molecules synthesised in *Streptomyces* and corresponding plurality of biosynthetic gene clusters, it was not a straightforward matter to identify and clone the correct gene cluster for BE-14106; a considerable effort and ingenuity in terms of sequence analysis and design or selection of probes was required.

The present inventors have isolated and purified BE-14106 from a previously unknown source, bacterial isolate MP28-13, believed to be a novel strain of *Streptomyces* (deposited under the deposit number DSM21069, on 25 Jan. 2008, at the Deutsche Sammlung von Mikroorganismem and Zellkulturen GmbH (DSMZ)) which was isolated from shallow water sediment in the Trondheim fjord, Norway. The isolation of this novel microorganism has enabled the inventors to clone and sequence the entire BE-14106 biosynthetic gene cluster. This cluster contains 22 genes that encode proteins presumed to be involved in the biosynthesis of the BE-14106 molecule (see Table 1).

To perform this cloning, specially designed oligonucleotide primers representing sequences encoding parts of the ketosynthase (KS) domain were used for amplification of KS domain coding regions from isolate MP28-13. Once amplified sequences had been obtained and characterised, based on complex and extensive bioinformatic analysis, one of the sequences was chosen as a probe. This probe was used for screening the genomic library that was constructed for MP28-13. The cosmids that were identified in this manner were analysed and sequenced to provide the whole biosynthetic cluster. The sequence has been fully annotated and a two-part pathway for BE-14106 biosynthesis has been elucidated, as set out in FIGS. 2A and 2B. The first part of the pathway for biosynthesis of the starter aminoacyl unit is shown in FIG. 2A and the second part, elongation of the aminoacyl chain, its cyclisation resulting in the formation of macrolactam ring and post PKS modification, is depicted in FIG. 2B. Thus, it is proposed that the BE-14106 biosynthetic gene cluster encodes a first enzyme system or complex comprising PKS and other enzymes or proteins for synthesis of the aminoacyl chain and an additional PKS enzyme system or enzyme complex for elongation of said aminoacyl chain, as well as an enzyme for post PKS modification of the molecule, proteins for regulation of the pathway, and resistance/efflux proteins.

Based on the knowledge of the sequence, a method for genetic manipulation of *Streptomyces* species MP28-13 was developed. In this way it was possible to show that the novel sequence was indeed responsible for BE-14106 biosynthesis.

Furthermore, as will be described in more detail below, manipulation of functional DNA sequences within the novel biosynthetic gene cluster which has been identified, can lead to the synthesis of novel molecular structures, e.g. BE-14106 derivatives or analogues with the altered, e.g. improved function or properties. As such the BE-14106 gene cluster can be manipulated to obtain not only beneficial new BE-14106 derivatives or analogues, but also to improve and facilitate the biosynthetic production process (for example to improve yield, or production conditions, or to expand the range of available host cells) or more preferably to provide novel compounds with new activities and/or properties.

The complete coding sequence for (i.e. the complete nucleotide sequence encoding) the BE-14106 biosynthetic gene cluster is shown in SEQ ID No. 1. This has been shown to contain a number of genes or ORFs, which encode the various proteins and polypeptides which are responsible for the activities that are required for BE-14106 biosynthesis.

The biosynthetic gene cluster contains genes and ORFs that are believed to encode all of the proteins and polypeptides that are required for normal BE-14106 biosynthesis. However, not all of the encoded proteins and polypeptides have yet been ascribed a role in the biosynthesis and so it may be that not all of the encoded proteins or polypeptides of the cluster are essential for BE-14106 biosynthesis. The various genes and ORFs may encode enzymes that catalyse one or more biochemical reactions, or proteins that do not have catalytic activity but instead are involved in other processes such as the regulation of the process of BE-14106 synthesis, or BE-14106 transport, for example.

Several of the enzymes are polyketide synthases (PKSs), and it is possible that a number of these PKSs may physically associate to form an enzyme complex, although this has not yet been established. Such a group or set of enzymes is referred to herein as a polyketide biosynthetic enzyme system or complex or PKS enzyme system or complex, although not all of the enzymes/proteins in the system/complex need be actual polyketide synthases, i.e. have polyketide synthase activity; they may have other activities or functional roles in BE-14106 synthesis. For example, a discrete adenylation domain of non-ribosomal peptide synthetase (NRPS) (BecL), along with some other accessory proteins (e.g. BecJ, BecS, BecU) encoded by the cluster are involved in the synthesis of the starter unit for biosynthesis of BE-14106 by activating an amino acid (presumed to be a glycine) and its loading on one of several BE-14106 PKS modules for further elongation.

Other proteins, such as BecO, perform hydroxylation of the macrolactam ring at C-8. A group or set of enzymes comprising such a NRPS domain and PKS enzymes may be referred to as a hybrid NRPS-PKS enzyme system or enzyme complex. The group of proteins and polypeptides encoded by the gene cluster as a whole are collectively referred to as the biosynthetic machinery for the biosynthesis of BE-14106.

Thus in one aspect, the present invention provides a nucleic acid molecule comprising:

(a) a nucleotide sequence as shown in SEQ ID No. 1; or (b) a nucleotide sequence which is the complement of SEQ ID No. 1; or (c) a nucleotide sequence which is degenerate with SEQ ID No. 1; or (d) a nucleotide sequence having at least 85% sequence identity (preferably at least 87%, 90%, 91%, 92%, 93%, 94%, 95%, 96%, 97%, 98% or 99% sequence identity) with SEQ ID No. 1; or (e) a part of any one of (a) to (d) wherein said part preferably comprises a sequence which corresponds to a BE-14106 biosynthetic gene or open reading frame (ORF), or is complementary thereto or degenerate therewith.

More particularly such a nucleic acid molecule encodes (or comprises a nucleotide sequence encoding) one or more polypeptides, or comprises one or more genetic elements, having functional activity in the synthesis of a polyketide or macrolactam molecule, more particularly the synthesis of BE-1406 or a derivative thereof, or BE-1406 related molecule, or which is the complement of such a nucleic acid molecule. Such functional activity may be enzymatic activity, e.g. an activity involved in the synthesis or transport or transfer of a polyketide or macrolactam molecule (this can be polyketide chain or macrolactam ring synthesis or any step contributory thereto, or macrolactam ring or polyketide chain modification etc) and/or it may be a regulatory activity, e.g. regulation of the expression of the genes (e.g. a transcriptional regulator) or proteins involved in the synthesis, or regulation of the synthetic process, and/or it may be a "transporter activity". Thus, included generally are also transport proteins involved in the transfer or transport of polyketide or macrolactam moieties e.g. in the transport or efflux of the synthesised molecule within or out of the cell.

Whilst nucleotide sequences encoding a desired product are preferred according to the invention, also encompassed are nucleotide sequences comprising functional genetic elements such as promoters, promoter-operator regions, enhancers, other regulatory sequences etc. Thus, the nucleic acid molecule of the invention need not comprise the entire PKS gene cluster but may comprise a portion or part of it e.g. a part encoding a polypeptide having a particular function or a regulatory sequence. This may comprise one or more genes, and/or regulatory sequences, and/or one or more modules or, enzymatic domains, or non-coding or coding functional genetic elements (e.g. elements controlling gene expression, transcription, translation etc). Generally speaking, a nucleic acid molecule of the invention will comprise a number of different genes and/or regulatory sequences leading to the synthesis of a polyketide-based or macrolactam molecule, e.g. a BE-14106 derivative or a modified BE-14106 molecule.

A "BE-14106 biosynthetic gene or ORF" is defined further below, but briefly in the context of section (e) above means a gene or ORF which encodes a protein or polypeptide that is functional in the biosynthetic process of BE-14106 or a BE-14106 derivative or analogue or BE-14106-related molecule. As noted above, this could be an enzyme that is involved in the activation of the starting amino acid, transfer of the activated amino acid/aminoacyl chain to a PKS enzyme, generation of the polyketide chain or modification thereof, or a protein that is required for regulation, or for transport or transfer of the molecule at any stage of its biosynthesis.

A nucleic acid molecule of the invention may be an isolated nucleic acid molecule (in other words isolated or separated from the components with which it is normally found in nature) or it may be a recombinant or a synthetic nucleic acid molecule.

As discussed elsewhere herein, the BE-14106 biosynthetic gene cluster is a large nucleic acid molecule which contains the various genetic elements or different genes or ORFs that encode the proteins or peptides that are required for the biosynthesis of the BE-14106 molecule or a BE-14106 derivative or analogue or BE-14106-related molecule. Each BE-14106 biosynthetic gene or ORF encodes a single polypeptide chain (which can alternatively be described as a protein) that has or is believed to have a function in the biosynthesis of the BE-14106 molecule or a BE-14106 derivative or analogue or BE-14106-related molecule. 22 such genes or ORFs have been identified (see Table 1). As shown in FIGS. 2A and 2B, 14 of these are ascribed a direct role in the biosynthesis of BE-14106. As explained further below, certain others are also believed or proposed to play a role in BE-14106 biosynthesis. Thus for example, becH and M are believed to encode regulators, BecL is believed to be involved in the glycine activation, BecU is believed to mediate the protein interaction between the ACP of BecC and PCP BecS, BecN is believed to be involved in efflux and/or resistance, BecP is thought to assist the cyclisation of the macrolactam ring and BecQ in the release of the initiating aminoacyl chain from the BecC-BecU-BecS complex.

Certain of the proteins have enzymatic activity and can thus be defined as being enzymes. Various of these enzymes can be described as polyketide synthases (PKSs). Such enzymes contain one or more than one module, and each module can contain from one to six, preferably two, three, four or five enzyme domains, each of which is responsible for a different activity in the biosynthesis of the BE-14106 molecule or a BE-14106 derivative or analogue or BE-14106-related molecule. As such, in these PKSs multiple active sites can be present in a single polypeptide or enzyme.

For example, the enzyme BecB is a PKS and has three modules; module 1 (the "loading module" in FIG. 2B) has a single active site or domain (ACP), and each of modules 2 and 3 (Modules 1 and 2 in FIG. 2B) have five active sites or domains having KS, AT, DH, KR and ACP activities. Other PKSs encoded by the gene cluster are BecA, BecC, BecD, BecG, BecF and BecE. Such PKSs can contain numerous domains, each possessing catalytic activity to extend and/or alter the structure of the polyketide. The polyketide passes along the protein such that the different activities are carried out sequentially on the growing polyketide chain. As discussed above, various of the PKSs encoded by the gene cluster may associate to form a biosynthetic enzyme complex.

The nucleic acid molecule of the invention encodes (or comprises a nucleotide sequence encoding) some, or more preferably all, of the polypeptides or proteins that are involved in the biosynthesis of the molecule BE-14106 or a BE-14106 derivative or analogue or BE-14106-related molecule. For example, the nucleic acid molecule may contain each of the 22 genes or ORFs and thus encode each of the proteins that are involved in the biosynthesis of the molecule BE-14106 as set out in Table 1, or it may comprise a portion or part of the nucleotide sequence of SEQ ID No. 1 e.g. a sequence encoding a single protein or polypeptide encoded by a single gene or ORF within the BE-14106 biosynthetic gene cluster. Parts comprising e.g. at least 11, 12, 13, 14, 15, 16, 17, 18, 19, 20, 21, or up to 2, 3, 4, 5, 6, 7, 8, 9, 10, 11, (e.g. 1-21, 2-20, 3-19, 4-18, 5-17, 6-16, 7-15, 8-14, 9-13, 10-12) genes or ORFs are contemplated. Preferably the nucleic acid molecule of the invention encodes all of the proteins that are involved in the biosynthesis of the molecule BE-14106 as set out in Table 1. Alternatively it may comprise all of the ORFs/genes as set out in Table 1 except any one or more of becR and ORF6. Since Table 1 sets out all of the genes or ORFs which have been characterised, a nucleic acid molecule encoding all of the proteins that are involved in the biosynthesis of the molecule BE-14106 as set out in Table 1 can be defined as a sequence which comprises the BE-14106 biosynthetic gene cluster.

The nucleic acid molecule of the invention thus encodes one or more polypeptides involved in the biosynthesis of or having functional activity in the synthesis of BE-14106 or a BE-14106 derivative or analogue or BE-14106-related molecule. Alternatively it may encode one or more functionally equivalent variants or functional equivalents thereof. As defined above, the nucleic acid molecules of the invention may comprise functionally equivalent variants of SEQ ID No. 1 and such variants may include parts, degenerate sequences, or homologues defined by a % sequence identity to SEQ ID No. 1. Such functionally equivalent variants encode proteins/polypeptides having functional activity as defined above. Such functional activity may be enzymatic activity e.g. an activity involved in the synthesis or transport or transfer of a polyketide moiety or a macrolactam molecule (this can be chain or ring synthesis or any step contributory thereto, or modification etc at any stage of biosynthesis, e.g. BecA, BecU, BecB, BecJ, BecK, BecS, BecO, BecD, BecG, BecF, BecE, BecT, BecQ, BecP, BecC, BecI, BecL) and/or it may be a regulatory activity, e.g. regulation of the expression of the genes or proteins involved in the synthesis, or regulation of the synthetic process e.g. BecH, BecM, and/or it may be a "transporter activity" or resistance e.g. BecN. Thus, included generally are also transport proteins involved in the transfer, transport or efflux of the synthesised molecule within or out of the cell. Also contemplated are sequences that encode one or more modules or enzymatic domains.

Such molecules may be at least 200 bases in length, more preferably at least, 300, 500, 600, 700, 800, 900, 1000, 1500, 2000, 3000, 5000, 10000, 15000, 20000, 30000, or 50000 bases. Representative fragment lengths thus include fragments that are 100 bp to 18000 bp in length, e.g. 100-3000 bp, 200-2500 bp, 2000-8000 bp, 3000-5000 bp, 4000-17000 bp, 7000-12000 bp or 8000-11000 bp in length. As mentioned above, a number of genes and ORFs have been identified within SEQ ID NO:1 and parts or fragments which comprise such genes or ORFs represent preferred "parts" or fragments of SEQ ID NO:1. These are tabulated in Table 1 below:

TABLE 1

| Name | Start position in SEQ ID NO: 1 | End position in SEQ ID NO: 1 | Putative function of encoded protein | SEQ ID NO: (nucleic acid/ protein) |
|---|---|---|---|---|
| becH | 458 | 3313 | LuxR-type transcriptional regulator | 2/3 |
| becA | 3664 | 20412 | PKS type I, loading + mod 1 + mod 2 + incomplete mod 3 | 4/5 |
| becI | 21832 | 20744 C | glycine oxidase/FAD-dependent oxidoreductase | 6/7 |
| becC | 23913 | 21829 C | PKS type I, incomplete module 3 | 8/9 |

TABLE 1-continued

| Name | Start position in SEQ ID NO: 1 | End position in SEQ ID NO: 1 | Putative function of encoded protein | SEQ ID NO: (nucleic acid/ protein) |
|---|---|---|---|---|
| becU | 24508 | 23945 C | homolog of *S. avermitilis* SAV_606, putative NRPS accessory protein | 10/11 |
| becB | 35088 | 24505 C | PKS type I, modules 1, 2 and 3 | 12/13 |
| becJ | 36752 | 35154 C | putative acyl CoA synthase/ligase | 14/15 |
| becK | 36947 | 37918 | acyl transferase | 16/17 |
| becS | 38170 | 37934 C | peptdyl/acyl carrier protein | 18/19 |
| becL | 38288 | 39805 | NRPS, adenylation domain | 20/21 |
| becM | 40384 | 39788 C | TetR-type transcriptional regulator | 22/23 |
| becN | 40486 | 42060 | MFS-type efflux pump | 24/25 |
| becO | 43388 | 42153 C | P450 monooxyganase | 26/27 |
| becD | 53553 | 43435 C | PKS type I, modules 4 &5 | 28/29 |
| becP | 54502 | 53561 C | L-amino acid amidase/proline Iminopeptidase | 30/31 |
| becG | 60565 | 54605 C | PKS type I, module 9 + TE domain | 32/33 |
| becF | 70706 | 60573 C | PKS type I, modules 7 and 8 | 34/35 |
| becE | 75649 | 70754 C | PKS type I, module 6 | 36/37 |
| becT | 76241 | 75954 C | SimX2-like protein, putative subunit of propionyl Coa carboxylase | 38/39 |
| becQ | 76563 | 77336 | thioesterase, type II | 40/41 |
| becR | 77489 | 78202 | PlsC-type phospholipid/glycerol acyltransferase | 42/43 |
| orf6 | 79912 | 78302 C | tripeptydylaminopeptidase, secreted | 44/45 |

In the above Table, "C" indicates that the protein is encoded by the complement strand The sequences set out above thus represent BE-14106 biosynthetic genes or ORFs. In other words, such genes/ORFs are found within the BE-14106 biosynthetic gene cluster and encode proteins or polypeptides which have or are proposed to have a role in the biosynthesis of BE-14106 in *Streptomyces*. The term "BE-14106 biosynthetic gene" or "BE-14106 biosynthetic ORF" also includes genes and ORFs which encode proteins that share activity or function with the above proteins, and for example share high levels of sequence identity, as discussed elsewhere herein. They can alternatively be described as "functionally equivalent variants" or "functional equivalents".

In general the term "gene" includes the ORF which encodes the protein, together with any regulatory sequences such as promoters; whereas the term"ORF" refers only to the part of the gene which is responsible for encoding the protein.

As referred to herein "functionally equivalent variants" or "functional equivalents" retain at least one function of the entity to which they are related (or from which they are derived), e.g. encode a protein with substantially the same properties, or exhibit substantially the same regulatory or other functional properties or activities. The properties or activities can be tested for using standard techniques that are known in the art.

Whilst nucleotide sequences encoding a desired product (e.g. ORFs and genes) are preferred according to the invention, also encompassed are nucleotide sequences comprising functional genetic elements such as promoters, promoter-operator regions, enhancers, other regulatory sequences etc. Thus, the nucleic acid molecule of the invention need not comprise the entire gene cluster but may comprise a portion or part of it e.g. a part encoding a polypeptide having a particular function or a regulatory sequence. This preferably comprises one or more genes, and/or regulatory sequences. Also contemplated are sequences that in general will be smaller than this and encode one or more modules or, enzymatic domains, or non-coding or coding functional genetic elements (e.g. elements controlling gene expression, transcription, translation etc).

The invention thus extends to a nucleic acid molecule comprising a nucleotide sequence selected from SEQ ID NO:2, 4, 6, 8, 10, 12, 14, 16, 18, 20, 22, 24, 26, 28, 30, 32, 34, 36, 38, 40, 42 and 44 (as identified by reference to nucleotide start and end positions in SEQ ID No. 1 as shown in Table 1) or a nucleotide sequence which is complementary thereto or degenerate therewith.

Also provided are nucleic acid molecules comprising nucleotide sequences which exhibit at least 80% (preferably at least 85%, 87%, 90%, 91%, 92%, 93%, 94%, 95%, 96%, 97%, 98% or 99%) sequence identity with any one of SEQ ID NO:2, 4, 6, 8, 10, 12, 14, 16, 18, 20, 22, 24, 26, 28, 30, 32, 34, 36, 38, 40, 42 and 44 or a nucleotide sequence which is complementary thereto or degenerate therewith.

The invention further relates to a nucleic acid molecule comprising a nucleotide sequence encoding one or more amino acid sequences selected from SEQ ID NO:3, 5, 7, 9, 11, 13, 15, 17, 19, 21, 23, 25, 27, 29, 31, 33, 35, 37, 39, 41, 43 or 45 or a nucleotide sequence which is complementary thereto or degenerate therewith.

Also provided are nucleic acid molecules comprising nucleotide sequences which encode one or more amino acid sequences (i.e. polypeptides) which exhibit at least 80% (preferably at least 85%, 87%, 90%, 91%, 92%, 93%, 94%, 95%, 96%, 97%, 98% or 99%) sequence identity with any one of SEQ ID NO:3, 5, 7, 9, 11, 13, 15, 17, 19, 21, 23, 25, 27, 29, 31, 33, 35, 37, 39, 41, 43 or 45 or a nucleotide sequence which is complementary thereto or degenerate therewith.

In each case, the nucleic acid molecule is preferably a BE-14106 biosynthetic gene or ORF, as defined herein.

Nucleotide or amino acid sequence identity may be assessed by any convenient method. However, for determining the degree of sequence identity between sequences, computer programs that make multiple alignments of sequences are useful, for instance Clustal W (Thompson, J. D et al., 1994, "CLUSTAL W: Improving the sensitivity of progressive multiple sequence alignment through sequence weighting, position-specific gap penalties and weight matrix choice". Nucleic Acids Res 22: 4673-4680). Programs that compare and align pairs of sequences, like ALIGN (E. Myers and W. Miller, 1988, "Optical Alignments in Linear Space", CABIOS 4: 11-17), FASTA (W. R. Pearson and D. J. Lipman, 1988, "Improved tools for biological sequence analysis", PNAS 85:2444-2448, and W. R. Pearson, 1990, "Rapid and sensitive sequence comparison with FASTP and FASTA" Methods in Enzymology 183:63-98) and gapped BLAST (Altschul, S. F., et al., 1997, "Gapped BLAST and PSI-BLAST: a new generation of protein database search programs". Nucleic Acids Res. 25: 3389-3402) are also useful for this purpose. Furthermore, the Dali server at the European Bioinformatics institute offers structure-based alignments of protein sequences (Holm, 1993, J. of Mol. Biology, 233: 123-38; Holm, 1995, Trends in Biochemical Sciences, 20: 478-480; Holm, 1998, Nucleic Acid Research, 26: 316-9).

For example, nucleotide sequence identity may be determined using the BestFit program of the Genetics Computer Group (GCG) Version 10 Software package from the University of Wisconsin. The program uses the local homology algorithm of Smith and Waterman with the default values: Gap creation penalty=50, Gap extension penalty=3, Average match=10,000, Average mismatch=−9.000.

Nucleotide sequences according to the invention may exhibit at least 85%, 87%, 90%, 91%, 92%, 93%, 94%, 95%, 96%, 97%, 98% or 99% sequence identity with SEQ ID NO: 1 and such sequences will preferably encode or are complementary to a sequence which encodes some or all of the proteins that are involved in the biosynthesis of the molecule BE-14106. Nucleotide sequences meeting the % sequence identity criteria defined herein may be regarded as "substantially identical" sequences.

A further aspect of the invention provides polypeptides encoded by a nucleic acid molecule of the invention as defined herein.

As discussed above, SEQ ID NO:1 encodes several proteins or polypeptides and as such this aspect of the invention provides a polypeptide comprising:

(a) all or part of an amino acid sequence as shown in any one or more of SEQ ID Nos. 3, 5, 7, 9, 11, 13, 15, 17, 19, 21, 23, 25, 27, 29, 31, 33, 35, 37, 39, 41, 43 or 45; or
(b) all or part of an amino acid sequence which has at least 80% sequence identity with any one or more of SEQ ID Nos. 3, 5, 7, 9, 11, 13, 15, 17, 19, 21, 23, 25, 27, 29, 31, 33, 35, 37, 39, 41, 43 or 45.

In particular the amino acid sequence may exhibit at least 80%, 85%, 87%, 90%, 91%, 92%, 93%, 94%, 95%, 96%, 97%, 98% or 99% identity with the polypeptide of any one of SEQ ID Nos. 3, 5, 7, 9, 11, 13, 15, 17, 19, 21, 23, 25, 27, 29, 31, 33, 35, 37, 39, 41, 43 or 45. Alternatively, the amino acid sequence may exhibit at least 80%, 85%, 87%, 90%, 91%, 92%, 93%, 94%, 95%, 96%, 97%, 98% or 99% similarity with the polypeptide of any one of SEQ ID Nos. 3, 5, 7, 9, 11, 13, 15, 17, 19, 21, 23, 25, 27, 29, 31, 33, 35, 37, 39, 41, 43 or 45.

Amino acid (polypeptide) sequences meeting the % sequence identity or similarity criteria herein are regarded as "substantially identical".

The polypeptide of the invention may be an isolated, purified or synthesized polypeptide. The term "polypeptide" is used herein to include any amino acid sequence of two or more amino acids i.e. both short peptides and longer lengths (i.e. polypeptides or proteins) are included.

Programs for determining amino acid sequence identity are mentioned above, for example amino acid sequence identity or similarity may be determined using the BestFit program of the Genetics Computer Group (GCG) Version 10 Software package from the University of Wisconsin. The program uses the local homology algorithm of Smith and Waterman with the default values: Gap creation penalty—8, Gap extension penalty=2, Average match=2.912, Average mismatch=−2.003. A "part" of the amino acid sequence of any one of SEQ ID Nos. 3, 5, 7, 9, 11, 13, 15, 17, 19, 21, 23, 25, 27, 29, 31, 33, 35, 37, 39, 41, 43 or 45 (or of a "substantially identical" sequence as defined above) may comprise at least 20 contiguous amino acids, preferably at least 30, 40, 50, 70, 100, 150, 200, 300, 400, 500, 1,000, 2,000, 5,000 or 10,000 contiguous amino acids.

The polypeptide, and preferably also the part thereof, is functionally active according to the definitions given above, e.g. is enzymatically active or has a regulatory or transport functional activity in the biosynthesis of BE-14106 or a derivative of BE-14106 or a modified version thereof. The part may thus correspond to or comprise an active site or domain or a module as discussed above.

The nucleotide and polypeptide sequences of the invention have been characterised and various functional regions within them have been identified. Such functional regions form separate aspects of the invention. "Parts" as defined herein thus preferably correspond to at least one module or enzymatic domain, or non-coding or coding functional genetic element. Table 2 below shows the functional regions identified with the translation products of the ORFs identified in SEQ ID No. 1 which encode PKS enzymes.

TABLE 2

| Domain boundaries in BE-14106 PKS proteins | | | | |
|---|---|---|---|---|
| Type | Start | End | Name | Description |
| BecA (SEQ ID No. 5) Molecule: BecA, 5582 aas Protein Molecule Features: | | | | |
| REGION | 17 | 436 | KSq | KS-like domain, loading module |
| REGION | 543 | 858 | AT0 | AT domain, loading module, propionate |
| REGION | 933 | 1004 | ACP0 | ACP domain, loading module |
| REGION | 1027 | 1450 | KS1 | KS domain, module 1 |
| REGION | 1561 | 1879 | AT1 | AT domain, acetate, module 1 |
| REGION | 1892 | 2095 | DH1 | DH domain, module 1 |
| REGION | 2415 | 2662 | KR1 | KR domain, module 1 |
| REGION | 2698 | 2771 | ACP1 | ACP domain, module 1 |
| REGION | 2795 | 3220 | KS2 | KS domain, module 2 |
| REGION | 3331 | 3649 | AT2 | AT domain, acetate, module 2 |
| REGION | 3663 | 3868 | DH2 | DH2 domain, module 2 |
| REGION | 4189 | 4435 | KR2 | KR domain, module 2 |
| REGION | 4472 | 4545 | ACP2 | ACP domain, module 2 |
| REGION | 4572 | 4995 | KSx | KS domain, module 3 |
| REGION | 5103 | 5416 | ATx | AT domain, acetate, module 3 |
| BecB (SEQ ID No. 13) Molecule: BecB, 3527 aas Protein Molecule Features: | | | | |
| REGION | 10 | 90 | ACP1 | ACP domain, module 1 |
| REGION | 112 | 537 | KS2 | KS domain, module 2 |
| REGION | 645 | 961 | AT2 | AT domain, acetate, module 2 |
| REGION | 975 | 1169 | DH2 | DH domain, module 2 |
| REGION | 1424 | 1672 | KR2 | KR domain, module 2 |
| REGION | 1709 | 1782 | ACP2 | ACP domain, module 2 |
| REGION | 1801 | 2225 | KS3 | KS domain, module 3 |
| REGION | 2332 | 2651 | AT3 | AT domain, propionate, module 3 |
| REGION | 2665 | 2865 | DH3 | DH domain, module 3 |
| REGION | 3132 | 3374 | KR3 | KR domain, module 3 |
| REGION | 3411 | 3485 | ACP3 | ACP domain, module 3 |
| BecC (SEQ ID No. 9) Molecule: BecC, 694 aas Protein Molecule Features: | | | | |
| REGION | 346 | 600 | KR | KR domain, module 3 |
| REGION | 615 | 689 | ACP | ACP domain, module 3 |
| BecD (SEQ ID No. 29) Molecule: BecD, 3372 aas Protein Molecule Features: | | | | |
| REGION | 38 | 447 | KS4 | KS domain, module 4 |
| REGION | 561 | 861 | AT4 | AT domain, acetate, module 4 |
| REGION | 875 | 1070 | DH4 | DH domain, module 4 |
| REGION | 1321 | 1570 | KR4 | KR domain, module 4 |
| REGION | 1586 | 1659 | ACP4 | ACP domain, module 4 |
| REGION | 1678 | 2089 | KS5 | KS domain, module 5 |
| REGION | 2173 | 2466 | AT5 | AT domain, acetate, module 5 |
| REGION | 2480 | 2672 | DH5 | DH domain, module 5 |
| REGION | 2934 | 3178 | KR5 | KR domain, module 5 |
| REGION | 3217 | 3290 | ACP5 | ACP domain, module 5 |
| BecE (SEQ ID No. 37) Molecule: BecE, 1631 aas Protein Molecule Features: | | | | |
| REGION | 34 | 445 | KS6 | KS domain, module 6 |
| REGION | 529 | 822 | AT6 | AT domain, acetate, module 6 |
| REGION | 836 | 984 | DH6i | DH domain, module 6, C-term deletion, probably inactive |
| REGION | 1201 | 1448 | KR6 | KR domain, module 6 |
| REGION | 1476 | 1550 | ACP6 | ACP domain, module 6 |
| BecF (SEQ ID No. 35) Molecule: BecF, 3377 aas Protein Molecule Features: | | | | |
| REGION | 37 | 447 | KS7 | KS domain, module 7 |
| REGION | 558 | 864 | AT7 | AT domain, propionate, module 7 |
| REGION | 878 | 1079 | DH7 | DH domain, module 7 |

TABLE 2-continued

| Domain boundaries in BE-14106 PKS proteins | | | | |
|---|---|---|---|---|
| Type | Start | End | Name | Description |
| REGION | 1341 | 1585 | KR7 | KR domain, module 7 |
| REGION | 1618 | 1691 | ACP7 | ACP domain, module 7 |
| REGION | 1710 | 2121 | KS8 | KS domain, module 8 |
| REGION | 2203 | 2496 | AT8 | AT domain, acetate, module 8 |
| REGION | 2510 | 2702 | DH8 | DH domain, module 8 |
| REGION | 2944 | 3186 | KR8 | KR domain, module 8 |
| REGION | 3221 | 3294 | ACP8 | ACP domain, module 8 |
| BecG (SEQ ID No. 33) Molecule: BecG, 1986 aas Protein Molecule Features: | | | | |
| REGION | 35 | 445 | KS9 | KS domain, module 9 |
| REGION | 553 | 847 | AT9 | AT domain, acetate, module 9 |
| REGION | 861 | 1066 | DH9 | DH domain, module 9 |
| REGION | 1341 | 1586 | KR9 | KR domain, module 9 |
| REGION | 1616 | 1690 | ACP9 | ACP domain, module 9 |
| REGION | 1767 | 1986 | TE | TE domain |

The pathway for biosynthesis of BE-14106 has been elucidated as follows and is shown in FIGS. 2A and 2B.

Biosynthesis of BE-14106 starts with assembly of a C17-C25 acyl moiety by the proteins BecA (which has the sequence SEQ ID NO:5 and is encoded by SEQ ID NO:4) and BecC (which has the sequence SEQ ID NO:9 and is encoded by SEQ ID NO:8) from 1 propionate and 2 acetate units (FIG. 2A). The KR domain in BecC is most likely inactive, leaving a carbonyl group at C19 of the synthesized polyketide chain. Biosynthesis of that aminoacyl starter continues with the activation of glycine by the discrete NRPS adenylation domain BecL (which has the sequence of SEQ ID NO:21 and is encoded by SEQ ID NO: 20) and loading of the activated glycine onto discrete peptidyl carrier protein BecS (which has the sequence of SEQ ID NO: 19 and is encoded by SEQ ID NO:18). BecU (which has the sequence of SEQ ID NO:11 and is encoded by SEQ ID NO:10) is thought to mediate the interaction between the ACP of BecC and BecS, bringing the substrates into proximity to each other. D-amino acid oxidase BecI presumably catalyzes the oxidative deamination of glycine, releasing ammonium, which makes a nucleophilic attack on the C-17 carbonyl to afford a C-17 imino group, which is subsequently reduced to an amino group. The latter reduction supposedly leads to the oxidation of the acyl chain and migration of double bonds. Thioesterase BecQ (which has the sequence of SEQ ID NO:41 and is encoded by SEQ ID NO:40) releases the aminoacyl chain from BecC-BecU-BecS complex, resulting in the formation of a aminoacyl-carboxylic acid. Putative acyl-CoA ligase, BecJ (which has the sequence of SEQ ID NO:15 and is encoded by SEQ ID NO:14), is assumed to activate the resulting aminoacyl-carboxylic acid through adenylation and subsequent ligation with CoA, making the aminoacyl-CoA an acceptable substrate for the acyl transferase BecK (which has the sequence of SEQ ID NO:17 and is encoded by SEQ ID NO:16). A discrete acyltransferase BecK transfers the activated aminoacyl chain to the ACP domain in module 1 on PKS BecB, which has the sequence of SEQ ID NO:13 and is encoded by SEQ ID NO:12. The latter PKS lacks all domains in module 1 except for ACP (loading module of FIG. 2B). Modules 2 and 3 (modules 1 and 2 in FIG. 2B) of BecB elongate the aminoacyl moiety from C17 with 1 acetate and 1 propionate unit (C16-15 and C14-13), respectively.

The growing chain is then passed to BecD, which has the sequence SEQ ID NO:29 and is encoded by SEQ ID NO:28, for further elongation and modification BecD contains modules 4 and 5 (modules 3 and 4 in FIG. 2B), which elongate the chain with 2 acetate units (C12-11 and C10-9).

The chain is then passed to BecE which has the sequence SEQ ID NO:37 and is encoded by SEQ ID NO:36. Module 6 (module 5 in FIG. 2B) of BecE PKS elongates the chain with one acetate unit (C8-7). The fact that the DH domain in this module is inactive is responsible for appearance of the C-9 hydroxy group. (The DH domain is believed to contain a deletion at the C-terminal region which eliminates the activity).

The chain is then passed to BecF which has the sequence SEQ ID NO:35 and is encoded by SEQ ID NO:34. Modules 7 and 8 (modules 6 and 7 in FIG. 2B) of BecF PKS elongate the chain with one propionate (C6-5) and one acetate (C4-3) unit, respectively.

The chain is then passed to BecG which has the sequence SEQ ID NO:33 and is encoded by SEQ ID NO:32. Module 9 (module 8 in FIG. 2B) of the BecG PKS extends the chain with one acetate unit and the TE domain of BecG is responsible for the hydrolysis of the thioester bond and the release of the completed aminated polyketide chain from the PKS. This causes the cyclisation of the macrolactam ring, probably assisted by the putative homolog of proline iminopeptidase BecP (which has the sequence SEQ ID NO:31 and is encoded by SEQ ID NO:30). The biosynthesis is completed by P450 monooxygenase BecO (which has the sequence SEQ ID NO:27 and is encoded by SEQ ID NO:26), which hydroxylates 8-deoxy BE-14106 at C-8.

No clear role in the biosynthesis of BE-14106 could be defined for BecT (which has the sequence SEQ ID NO:39 and is encoded by SEQ ID NO:38). BecR (which has the sequence SEQ ID NO:43 and is encoded by SEQ ID NO:42) is not involved in the biosynthesis of BE-14106, as proven by the gene inactivation experiment (Example 10).

Proteins that are thought to be involved in the regulation of the pathway include the LuxR-type protein BecH (which has the sequence SEQ ID NO:3 and is encoded by SEQ ID NO:2) and the TetR-type regulator BecM (which has the sequence SEQ ID NO:23 and is encoded by SEQ ID NO:22).

The MFS-type efflux pump BecN (which has the sequence SEQ ID NO:25 and is encoded by SEQ ID NO:24) is thought to be responsible for BE-14106 efflux/resistance.

The nucleotide sequences of the present invention provide important tools and information which can be utilised in a number of ways to manipulate BE-14106 biosynthesis, to synthesise new BE-14106 derivatives or analogues or novel polyketide-based or macrolactam molecules or structures, and to provide novel or modified PKS biosynthetic machinery for the biosynthesis of such novel polyketide or macrolactam molecules or structures. By PKS biosynthetic machinery is meant a group of proteins (e.g. encoded by a gene cluster) that comprises one or more PKSs that may form a protein complex, collection or assembly, which is functional in polyketide synthesis, but which is not necessarily restricted only to the presence of PKS enzymes or enzymatic domains, and which may contain also other functional activities, e.g. other enzymatic (e.g. modificatory) or transporter or regulatory functional proteins). The proteins encoded by the gene cluster may thus be viewed as an "enzyme system" or "enzyme complex" or "protein system" or "protein complex" without necessarily implying that the proteins in the system are physically associated in any way. They are "functionally" associated in the sense of constituting the biosynthetic machinery for BE-14106. They may alternatively be termed a "biosynthetic system" or "biosynthetic complex" or "assembly".

Thus, for example, the entire BE-14106 biosynthetic gene cluster or biosynthetic machinery or a constituent enzyme or enzyme complex as provided herein, or a portion thereof, may be subjected to modification. The modification takes place by modifying one or more genes or ORFs in the gene cluster so as to cause the modification of one or more encoded proteins or peptides (e.g. enzymes or modules, or enzymatic domains, or functional sequences within the encoded protein/peptide or enzyme). Thus, enzyme activity may be altered or inactivated so as to result in modification to the molecule (e.g. polyketide or macrolactam structure) which is synthesised. Such modified or derivatised NRPS-PKS biosynthetic machinery may thus be used to synthesize novel or modified polyketide or macrolactam moieties, as will be described in more detail below. In this situation, the BE-14106 biosynthetic gene cluster or enzyme complex or groups of enzymes provided herein, or a fragment or portion thereof, may function as an "origin" or "template" or "source" system or sequence for modification. Thus the NRPS-PKS biosynthetic machinery may be seen as a NRPS-PKS biosynthetic system, or "NRPS-PKS system".

As described in more detail below, in one embodiment the modification of the gene cluster may take place in situ. In other words, the endogenous gene cluster as contained in a microorganism which produces BE-14106 may be modified, for example by gene replacement or gene inactivation. Thus, the native gene cluster as it naturally occurs in a microorganism may be modified. Whilst recombinant expression of a nucleic acid molecule of the invention is a possibility (i.e. the introduction of the nucleic acid molecule into a host cell (e.g. a heterologous host cell) and the culturing (or growth) of that host cell under conditions which allow the nucleic acid molecule to be expressed and the polyketide or macrolactam molecule to be produced (i.e. conditions which allow the expression product of the nucleic acid molecule to synthesise the polyketide/macrolactam molecule), this is less preferred. In such a recombinant expression system, the nucleic acid molecule may be subject to modification before being introduced into the host cell and expressed.

According to the invention and as further described below, the non-functional parts (e.g., non-biologically active parts, for example non-coding parts) of said system (i.e. of the gene cluster or protein complex or assembly or biosynthetic machinery) may be utilised as a "scaffold", and left unmodified and the functional parts (e.g. sequences encoding enzymatic portions) may be modified to yield the derivative or modified NRPS-PKS system. In preferred embodiments only a single selected, or few selected functional (e.g. enzymatic) regions, modules or domains may be modified, leaving the remaining sequence or structure largely intact.

Included within the scope of the invention are synthetic or recombinant polyketide synthase or other enzymes and complexes or systems containing such enzymes, or other proteins of the biosynthetic machinery, i.e. enzymes or proteins or complexes or systems derived from the scaffold encoded by the BE-14106 biosynthetic gene cluster which are modified in order to change the properties of at least one protein encoded by the BE-14106 biosynthetic gene cluster.

For example such a modification could be to include sequences encoding one or more functional units (e.g. modules or domains or even whole genes/ORFs) derived from other modular enzymes. Alternatively, such a modification could be to introduce sequences encoding one or more functional units derived from the BE-14106 biosynthetic gene cluster but which are found at a different location in the naturally occurring sequence. The modification could also be modification which results in the inactivation or deletion of an encoded domain, module, enzyme or other functional unit in the BE-14106 biosynthetic machinery.

Such functional units may be catalytic or a transport or regulatory protein domain. To perform such manipulations, the sequences that are used can be from the nucleic acid molecule of the invention, or appropriate sequences encoding domains can be derived from nucleotide molecules encoding other polyketide synthesising enzymes, peptide synthesising enzymes, hybrid peptide polyketide synthesising enzymes, fatty acid synthesising enzymes or other enzyme domains known in the art.

Thus, in a very general sense, the present invention provides the use of the nucleic acid molecules of the invention as defined herein in the preparation of a modified BE-14106 biosynthetic gene cluster, the encoded biosynthetic machinery (or protein system) and the resultant modified molecules that are synthesised therefrom.

The nucleotide sequence of the nucleic acid molecules of the invention may be utilised in this way according to the present invention in a random or directed or designed manner, e.g. to obtain and test a particular predetermined or predesigned structure, or to create random molecules, for example libraries of polyketide structures, e.g. for screening.

By modified BE-14106 molecule or BE-14106 derivative it is meant that the chemical structure of BE-14106 has been changed relative to that which is depicted in FIG. 1. Such modifications can alter the functional properties of BE-14106 such that the strength or potency of the molecule (e.g. cytotoxic effects or antiproliferative activity) is enhanced or reduced, for example, or they can influence selective toxicity, solubility, pharmacokinetics, affinity to cellular target(s) or other properties of the compound.

Alternatively, the modifications described herein can be used to change the way that the BE-14106 molecule is transported or its biosynthesis regulated.

Such a novel or modified biosynthetic gene cluster, the encoded biosynthetic machinery including the constituent proteins or protein system and the resultant modified molecules that are synthesised therefrom each form a separate aspects of the present invention. Also included as part of the invention are cells into which a biosynthetic gene cluster has been introduced or cells containing or comprising such a modified biosynthetic gene cluster or the modified encoded biosynthetic machinery.

The genes or genetic elements which can be modified include not only the actual PKS genes or ORFs (which encode BecA, BecB, BecC, BecD, BecE, BecF, BecG) or the individual modules or domains thereof, but also genes or ORFs encoding other enzymes or functional proteins involved in BE-14106 biosynthesis (e.g. which encode BecU, BecI, BecP, BecJ, Beck, BecS, BecL, BecO, BecT, BecQ) and transport (e.g. which encode BecN) or regulation (e.g. which encode BecH, BecM), all of which are referred to herein collectively as "BE-14106 biosynthetic genes".

As regards the actual PKS genes, as will be described in more detail below, these may be modified to change the nature of a loading module domain which determines the nature of the starter unit, the number of modules, the nature of the extender, as well as the various dehydratase, reductase and synthase activities which determine the structure of the polyketide chain.

Thus, for example, the number of modules of a PKS enzyme may be increased or decreased, e.g. one or more modules of a PKS enzyme may be deleted; KS, DH and/or KR domains of a PKS enzyme may be deleted, inactivated or introduced (e.g. from the same PKS gene or another PKS gene), an AT domain of a PKS enzyme may be modified to alter its specificity for a starter or extender unit; the $KS^Q$ domain of a BecA (SEQ ID No. 4/5) may be modified (e.g. inactivated) to alter the nature of the starter unit which will constitute part of the side chain.

Change of specificity of BecO hydroxylase may provide for hydroxylation at carbon atoms of BE-14106 (or its analogues) other than C-8.

In addition to modification of the NRPS or PKS enzymes to change the nature of the synthesised molecules, the nucleic acid molecules of the invention can also be utilised to manipulate or facilitate the biosynthetic process, for example by extending the host range or increasing yield or production efficiency etc.

To enable recombinant expression of a nucleic acid molecule of the invention, the invention also provides a vector, for example a cloning or expression vector, comprising the nucleic acid of the invention and a host cell containing such a molecule. However, as noted above, this aspect of the invention is less preferred.

In practice, the modification advantageously can be carried out by manipulating the BE-14106 biosynthetic gene cluster sequence in situ in a cell (which may be viewed herein as a "host cell") e.g. to alter the nucleotide sequence encoding an enzyme activity, so as to inactivate or modify that activity or to introduce an activity. Appropriate genetic constructs can be generated which contain sequences having the required modifications that are to be introduced into the BE-14106 biosynthetic gene cluster sequence (e.g. into SEQ ID No. 1) as contained in an endogenous nucleic acid molecule (in other words a nucleic acid molecule contained in the host cell). Introduction of a vector (e.g. a plasmid) with this sequence into the appropriate host cell can then be carried out. This ultimately leads to the integration of the modified sequence into the gene cluster (e.g. within the genome of the host cell) near the corresponding (e.g. endogenous or naturally occurring) portion of the biosynthetic gene cluster via homologous recombination. Upon a second recombination event, the endogenous portion of the gene cluster is replaced by the modified version and the vector is eliminated.

The resultant modified host cell will therefore contain a modified BE-14106 biosynthetic gene cluster, which encodes a modified BE-14106 enzyme system. The modified BE-14106 biosynthetic machinery thus synthesises a modified BE-14106 molecule.

As noted above, the gene cluster which is modified may be the native gene cluster which is naturally present in a host cell (microorganism) which produces BE-14106 or a derivative thereof (and hence a native nucleic acid or endogenous nucleic acid molecule is modified). Less preferably, but still encompassed by the present invention, the nucleic acid molecule of the invention may be introduced into the host cell before modification. Alternatively, the nucleic acid molecule is introduced into the host cell after modification. Hence an exogenous nucleic acid molecule may be modified.

Given that the invention provides the sequence of the full length BE-14106 gene cluster, this gene replacement strategy is of general application to modify the BE-14106 gene cluster. The strategy can e.g. be used to delete a portion of the gene cluster, to introduce activities or to substitute activities found within the modules in the native or wild-type sequence. The strategy requires knowledge of the gene cluster sequence but does not necessarily require the complete gene cluster to be isolated from a host cell in order to carry out the manipulation.

Thus, in a further aspect the present invention provides a method for preparing a nucleic acid molecule encoding a modified BE-14106 NRPS-PKS biosynthetic machinery (or modified BE-14106 NRPS-PKS system), said method comprising modifying a nucleic acid molecule, as hereinbefore defined, encoding said BE-14106 NRPS-PKS biosynthetic machinery (or modified BE-14106 NRPS-PKS system).

The nucleic acid molecule is modified by modifying its sequence, and more particularly the nucleic acid molecule may be modified by introducing, mutating, deleting, replacing or inactivating a sequence encoding one or more activities (or proteins) encoded by said nucleic acid molecule. Thus, one or more sequences may be modified that encode enzymatic or other functional activities. Such modification results in a nucleic acid molecule which encodes a BE-14106 NRPS-PKS biosynthetic machinery (or BE-14106 NRPS-PKS system) which has altered function or activity or altered properties as compared to the native or wild-type BE-14106 NRPS-PKS biosynthetic machinery (or BE-14106 NRPS-PKS system). Thus the modified biosynthetic machinery (or NRPS-PKS system) may have one or more altered or modified enzymatic activities and may result in the synthesis of a molecule (e.g polyketide or macrolactam molecule) which is other than (or different to) the molecule synthesised from the native (i.e unmodified) biosynthetic machinery (or NRPS-PKS system). Alternatively, as noted above modification of the biosynthetic machinery may result in an improvement in the biosynthetic process e.g. increased yield etc.

The nucleic acid which is modified may be contained within a cell or organism, which may be the cell or organism used for production of the polyketide/macrolactam molecule which is synthesised by the modified biosynthetic machinery.

As noted above, the nucleic acid molecule which is modified may advantageously be the nucleic acid molecule which is endogenously (or naturally) present in an organism which produces BE-14106 (or a derivative thereof). Thus, the method of the invention may involve modifying in situ a native nucleic acid molecule (more particularly modifying the sequence of a nucleic acid molecule) within a cell or organism (generally a microbial cell or a microorganism) which produces BE-14106 or a derivative thereof. The nucleic acid molecule is or represents the BE-14106 biosynthetic gene cluster or a part thereof and may thus be seen as a nucleic acid molecule encoding the BE-14106 biosynthetic machinery or BE-14106 NRPS-PKS system or a part thereof.

A number of different microorganisms may produce BE-14106 and it is further known that some microorganisms may produce naturally occurring derivatives of BE-14106 such as the 8-deoxy derivative (Takahashi et al., supra). Reference to a BE-14106 gene cluster or biosynthetic machinery (or NRPS-PKS system etc) is intended to include gene clusters or biosynthetic machinery etc that produce not only BE-14106 itself but also naturally occurring derivatives such as the 8-deoxy derivative (designated GT32-B).

The invention further provides a method for preparing a modified BE-14106 NRPS-PKS biosynthetic machinery (or modified BE-14106 NRPS-PKS system), said method comprising expressing a modified nucleic acid molecule prepared (or obtained) as defined above. This may be achieved simply by modifying the nucleic acid molecule contained in the cell, as described above, and allowing the cell to grow under conditions in which the modified nucleic acid molecule is expressed. Thus, for example, the native nucleic acid molecule in the cell may be modified in situ and the cell may be allowed to grow.

This aspect of the invention may also provide the modified BE-14106 NRPS-PKS biosynthetic machinery (or modified BE-14106 NRPS-PKS system) obtained by such a method.

The invention also provides a method for preparing a modified polyketide or macrolactam molecule, said method comprising expressing a modified nucleic acid molecule prepared (or obtained) as defined above.

Generally speaking, the nucleic acid molecule will be expressed in a host cell under conditions in which the modified biosynthetic machinery may be expressed. As outlined above, this may be achieved by introducing the nucleic acid molecule into a host cell, but generally the "host cell" will be the cell or organism in which the nucleic acid molecule is naturally or endogenously present and in which the nucleic acid molecule is modified. The host cell will be grown or cultured under conditions which allow the modified nucleic acid molecule and biosynthetic machinery to be expressed, and the molecule produced from the biosynthetic machinery to be synthesised.

Thus, the nucleic acid molecule may be expressed in any desired host cell, but preferably it will be expressed in the cell or microorganism from which it was (or from which it may be) derived and in which the (unmodified) molecule is natively present.

The method of the invention for preparing a modified polyketide or macrolactam molecule may include the further step of recovering (e.g. isolating or purifying) the molecule e.g. from the culture medium in which the host cell was grown or from the host cell. Thus, this aspect of the invention may also provide the modified polyketide or macrolactam molecule obtained by such a method A further aspect of the present invention thus provides a cell or microorganism containing a nucleic acid molecule encoding a modified BE-14106 NRPS-PKS biosynthetic machinery (or modified BE-14106 NRPS-PKS system) obtained by a method as hereinbefore defined. Alternatively, the cell or microorganism may contain a modified BE-14106 NRPS-PKS biosynthetic machinery (or modified BE-14106 NRPS-PKS system) obtained by a method as defined above.

In an alternative but less preferred embodiment the invention may also provide a host cell containing a nucleic acid molecule as defined above, wherein said molecule has been introduced into said host cell.

By way of representative example, it is envisaged that such manipulations of the gene cluster can be performed with the aim of generating a modified BE-14106 molecule in which a hydroxyl group is introduced in any one or more of positions C-2, 3, 4, 7, 11, 13, 15, 17, 21 and 23 of BE-14106 or a derivative or modified version thereof. This can be achieved by inactivating or deleting the appropriate DH domain(s) in the BE-14106 biosynthetic gene cluster. According to the biosynthetic pathway proposed herein the following modifications should be made:

TABLE 3

| Position at which —OH group is to be introduced | DH domain to be inactivated/deleted |
|---|---|
| 3 | BecG module 9 DH domain |
| 5 | BecF module 8 DH domain |
| 7 | BecF module 7 DH domain |
| 11 | BecD module 5 DH domain |
| 13 | BecD module 4 DH domain |
| 15 | BecB module 3 DH domain |
| 17 | BecB module 2 DH domain |
| 23 | BecA module 1 DH domain |

In addition to or as an alternative, it is envisaged that such manipulations of the gene cluster can be performed with the aim of generating a modified BE-14106 molecule in which an oxo (keto) group is introduced in any one or more of positions C-2, 3, 4, 7, 9, 11, 13, 15, 17, 21 and 23 of BE-14106 or a derivative or modified version thereof. This can be achieved by inactivating or deleting the appropriate KR domain(s) in the BE-14106 biosynthetic gene cluster. According to the biosynthetic pathway proposed herein the following modifications should be made:

TABLE 4

| Position at which oxo group is to be introduced | KR domain to be inactivated/deleted |
|---|---|
| 3 | BecG module 9 KR domain |
| 5 | BecF module 8 KR domain |
| 7 | BecF module 7 KR domain |
| 9 | BecE module 6 KR domain |
| 11 | BecD module 5 KR domain |
| 13 | BecD module 4 KR domain |
| 15 | BecB module 3 KR domain |

TABLE 4-continued

| Position at which oxo group is to be introduced | KR domain to be inactivated/deleted |
|---|---|
| 17 | BecB module 2 KR domain |
| 23 | BecA module 1 KR domain |

Thus, a further aspect of the present invention provides a BE-14106 analogue which may be produced by modifying the genes/proteins of the BE-14106 biosynthetic pathway. A BE-14106 analogue of the invention includes, but is not limited to, a molecule comprising a modification selected from any one or more of the group comprising 8-deoxy BE-14106, 3-, 5-, 7-, 11-, 13-, 15-, 17- or 23-hydroxy BE-14106 and 3-, 5-, 7-, 9-, 11-, 13-, 15-, 17- or 23-oxo BE-14106 or combinations thereof. A selection of the structures of such representative BE-14106 analogues of the invention, and modules which require inactivation to generate said analogues, are shown in table 5.

TABLE 5

BE-14106 analogues that can be produced upon engineering of the polyketide synthase genes

| Name | Structure | Mutation(s) |
|---|---|---|
| BE-14106 | 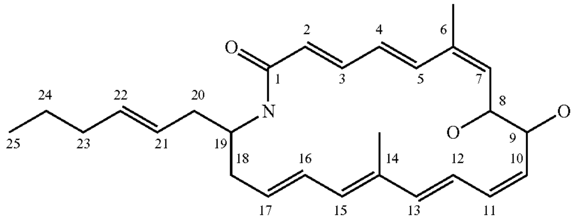 [SMILES: CCC/C=C/CC1C/C=C/C=C(C)/C=C/C=C\C(O)C(O)\C=C(C)/C=C/C=C/C(=O)N1] | none |
| 8-deoxy BE-14106 | 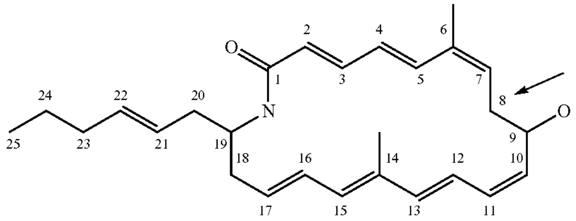 [SMILES: CCC/C=C/CC1C/C=C/C=C(C)/C=C/C=C\C(O)C\C=C(C)/C=C/C=C/C(=O)N1] | BecO |
| (1) 17-hydroxy BE-14106 | 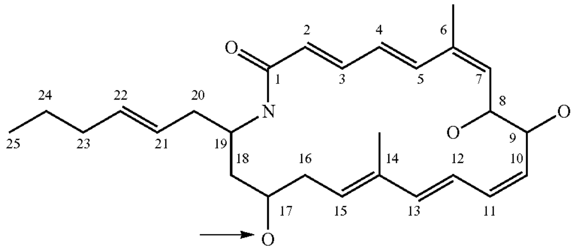 [SMILES: CCC/C=C/CC1CC(O)C/C=C(C)/C=C/C=C\C(O)C(O)\C=C(C)/C=C/C=C/C(=O)N1] | DH2 (BecB) |
| (2) 15-hydroxy BE-14106 | 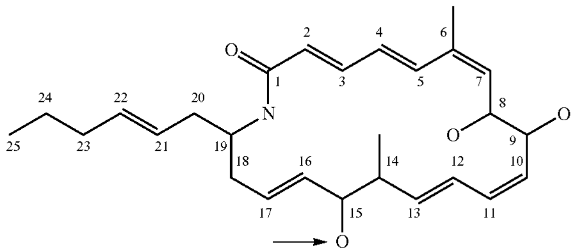 [SMILES: CCC/C=C/CC1C/C=C/C(O)C(C)/C=C/C=C\C(O)C(O)\C=C(C)/C=C/C=C/C(=O)N1] | DH3 (BecB) |

TABLE 5-continued
| BE-14106 analogues that can be produced upon engineering of the polyketide synthase genes | | |
|---|---|---|
| Name | Structure | Mutation(s) |
| (3) 3-oxo BE-14106 | 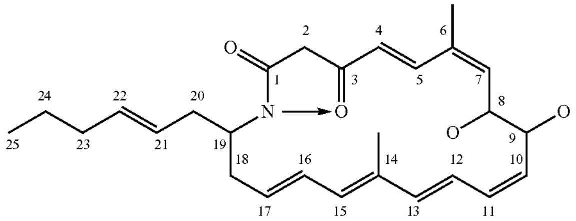 [SMILES: CCC/C=C/CC1C/C=C/C=C(C)/C=C/C=C\C(O)C(O)/C=C(C)\C=C\C(=O)CC(=O)N1] | KR9 (BecG) |
| (4) 3-hydroxy BE-14106 | 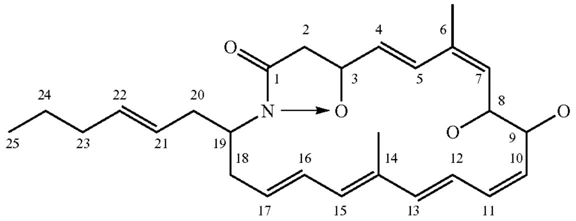 | DH9 (BecG) |
| (5) 11-oxo BE-14106 | 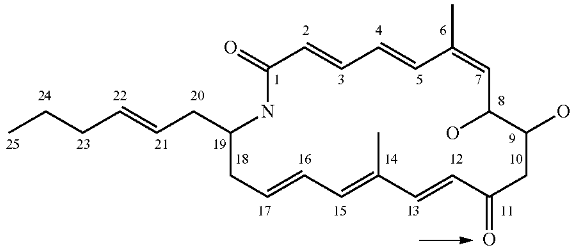 [SMILES: CCC/C=C/CC1C/C=C/C=C(C)/C=C/C(=O)CC(O)C(O)\C=C(C)/C=C/C=C/C(=O)N1] | KR5 (BecD) |
| (6) 11-hydroxy BE-14106 | 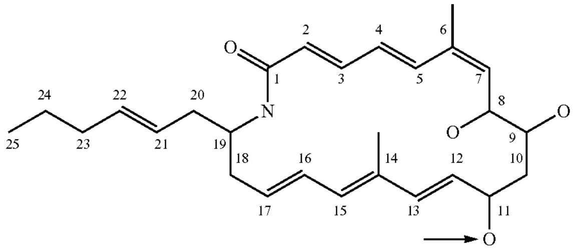 [SMILES: CCC/C=C/CC1C/C=C/C=C(C)/C=C/C(O)CC(O)C(O)\C=C(C)/C=C/C=C/C(=O)N1] | DH5 (BecD) |
| (7) 17-oxo BE-14106 | 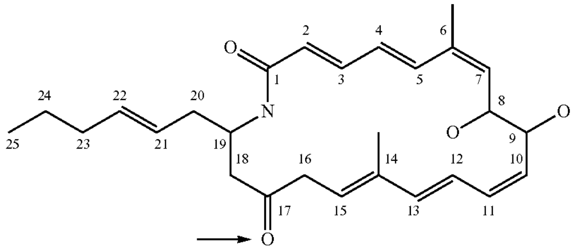 [SMILES: CCC/C=C/CC1CC(=O)C/C=C(C)/C=C/C=C\C(O)C(O)\C=C(C)/C=C/C=C/C(=O)N1] | KR2 (BecB) |
| (8) 15-oxo BE-14106 | 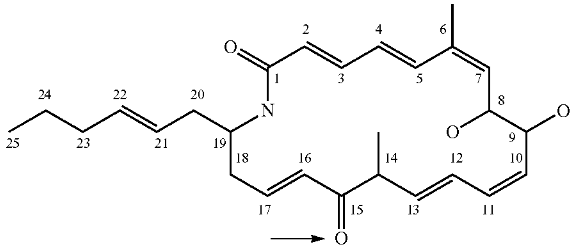 | KR3 (BecB) |

TABLE 5-continued

BE-14106 analogues that can be produced upon engineering of the polyketide synthase genes

| Name | Structure | Mutation(s) |
|---|---|---|
| (9) 7-oxo BE-14106 | 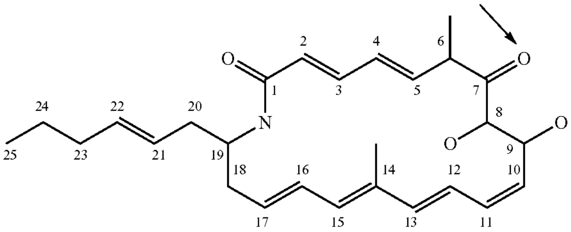 [SMILES: CCC/C=C/CC1C/C=C/C=C(C)/C=C/C=C\C(O)C(O)C(=O)C(C)/C=C/C=C/C(=O)N1] | KR7 (BecF) |
| (10) 7-hydroxy BE-14106 | 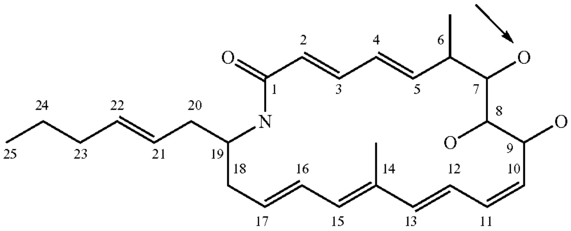 [SMILES: CCC/C=C/CC1C/C=C/C=C(C)/C=C/C=C\C(O)C(O)C(O)C(C)/C=C/C=C/C(=O)N1] | DH7 (BecF) |
| (11) 13-hydroxy BE-14106 | 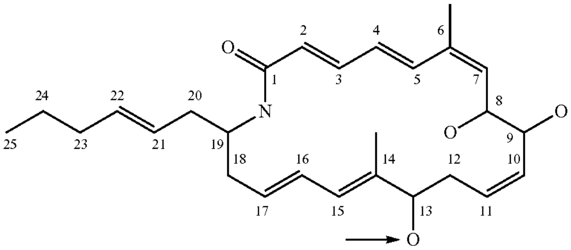 [SMILES: CCC/C=C/CC1C/C=C/C=C(\C)C(O)C/C=C\C(O)C(O)\C=C(C)/C=C/C=C/C(=O)N1] | DH4 (BecD) |
| (12) 13-oxo BE-14106 | 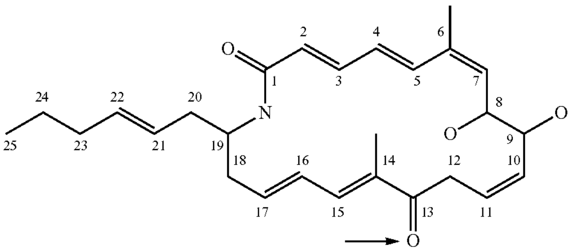 | KR4 (BecD) |
| (13) 9-oxo BE-14106 | 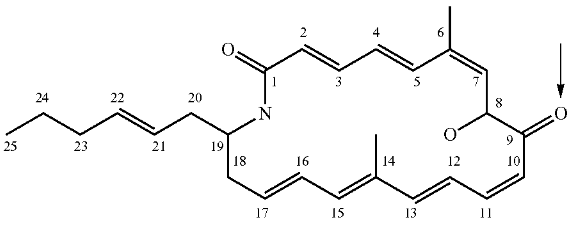 [SMILES: CCC/C=C/CC1C/C=C/C=C(C)/C=C/C=C\C(=O)C(O)\C=C(C)/C=C/C=C/C(=O)N1] | KR6 (BecE) |

In addition to or as an alternative to the above modifications, the C20-C25 side chain can be shortened by deletion of the DNA regions in becA encoding entire module(s) of BecA PKS. Alternatively, one or more molecules of BecA may be deleted to shorten the side chain. For example, deletion of one entire module of BecA may shorten the side chain.

In addition to or as an alternative to the above modifications, one or more of the PKS modules (e.g. of BecA, BecB, BecD, BecE, BecF, BecG) can be deleted in order to produce analogues having macrolactam rings having fewer members (e.g. 18-, 16-, 14-, 12-, 10- and 8-membered rings).

As shown in Table 5, and in addition to or as an alternative to other modifications described or tabulated above, BecO can be inactivated or deleted so as to eliminate the hydroxyl group at position 8.

Further modifications which may be made in addition to or as an alternative to the above modifications include substitution of the C-1 carbonyl of BE-14106 with thio-carbonyl (C═S) or carboxamide (C═NH) to increase the stability of the molecule (for example against protease degradation to which BE-14106 may be susceptible due to the similarity of the —N—C═O linkage in BE-14106 to a peptide bond); glycosylation of BE-14106 or a modified BE-14106 molecule, e.g. with monosaccharide moieties; acylation of free hydroxyl groups, and reduction of the C21-C22 double bond is the side chain of BE-14106.

Regulator proteins can be overexpressed in order to increase production of the molecule synthesised, e.g. BE-14106 or a derivative or analogue thereof.

As such, a method of producing a modified BE-14106 biosynthetic gene cluster is provided, in which one or more of the modifications as set out above is made to the nucleic acid molecule of the invention as defined herein. Conveniently, said modifications may be made by carrying out gene replacement in a host cell which endogenously contains the nucleic acid molecule of the invention.

By "gene replacement" it is meant any method in which a gene or ORF or portion thereof (e.g. module, domain or other functional unit) as found in the nucleic acid molecule of the invention is effectively replaced with or substituted by a modified version thereof. The modified version thereof can be one in which the gene or ORF or portion thereof (e.g. the sequence encoding the protein or peptide or domain or module thereof) is changed or altered (e.g. mutated such as by substitution, deletion or insertion of one or more nucleotide residues). Such changes could result in changes to the activity of the encoded polypeptide, but also includes changes which result in one or more proteins or polypeptides or domains or modules thereof being deleted or inactivated. Preferably, the modified version is one in which the sequence encoding said protein or polypeptide or one or more modules or domains thereof is inactivated or deleted.

It should be noted that the method does not require that the whole gene or ORF is physically removed and replaced, but rather that some or all of the sequence as found in the nucleic acid molecule of the invention is replaced with a modified version thereof.

Gene replacement can be performed according to techniques that are known in the art (see for example Sekurova et al., 1999 FEMS Microbiol. Lett., 177, 297-304).

A host cell (e.g. microorganism) which endogenously contains the nucleic acid molecule of the invention is preferably subjected to modification of the nucleic acid molecule e.g. by gene replacement, so as to change or alter the BE-14106 biosynthetic gene cluster that is present in said host cell. A host cell endogenously contains the nucleic acid molecule of the invention if said nucleic acid molecule of the invention is normally found in that host cell or naturally occurs in that host cell (i.e. the nucleic acid molecule is present in the genetic material of the host cell). In other words, the nucleic acid molecule of the invention is not present in the host cell merely by virtue of it having been introduced (e.g. transfected or transferred) into the host cell e.g. in a recombinant DNA molecule such as a plasmid.

Whether or not a host cell contains the nucleic acid molecule of the invention can be ascertained by determining whether the host cell can synthesise BE-14106 or a derivative thereof. Alternatively or additionally, genetic techniques to analyse the sequences of the nucleic acid molecules present in the host cell can be carried out (e.g. PCR, Southern Blotting and other standard techniques that are known in the art). Such genetic techniques can be used to determine whether the nucleic acid molecule is present endogenously.

The host cell for use in the methods of the invention may be any desired cell or organism, prokaryotic or eukaryotic, but generally it will be a microorganism particularly a bacterium. More particularly, the host cell will be an actinomycete.

Preferred host cells include *Streptomyces* strains, preferably that endogenously contain the nucleic acid molecule of the invention. A suitable example is *Streptomyces* strain espiA14106 (FERMP-11378, as referred to in JP4001179). The novel isolated strain referred to above, from which the gene cluster was sequenced (isolate MP28-13) as deposited under deposit number DSM21069 at the DSMZ is particularly preferred.

Further, a method of producing a modified polypeptide encoded by the BE-14106 biosynthetic enzyme system is provided, in which a modified BE-14106 biosynthetic gene cluster obtainable by the above described methods is expressed in a host cell. Once the appropriate modifications have been made to the BE-14106 biosynthetic gene cluster, e.g. by the methods set out above, the host cell can be grown or cultured under conditions which allow the expression of polypeptides and proteins from the modified gene cluster so as to produce the modified BE-14106 biosynthetic polypeptide(s).

As such, the modified host cell containing the modified BE-14106 biosynthetic gene cluster will express the polypeptides and proteins encoded by the gene cluster and this will lead to the production of a modified polypeptide or protein, as well as the other proteins encoded by the gene cluster. As a result of the presence of one or more modified polypeptides or proteins in the biosynthetic machinery, the properties of the biosynthetic machinery for BE-14106 will be changed. Depending on the nature of the modification(s) that was made to the BE-14106 biosynthetic gene cluster, the properties of the encoded polypeptides, proteins and enzymes will be different to those of the wild type.

For most purposes, the production of the BE-14106 biosynthetic machinery within the cell will suffice. Alternatively, the proteins which make up the BE-14106 biosynthetic machinery can be purified from the cell in which it was expressed.

A further aspect of the invention provides a polypeptide encoded by the nucleic acid molecule of the invention which has been modified as defined above.

A method of producing a modified BE-14106 molecule is also provided. According to this method, a modified BE-14106 biosynthetic gene cluster obtainable by the above described methods is expressed in a host cell. This is achieved by growing or culturing a host cell in which a modified BE-14106 biosynthetic gene cluster obtainable by the above described methods is present under conditions which allow the expression of the polypeptides, proteins and enzymes encoded by the modified BE-14106 biosynthetic gene cluster. The cell will thus contain the biosynthetic machinery necessary for the biosynthesis of the modified BE-14106 molecule and synthesis of this molecule will ensue.

The method may further comprise the step of recovering, e.g. isolating or purifying the modified BE-14106 molecule. This can be isolated or purified from the cell culture medium into which it has been transported or secreted if appropriate, or otherwise from the host cell in which it has been included. Thus, for example, the cells of the producing organism may be harvested, e.g. by centrifugation, and may be extracted, for example with organic solvent(s) (e.g., methanol or other alcohols). The molecules may be recovered from such an extract, for example by precipitation. Further purification of a crude product obtained in this way may include e.g. chromatography, e.g. HPLC.

In order to enable practice of the invention according to the principles above, the invention also provides a host cell containing the nucleic acid molecule as herein defined, and more particularly a cell containing a nucleic acid molecule of the invention modified as defined above.

In general, the methods of the invention can be carried out on any host cell which contains the nucleic acid molecule of the invention, preferably host cells which endogenously contain the molecule. As noted above, preferred host cells include cells of *Streptomyces* spp. More preferred cells are *Streptomyces* cells which have the antibiotic resistance and sensitivity characteristics as set out in Table 6.

In a highly preferred embodiment, the methods are carried out using the novel strain of *Streptomyces* MP28-13 deposited under number DSM21069 at the DSMZ) or a mutant or modified strain thereof which produces BE-14106 or a derivative thereof.

The invention thus further provides a microorganism, particularly a bacterium and especially a *Streptomyces*, obtainable by the methods as described herein.

In an important aspect the invention also provides a strain of *Streptomyces* as deposited under number DSMZ 21069 at the DSMZ, or a mutant or modified strain thereof which produces BE-14106 or a derivative thereof.

The methods of the invention may be seen to result in the production of derivative nucleic acid molecules, derived from the nucleic acid molecules of the invention defined above.

The derivative nucleic acid molecule may be formed in situ in host cells or microorganisms in which the unmodified nucleic acid molecules are contained. Alternatively, but less preferably, they may be formed in host cells in which the nucleic acid molecules are introduced. Such "modified" microorganisms containing the derivative or modified nucleic acid molecules according to the present invention may be used to form libraries, for example libraries of polyketides or polyketide-based or macrolactam molecules wherein the members of the library are synthesized by modified BE-14106 biosynthetic machineries or NRPS-PKS systems derived from the naturally occurring BE-1406 system provided herein. Generally, many members of these libraries may themselves be novel compounds, and the invention further includes novel members (compounds) of these libraries. The methods of the invention may thus be directed to the preparation of an individual compound. The compound may or may not be novel, but the method of preparation permits a more convenient method of preparing it. The resulting compounds (e.g. polyketides) may be further modified, for example, to convert them to further active molecules, e.g. antibiotics, for example by glycosylation. The invention also includes methods to recover novel compounds with desired activities by screening the libraries of the invention.

The invention provides libraries or individual modified forms, ultimately of polyketide-based, or macrolactam molecules, by generating modifications in the BE-14106 NRPS-PKS gene cluster so that the proteins produced by the cluster have altered activities in one or more respects, and thus produce compounds other than the natural product of the NRPS-PKS system encoded by the gene cluster (i.e. BE-14106). Novel compounds may thus be prepared, or compounds in general prepared more readily, using this method. By providing a large number of different genes or gene clusters derived from the naturally occurring BE-14016 gene cluster, each of which has been modified in a different way from the native cluster, an effectively combinatorial library of compounds can be produced as a result of the multiple variations of these activities. The modified NRPS-PKS encoding sequences and biosynthesis machinery/systems used in the present invention thus represent encoding sequences and enzyme/protein machinery or systems "derived from" a naturally occurring BE-14106 NRPS-PKS biosynthetic machinery or system.

By a biosynthetic machinery or NRPS-PKS system "derived from" the BE-14016 biosynthetic machinery is meant a biosynthetic machinery or NRPS-PKS system in which at least one enzymatic or functional activity is mutated, deleted, inactivated or replaced, so as to alter the activity. Alteration results when these activities are deleted or are replaced by a different version of the activity, or simply mutated in such a way that a compound (e.g. a polyketide or macrolactam) other than the natural product results from these collective activities. This occurs because there has been a resulting alteration of the starter unit and/or extender unit, and/or stereochemistry, and/or chain length or cyclization and/or reductive or dehydration cycle outcome at a corresponding position in the product compound. Where a deleted activity is replaced, the origin of the replacement activity may come from a corresponding activity in a different naturally occurring NRPS or polyketide synthase or from a different region of the same NRPS-PKS system/machinery.

Modification or manipulation of the modular NRPS-PKS may involve truncation, e.g. gene or domain or module deletion or domain/gene/module swapping, addition or inactivation, which may involve insertion or deletion. Alternatively, random or directed modifications (i.e. mutations) may be made in the nucleotide sequence of the selected portion (e.g. in a gene/domain/module etc).

Advantageously, a biosynthetic machinery or NRPS-PKS system "derived from" the BE-14106 machinery or system contains at least an NRPS adenylation domain and at least two modules of a PKS enzyme and may optionally contain mutations, deletions, or replacements of one or more of the activities of these functional domains or modules so that the nature of the resulting compound is altered. This definition applies both at the protein and genetic levels. Particular preferred embodiments include those wherein a KS, AT, KR or DH has been inactivated or deleted or replaced by a version of the activity from a different machinery or PKS/NRPS system or from another location within the same machinery or NRPS-PKS system. Also preferred are derivatives where at least one noncondensation cycle enzymatic activity (e.g. KR or DH) has been deleted or wherein any of these activities has been mutated so as to change the ultimate compound synthesized.

Thus, there are five degrees of freedom for constructing a PKS biosynthetic machinery or system in terms of the compound that will be produced. First, the polyketide chain length will be determined by the number of modules in the machinery or system. Second, the nature of the carbon skeleton of the polyketide will be determined by the specificities of the acyl transferases which determine the nature of the extender units at each position, e.g. malonyl, methyl malonyl or ethyl malonyl, etc. Third, the loading domain specificity will also have an effect on the resulting carbon skeleton of the polyketide. Thus, the loading domain may use a different starter unit, such as acetyl, propionyl, and the like. Fourth, the oxidation state at various positions of the polyketide will be determined by the dehydratase and reductase portions of the modules. This will determine the presence and location of ketone, alcohol, double bonds or single bonds in the polyketide.

Finally, the stereochemistry of the resulting polyketide is a function of various aspects of the synthase. The first aspect is related to the AT/KS specificity associated with substituted maloyls as extender units, which affects stereochemistry only when the reductive cycle is missing or when it contains only a ketoreductase since the dehydratase would abolish chirality. Second, the specificity of the ketoreductase will determine the chirality of any β-OH.

By modifying the PKS involved in the biosynthesis of the aminoacyl "starter", the compound that is produced can be altered.

Thus the modified machinery or NRPS-PKS system may permit a wide range of compounds to be synthesized.

The size of the synthesized product can be varied by varying the number of modules.

The polyketide/macrolactam products of the modified biosynthetic machinery may be further modified for example by glycosylation or other derivatisation, in order to exhibit or improve activity e.g. antibiotic activity. Methods for glycosylating polyketides are generally known in the art; the glycosylation may be effected intracellularly by providing the appropriate glycosylation enzymes or may be effected in vitro using chemical synthetic means.

In order to obtain nucleic acid molecules encoding a variety of derivatives (or analogues) of the naturally occurring BE-14016 NRPS-PKS system, and thus a variety of polyketides macrolactam-based compounds, a desired number of constructs can be obtained by "mixing and matching" enzymatic activity-encoding portions, and mutations can be introduced into the native host nucleic acid molecule/gene cluster or portions thereof.

Mutations can be made to the native sequences using conventional techniques. The substrates for mutation can be an entire cluster of genes or only one or two of them; the substrate for mutation may also be portions of one or more of these genes. Techniques for mutation are well known in the art and described in the literature. Such techniques include preparing synthetic oligonucleotides including the mutation(s) and inserting the mutated sequence into the gene using restriction endonuclease digestion. Alternatively, the mutations can be effected using a mismatched primer (generally 15-30 nucleotides in length) which hybridizes to the native nucleotide sequence, at a temperature below the melting temperature of the mismatched duplex. The primer can be made specific by keeping primer length and base composition within relatively narrow limits and by keeping the mutant base centrally located. Primer extension is effected using DNA polymerase, the product cloned and clones containing the mutated DNA, derived by segregation of the primer extended strand, selected. The technique is also applicable for generating multiple point mutations. PCR mutagenesis will also find use for effecting the desired mutations.

The vectors used to perform the various operations to replace the enzymatic activity in the host genes or ORFs or to support mutations in these regions of the host genes or ORFs may be chosen to contain control sequences operably linked to the resulting coding sequences in a manner that expression of the coding sequences may be effected in the host. However, simple cloning vectors may be used as well.

The invention will now be described in more detail in the following non-limiting Examples with reference to the drawings in which.

EXAMPLE 1

Figure 1:
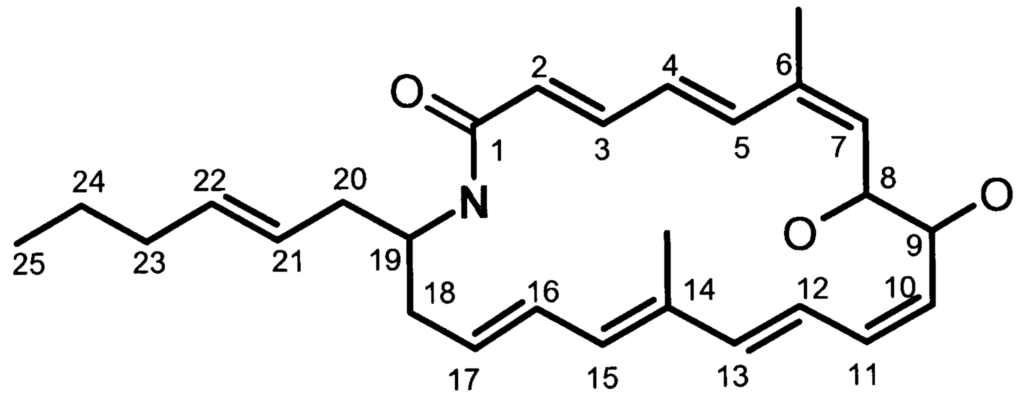
FIG. 1 shows the chemical structure of the macrolactam antibiotic BE-14106.
Figure 2:
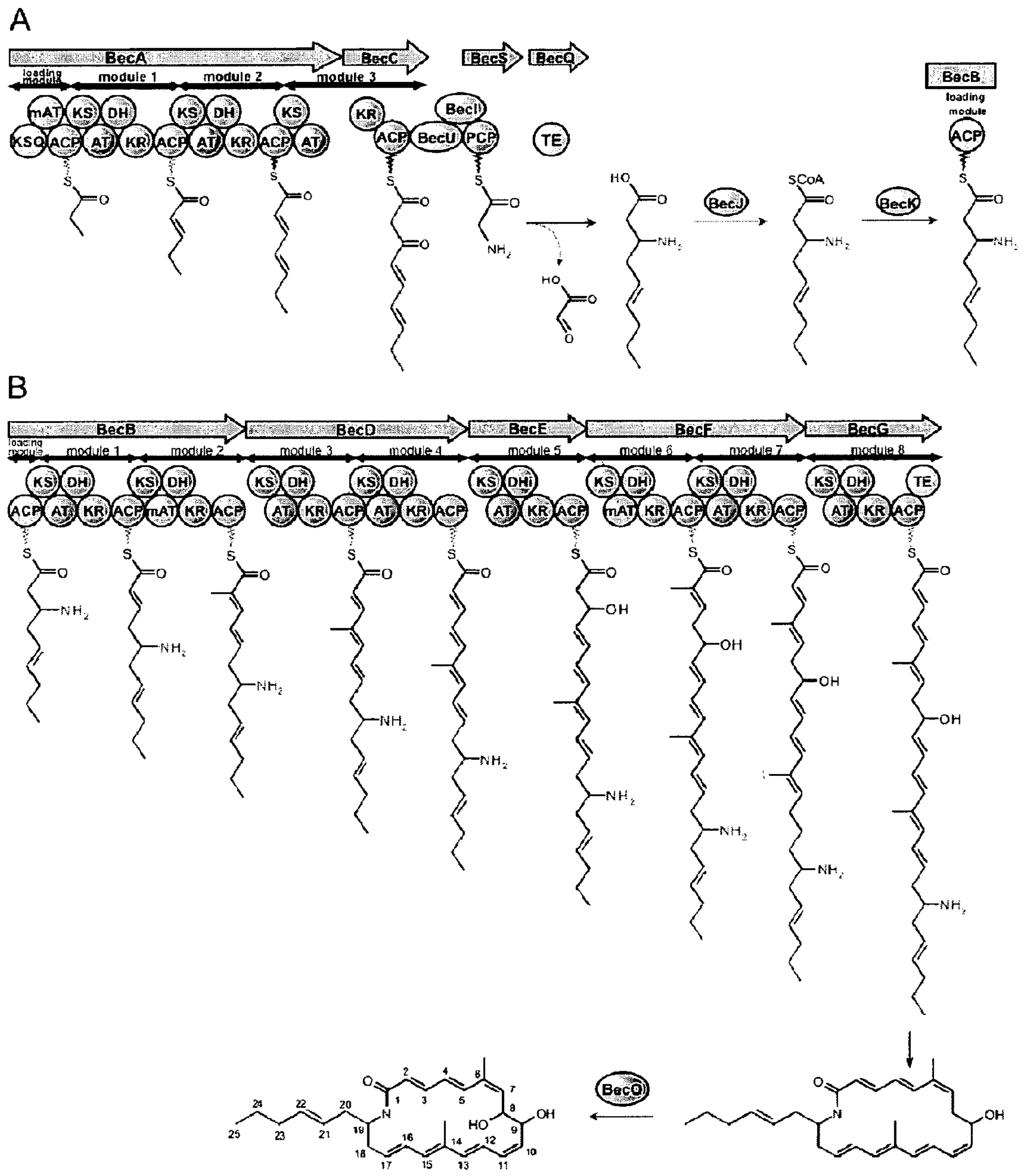
FIG. 2A shows the proposed initiation of biosynthetic pathway for BE-14106.
FIG. 2B shows the proposed completion of the BE-14106 biosynthesis.

Characterisation of Isolate MP28-13 (*Streptomyces* Strain DSM 21069)

On ISP2 agar growth medium (Difco, USA): The substrate mycelium is pale yellow, the same color as the ISP2-agar plates. The aerial mycelium is white and the spores are almost white, just slightly greenish.

On SFM agar growth medium (soya flour, 20 g/l; mannitol, 20 g/l; agar, 20 g/l): The substrate mycelium is more beige than on ISP2, aerial mycelium and spores the same as on ISP2.

On ISP2 plates growth is visible after 2 days, but sporulation takes about 20 days. Sporulation is quite poor on both media.

Growth in liquid media: Grows well in TSB liquid growth medium (Oxoid, UK), with shaking at 225 rpm and glass beads (3 mm). 2 days at 25° C. is necessary to obtain sufficient mycelium.

The strain grows at 20° C., 25° C. and 30° C., but the optimal temperature is around 25° C. At 30° C. the sporulation is affected.

The 16S RNA gene sequence of strain DSM 21069 (isolate MP28-13) is shown in SEQ ID No. 46.

Table 6 shows the antibiotic resistance characteristics of strain DSM 21069

TABLE 6

| | Antibiotic resistance | | | |
|---|---|---|---|---|
| Antibiotic | 5 μg/ml | 10 μg/ml | 20 μg/ml | 50 μg/ml |
| Apramycin | sensitive | sensitive | sensitive | sensitive |
| Kanamycin | sensitive | sensitive | sensitive | sensitive |
| Neomycin | sensitive | sensitive | sensitive | sensitive |
| Rifamycin | resistant | resistant | resistant | sensitive |
| Streptomycin | resistant | resistant | resistant | resistant |
| Thiostrepton | sensitive | sensitive | sensitive | sensitive |

EXAMPLE 2

Generation of a Probe for the BE-14106 Biosynthesis Gene Cluster

Total DNA was isolated from DSM 21069 (MP28-13) using the DNeasy Blood & Tissue Kit (QIAGEN). β-ketoacyl synthase (KS) domains were amplified using the degenerate primers KSMA-F (5'-TS GCS ATG GAC CCS CAG CAG-3' [SEQ ID No. 47]) and KSMB-R (5'-CC SGT SCC GTG SGC CTC SAC-3' [SEQ ID No. 48]) described by Izumikawa et al. ((2003) Bioorg. Med. Chem., 11, 3401-3405). The 50 μl reaction mix contained total DNA isolated from MP28-13 (10-20 ng), 1× ThermoPol Reaction Buffer (New England Biolabs), 400 nM of each primer, 200 μM of each dNTP and 2.5 U of Taq DNA Polymerase (New England Biolabs). The reaction was run at 95° C. for 5 min, then 35 cycles of 1 min at 95° C., 1 min at 60° C. and 2 min at 72° C., and then a final 5 min extension at 72° C.

The 50 μl reaction mix was subjected to a gel electrophoresis and the resulting DNA fragment of about 700 bp was purified using the QIAEX II Suspension (QIAGEN). The purified PCR-product was cloned in the pDrive vector (QIAGEN) in *E. coli* EZ-cells using the QIAGEN PCR Cloning Kit (QIAGEN). Plasmid DNA from the transformants was isolated using the Wizard® Plus SV Minipreps DNA Purification System (Promega).

8 recombinant plasmids were sequenced using the pDrive-specific primers M13 forward (−20) (5' GTA AAA CGA CGG CCA GT 3' [SEQ ID No. 49]) and M13 reverse (5' AAC AGC TAT GAC CAT G 3' [SEQ ID No. 50]) described in the QIAGEN PCR Cloning Handbook (QIAGEN, 2001). The sequencing was performed using BigDye® Terminator v1.1 Cycle Sequencing Kit (Applied Biosystems). Of the 8 sequences obtained 5 were different from each other. Translation into protein sequences and BLAST searches gave a match for PKS type I for all of the sequences (see Table 7).

The most interesting sequences were no. 1, 3, 6, 7 and 8. Sequence no. 1 matched a PKS involved in the biosynthesis of meridamycin in *S. violaceusniger* (Sun et al., 2006 Microbiol., 152, 3507-3515). Sequences no. 3, 7, 8 gave a match to LnmJ involved in the biosynthesis of leinamycin in *S. atroolivaceus* (Cheng et al., 2003 Proc. Natl. Acad. Sci. USA, 100, 3149-3154). Sequence no. 6 gave a strong match to VinP1 involved in the biosynthesis of the macrolactam vicenistatin in *S. halstedii* (Ogasawara et al., 2004 Chem. & Biol., 11, 79-86) and also to AVES 2 involved in the biosynthesis of the macrolide avermectin in *S. avermitilis* (Ikeda et al., 1999 Proc. Natl. Acad. Sci. USA, 96, 9509-9514).

Sequence no. 6 (SEQ ID No. 51) was chosen as a probe for screening the genomic library constructed for DSM 21069 (MP28-13). A digoxygenin (DIG) labeled probe was generated using the PCR DIG Probe Synthesis Kit (Roche Applied Science) and the M13 primers described above. The plasmid containing sequence no. 6 was used as a template. The reaction was run at 95° C. for 3 min, then 30 cycles of 45 sec at 95° C., 1 min at 44° C. and 3 min at 68° C., and then a final 7 min extension at 68° C. The resulting PCR product was subjected to a gel electrophoresis and the DNA fragment purified with the QIAEX II Suspension (QIAGEN).

TABLE 7

Sequencing of PCR amplified KS domains from DSM 21069

| Sequence | First hit | Other top hits |
|---|---|---|
| 1 | PKS from *S. aizunensis* | PKS from *S. violaceusniger*/polykelide meridamycin biosynthesis |
| 2, 4 | β-ketoacyl synthase from *Clostridium* sp. | PKS from *Bacillus* sp. |
| 3, 7, 8 | PKS from *S. atroolivaceus*/ leinamycin biosynthesis | PKS from *Bacillus* sp. |
| 5 | PKS from *Amycolatopsis orientalis* | PKS from *S. violaceusniger*/polyether nigericin biosynthesis |
| 6 (SEQ ID No. 51) | PKS from *S. halstedii*/ halstoctacosanolide biosynthesis | PKS from *S. halstedii*/macrolactam vicenistatin biosynthesis and PKS from *S. avermitilis*/macrolactone avermectin biosynthesis |

EXAMPLE 3

Optimisation of the Conjugation Procedure

To establish a procedure for genetically modifying strain DSM 21069 (MP28-13), conjugation with *E. coli* strain ET12567 (pSOK804+pUZ8002) (Sekurova et al., 2004, J. Bacteriol., 186, 1345-1354) was tested following the procedure described by Flett et al. (1997 FEMS Microbiol. Lett., 155, 223-229). A few modifications to the procedure were made. The *E. coli* donor was grown to an $OD_{600}$ of 0.4-0.5. Only fresh spore suspension of MP28-13 was used and the spore suspension was made with 2×YT (Sambrook et al., 2000 Molecular cloning: a laboratory manual. Cold Spring Harbor Laboratory Press, New York, N.Y.). Spores and the donor cells were mixed and pelleted by centrifugation, and the pellet was resuspended in a smaller volume and spread on two SFM plates. Conjugation plates were incubated 24 h before addition of antibiotics (0.9 mg/ml nalidixic acid and 1.5 mg/ml apramycin). The incubation temperature and the temperature and time of the heat shock were varied to find the optimum. The best results were obtained at an incubation temperature of 25° C. and a heat shock at 50° C. for 5 min.

EXAMPLE 4

Gene Inactivation Experiment

The PKS sequence no. 6 from strain DSM 21069 (MP28-13) cloned in the pDrive vector was excised from the plasmid using restriction enzymes BamH I and Hind III, and ligated with the 3.1 kb BamH I/Hind III fragment from the vector pSOK201 (Zotchev et al., 2000 Microbiol., 146, 611-619) and transformed into *E. coli* DH5α. The new construct was checked by restriction analysis, and then transformed into *E. coli* ET12567 (pUZ8002). The construct was transferred into DSM 21069 by conjugation following the procedure described above. The 3.1 kb BamH I/Hind III fragment from the vector pSOK201 does not contain genetic elements needed for autonomous replication in *Streptomyces*. Therefore, the transconjugants can only be obtained if this part of the vector is ligated with a fragment having high level of homology to the chromosomal DNA fragment in DSM 21069. Such homology allows for recombination leading to integration of the entire vector into the corresponding chromosomal region. If the cloned fragment does not contain start or stop codons of the gene, such integration will lead to gene disruption, effectively inactivating chromosomal copy of the gene.

A single transconjugant was obtained and analyzed for BE-14106 production. No production of BE-14106 was observed, verifying that sequence no. 6 belongs to the BE-14106 biosynthetic gene cluster.

EXAMPLE 5

Construction of the Genomic Library

The genomic library for DSM 21069 was constructed in the cosmid vector SuperCos 1 (Stratagene) according to manufacturer's instructions (Stratagene, 2005). Genomic DNA was isolated from DSM 21069 following the Kirby mix procedure (Kieser et al., 2000 Practical *Streptomyces* Genetics, The John Innes Foundation, Norwich, England.), partially digested with Mbo I and dephosphorylated before ligation with Xba I-, CIAP- and BamH I-treated SuperCos 1. *E. coli* XL1-Blue MR (Stratagene) was used as a host for the construction of the library.

EXAMPLE 6

Screening of the Genomic Library

The library was plated out on Luriana-Bertani (LB) agar plates (Corning® Low Profile Square BioAssay Dish) containing 100 μg/ml ampicillin to give ~2000 colonies per plate. 2304 colonies were picked using a Genetix QPixII Colony Picker and transferred to 24 96 well plates (Nunc) containing LB broth and 24 96 well plates containing Reduced Hi+YE-medium (120 μl in each well). The well plates were incubated with shaking (900 rpm) at 30° C. overnight. Glycerol were added to the 24 LB plates to give a final concentration of 15% (v/v) and then stored at −80° C.

Culture from the 24 Reduced Hi+YE plates were transferred to 6 384 well plates (Nunc) using a Tecan Genesis RSP 200 robotic liquid handling system and then stamped on a filter (4 replica stampings) using the Genetix QpixII Colony Picker. The process was repeated 4 times to give 4 replica filters. The filters were dried for 20 min under a sterile hood.

Cultures were lysed by placing the filters on 3MM Whatman filter paper saturated with 10% SDS for 5 min. DNA was denatured by placing the filters on 3MM Whatman filter paper saturated with NaOH/Chloride Buffer (1.5 M NaCl, 0.5 M NaOH) for 10 min and neutralized with Tris/NaCl Buffer (3 M NaCl, 1 M Tris-Cl, pH 7.4) for 10 min. Finally the filters were submerged in 2×SSCP Buffer (2×SSC+0.1% (w/v) Sodium Pyrophosphate) to remove colony debris and baked at 80° C. for 2 hrs. The filters were stored at 4° C. until hybridization was started. Hybridization was carried out as described for the DIG System (Roche Applied Science) using the probe obtained from DSM 21069. By exposing the filter to an X-ray film, 3 candidate cosmids were identified and their corresponding hosts could be restreaked from the LB-plates stored at −80° C.

Cosmid DNA was isolated from overnight cultures using the Wizard® Plus SV Minipreps DNA Purification System (Promega) and end-sequenced using primers designed for the cosmid regions flanking the insert site (SuperCos_forw; 5' GGC CGC AAT TAA CCC TCA C 3' [SEQ ID No. 52] and SuperCos_rev; 5' GGC CGC ATA ATA CGA CTC AC 3' [SEQ ID No.53]). The sequencing was performed using BigDye® Terminator v1.1 Cycle Sequencing Kit (Applied Biosystems). Results are given in Table 8.

TABLE 8

End-sequencing of cosmid 1, 2 and 3.

| Cosmid | SuperCos_forw primer | SuperCos_rev primer |
|---|---|---|
| cosmid 1 | Biotin synthase | PKS (AT-DH domain linker) |
| cosmid 2 | PKS (KS domain) | PKS (AT domain) |
| cosmid 3 | Peptide deformylase | PKS (DH domain) |

The results indicated that cosmid 1 might contain one end of the cluster and cosmid 3 the other end. The 3 cosmids were tested to see if they contained any overlapping sequences by designing primers for the end-sequences and using those primers for sequencing the other cosmids. From these results it was concluded that cosmid 2 and cosmid 3 were overlapping, but cosmid 1 did not have any overlap with cosmid 2 and 3. Primers were designed for the forward primer end-sequence of cosmid 2 for amplifying a new probe for the missing part of the cluster. A digoxygenin (DIG) labelled probe was generated using the PCR DIG Probe Synthesis Kit (Roche Applied Science) with cosmid 2 as a template. The reaction was run at 95° C. for 5 min, then 35 cycles of 1 min at 95° C., 1 min at 60° C. and 2 min at 72° C., and then a final 5 min extension at 72° C. The resulting PCR product was subjected to a gel electrophoresis and the DNA fragment purified with the QIAEX II Suspension (QIAGEN). One of the replica filters was used for hybridization with the new probe and 2 new candidate cosmids were identified (cosmid 4 and 5). The process with end-sequencing and cross-sequencing with the other cosmids was repeated and cosmid 4 was found to overlap with both cosmid 1 and 2.

EXAMPLE 7

Verification of BecA Function

To verify that the gene cluster contained in cosmids 1-4 was responsible for the BE-14106 production, another gene inactivation experiment was carried out. PKS fragments were amplified from cosmid 2 and 3 using one cosmid primer (SuperCos_forw [SEQ ID No. 52] or SuperCos_rev [SEQ ID No. 53]) and one degenerate primer for the KS domain (KSMA-F [SEQ ID No. 47] or KSMB-R [SEQ ID No. 48]). A 1.2 kb fragment was obtained for cosmid 2 and a 3.7 kb fragment for cosmid 3. Both fragments were cloned in pDrive and pSOK201 as described above and the construct was transferred into MP28-13 by conjugation. For the cosmid 2 fragment only one transconjugant was obtained. For the cosmid 3 fragment several transconjugants were obtained and 6 were chosen for further analysis.

TABLE 9

Analysis of BE-14106 production in knock-out mutants

| | BE-14106 production compared to WT (%) |
|---|---|
| MP28-13 (WT) | 100 |
| cosmid 2 mutant | 0 |
| cosmid 3 mutant 1 | 0.7 |
| cosmid 3 mutant 2 | 0.9 |
| cosmid 3 mutant 3 | 0.6 |
| cosmid 3 mutant 4 | 0.6 |
| cosmid 3 mutant 5 | 0.6 |
| cosmid 3 mutant 6 | 0.7 |

Based on the results from the cross-sequencing of the cosmids and the gene inactivation experiment, cosmids 1, 2, 3 and 4 were sequenced.

EXAMPLE 8

Production, Purification and Identification of BE-14106

Cultivation of MP28-13

Preparation of Standard Inoculum

Inoculum: Spores from an agar plate was transferred to a shake flask (250 ml, baffled) with 50 ml modified TSB-medium supplemented with glucose (composition given in Table 9). To increase the shear forces in the shake-flask, 3 g of 3 mm glass beads was added.

Incubation: The culture was incubated at 25° C. for 3 days at 225 rpm (Infors Multitron shaking incubator, orbital movement, amplitude 2.5 cm).

Preservation: Glycerol was added to the culture to a concentration of 15%. The mixture was transferred to cryo vials and stored at −80° C.

Preparation of Pre-Culture for Production

Inoculum: 1.5 ml standard inoculum was transferred to a shake flask (250 ml, baffled) with 50 ml modified TSB-medium supplemented with glucose (composition given in Table 10) and 3 g of 3 mm glass beads.

Incubation: The culture was incubated at 25° C. for 2 days at 200 rpm (Infors Multitron shaking incubator orbital movement, amplitude 2.5 cm Production Culture Inoculum: 3 ml pre-culture for production was transferred to a shake flask (500 ml, baffled) with 100 ml 0.3×BPS-medium supplemented with glucose (composition given in Table 11) and 5 g of 3 mm glass beads.

Incubation: The culture was incubated at 25° C. for 2 days at 200 rpm (Infors Multitron shaking incubator orbital movement, amplitude 2.5 cm.

Composition of Media used for Production

TABLE 10

Composition of modified TSB- medium supplemented with glucose

| Compound | Concentration (g/l) |
|---|---|
| Tryptic soy broth | 18.5 |
| Glucose[a] | 20 |

[a]Autoclaved separately.

TABLE 11

Composition of 0.3 x BPS medium supplemented with glucose

| Compound | Concentration (g/l) |
|---|---|
| Oatmeal | 9.0 |
| Malt extract | 1.5 |
| Yeast extract | 0.9 |
| $MgSO_4•7H_2O$ | 0.12 |
| NaCl | 0.3 |
| $CaCO_3$ | 1.5 |
| Starch soluble | 9.0 |
| MOPS | 11.1 |
| Glucose[a] | 20 |
| Phenol red solution (10 mg/ml)[a,b] | 1.5 |

[a]Autoclaved separately.
[b]10 mg/ml phenol red solution, pH-adjusted to 8.2 with NaOH.

The components were added to pre-heated water and the components were swelling for 10 minutes before the medium was autoclaved. pH of the medium was adjusted after autoclaving with HCl or NaOH until orange color was obtained which occurs at pH=7 when phenol red is used as pH-indicator.

Purification of BE-14106

Harvesting and Homogenization of Cell Mass

The cell mass in the production culture was harvested by centrifugation and freeze dried. Freeze dried pellet was homogenized with magnetic iron beads until fine pellet.

Crude Purification of BE-14106

The freeze dried cell pellet was extracted with 240 ml methanol/g for 1 hour. Glass beads were added to increase shear forces. Cell pellet was removed by centrifugation followed by filtration to remove all insoluble matter. The clear supernatant was added water and kept on ice for approximately 30 minutes in order to precipitate BE-14106. The precipitate was collected by centrifugation, washed with water to remove remaining methanol and freeze-dried. The freeze dried product represents a crude product.

Preparative HPLC Purification of Crude Product

The crude product was dissolved in DMSO and the purification was performed on a reverse-phase column.

Preparative method: BIOP PREP BE14106_KFD.M

HPLC system: Agilent 1100 series preparative HPLC with fraction collection system Column: PREP-C18, 50×250 mm (PN410910)

Column temperature: Ambient

Mobile phase: 10 mM ammonium acetate pH 4.0 (A) and methanol (B).

| Time | % B |
|---|---|
| 0.00 | 85 |
| 8.50 | 85 |
| 8.60 | 100 |
| 10.60 | 100 |
| 10.70 | 85 |
| 13.00 | 85 |
| Eluent flow: | 85 ml/min |

The fractions were added 1% of a 2 M NH3 solution and stored at −20° C.

Concentration of Product in the Preparative HPLC-Fractions

Most of the methanol in the fractions was vaporized at a rotational vacuum evaporator at 50° C. The remaining water phase containing BE-14106 was frozen to increase the precipitation yield and the precipitate was pelleted by centrifugation. The pellet was washed with water and freeze dried to give the final product.

LC-DAD-TOF Analysis of BE14106 Purified by Preparative HPLC

Calculation of Purity by LC-DAD-TOF

After purification by preparative LC, BE-14106 was shown to constitute >99% of compounds in the sample which is absorbing at 291 nm as determined by UV and TOF data. It is assumed that the extinction coefficient for the contaminants is the same as for BE-14106.

TOF-MS Data of BE-14106

The TOF-MS enable a LCTOF plot of purified BE-14106 to be obtained. From this a theoretical accurate m/z (negative ion) of BE-14106 ($C_{27}H_{73}NO_3$) is 422.2701. This m/z was observed with acceptable accuracy and the 422 peak correlates well with the heptaene UV-peak.

LCTOF Method: BIOP BE14106 SE.M

Column: Zorbax Bonus-RP 2.1×50 mm, (Agilent Technologies).

Mobile phase A: 10 mM ammonium acetate (Riedel-de-Haën Cat#: 34674),

Mobile phase B: 100% acetonitrile supergrade (Labscan UN1648)

Flow: 0.3 ml/min

Column temperature: Ambient

| Time | % B |
|---|---|
| 0.00 | 40 |
| 10.00 | 70 |
| 10.10 | 90 |
| 12.00 | 90 |
| 12.10 | 40 |
| 17.00 | 40 |

TOF-MS Parameters:

Negative API-ES Ionization

Drying gas: 10 l/min

Nebulizer pressure: 40 psig

Drying gas temp.: 350° C.

Capillary voltage: 3000 V

Fragmentor: 200 V

EXAMPLE 9

Characterisation of Strain DSM 21069 Antifungal Activity

The strain DSM 21069 was investigated for production of antifungal activity. Growth conditions of 25° C. on medium PM2 (Bredholt et. al, 2008, *Marine Drugs,* 6(1) pp. 12-24) for 7 days, resulted in strong antifungal activity. After incubation the medium was dried and then extracted with DMSO. After filtration, the DMSO extracts were used as samples in a robotic bioassay procedure with the strains *Candida albicans* CCUG3943 and *C. glabrata* CCUG3942 as indicator organisms. The latter strain has a high level of resistance against polyene antibiotics, while the *C. albicans* strain is sensitive to polyenes. The medium used in the bioassay was AM19(B) (9.4 g/l peptone [Oxoid], 4.7 g/l yeast extract [Oxoid], 2.4 g/l beef extract [Difco], 10 g/l glucose [BDH], distilled water).

Samples of DMSO-extracts with interesting bioactivity were fractionated using an Agilent 1100 series HPLC system equipped with a diode array detector (DAD) and a fraction collector. Each sample was fractionated in parallel using 2 different types of LC-columns: Agilent ZORBAX Eclipse XDB-C18, 5 um, 4.6×150 mm and Agilent SB-CN 3.5 um, 4.6×75 mm. For both types of columns, a flow of 1 ml/min of a mixture of 0.005% formic acid in deionized water and acetonitrile was used as mobile phase. In both cases the concentration of acetonitrile was kept at 40% the first minute, then increased linearly from 40 to 95% during the next 9 minutes and kept at a concentration of 95% for the rest of the run. The fraction collector was used to collect 12 fractions of the eluent from 1 minute until 13 minutes from injection.

The samples were dryed in a SpeedVac instrument (Thermo Scientific), dissolved in DMSO and the bioactivity of the fractions was measured (assay described above).

The fractions with bioactivity were analysed using an Agilent 1100 series HPLC system connected to a diode array detector (DAD) and a time of flight (TOF) mass spectrometer. The same columns and buffers were used in this analysis as described above for the fractionation step. Electrospray ionization was performed in the negative (ESI−) mode. The DAD plots were used to identify the approximate retention time of the bioactive compounds in the fractionation runs compounds and in the LC-MS-TOF analysis. Molecular masses corresponding to significant peaks identified in bioactive samples from parallel fractionations (C18 and CN columns) were compared and molecular masses common to fractions from the C18 and CN columns were identified. These molecular masses (10 ppm window) were submitted to the online version of the Dictionary of Natural Products at the website dnp.chemnetbase.com in order to search for previously characterized compounds with bioactivity.

In LCMS analysis of the bioactive fractions, significant peaks with a molecular mass corresponding to Antibiotic BE14106 was identified. The molecular mass observed in the LC-MS-TOF analysis was within 1 ppm of the molecular mass given in DNP (Accurate mass 423.277344). In addition, the DAD-profiles of these extracts were compared to the information given in DNP about the UV-absorbance spectra of Antibiotic BE14106. A good correlation was observed between the data given in DNP and the DAD profile of the compound identified in the extracts.

EXAMPLE 10

Characterisation of BecI, BecO, BecR, BecC and BecP Functions

In order to verify the roles of certain genes in the biosynthesis of BE-14106, a series of gene inactivation experiments was carried out. As described above (Example 7), a gene inactivation experiment using PCR amplified fragments from cosmids 2 and 3 has also been accomplished. Sequencing of these fragments and comparison with the BE-14106 cluster showed both of these fragments to be a part of the becA gene, the 1.1 kb fragment encoding parts of the KS and AT domains of module 2 and the 3.7 kb fragment encoding the KS, AT and DH domains of module 2. The production of BE-14106 was clearly affected in both mutants (Table 9).

Construction of Vectors for Gene Inactivation Experiments becI Replacement Vector:

The 3.63 kb Bgl II-Kpn I fragment from cosmid 2 was cloned into pGEM3Zf(−) digested with BamH I-Kpn I, resulting in construct pBIR1. From this construct a 0.8 kb Nru I-FspA I fragment was removed and the construct was religated, resulting in construct pBIR2. From the new construct a 2.86 kb EcoR I-Hind III fragment was excised and ligated with a 3.11 kb EcoR I-Hind III fragment of pSOK201, resulting in the becI replacement vector, pBIR3.

becO Replacement Vector:

The 14.77 kb Sph I fragment from cosmid 4 was cloned into pGEM3Zf(−) digested with Sph I, resulting in construct pBOR1A. From pBOR1A a 3.71 kb Sph I-Xba I fragment was excised and ligated into the Sph I-Xba I digested pGEM3Zf(−), yielding construct pBOR1B. The 6.37 kb EcoN I-Age I fragment from pBOR1B was treated with Klenow to fill in ends and religated as construct pBOR2. A 3.23 kb EcoR I-Hind III fragment was excised from construct pBOR2 and ligated with the 3.11 kb EcoR I-Hind III fragment from pSOK201, resulting in the becO replacement vector pBOR3.

becR Replacement Vector:

The 4.35 kb Hind III-BamH I fragment from cosmid 1 was cloned into pGEM3Zf(−) digested with Hind III-BamH I, resulting in construct pBRR1. A 0.4 kb SnaB I-BsaB I fragment was removed from pBRR1 and religation resulted in the new construct, pBRR2. The 3.96 kb EcoR I-Hind III fragment from construct pBRR2 was ligated with the 3.11 kb EcoR I-Hind III fragment of pSOK201, resulting in the becR replacement vector, pBRR3.

becC Replacement Vector:

The 5.24 kb BamH I-Sac I fragment from cosmid 4 was cloned into pGEM3Zf(−) digested with BamH I-Sac I, yielding construct pBCR1. The 7.48 kb Not I-Acc65 I fragment from pBCR1 was treated with Klenow to fill in ends and religated as construct pBCR2. A 4.33 kb EcoR I-Hind III fragment was excised from construct pBCR2 and ligated with the 3.11 kb EcoR I-Hind III fragment from pSOK201, resulting in the becC replacement vector pBCR3.

becP Replacement Vector:

The 6.49 kb Sac I-Sph I fragment from cosmid 4 was ligated into pGEM3Zf(−) digested with Sac I-Sph I, resulting in construct pBPR1A. A 3.74 kb Hind III-Bcl I fragment was excised from pBPR1A and ligated into pLITMUS28 digested with Hind III-BamH I, resulting in construct pBPR1B. The 5.85 kb Xmn I-BbvC I fragment from pBPR1B was treated with Klenow to fill in ends and religated as construct pBPR2. The 1.82 kb EcoR I-Apa I fragment and 1.23 kb Hind III-Apa I fragment from pBPR2 was ligated with the 3.11 kb EcoR I-Hind III fragment from pSOK201, resulting in the becP replacement vector pBPR3.

All replacement vectors were introduced into ET12567 (pUZ8002) and then used for conjugation with *Streptomyces* sp. DSM 21069 following the procedure described by Flett et al., 1997 (*FEMS Microbiol. Lett.,* 155, pp, 223-229), but with the donor cells grown to an $OD_{600}$ of 0.4-0.5 and the heat shock time reduced to 5 min. Antibiotics were added after 24 hrs incubation.

BecR was initially assigned a putative role of linking together the C20-C25 acyl side chain made by BecA and the macrolactam ring. The mutant, verified by a Southern blot analysis, was tested for BE-14106 production by LC-MS of fermentation extracts. The BE-14106 production was not affected in the ΔbecR mutant, implying that it is not involved in the biosynthesis.

In addition to the role of BecR there were also questions about the roles of BecI, BecC and BecP in the biosynthesis of BE-14106, and the suggested role of BecO as a C-8 hydroxylase needed to be verified. Using the above vectors, second crossover mutants were obtained for all genes and verified by Southern blot analyses. The BE-14106 production for each mutant strain was tested by LC-MS of fermentation extracts. For the ΔbecO mutant, the expected mass corresponding to the stoichiometric formula ($C_{27}H_{37}NO_2$) of the suggested 8-deoxy BE-14106 was found with 1.0 ppm difference from the theoretical mass, thereby confirming the role of BecO as a P450 monooxygenase hydroxylating BE-14106. The C-8 carbon represents the only likely target of BecO, since the hydroxyl group at the C-9 appears due to the lack of the DH domain activity in BecE PKS involved in the biosynthesis of the macrolactam ring.

LC-MS analyses of fermentation extracts from the ΔbecI, ΔbecC and ΔbecP mutants all showed complete absence of BE-14106 production, and no putative BE-14106 analogues/precursors could be identified. This might indicate that all three enzymes function very early in the biosynthesis, presumably being involved in the synthesis of the starter aminoacyl unit.

EXAMPLE 11

Feeding Studies to Determine Amino Acid Incorporation to BE-14106

Feeding studies of DSM 21069 were performed using a defined production medium based on the $^{15}N$ Silantes OD2 medium (Silantes pr. No. 103202). The composition of the media was $^{15}N$ Silantes OD2 medium 536 ml/l and in addition g per l: $MgSO_4 \times 7H_2O$, 0.4; $CaCO_3$, 5.0; $(^{15}NH_4)_2SO_4$, 0.54; $KH_2PO4$, 0.2 and glucose, 10. The medium was supplemented with trace mineral solution TMS1 (Borgos et al., 2006, *Arch. Microbiol.,* 185, pp. 165-171) 3 ml/l. Incorporation of unlabeled amino acids was tested by adding 0.14 g/l D-asparagine or 0.06 g/l glycine or 0.10 g/l Na-glutamate or no addition of unlabeled amino acid. The production cultures were inoculated with 3% of a 0.5×TSB pre-culture cultivated as described above, except that the cells were washed with the production medium once before inoculation to remove components from the pre-culture. Both the production culture and the pre-culture were cultivated in baffled shake flasks with glass beads as described above.

Quantitative and qualitative LC-MS analyses of BE-14106 and 8-deoxy BE-14106 were performed on methanol extracts from culture pellets using an Agilent 1100 series HPLC system connected to a diode array detector (DAD) and a TOF mass spectrometer. Electrospray ionization was performed in the negative (ESI−) or positive (ESI+) mode, essentially as described previously (Bruheim et al., 2004, *Antimicrob. Agents Chemother,* 48, pp. 4120-4129), but with the following modifications: LC separation were performed on an Agilent ZORBAX Bonus-RP 2.1×50 mm column. The acetonitrile concentration was increased linearly from 40 to 70% for the first 10 min and was then kept at a concentration of 90% for the rest of the run. Concentrations of BE-14106 were determined by UV peak absorption at 291 nm using BE-14106 purified by preparative HPLC as a standard.

All nitrogens in the media before addition of the amino acids to be tested for incorporation in the biosynthesis were $^{15}N$ isotope labeled. The amino acids to be tested were added as $^{14}N$. In addition to D-asparagine and glycine, addition of L-glutamate and no addition of extra amino acids were used as controls in the experiment. The concentration of relevant $^{15}N$ amino acids in the media was: asparagine 0 μM (aspartate 54 μM), glycine 29 μM (serine 11 μM) and glutamate 29 μM. The addition of the unlabeled amino acids were added to 20× concentration of $^{15}N$ aspartate, 27× concentration of $^{15}N$ glycine and 20× concentration of $^{15}N$ glutamate for D-asparagine, glycine and glutamate respectively. The production cultures were extracted in DMSO and the extracts were analyzed on LC-DAD-TOF. The BE-14106 molecule contains one nitrogen atom and it is therefore expected that if N from one of the added $^{14}N$ amino acids is incorporated, a BE-14106 molecule with an accurate mass (M-H) of 422.27 will be observed in a LC-TOF-spectra whereas $^{15}N$ labeled BE-14106 will have the accurate mass (M-H) of 423.28. The production cultures were extracted in DMSO and the extracts were analyzed on LC-DAD-TOF. The TOF-mass spectra showed that addition of unlabeled glycine resulted in 20% incorporation of $^{14}N$, whereas the incorporation ratio by addition of D-asparagine and glutamate were 3%, which is the same as for the control.

The invention claimed is:

1. A non-native recombinant or synthetic nucleic acid molecule comprising a nucleotide sequence having at least 95%, but less than 100%, sequence identity with SEQ ID No. 1 and containing a recombinantly- or synthetically-provided substitution, insertion or non-terminal deletion as compared with SEQ ID No. 1, wherein the substitution, insertion or non-terminal deletion comprises one or more of:

(i) deletion or inactivation of a DH domain-encoding nucleotide sequence as set out in Table 3;

(ii) deletion or inactivation of a KR domain-encoding nucleotide sequence as set out in Table 4;

(iii) deletion or inactivation of becA (SEQ ID No. 5) or a module thereof;

(iv) deletion or inactivation of one or more nucleotide sequences encoding a module of BecB, BecD, BecE, BecF or BecG as defined by the nucleotide positions indicated in Table 2; or (v) deletion or inactivation of becO (SEQ ID No. 26);

wherein said non-native nucleic acid molecule encodes one or more polypeptides having functional activity in the synthesis of a polyketide-based or macrolactam molecule.

2. The nucleic acid molecule of claim 1, wherein said molecule encodes an NRPS-PKS biosynthetic system for synthesis of a polyketide-based or macrolactam molecule.

3. A method for preparing a polyketide-based or macrolactam molecule, said method comprising expressing in a microorganism a recombinant or synthetic nucleic acid molecule according to claim 2.

4. The method of claim 3, further comprising recovering the polyketide-based or macrolactam molecule.

5. The recombinant or synthetic nucleic acid molecule of claim 1, wherein said nucleic acid molecule comprises a nucleotide sequence having at least 96% sequence identity with SEQ ID No. 1.

6. The recombinant or synthetic nucleic acid molecule of claim 1, wherein said nucleic acid molecule comprises a nucleotide sequence having at least 97% sequence identity with SEQ ID No. 1.

7. The recombinant or synthetic nucleic acid molecule of claim 1, wherein said nucleic acid molecule comprises a nucleotide sequence having at least 98% sequence identity with SEQ ID No. 1.

8. The recombinant or synthetic nucleic acid molecule of claim 1, wherein said nucleic acid molecule comprises a nucleotide sequence having at least 99% sequence identity with SEQ ID No. 1.

9. A vector comprising a nucleic acid molecule comprising:

(a) a nucleotide sequence as shown in SEQ ID No. 1; or (b) a nucleotide sequence which is complementary along the full length of SEQ ID No. 1; or (c) a nucleotide sequence which is degenerate with SEQ ID No. 1; or (d) a nucleotide sequence having at least 95% sequence identity with SEQ ID No. 1; or (e) a part of any one of (a) to (d), wherein said part comprises:

(i) a nucleotide sequence as shown in any one of SEQ ID Nos. 2, 6, 8, 10, 12, 14, 16, 18, 20, 22, 24, 26, 28, 30, 32, 34, 36, 38, 40 or 44, or a nucleotide sequence which is complementary along the full length of a nucleotide sequence as shown in any one of SEQ ID Nos. 2, 6, 8, 10, 12, 14, 16, 18, 20, 22, 24, 26, 28, 30, 32, 34, 36, 38, 40 or 44, or which is degenerate therewith, or which has at least 95% sequence identity therewith; or (ii) a nucleotide sequence encoding one or more amino acid sequences selected from SEQ ID Nos. 3, 7, 9, 11, 13, 15, 17, 19, 21, 23, 25, 27, 29, 31, 33, 35, 37, 39, 41 and 45, or which has at least 95% sequence identity therewith, said vector further comprising a heterologous nucleic acid sequence, wherein said nucleic acid molecule encodes or is complementary along its full length to a nucleic acid molecule encoding one or more polypeptides having functional activity in the synthesis of a polyketide-based or macrolactam molecule.

10. The vector of claim 9, wherein the nucleic acid molecule contains a substitution, insertion or non-terminal deletion as compared with SEQ ID No. 1, introducing, deleting, replacing or inactivating a sequence of SEQ ID No. 1 encoding one or more activities or proteins.

11. The vector of claim 9, wherein the nucleic acid molecule contains a substitution, insertion or non-terminal deletion as compared with SEQ ID No. 1 and wherein the substitution, insertion or non-terminal deletion comprises one or more of the following:

(i) modification of a PKS-encoding sequence to modify a domain of a loading module to alter the nature of the starter unit;

(ii) modification of a PKS-encoding sequence to modify the number of modules;

(iii) modification of a PKS-encoding sequence to modify an AT domain to alter its specificity for an extender unit;

(iv) modification of a PKS-encoding sequence to alter the activity of a dehydratase (DH) or ketoreductase (KR) domain;

(v) modification of a hydroxylase encoding sequence (becO; SEQ ID No. 26) to inactivate the hydroxylase enzyme or alter its specificity;

(vi) deletion of a PKS-encoding sequence or modification of a PKS-encoding sequence to inactivate the encoded PKS enzyme; or (vii) introduction of a nucleotide sequence encoding a glycosylation enzyme.

12. The vector of claim 11, wherein the substitution, insertion or non-terminal deletion comprises one or more of:

(i) deletion or inactivation of a DH domain-encoding nucleotide sequence as set out in Table 3;

(ii) deletion or inactivation of a KR domain-encoding nucleotide sequence as set out in Table 4;

(iii) deletion or inactivation of becA (SEQ ID No. 5) or a module thereof;

(iv) deletion or inactivation of one or more nucleotide sequences encoding a module of BecB, BecD, BecE, BecF or BecG as defined by the nucleotide positions indicated in Table 2; or (v) deletion or inactivation of becO (SEQ ID No. 26).

13. The vector of claim 9, wherein said nucleic acid molecule part comprises a nucleotide sequence having at least 96% sequence identity with a nucleotide sequence encoding one or more amino acid sequences selected from SEQ ID Nos. 3, 7, 9, 11, 13, 15, 17, 19, 21, 23, 25, 27, 29, 31, 33, 35, 37, 39, 41 and 45.

14. The vector of claim 9, wherein said nucleic acid molecule part comprises a nucleotide sequence having at least 97% sequence identity with a nucleotide sequence encoding one or more amino acid sequences selected from SEQ ID Nos. 3, 7, 9, 11, 13, 15, 17, 19, 21, 23, 25, 27, 29, 31, 33, 35, 37, 39, 41 and 45.

15. The vector of claim 9, wherein said nucleic acid molecule part comprises a nucleotide sequence having at least 98% sequence identity with a nucleotide sequence encoding one or more amino acid sequences selected from SEQ ID Nos. 3, 7, 9, 11, 13, 15, 17, 19, 21, 23, 25, 27, 29, 31, 33, 35, 37, 39, 41 and 45.

16. The vector of claim 9, wherein said nucleic acid molecule part comprises a nucleotide sequence having at least 99% sequence identity with a nucleotide sequence encoding one or more amino acid sequences selected from SEQ ID Nos. 3, 7, 9, 11, 13, 15, 17, 19, 21, 23, 25, 27, 29, 31, 33, 35, 37, 39, 41 and 45.

17. The vector of claim 9, wherein said nucleic acid molecule part comprises a nucleotide sequence having at least 96% sequence identity with a nucleotide sequence as shown in any one of SEQ ID Nos. 2, 6, 8, 10, 12, 14, 16, 18, 20, 22, 24, 26, 28, 30, 32, 34, 36, 38, 40 or 44.

18. The vector of claim 9, wherein said nucleic acid molecule part comprises a nucleotide sequence having at least 97% sequence identity with a nucleotide sequence as shown in any one of SEQ ID Nos. 2, 6, 8, 10, 12, 14, 16, 18, 20, 22, 24, 26, 28, 30, 32, 34, 36, 38, 40 or 44.

19. The vector of claim 9, wherein said nucleic acid molecule part comprises a nucleotide sequence having at least 98% sequence identity with a nucleotide sequence as shown in any one of SEQ ID Nos. 2, 6, 8, 10, 12, 14, 16, 18, 20, 22, 24, 26, 28, 30, 32, 34, 36, 38, 40 or 44.

20. The vector of claim 9, wherein said nucleic acid molecule part comprises a nucleotide sequence having at least 99% sequence identity with a nucleotide sequence as shown in any one of SEQ ID Nos. 2, 6, 8, 10, 12, 14, 16, 18, 20, 22, 24, 26, 28, 30, 32, 34, 36, 38, 40 or 44.

21. A method of producing BE-14106 comprising:

(i) introducing the vector of claim 9 into a heterologous host cell; and (ii) culturing said host cell under conditions which allow the vector to be expressed and the BE-14106 molecule to be produced.

22. The vector of claim 9 wherein the substitution, insertion or non-terminal deletion comprises one or more of:

(ii) modification of a PKS-encoding sequence to decrease the number of modules; or (iv) modification of a PKS-encoding sequence to inactivate or delete a DH or KR domain.

23. The method of claim 21, wherein said heterologous host cell is *Streptomyces* sp as deposited with the DSMZ on 25 Jan. 2008 under deposit number DSM21069 or a mutant or modified strain thereof which produces BE-14106 or a derivative thereof.

24. The method of claim 21, further comprising recovering the BE-14106 molecule.

25. A non-native recombinant or synthetic nucleic acid molecule comprising a nucleotide sequence having at least 95%, but less than 100%, sequence identity with SEQ ID No. 1 and containing a recombinantly- or synthetically-provided insertion or non-terminal deletion as compared with SEQ ID No. 1, wherein:

(i) the non-terminal deletion comprises deletion of one or more nucleotide sequences as shown in any one of SEQ ID Nos. 2, 4, 6, 8, 10, 12, 14, 16, 18, 20, 22, 24, 26, 28, 30, 32, 34, 36, 38, 40, 42 or 44, and results in the inactivation of a functional protein, or a functional domain or module thereof, encoded by said nucleotide sequence as shown in said SEQ ID No.; and (ii) the insertion comprises the insertion of a nucleotide sequence as shown in any one of SEQ ID Nos. 2, 4, 6, 8, 10, 12, 14, 16, 18, 20, 22, 24, 26, 28, 30, 32, 34, 36, 38, 40, 42 or 44, or which has at least 95% sequence identity therewith, and encodes a functional protein, or a functional domain or module thereof;

wherein said non-native nucleic acid molecule encodes one or more polypeptides having functional activity in the synthesis of a polyketide-based or macrolactam molecule.

26. The nucleic acid molecule of claim 25, wherein the nucleic acid molecule comprises a nucleic acid sequence containing a non-terminal deletion, and the non-terminal deletion comprises deletion of a nucleotide sequence as shown in any one of SEQ ID Nos. 4, 8, 12, 28, 32, 34 or 36.

* * * * *

SEQUENCE LISTING

<160> NUMBER OF SEQ ID NOS: 53

<210> SEQ ID NO 1
<211> LENGTH: 80060
<212> TYPE: DNA
<213> ORGANISM: Streptomyces sp. MP28-13

<400> SEQUENCE: 1 ccccttggt taccgggcag ttaaggctgg tcttcaatat ggccgaaatc agccctgcgt 60
tgtgcgccga cgacggccga acccattggt aaccatgacc ggcgaccggg accgcatcac 120
cgtacaagtg gtctgtgaag cggccgagtc aggcactgtc acccccgcaa ttcgccccga 180
acggcagcag accccgctcg gcgcccttgc gaagttccca gccacggaga aatcgctgcg 240
aggttgctag gagatttcgc acacccgtct cgactacccc ttagccccgc accgattacc 300
ctatcgccga gtgggtgacc gaatgcggtc gctggcttct tgatgttatc gaatatggtc 360

-continued gctagcttct tgatattgat gactaggttc cgcttctggc tgccggaaac cgacgagctc 420
cacgatcaaa aggtgtcaac aggggggaaa gtaagctgtg ttgaaggaac gggacaagat 480
actcgaacag ctcgatgccc tactgatcca gtccacgcgg ggcagggggg ccatcgccgc 540
gatcagcggt tcgaccgcga tcggcaagac cacgacactc aacgccctgg ccgaacgggc 600
gacttcggcg gacatcacgg tgctcagcgt ggtgagttcg ccgcacgagc gcgaggttcc 660
ctacagcgcc ctcgcccagc tgctgcattc gatcgaagcc cagtgcacca ccgccgacgt 720
tccgcgcgcc gggggcgccg ggaccgtcca tgccggcagg caggcggacg aggccgccgc 780
cctcgccccg ccgttggccc aggacgaccc gatgacagtc gcacggcgga cctaccagat 840
catcgccgag ctgaccgccc tgcggcctct gctgatcacg gtggacgaca tccagcacac 900
cgacacggcc accctcacgt gcctgcgcta cctggcgcag cgtctgaccc agctctcact 960
cgcgctggtg ttcacgcacg ggatctccgt cgacgagcag ccggctcgtg tcctggacga 1020
cctcctctac cgcacgagcg cgcgccactt ccacctggag ccgctctcgc gggtggacat 1080
catggggctg gccgcgaacc ggctcccggt cctcccgtcg gaccggctca tcgtcgagat 1140
ccaccggctg agcgggggca atccgctgct cgcccaggca ctcatcgagg agcacaggct 1200
gcgtctcgcg tccgattccg tcgcggggcc gatgccgccg cagagcgacg gcatcggccg 1260
ccggtcgacc accgagggcg gggcgtcgat cggccccgcc ttctaccagg ccgtcctcgc 1320
ctacctgcac cggctcggcc cgcgcgcggt ccgtctcgcc cggtgcgtcg ccctcctgga 1380
cgaggcgacg actccccttc tgttgagtcg gctcagcggt atcgacacgg aactgtcgaa 1440
acgttactta cggttgttca ccggcttggg cgtgctggag ggcgcgcggt tgcggcacgc 1500
gggcgtacgg caggccgtac tgggtgagat gcctcacggc gaggcgaccc agcagcgcta 1560
ccgcgccgct cgcctcctga acgagggagg agcgccgccg caagccgtcg ccatgcatct 1620
gctcggcgtc ggtccgctcc acgacggatg ggtgctgccc gtactccagg aggccgcggc 1680
ccacgccatg gaggacggtg acgtaccgca gggcatccgt tatctggagc tggcctgcga 1740
atgctccctg gacgagggac agcggctctc ggcgaagtcg ctgtacgcct tcggccagtg 1800
gcagctcagg cccgccgagt ccgccccgca cttccgcgcg ctcaagggcc ccatccttga 1860
ggggaagctc acgggcaccg acgccctgtg ggtcgccgag ggcatgctct tccacctcga 1920
cttcgacgag gccgtcgagg ttgtcgacca tgtcaacagc ggcgaggcgg acatgtccac 1980
cgcgctgcac agcacccgga tgctcatggc cgcggaggtc ccgggcctgc tcgaacggct 2040
ggagcaccca ctgccggcca caaccgcccc ggcgacgtcc cattcggagt taagagcccg 2100
tcacgccctc gccctcatcc ttgagaacgg agcggacaag tacgccatcg ccctggccga 2160
ccaggtgttc cagggcagcc agaactggcc gacgtcgaag ctcagcggcc tgccgaaggc 2220
gctgctggcc ctgtgctacg cggatcaact cgacaccgcc gccgcgtggt acgacctgct 2280
cgcggccgag gtggaacgac acgacgcccc tggctggtgg gcccagatcg aaagcgtcgg 2340
cgcgctcctg gcgctgcggc gcgggcggct ggcggacgcc gtacgccagg cggagacggc 2400
ccacgcccgg ctgtccgggc cgaggtggaa cgtcagcagc gcgcttgcgc tgaccgtgct 2460
catcgaggcc cacaccgcca tgggcaacca tcagaccgcg gccaagtatc tggagacgtc 2520
cgagccgccg cccgcgctgt tcctcacccg cgcggggctg cactacctgt acgcgcgcgg 2580
ccgtcatcac ctcgcgaccg gcaacaccta cctggctctg tccgacttcc aggagtgcgg 2640
cacgctgatg cgtcgctgga acatcgacac accctccctg gcgccctggc ggctgggaga 2700
ggcggaggtg tggctgcgcc tgggcgacca gaaacaggcg gcccggctcg tcgagaagca 2760

-continued

```
gctggccaac ccggacgccg ggctcacccg gtcgcgcggt atgaccctgc acgccctggc   2820
cctggtccag gcaaccgcca agcagccccc gatcctgcgg gacgcgttcc gtctgctgga   2880
ggccgcgggc gcgcgttacg aggctgcccg tgtcctggcc gatctcagcc gcgcctacca   2940
gcagttgggc gacaaacagg cccggccgac cgcacggcgg gcctggcggc tcgccaagag   3000
ctgccaggcg gagtccctct gccaggctct gctcccgaca tccatacccc agaacatgga   3060
cacaaagccg agcgaggggt cctgcggcgc cgaccgcgcg ggccaggaca gcttcggcac   3120
actcagtgaa tccgaacggc gcgtcgccac actggccgcc caggggtacg ccaaccgtga   3180
gatcgccgag aggctgttca tcacggtcag caccgtggag cagcatctga cccgcgtcta   3240
ccgcaagatg ggcatcagga accgcgagca gctcctgcag agagcccacg cggtcagcta   3300
cgagtccgtc tgatccgttc gacccccacc ccgtaagcgc cccgttccgc ctgcccgtcg   3360
accgacgggc aggcggtggc gttcggaggg cgagcaagga ctgcacgacc gctcctgcga   3420
gctgaggcgg tcccgcaagc tcgggccggc ccggatcgga ccggtcctgg gcctgccgca   3480
aaggcctggc ccggaaagcc gccctggccg acctcggcgc gaccggcaaa ccacccatca   3540
cccgcgtcaa caaccctccg agccaataca cctagggggc tctacgggta gctgggggtg   3600
agcggcggag atgatgatcg ttccctcaag acgaacgcct gcccggcgtt ttcgaagcac   3660
gcgatgaggg aggcactcgc catcatgtcg agtgatcttg ttcacggcac ggacgcaatc   3720
gcaatcaccg gcatgtcatg ccgcctcccc caggcacccg acgccaactc cttctgggag   3780
ttgctgcggt cgggccgtag tgcgatcacc gaggtgccgc cggaccgctg ggacccggac   3840
gaggtgctgc cggactcacc ggagcggcac cgcgcagcgc tgcgccacgg cgggttcctc   3900
gaccgagtgg accagttcga cgcggccttc ttcgggatct cgccgcgcga ggccgtggcg   3960
atcgacccgc agcagcggct cttcgccgag ctggcctggg aggcgctgga ggacgcggga   4020
atcgtccccg agacgctgcg gtccaccgcg accgccgtca tcgtgggagc gatcgccggg   4080
gactacgcgg cgctggcaca ccgcggcggt gcgatcacac agcactcgct gccggggctg   4140
aaccgcggtg tcatcgccaa ccgggtgtcc tacgcgctgg gactgaacgg cccgagcatg   4200
gcggtcgact cggcgcagtc gtcgtcgctc gtggcggtgc atctggccgt ggagagtctg   4260
cgcaagggtg agtgcaccct ggccctggcg ggcggtgtgg cgctcaactt cgcgcccgag   4320
agcgccgaag tcgccggaat gttcggcggg ttgtcgccgg acggacgctg cttcaccttc   4380
gacgcgcggg ccaacggcta cgtgcgcggt gagggcggcg gcgtcgtcgt actgaagccg   4440
ctggcacacg cggtgcgcga cggcgacacg gtgtacgggg tcatccgtgg caccgcggtc   4500
aacaacgacg gctccaccga cgggctcacg gtgcccagcg ccgaggccca ggcgaccgtg   4560
ctgcgccagg cgtgcgagga cgccggcgtg gacccggccg aggtccgtta cgtggaactc   4620
cacggcacgg gcactccgac gggcgatccg ctggaggcgg cgggtgtggg cgccgcgtac   4680
ggcagcgcgc gtcctgcggg ctcaccggta ctcgtcggct cggccaagac caacgtcggg   4740
cacctggagg gcgcggcggg catcgtcggg ctgatcaaga cggcgctgag catccggcac   4800
cgggagatcc cggccagcct caactacgag acgcccaacc cgcggatcga ccccgaggcg   4860
ctgaatctgc gcgtccagac cgcgtccggc ccgtggccgg acgcgccgct gctggccggg   4920
gtcagctcct tcggtgtggg cggaacgaac tgccatgtcg tactggccga ggcgcccgag   4980
cgggccgcgt ccgaggagga cgcgccgcag ggcgacgagc cggagatccc gctggctccg   5040
tggctggtgt ccgggcgtac cgaggcggct ctgcgcgccc aggccgggcg gctgctggag   5100
```

-continued cggcggacgg cggacgccga cgcgttcgac atcggccgct cgctcgcggg cacccgtacc 5160
cacttcgagc accgcgccgt cgcgctcggg ctcggacacg acgcgcagct tgaggcgttg 5220
cggtccggcg ccgacgtacc ggggctcgtc acgggggtca ccggcgacca cgggaagatc 5280
gcgctggtgt tcccggggca gggctcgcag tgggagggca tggcgcgcga gttgatgcgc 5340
acgtcggcgg tcttccgcgc gtcgatcgag gcgtgccacg aagccctcgc gccgtacgtc 5400
gactggtcgc tgctggacac gctcaccgat gagtccggcg cgacgtccct cgaccgcgcg 5460
gacgtcgtcc agcccgtgct gttcgcggtg atggtctcgc tcgccagggt gtgggagtcg 5520
ctgggtgtac ggcccgacgc ggtcatcggg cactcgcagg gcgagatcgc ggcggcgcac 5580
atcgcgggag cgctcgacct ggcggacgcc gccaggatcg tggccctgcg cagccagacg 5640
atcatgacgc tggcgggtac cggggccatg gcgtcggtgc cgctggcggc cgaccgggtc 5700
accgagtaca tcgccccctt cggcgacggg ctgagcatcg ccgcggtcaa cgggccgacc 5760
accactgtcg tggccggaaa ccccgacgcc atcgccgagt tgctggcccg ctgcgaggcg 5820
gaggggattc gcgcgagggc cgtctcggcc gtggacttcg cctcccactc ttcgcacatg 5880
gaggcggtca aggaccggtt gctggagcag ttcgccgagg tgacgccgcg ttcgtgcgac 5940
atcgcgttct actccacggt caccgcgagc gccatcgaca cggccggtct cgacgccggc 6000
tactggtact ccaaccttcg ccggcccgtc ctcttcgagg cgacgctcag ggccatggcg 6060
gaggacggct tcggcacgtt cgtcgagtcg agtccgcacc ccgttctcac gctcggattg 6120
cgggcgacgc tgccggacgc gctggtcgcg gactcgctgc gccgtaacga ggctccgtgg 6180
ccgcagctgc tgacctccct ggcggaactg cacgtatccg gcctgcccgt ggactggtcc 6240
gccgtcttca aggggcgtac accgggtcgc gtggcgctgc ccacgtacgc cttccagcgc 6300
gagcgctact ggcccgaggt ctcgaccgcg ttcgagcccg ggacgcgcgg cgccgtccag 6360
caccaggaag ccgcgcgcga ggagatcccc gcggcgagct ccacctggtc ggatcggctg 6420
gccggactgc cggcggacga gcgctcccgt gaggcgctgg agctggtgcg gctgcgcacg 6480
gcgatcgtgc tcggtcatct gagcacggac ggggtcgatg tcggccaggc gttccgcgag 6540
ctgggcatgg actccacgat ggccgtccag ctccgtcaga acctcgtgga catcaccggg 6600
ctggcgctgc cggagaccgt cgtcttcgac tacgcgagcc cgtcccggct ggccagccgg 6660
ctctgcgaac tggccctggg cgaggacacg tcgtcggccg cgtccgcgct gtcgcggtcg 6720
gcgtcggtgc tggacgccga cgatccgatc gtgatcgtcg gcatggcctg ccgttacccc 6780
ggcggcgcca gcaccccgga cgagctgtgg cagctcgtcg acgacggcgt gagcgcgatc 6840
tcgggcttcc ccaccgatcg cgggtgggac ctggacgccc tgtacgaccc cgagcccggg 6900
gtgcgcggca agacctacac acggcacggc gggttcctcg acgaggccgc cgagttcgac 6960
accgagttct tcgggatcag cccgcgcgag gccaccgcga tggacccgca gcagcggctg 7020
ctcctccagg tcacctggga ggcgctggaa cgcgccggga tcgacccgga cggcctccag 7080
ggcagcagca ccggtgtgtt cgtgggcgcg atgtcgcagg agtacggccc ccggctgcac 7140
gagggcgacg acggactggg cggctatctg ctcaccggca ccaccgcgag tgtcgtctcc 7200
gggcggatct cgtacacctt cggtcttgag ggcccggcgg tcaccgtcga cacggcctgc 7260
tcgtcgtcgc tcgtcgcgat gcaccaggcg gcgcaggcgc tgcgcgtcgg ggagtgctcg 7320
ctggccctgg cgggcggcgt cgcggtcatg gcgacgcccg gcatgttcgt ggagttcgga 7380
cagcagcgtg gtctggctcc cgacggccgg tgcaagtcgt tcgccggtgc ggcggacggc 7440
accatctggg ccgagggcgc gggcatggtc ctcctggagc gtctgtccga cgcgaaggcc 7500

-continued

```
aacggacaca cggtcctggc cgtcatccgc ggctccgcgg tcaaccagga cggcgccagc   7560
aacggcctca ccgcccccaa cgggccctcg cagcagcggg tcatcaccgc cgctctggcc   7620
ggcgcgggcc tcacgcccga ccaggtcgac gcggtcgagg cacacggcac cggaaccccg   7680
ttgggcgacc cgatcgaggc ccaggcgctc ctggccacct acggccagaa ccgtgaagaa   7740
ccgctgtggc tcgggtcgtt gaagtcgaac atcggccaca cgcaggccgc cgccggtatc   7800
ggcggggtca tcaagatgat ccaggccatg cgccacggca ccctgccccg gaccctgcac   7860
gtcgacgagc ccagcccgca catcgactgg gactccggca acgtgcggct cctcaccgag   7920
gcccgggcct ggcccgagac cgaccacccg cgccgctccg ccgtctcctc cttcggcatc   7980
agcggcacca acgcccacct catcctcgaa caggcccccg cgacgccgga gcccgtggac   8040
ggcgacgacg agcaggagac cccgcagggg gccctcgttc cctggttcct gtccgccaag   8100
agcgcccccg cgctccgcga ccaggcccag cgcctcctcg accatgtcat cgcgcgcccc   8160
ggggtcgacc cggcgcacat cggccgtgcc ctgacagcca cccgcgcccg tttccagcac   8220
cgtgcggtgg tggtgggaga gggccgtgac gaactactcg cgggtcttcg ggcgctgagc   8280
aacgacgagt catcccgcgc ggtcgtcacc ggcacggcac gggaaggcac caccgcgttc   8340
ctgttcacgg gacagggcgc gcagcgggcc ggcatgggcc gcgagctcta cgacacgtac   8400
ccggtcttcc gggacagctt cgacgaggtc tgcgccaccc tcgaccggca tctgaacgcc   8460
gaacagccgg tcaaggacgt cgtcttcgcc gacgacgcca ccctgctcaa ccagacccgc   8520
tacacccagg ccgctctctt cgcgatcgag acctcgctct accgcctggt cgaatcattc   8580
gggatcaccc cgcagcacct gaccggccac tccatcggtg aactcaccgc cgcccatatc   8640
gcgggcgtct tcaccctgaa cgacgcctgc cggctcgtcg ccgcgcgcgg ctcactgatg   8700
caggccctgc ccgccaacgg cgcgatgatc tccctgcgcg ccaccgagga gcagatcctt   8760
ccgttcctcg aaggccacga gcaccacgtc gccatcgcgg cggtcaacgg gcccaactcg   8820
atcgtcatat cgggcgacca ggaagccacc accgccatcg cggaagccct ggccgagaca   8880
ggtgtcaaga cgcggcgcct cacggtctcc cacgcgttcc actcccccca catggacccc   8940
atgctggagg agttcgagcg tacggcggcg gacctgacgt accacgcccc gacgagcccg   9000
atcgtctcca acctcaccgg ccaactcgcc gaccaccgca tcaccacccc gcagtactgg   9060
gtccagcacg tccgggacgc cgtgcgcttc gccgacacca tcaccaccct cgatcagctc   9120
ggcacccggc actacctcga actcggaccc gaccccgtcc tcaccactct cgtcaacgag   9180
accctcggca agacccgggg caccatcccc accgccgtcc tgcgcaaggg gcactccgaa   9240
gccgccacgc ttctcacggc gctcgccacc gcgtacaccg ccggcgcgcc cgtcaacctc   9300
agcagccacc tcccggcccc ccacacccac cccgacctgc ccacgtaccc cttccagcgc   9360
cagcgttact ggcacgcggc caccaccgcc acgggagacg tgtcgtcggc cgggctgacc   9420
gccacgggac acccggtgct gaccacggcc gccgagcttc ccgatccggg cgggttgctg   9480
ctgaccggcc gggtgaacgc ggcgtcaccc gcctgggcgg cggaccacgc cgtcttcggc   9540
accccggtca tgccgggcgt ggcgttcgtc gacatgctgc tgcacgccgc ggcgctggtc   9600
gggcgccctc gtatcgagga actcacccac catgtcttcc tggccctgcc ggaacacggc   9660
gccctccagc tgagggtggt cgtccgcccg gcggacgact ccgggcggcg gtccttcgcc   9720
gtccactcgc ggcccgagga cgccccgctg ggcgccgact ggacctgcca cgccaccggt   9780
gcgctgggcg tcgccccggc cgtaccgccg gcccttccgc ccgtggacgc ggcctggccc   9840
```

-continued

```
ccggcctccg ccgcggtcct cgacaccgac ggcttctacc ggcggatcgc cgaggccggg   9900
ttcggctacg ggccggtctt ccaggggctc gccgccgcct gggaggacgg agacacgctg   9960
tacgccgagg tcgccctgcc cgcggggacc tccccgggct cgtacggcgt ccaccccggc  10020
ctgctcgact ccgcgctgca cccgatcgcc ctggccgcga ccggtgccga gacggacggc  10080
acactccatg tgccgttctc ctggagcggt gtgacgctcc acgcgtccgg cgcgcacacc  10140
ctgcgcgtcc ggctcgtgcg ctccacgccg gagacggtcg cgctgaccgt cacggacccg  10200
tccggcgcgc cggtgctgac cgtcgactcc ctcgccatgc gcggggtccg tgccgagcag  10260
ctcgaagccg ccaggcccga ccgcgacggt gcgctgcacg acgtcgcctg gcgcgcggtg  10320
cccgcgccgc cacgcgccaa ctcgcgcccc gacggcgtcg gctgggccgt ggtgggagac  10380
acccgtgacc cgcgagtcgc cgccgtgctg gcatcgctcg gtgcggccgc cgagtcgtac  10440
ccggacgccg aagcgctgcg cgcctcgttg cgggccggcg cggtccggcc ctcgacgatc  10500
gtcgcccgct tcgccaccgg gaccgccgaa gacggcgccg acccggtcgc ggcggcacac  10560
accgggacac gccacgccat gcacctgctc caggccgtcc tggccgacgg ggcaccggac  10620
tcccggctgg tgatcctcac cgagaacgcg agatacaccg gaaccggcga cgcggcggcc  10680
gacatggccg gtgcggcggt ctggggcctg atccgttcgg cccagtccga gcaccccgac  10740
cggttcacgc tcctcgacgt cgacggctcg cgggcctccg acgaggccgt cgtcgcggcg  10800
ctctccgccg gtgagcccca actggccgta cgcgaaggcc ggctgttcgt tccccgcctc  10860
gcccgtctga ccccgggcgc gattcccgcc acgttcgacg cgcggcgtac ggtgctcatc  10920
accggcggca ccggcgcgct gggctcgatt ctcgcgcgcc acctggtcac ccggcacggc  10980
gtcaggaagc tgctgctgac cagcaggagc ggtcgtacgg cggacagcac cgtcgtcgcg  11040
gaactcgccg gactcggcgc cgaggtcacc gtcgcggcct gcgacgtcac cgaccggctg  11100
tcgctggaga ccctgctcgc gggcctgccg acggagcatc cgctcggcgc ggtcgtgcac  11160
tgcgcgggcg tcctggacga cggtgtggtc acggagctga ccgaggaccg gctggacgcg  11220
gtgctccgcc cgaaggtgga cggcgcgtgg aacctgcacc aggtgacccg tgacatgggc  11280
ctggacctgg acgccttcgt gctgttctcg tccgtggtcg gtgtcctcgg ctcgcccgga  11340
caggccaact acgccgccgc caactccttc ctcgacgaac tcgccgagca ccgccgtacg  11400
gccgggctcc ccgccaagtc cctcgcctgg ggactgtggg agagcggcat ggccgacacc  11460
ctcgacgagc aggaccgggc gcggatgagc cgcggcggac tctcgccgat gcccgccgag  11520
cgggcgctcg cgctcttcga ctcggcactc gcgacggcgc gggcggtgct cgtgcccgcc  11580
ggggtcgatg tctcccacgc gcgcacgcag cgggcgtcga tgctctcccc tctgctcgcc  11640
gaactgctcc cggcccaggc ggcgcccgcc gaacgaggcg gtgaagcggt cgacgagtcc  11700
tcgctgcgcc agcagttggc cctcctgccc gagcccgaac agcgcgaact cctcctggag  11760
gtcctgcgca agcatgtcgc ggcggttctg ggccacagct ctccgctcgt catcgacccc  11820
gagagctcgt tcaaggacct cggtttcgac tcgctcgccg gcatcgaact cctcatggtg  11880
ctgggcgagt ccatggggct gcacctgccg tccacgatgc tgttcgacca cccgacgccc  11940
gagttgctga tcacccacct cagggacgaa ctggtcgacg acgaggccgt acctgtcacc  12000
gccgcggaca ccgcggccgt cgccgtggca ccacgcgacg acgacgaacc catcgccgtg  12060
atcggcatgg ggtgccgcta cccgggcggc gccaccacgc cggacgagct gtggcgactg  12120
gtcaccgagg gggtggacgc catcggctcc ttccccacca accgcggctg ggatctggag  12180
gagctgttcg atcccgaccc cgacatgcgc gggaagacct atgcccgcaa gggcgggttc  12240
```

ctctacgacg ccgaccgttt cgaccccgag ttcttcggca tcagcccccg cgaggccctg 12300
gcgctcgacc cgcagcagcg actcctcctg gagaccacct gggagacgtt cgagaacgcg 12360
ggcatccgcc ccgacaccct gcgcggcaag cccgtcggcg tcttcgccgg cgtcgtcacc 12420
caggagtacg gctccctcgt ccaccggggc accgagccgg tcgacggctt cctgctgacg 12480
ggtacgacgg cgagtgtcgc ctccgggcga ctggcctaca cgctgggtct tgagggcccg 12540
gcggtcaccg tcgacaccgc gtgctcctcc tcgctggtcg cgatgcacct ggcctgccag 12600
tcgctgcgga acaacgagtc cacgatggcc ctggccggtg gcgccacggt gatggccaac 12660
cccggaatgt tcctggagtt cagccgccag cgcggtctgg ctcccgacgg ccggtgcaag 12720
tcgttcgccg gtggcgccga cggcaccatc tgggccgagg gcgcgggcat ggtcctcctg 12780
gagcgtctgt cggacgccaa ggccaacgga cacaccgttc tcgccgtgat ccgcggctcg 12840
gccgtcaacc aggacggcgc cagcaacgga ctgaccgctc cgagcggccc gtcccagcag 12900
cgggtcatca ccgccgctct ggccggcgcg ggcctcacct ccgaccaggt cgacgcggtc 12960
gaaggacacg gcaccggaac cccgttgggc gacccgatcg aggcccaggc gctcctggcg 13020
acgtacggcc agggccgtga agccgaccag ccgctgtggc tcgggtcgtt caagtcgaac 13080
atcggccacg cgcaggccgc cgccggtatc ggcggggtca tcaagatgat ccaggccatg 13140
cgccacggca ctctcccccg gaccctgcac gtcgacgagc ccagcccgca catcaactgg 13200
gcctcgggca acgtgcggct cctcaccgag gagcgcgcct ggcccgagac cgaccacccg 13260
cgccgctccg ccgtctcctc cttcggcatc agcggcacca acgcccatgt catcctcgaa 13320
caggcccccg cgacgccgga gcccgccgag gatgaccacg agcaggacgc gccgcaggcg 13380
accctggtcc cgtgggtcct gtccggcaag acggagcagg ccctccgcga ccaggcgcag 13440
cagctgcgca cgtacctcga actcaacccc gggctgcgca cggaccgagt cgctcacgcg 13500
ctcgccacca cccgcgccca gttccagtac cgggccgtgg tgctcggcac cgaccaccag 13560
gcgttcgacc gtgccctggg cacgctcacc ctcggcgagc cgtccccggc gctggtacgc 13620
gggacgccgc accccggcaa gacagccttc atgttcacgg gacagggcgc gcagcgggcc 13680
ggcatgggcc gcgagctcta cgacacgtac ccggtcttcc gggacacgtt cgacgaggtc 13740
tgcgccaccc tcgaccggca tctgaacgcc gaacagccgg tcaaggacgt cgtcttcgcc 13800
gacgacgcca tcctgctcaa ccagacccgc tacacccagg ccgctctctt cgcgatcgag 13860
acctcgctct accgcctggt cgaatcattc gggatcaccc cgcactacct gaccggccac 13920
tcgatcggtg agatcacggc cgcccacgtg gccgggatct tcaccctcga cgacgcctgc 13980
cgactggtcg ccgcgcgcgg ctcactgatg caggctctgc ccgccaacgg cgtcatgatc 14040
tcgctgcggg ccaccgagga gcagatcgtc ccgttcctcg aaggccacga gcaccacgtc 14100
agcgtcgcgg cggtcaacgg gcccagctcg atcgtcatct cgggcgacca ggaagccacc 14160
accgccatcg ccggcgctct cgccgagacg ggtgtcaaga cgcggcgcct cacggtctcc 14220
cacgcgttcc actcccccca catggacccc atgctggacg agttcgaact cgtggccgga 14280
gagctgacct accacgcccc gacgatcccg atcgtctcca acctcaccgg ccaactcgcc 14340
gaccactaca tcaccacccc gcagtactgg gtccagcacg tccgggaggc cgtccgcttc 14400
tccgacggca tcaccaccct cgaccggctc ggcacccggc actacctcga actcggaccc 14460
gaccccgtcc tcaccaccat ggcgcaggac agcgtggccg atgacagcga cgccgccctc 14520
gtcgccaccc tgtaccgcga ccgggacgag aaccacagct tcctcaccgc cctggccacg 14580

-continued

```
gcacacgccc atggcatcca ggtcggctgg acccccgtgg tcggtgagac ctcggtcccc  14640
gccctcggcc tccccaccta ccccttccag cgccagcact actggctgga ggcggcgaag  14700
cccacctcgg gtgccgacgg tctggggctg acggcgaccg accatccggt gctgaccacc  14760
ttggccgaac tcccggacgg aggcgggcac ctgttcaccg gccgcgtctc cgggaacgat  14820
ccggactggg tggccgagca catcatcttc gggacaatga tcgttccggg tgtggccttc  14880
gtcgacctcc tgctccacgc ggcacgccat gtggactgcg agcacatcga ggaactcacc  14940
caccacgtgt tcctcgccgt gccggagcgc gccgccctcc agctgcggct cctgatcgag  15000
ccggcggaca gctccggaag ccgggccttc gcgttctact cgcggccgga ggacgtcccg  15060
gtcgaaaccg actggaccct ccacgccacg ggcgcgctcg gagccgaacg cagggaagtc  15120
cccgcgggcg ccgactcgct caggaacgag gtctggccgc ctgacatctc ggacaccatg  15180
gacgtggggg agttctaccg ccgggtcacg gacggtggct tcggctacgg accgctgttc  15240
cgagggctca agaaggcctg gcaggacggg aacacgacgt acgcggaagt ctccttgccc  15300
gccggctccg atcccggcga ctacggcatc caccccggtc tgctcgactc ggcgctccag  15360
ccggccgcgc tcatcatggg agagaccgag gcggccgact cgatccgggt gccgttctcc  15420
tgggccggtg tgtccctcca cgcgacgggg gccgactccc tgcgtatccg ccacacgtgg  15480
accacaccgg acaccgcgtc gctggtcatc gccgaccaga cggggacacc ggtcatgacg  15540
atcgactccc tcgccatgcg gacggtcggc gccgaccaac tcgccgccac ccgtgcggcg  15600
gacgccggag agctgtacaa ggtcgactgg ttcgacgtcc agaccgtgga ggacaagacc  15660
cagggcgcgg gcaccgccaa gtgggcggtg gtcgccgacc cggggaacac ccaggtcgcc  15720
gcggcactct ccccgctcgg cgccgcggtc gaggtggagc cggacgcggt gacgctcccg  15780
acgacaccgg gggacgacac cacccggccg gacgtggtct tcacatggtg cgtctccgag  15840
cccggcgccg acccggcaca ggccgcgcgc tccttcaccc accgcgtgct cggcctcgtc  15900
caggcggtcc tctccgacga tcggccggac tcccgcctgg tgatcctcac caagggcgcg  15960
atgtccgccg gtagcggcgg cgcggccgac ctggccggag ccgcggtctg gggctgatc   16020
cgcaccgctc agaccgaaca ccccgatcgg ttcatcctga tggacctcga cggttcggat  16080
gcgtcgctgc gggccgtggg cgctgccctg aacgccggcg aaccccaact cgccgttcgc  16140
gacggccggc tcctcgcccc tcgcctcgcc cgtatcggca ccgccgactc cgagccgacc  16200
gccgcaccgg cgtcgttcga cccggacaag acggtgctca tcaccggcgg caccggcgcc  16260
ctgggcacgc tcctcgcccg tcacctggtc acccgccacg gtgtgaagaa gctgctcctg  16320
accagccggc gcggccgtcc ggcaggcagc accatcaccg cggaactcgc cgaactcggc  16380
gccgaggtca ccatcgtggc ctgcgacgcg gcggaccggg agtcgctgga agccctgctc  16440
gcgagcctgc cggacgagca tccgctcgga gcggtggtgc actgcgcggg aacgctcgac  16500
gacggcatcg tcacggcgct gacacctgac cggttcgacg aggtgctccg gccgaaggtg  16560
gacggcgcgt ggaacctgca cgagctgacc cgtgacctgg acctggacgc cttcgtgacg  16620
ttctcgtccg tggtcggtgt cctcggctcg ccgggacagt ccaactacgc cgccgcgaac  16680
gtcttcctcg acgagctggc cgaacaccgc cgtacggccg gactgcccgc caagtccctc  16740
gcctggggac tgtgggagag cggcatggcc gacaccctcg acgagcagga ccaggcgcgg  16800
atgaaccgcg gcggcctcct gccgatgccc gccgaacagg cactcgggca cttcgactcg  16860
gcgctcgcga ccgaccagac cgtcgtggtc ccggccaagc tcgacctcgc cgggctccgt  16920
gcccgcgccg cgacggtccc ggtggcgccg atcttccgtg ggctggtccg tacgccgctg  16980
```

-continued cgcagcgccg cccaggcggg cggcgcggga gcggaggtcg gagccctggg gcagtcgatc 17040
gcgggccgcc cggaggccga gcaggaccag atcatcctgg acttcctgcg caatcacgtg 17100
gccaccgtcc tcggacacgg ctcggcgaac gcgatcgacc ccgcgcactc cttcaaggag 17160
ctgggcttcg actcgctcag ctcggtggaa ctgcgcaact cgctcaacaa ggcgtccggg 17220
atgcgactcc cgtccaccct gttgttcgac taccccaccc cctcggtact ggccggctac 17280
atccgcaacc aactggcggg cggcaagcag gcggaggcag gcgcgcaagt ggcccgccgc 17340
accgttcgcc cggcgtcctc gcggagcgac gcggccgacc cgatcgtgat cgtgggcatg 17400
gggtgccgct tccccggtgg cgccgacacg cccgaggcgc tgtggaagct ggtcgcggac 17460
gagcgtgacg cggtgggggc cttccccgac aaccgcggct gggacatcga gaacctcttc 17520
gacgacgacc ccgacgtacg gggggaagtcg tacgccagtg agggcgggtt cctctacgac 17580
gccgaccgtt tcgaccccga gttcttcggc atcagccctc gcgaggccct ggcgctcgac 17640
ccgcagcagc ggctgctgct cgaaaccacc tgggaagcgt tcgagaacgc gggcatccgc 17700
cccgacactc tgcgcggcaa gcccgtcggc gtcttcgccg gcgtcgcggc cggggagtac 17760
gtctcgctca cccaccacgg cggcgagccc gtcgagggtt acctgctgac gggtacgacg 17820
gcgagtgtcg cctccgggcg catctcgtac acgctgggtc ttgagggccc cgcggtcacc 17880
gtcgacacgg cctgctcgtc gtcgctcgtc gcgatgcacc tggcgtgcca gtcactgcgg 17940
aacaacgagt ccacgatggc cctggccggc ggcgccacga tcatgtccaa cgcgggcatg 18000
ttcatggagt tcagccgcca gcgtggtctg gctcccgaca gccgtgccaa gtcctacgcg 18060
ggcgccgccg acggcaccat ctgggccgag ggcgcgggca tggtcctcct ggagcgtctg 18120
tcggacgcca aggccaacgg acacacggtc ctggccgtca tccgcggctc ggccgtcaac 18180
caggacggcg ccagcaacgg cctcaccgcc cccaacgggc cctcgcagca gcgggtcatc 18240
aacacggcgc tcgccagcgc gggtctcacc cccgaccagg tcgacgccgt cgaaggacac 18300
ggcaccggaa cgccgctggg tgacccgatc gaggcccagg ccctgctctc cacctacggc 18360
cagaaccgtg aagagccgct gtggctcgga tcgttcaagt ccaacatcgg ccacgcgcag 18420
gccgccgccg gcgtcggcgg ggtcatcaag atgatccagg ccatgcgcca cggcaccctg 18480
ccccggacgc tccacgtcga cgagcccagc ccgaacatcg actgggactc cggcaatgtg 18540
cggctcctga ccgaggcccg ggcctggccc gagaccgacc gcccgcgccg ctccgccgtc 18600
tcgtccttcg gcatcagcgg caccaacgcc cacctcatcc tggaggaagc gcccactccc 18660
acccaccctg agccggcccc cgagagcgca ccgcaggcaa ccacggtgcc ctggatactc 18720
tcgggcaaga gtgaacaggc cgtgcgggac caggcccagc gcttgctcga ccacgtcagc 18780
gagtaccccg agctccagcc ggtcgacatc gcgtactcgc tggccaccgc ccgtacctcc 18840
ttcgagcgcc aggccgtcgc gatcggcgcc acccatgacg aactcgtcga ccacctccgc 18900
tcgctgaccc aggaccccgg caccgccctc ctgcacggcc agtcccactc caagaaggtg 18960
gccctcctct tcaccggtca gggctcccag cacccgggca tgggccgtca gctctacgac 19020
acgcaccccg tctaccggga cgcgttcgac gaggtgaccg ccaccctgga ccagcacctc 19080
caggccgaac agccggtcaa ggacgtcgtc ttcgccgacg accccaccct gctcaaccag 19140
acccggtaca cccagcccgc catcttcgcc ctccaggtgg ccctcacccg gctcctcgtc 19200
gacgagttcg gcgtctcccc cacccatctc atcggccact cgatcggcga gatctcggcg 19260
gcccacacgg cggggatcct caccctcgac gacgcctgcc ggctggtcgc cgcccgcggc 19320

-continued actctcatgc agaccctccc cgccaccggc gcgatgacgg ccgtcgaggc gaccgaggaa 19380
gaggtgctcc cgcacctcac ggagcgggtc ggtatcgccg cggtgaacgg cccgcgttcg 19440
gtggtcgtct ccggggacga agccgctgtc atcgccgtcg gcgaggagtt cgccggtcag 19500
ggacgacgca tccgccgtct caccgtcagc cacgccttcc actcgcacca catggacccg 19560
atgctcggcg agctccacgc ggtggccgac acgctgacct accacgtgcc acgcaccccg 19620
ctcgtctcca ccgtcaccgg ccgcctggcc ggctccgaga tcaccagcgc cacctactgg 19680
agcgatcacg cccgcaacgc cacccgcttc cacgacggcc tcaacacgct tcacgagcag 19740
ggcgtcacca cgtacatcga ggtcggcccc gacgccgtac tcgccgcgct gacccgtgaa 19800
gcgctgcccg acgccaccgc cgtaccgctg atccgggcca aggcctccga gccggccact 19860
ctgctcgacg ggctcgtccg ggctcacgtg tccggcgcca cggtcgactg ggcagggttc 19920
ctcgcacgac gcgggggcag gagcgtcgac cttcccacgt acgccttcca gcgtcggcgc 19980
cactggctgg agaccgccga ccccgtcggt acggccgccg gcctcggtct ggagtccgcc 20040
tcccacccgc tgctggccac gaccaccgaa ctcccggacg gaaccgccct gttcacgggg 20100
cgggtgacgc tggccgacca cccgtggctc agcgaccaca ccgtcatggg aacggtcatc 20160
ctcccgggca cggccttcgt ggagctcgcg ctccacgcgg ccgagacggt gggtctcgac 20220
gagatagcgg aactcgtcct gcacgcgccg gtcaccttcg ggtcccagtc cgcggccctt 20280
ctccaggtga tcgtcggacc tgacgacccg tcggcgggcc ggaccctcac catcaggtcc 20340
cgttcggaag aggaccagtc ctggaccgag aacgcgaccg gcacgctcgg cgcactggtg 20400
ggggtctcct gaccccggcc ggcagcgcga ggccctgaca agcgcccaag gccgcccgca 20460
ccctctcagt ggagggtgcg ggcggccttg ggcgttcggc gttgtcgggg gttcggccac 20520
cggcgccggg cgctcggtct cacggacccg cgggcccggg cccagagccc gaccgggccc 20580
cgtgaacagc cacggccgtc ccactccccc ggctgcgagg gtatggacgg ccgtcgggcg 20640
acggggcggg tggacgacgg gcgggcgacg cgcgggcggg ctcgcgacgc acgaagtccc 20700
cctcctcgcc ggcgccggcg ggaaggggga ctcgtgggac cgatcaggag aagcggagcg 20760
gggtgaacgg cgccgtcgcg gcgtgcggga cggtgtcggt caggtaggcc gccatggcca 20820
cggccgtgac gggagccagc tggactccca tccggaagtg accgctcgcc aggtagacat 20880
cgggaaccgt ggtcggaccc atgacgggga ggtcgtcggg cgaggcggga cggagccccg 20940
cggtgatctc ggcgaaacgc agggcgccca cctcgggaat gacctcggcg gcgcggcgca 21000
gcaggctgcc ggtgccctcg gcggtgacgg tctcgtcgta gccgcgctcc tcgtaggtgg 21060
cgccgacgac gagttcaccg tccaggcggg gagccaggta gagggacttg cccttggaga 21120
tggcgcgggc cgtcacgttg agcagtggca cgtcggagcg caggcggagg atctggccct 21180
tgacgggacg gatctccggg atcgcgcccg cgggcagccc ctcgatctgg tgggtccagc 21240
agccggcggc caggacgaga cggtcgaagg gcaccttgtc accggtgtcg aggacgacgg 21300
tgtggtcctc gatccgggtg gctcccctgc gtacgacgct gccgcccagg gcttcgatgg 21360
cggtgatcag cgccgcgtcg agaacgcgcg ggtcgatggc gccgtcgtcc ggggacagca 21420
ggccgccgac cacgggggcg aaggccggct ggagcttggc gcactcctcg gcggtcagcc 21480
gttcggtgcg cacaccgatg gacttctgga aggccagttg gcggtcgagg atcggcaggg 21540
attcctcgtc gaacgccgcg tccaggacgc cgtcgcgccg gaagccggcc ggagcgaact 21600
cctccagttc ctcgacgaag gacgggtaca gctcacggga ggccaggcac aggcgcagga 21660
gttccggctg gtcgtacagc tggtcgttga tggccgggag cagtcccgcc gaggcgtggg 21720

-continued acgccttgct gcccggggca gggtcgatca ccgtgacgga gacgccttcg cgcgcggccc 21780
gccatgcggt ggccaggccg atgacaccac cgccgacgac aacagttctc atgaattgct 21840
ctcctggagg agtcgacgca ggtgggaggc gagttctgcg gggtgggat ggtcgaagac 21900 gagggtcgcc gggagccgca ggccggtggc ggccgccagg tggcggctga gttcgaggtt 21960
gccgatggag tcgagcccgg cggcgctgaa ctcccgctgc gggtcgatct cgtcgccgct 22020
ctcgtagccg aagaccaagg cggacaccga gcggacgaac tccagggcgg cggcgtcgcg 22080
ttcggcctcg ggcagctcgg ccagccggct gaccagggtg tcggtcacgg cgggcttgcc 22140
ggtacgggtg ggcgccagct cctccaggac gggcgggatg tccccggtga ggcccgcctc 22200
gttgagccgg acgggcgcca ggaccgcctc gtcgctgccg agcgtggcgt cgaagagagc 22260
caggccctgg tcgtgcccca ggggggcgaa gccggaccgc ttgatgcggt tgtggtcggc 22320
ggcggacagg tcggagccca tgccgttctc gctctcccac agaccccagg cgagcgagag 22380
gccctgcagt ctgcgggcac ggcggtggtg ggcgagcgcg tcgaggacgg cgttggcggc 22440
tgcgtagttg ccctgccccg cgttgccgac cagccccgcg acggacgaga acaccacgaa 22500
cgcgcagtcc gggtcctgga tcaggtcgtg caggtggagc gcggcgtcga ccttgggacg 22560
cagaaccttg tcgagtccgc gtggcgtgag ggtgccgatc gcgccgtcgg acagcacacc 22620
cgcggtgtgg atgacggcgg acggggcggg gatgccggcc agtgcgctct ccagcgacga 22680
gcggtcggcg acgtcgcagg cgaccacgtc gacacgggcg ccgagcgcgg tgagttcggc 22740
atccagctcg gcggcgccgg gcgagccggg accgcggcgg ctgagcagca cgaggtgccg 22800
gacgtcatgg ccggtgacga ggtgccgggc gagcaggcgg cccagttctc cggtgccgcc 22860
ggtgatcacg acggtacccg tgaggctcct gcgccgcggc ggcggtgggc tgcgtacgag 22920
acgcggcctg agcagcgcgc cgttgcgcac ggcgagttgg ggttcgccgg aggcgacggc 22980
ggcggcgagg gagcggcccg agttcccggg gtcgtcgacg tcgaccagga cgaagcggtc 23040
ggggtgttcg gactggacgc tgcggagcag tccccagacg gcggcgcccg acacgtcgga 23100
caggtcctcc ccggcgcggg cggcgacggc tccgctactg accagcacca ggcgggtctt 23160
ggcgaggcgg tggtcggcca ggcactcctg tacgaccatg agggcgcgtt gcgccgccga 23220
gcgtaccggc gagtcctcgt ccgtgcagga gacgacgatc acgtccggga cggctgtggc 23280
ggcccggagc acggagtcga gttcgcgcag cgtggggtag gagtcgaaca aggggcgggt 23340
ggccttcagc gcgccggtga ggccgatgcg gtcggttccg aggaatcccc agcgctgctg 23400
gtcggagttg tccgactgct gtacgacgga cttccatacg acgcgcagca gttgggtgcg 23460
ctgcgccgcg gcgtcgagct gctcggccgt gacgggccgg ctgacgacgg aaccgatcgt 23520
ggcgatcggc tcgccgtcgt cgccggtgag cgccagggag aagccgtcgt cgcccgggac 23580
ggtgtggatg cggacggcgc gggcgccgcc cttgtgcacc cgtatcccgc gcagcgcgaa 23640
cggcaggaac gtccggtcgt cgcggtcgat gtcggggacc agtgccgctt ggagcgcggt 23700
gtcgagcagg gccgggtgca ggaggtagtc gccgccggtc gcggtgtcga gcgctgagtc 23760
ggcgtagacc tcctcgccgt gcgaccacac ggcgcgcagg ccccggaagg ccggcccgta 23820
ctggagaccg cggtcggcga agcggctgta gaggtgctcg atgtcgacct cgcggactcc 23880
gtcaggaagc ccgggccgtt ctgctttact cattgtcgct tccttcgcga agtccgggcg 23940 gggtcagat cacgggcggg ttggtgacgg cggcggtgat ctcgccgtgg ctctcgccac 24000
cttgctcgtc ggcgtagtgg cacttggtcc gcaggatcac cagggcgtcg cgcaggtcgt 24060

```
tggcgtccca ttcggcgatg tcgatgatct cgatctcgcc ggtgaagcgg cggccctgca  24120
tcgcgctgcg gaagctgctc ttgaagtcgg tgatgaacac gtcggcgagc tgccgggtcc  24180
agaactgctc gatcgtccag ccggagaacg gctcgacgag tgactcccgt accgacatgg  24240
ccagcaggta gtaggccatc tggttgaagc agatgttgaa ctcgaccgag ttgaagtgcc  24300
cggtgtcgtc gatgtagcag gactcgggga tctcgaaggt gcaggtggcg atgagtcgtc  24360
cgccgtcgcg ggggtcgccc tccgaggtga ccgtggccga ggtgaggtac tcgcaccgct  24420
tggcccggta gggggtcagc acccggtgca gcagttcgtc gtcggtgggg aagacgcgcc  24480
ggtcggtgtc ttcgagaagc tgggtcatgt cgggtctcct gatcgtcgcg cggtgcggag  24540
aaggtcggcc aggctcatgt tctggatcgc ggcggtgcgg tccgcggcac cctcggccga  24600
ctcgggctcc ggttcgttct cggtacgtc gatcgccatt tcctcaagca ggtgccgagt  24660
gaggacgagc gaggtcgggt ggtcgaagac gagcgtcgcg ggcaggcgtt ccccgatgac  24720
ctcgccgagg gcgttgcgga accgcacggc ggcgagggag tcgaagccca tgtcgcggaa  24780
cgaccggtcg gcgtcgacct cgtcggcgtc gccgaagccg agggtggtgg cggcctgcgc  24840
ccggacgatg tcgagcagtg tctgttcgcg gcgggacgga gtcagccgtg ccagccggtc  24900
gcgcaggctc tcggccggtt cggcggcccg tgcggcggga tcgactacgc ggcgggacgg  24960
gccgcgtacg agatcgcgca tcagataggg cacgtcggac cggctctgcc cgctcaggtc  25020
gagccggacg ggcgccagga acgcccggtc gagcgcgccg gcggcgtcca gcatcgccag  25080
gccctcgtcg gagccgatgg gcaggacacc gtcgcgcacc atgccggcca cgtcggcgtc  25140
ggccagttcg ccggtcatgc cgctggcctc ttcccacagt ccccaggcca gggactgtgc  25200
cgagagcccg ttcgcgcgcc ggtgcgcggc gaggccgtcg aggaaggtgt tggcggcggc  25260
gtagttgccc tgtccggcgc cgccggtcac gcccgcggcg gacgagaaca tcacgaacgc  25320
cgagaggtct tgaccggcgg tgagttcgtg caggttcagc gccgcgtcga ccttggggcg  25380
catcaccgcg gccattctct ccggtgtcag cgaggagagg atcccgtcgt cgaggacgcc  25440
cgcggtgtgg acgattccgg tgagggtgcg gtccgccagc acggccgcca gcgcgtcgcg  25500
gtcggcggtg tcgcaggcga ccacctcgac acgggcgccg agcgcggtga gttcggcgtc  25560
cagttcggcg gcaccgggtg cggcggggcc gcggcggctg gtgagcagca ggtcggtgac  25620
gccgtgggtg gtgaccaggt gcctggcgac gaggctgccc agggtgccgg tgccgccggt  25680
gatcagtacg gtgccgggcc ggtcgccgaa gacggtggcg gcggtgccgc tcaggtcccc  25740
ggtgacgcgg gccagtcgcg ggcggtggag ggtgccggag cgtatggcga tctgggcctc  25800
gcccgtggcc accgccgcgt cgatgtcggc gtccgtgtgg tcggcgcggt cgtcgacggc  25860
gtccaggtcg atcaggacga cgcgtccggg gttctccgtc tgagcgctgc gtacgagtcc  25920
ccagacggcc gctccggcga ggtcggtgac gtcctcgccg ttcacggaca gggcgccgcg  25980
ggtgacgacg gcgagcacgg cgtcgtcggc gccgctctcc agccaggact ggaggacggc  26040
gagtgtcgtg gcggtctcgg cgtgggccga cgcggcggtg gtgccgcccg tgcagtggtg  26100
cacgacggtc cggggggcgg tgccgccagg tacgggtgcg gcgggtgccc agaccagctc  26160
gaacagcgag tcgtcgtacg cgccggtgcg gatcggcccg cccggggcca ccggacgcag  26220
tacgagcgac tcgacggagg cgacggggcg gcccgcggtg tcggtgaggc gcagcgccac  26280
ctcgtcatca cccaggctgg tcatccgcag tctgagcgcg gcggctcccg aggcgtgcag  26340
gtcgacccgt gtccaggcga acggcagggt gaccctttgg gcgtcggtgg cgagcagtcc  26400
ggtcgcgtgg agagcggcgt cgagtgcggc cgggtgcagc ccgaaccgct gggcctcggc  26460
```

-continued

```
ggcggcctgc tcggggagcg tgatctccgc gaacacctcg tcgccggagc gccaggcggc  26520
acgcaaaccc tggaacaccg gcccgtaggc gaggccgccg tcggcggccg gctcgtagaa  26580
gccggtgagg tcgacgggct cggcgcccgg cggcggccag gccgccggct cgtgggccgg  26640
ttcgggcgcg gcgtcggtga gcgtgccctg ggcgtggcgt gtccagaggg tgtcggcggg  26700
ggcgttgtcg ggccgcgagt ggatcgacac ggtacgcaga tcggcgtcga ccacgacctg  26760
gatggccacg ccgccgcgct cggggagagc cagcggtgct tcgagtgtca gttcttccac  26820
gcggccccgg ccgacctcgt caccggcccg gacggccagt tccacgaagc ctgacccggg  26880
gaacaggacg gtgccgccga cgacgtggtc ggcgagccat ggctggccgg agagcgagag  26940
gcgtccggtg agcagtactc cccggccccc ggcgaccggc acggccgccc cgagcagcgg  27000
gtggtcggtg ggtatctggc cgatgcccac ggcgtcgccg gtgtgctcgg acaggtgcag  27060
ccagtaccgc ttgcgctgga aggggtaggt gggcagttcg acgtgctggg ccccggttcc  27120
gacgaactgg gtgtcccagt cgacggtcgc gccccgcacg tacgcctcgg ccagcgaggt  27180
gacgaactgg cgcgggctgc cggagtcgcg gcgcagtgtg ccgacgagtg tggcggccac  27240
cccggccgac tcggcggtct cgtcgagtcc ggtcagcagg cccgggtgcg ggctggcctc  27300
gatgaaggtc tcgaagccgt cggcgagcag tgcccgcgtc gtgtcctcga accggacggt  27360
ctggcgcagg ttggtgtacc agtactcggc gtcgagaccg gcggtgtcca gggttcccgc  27420
ggtgacggtg gagtagaacg ggatggacga ggtacggggt gtcaggccgc tcagttcggt  27480
gagcagccgg tcgcggatct cctccacgaa catcgagtgg gaggcgtagt ccaccgggat  27540
acggcgggac tggacctcgt cggtgtccag ccggccccgc agttcgtcga gggcctccgg  27600
gccgccgcac acgacgacgg agctcgggcc gttgacgacg gcgagttgca ggcggccgtc  27660
ccagtcggcc aggtactcac tcgcgcggtc ggcggacagg gcgaccgaca tcatgccgcc  27720
ccggcccgcc aggtcctgcc ggatgacgcg gctgcgcagg gcgaccacgc gtgcgccgtc  27780
ctccagcgac agcgcgccgg cgacacaggc ggcggcgatc tcgccctggg agtggccgac  27840
gacggcggcc ggttcgacac cggccgcgcg ccaggcctcg gccagcgaca ccatcagcgc  27900
ccacagcgtg ggctggacga cgtcgacggc gtccagggcc ggtgcgccgg gcgcgccgtg  27960
gaccacgtcg agcaggttcc agtcgacgta cgattcgagt gccttggcgc attcgcccag  28020
gcgtgtcgcg aacgccggtg agtgctccag cagttcgacg cccatgccct gccactgcga  28080
gccctgtcct gggaagacca gcacggcgcg cgagtcgccg cgttgcaggc cctggaccac  28140
ggcggcggac gagttcccgg cggccagcgc gtcgagtccg gcgagcaggc cgtcgcggtc  28200
ggcgtccacg atcacggccc ggtgttccag ggcggcgcgg cctcgggcaa gcgtggcggc  28260
ggcgtccagt tcgtcgacgt cgccgttctc gcgcaggtgg gcggcgatgc gcgccgcctg  28320
ggcgcgcatc gcctcggggg tcgagcccga cacggtcagc gggacgaccg gaggccgctc  28380
gccgcgcggt tcgcccgggc cggccggcgg cgcctgctcg atgatcacgt gggcgttggt  28440
gccgctgacg ccgaaggagg agacggcggc gcggcgcggg cggccgtcgg ccgtccagtc  28500
cctgggctcg gtgagcagtt cgacggcgcc ctcggtccag tcgatgtgcg gagagggggt  28560
ctcggcatgc agggtgcgcg gcagtacgcc gtggcgcatc gccatcacca tcttgatgac  28620
gccggcgacg ccggcggcgg cctgggtgtg cccgaggttg gacttgaccg agccgagcca  28680
cagcggatcg tcgcggcgct cctggccgta ggtggccatc agcgcctgtg cctcgatcgg  28740
gtcgccgagg gtggtgccgg tgccgtggcc ctcgaccgcg tcgatgtcgg cgagtgtcag  28800
```

accggcggag gccacggcct gccggatcac ccgctgctgg gcggggccgt tgggggccgc 28860
gatgccgttg gacgcgccgt cctggttgat cgccgagccg cggatcaccg cgaccaccgg 28920
gtgaccgttg cggcgggcgt ccgacaggcg ttcgagcacc aggagtccgg cgccctcgcc 28980
ccagccggtg ccgtcggcgc cggcgccgta cgccttgcag cggccgtcgg cggcgaggcc 29040
gctctgcagg ctcatcccga cgaacgtctc gggcgtggcc atcacggtga cgccgccggc 29100
cagggcgagc gtgcactcgc cctgccgcag cgactgcatc gcccagtgca tggccaccag 29160
ggaggaggag caggcggtgt cgatggtgac cgcagggccc tggagaccca gggtgtaggc 29220
gatgcgtccg gaggcgatgc tgccgaggcc gcccccggcg gtgaagcccg cgaggtcctc 29280
ggggacggcg ccggagcggg tcgtccagtc gtggttcatg acaccggcga acacaccggc 29340
ggcggtgccg tgcagggagt gcggatcgat gccgccctgt tcgagggcct cccaggcgac 29400
ttcgaggagc atgcggtgct gggggtccat cgcctgggcc tccttcgggc tgatgccgaa 29460
gaaggcgggg tcgaactcgg cgacgtcgtg caggaagccg ccctcacggg tgtacgtggt 29520
gccgtgcttg ccgggctcgg ggtcgtagat gtcgtcggtg tgccagtccc ggtcgtccgg 29580
gaactcggtg atggcgtcgg tgccgccggc gaccagccgc cacagttcct cggcggaggt 29640
cacgccgccc gggtagcggc agcccatcgc cacgatcgcg atgggctcgt cggtcgcggt 29700
ccgcacggtg ggccgcggcg ccgcggtgac gggtacggct ccgcgtacgg tttcgagcac 29760
gtggtcgacc agggcgcgcg gggtcgggtg gtcgaagatc agcgtggagg tgagccgcag 29820
cccggtggcc gtaccgagcg cgttgcgcag ttcgatggcg gccagtgagt cgaagcccag 29880
ctcggtgaag gcgcggcggg ggtcgatcgc ggtgccgctg tcgtgtccga gtacggcggc 29940
gatctgggtc cggaccaggt cgaggacgat gcgttcgcgt tcggcgtccg gctttccggc 30000
gagccggtcg gccagtgcgc cgccggggcc ggtcgcggcc gccgcggcgg tgttccggcg 30060
ggcgggcggg cggaccagcc cccgcagcat cggcgggatg ccttcggagc gggcccgcag 30120
cgcgcgggcg tcgacgcgca gcgggacgag tgccggcgca ccggtgacga gcgcctggtc 30180
cagcagggcg aggttctcct cggcgtccag ggcggggagc ccggaacgct cggcccggcg 30240
gagggtgacc tcgtccaggc gggcgcccat tcccgcgtcg cccgcccaca ggttccacgc 30300
gagggaggtc gcggggaggc cctgggtgac gcggtgcgcg gcgagggcgt ccaggaaggc 30360
gttggcggcg gcgtagttgc cctgcccggc cgcctccatg gtcccggccg cggaggagaa 30420
caggacgaag gcggcgagcg ggaggccgcg ggtcagctcg tgcagatgcc aggcgccgtc 30480
ggccttgccg tggaagacgg tgtggacctg ctcgggcgtg agcgatccgg cgagcccgtc 30540
gtcgacgact ccggcgctgt ggacgacacc cgtcagcggg tgctcgccgg ggaccgtctc 30600
cagcagcgcg gccagggcgg cgcggtcggc gacatcacag gcggcgaccg tggcgtgggc 30660
gcccaagccg gccagttcgg cgacgagttc ggcggcgccg gggctgtcgg ggccgcgtcg 30720
cccggtgagc agcaggtgcc gcacgccgtg ctgttgtacg aggtggcggg cgaccacgcc 30780
gcccagaccg ccggtgccgc cggtgatcag caccgtgccg tccgggtccc acgcgacggg 30840
gcgcgggtcc tcgggtgcgg gcgtcctggc caggcggggc acgagtacct tgccgtcgcg 30900
cagggcgagt tggggttcgc cggtggccag ggcggcgcgc agttcgtgtt cgggcacgtc 30960
gtggtcggtg ccgacgagga cgaagcggcc ggggttctcg gcctgggcgg agcgcacgag 31020
cgcccacggg gacgcgaggg tgaagtcgta cggctcgccg cgggtgacga tcgcgaggcg 31080
ggtgtcgtcg cgcagcgcgt cctggatgag ggtgagggcg tgcagtgtcg ccgcccgggc 31140
cgcgtcggcg ggttcgccgg ggaaggtctc ggggacgtac gccagttgga actcgtgcga 31200

```
cgcggcgtcc ggctcggacg gggcctggac ggcggtccat tcgacgcgca gcagcgagcc  31260
gccgcccgag gcggacggcc gtacgccgtt gatcggcacg gggcgctgga cgagcgagcg  31320
gacggtggcg acgggtgccc cgttcgcgtc ggcgagttcg accgtgacct cgtccggggc  31380
ggtctggacg acgtggacgc gtacggcggt ggcgccggtg gcgtggagtt cgacaccgcg  31440
ccaggcgaac ggcagccgca cctggccgtc gtcctccggg ccttcggcgg cgtgcagtga  31500
ggagtccagc agcgcggggt gcagtccgaa ccggtcgcct ccggcgtcgt cgagggcgac  31560
ctcggcgaac acgtcgtccc cgcggcgcca cgcggcgcgc acgcgtcgga acgcgggccc  31620
gtagccgtac ccctgcgcgg cctggcgctc gtagaggccg tcgacgtcga tcggctcggc  31680
gtcggccggc ggccactggg cgaacacggc cgggtcggcc gtcgcgccct cgccgtgctc  31740
ggtcagcacc ccgctggcgt ggcgggtcca gttgtcctcg ctccgcgcgg ggcgcgagta  31800
gatgtcgacc gagcggcggc ccgaggcgtc gagcgcgccg acgacgacct ggatctcgac  31860
tccggcgtcg gtggtgaccg ccagcggtgt ctccagggtg agttcctcca ccgcggcgca  31920
gcccgcctcg tcgccggcgc ggacggccag ttcgacgagg gcggtgccgg gtacgaggac  31980
gacacccgcg atgacatggt cggccagcca gggctgtgcc cgggtggaca tccggcccgt  32040
caggatcact ccgtcggcgc ccgcgaggct gacggcgctg tccagcatcg ggtgcccgat  32100
cgtgccgggg tggctgcttc cggcgtccag ccagtagcgc ctgcgctgga acgagtaggt  32160
gggcagcgcg gtgcggtggg cgccgcggcc ggcgaagaag cggtcccagt cgaccgcgag  32220
accgtgggcg tgcgccaggc cgagcgcggt gagactctgg cgctcctcgt cgtgcccgtc  32280
gcgcagcagg gcggcgaacg cggcgtcggc gccgccgtcg gtcaggcagt cgcggcccat  32340
tgccgacagg acggcgtcgg ggcccagttc caggtaggtg gtgacgccct gggattcgag  32400
ccagctcatg gcgtcggcga accggaccgg ctcgcgcacg tggcgtaccc agtagtcggc  32460
gtcgaacgcg gcgacgggct cgccggtcag gttggacacc acggggatac gcggcggctg  32520
gtaggtcagg gtctcggcga cgcggcggaa gtcgtcgagc atcggttcca tcagcggcga  32580
gtggaacgcg tgcgagacgc gcagccgccg cgtcttgcgt ccctcctcgg tgaagcgggc  32640
ggcgacggcg agtacggcgt cggtctcacc ggacagcacg accgccagcg ggccgttgac  32700
ggcggcgatg cccaccttct cggtgagata cggggcgact tcggcctccg ccgcctggac  32760
ggcgaccatg gcgccgccgg cgggaagctc ctgcatcagc gtgccgcgcg cgccgaccag  32820
cagcgccgcg tcggccaggt tcatgacgcc ggcgacgtgc gcggcggcga tctcgccgat  32880
ggagtgtccg gtgaggagtc cgggcgtgac gccccacgac tccagcagcc ggaacatggc  32940
ggtctcgacg gcgaagaggg cggcctgcgc gtagcgggtc tgctggagca gttcggcctg  33000
cgccgaaccg ggctcggcga acagcacctc gcccaggggc tcgtcgaggt ggaggtcgag  33060
gtggtcggcg gcgtcctgga gcgcccgcgc gaacaccggg aaggcgcgca ccagttcgcg  33120
gcccatgcca agacgctggc tgccctggcc ggtgaagagg aacgcggtac ggcccgcggc  33180
cggcgtcgta ccggtgagca gtccgggcgc gctctcgccc gcggcgaggg cggtcagggc  33240
gcggcgcagt tcggcacggt cggcggccac gacggtggcg cggtcgcgca gcgcggcgcg  33300
cgtggtggcg gccgagtagg cgaggtccag cggcgaggcg tcgtcgaccg ccgtcaggag  33360
ccgttcggcc tggccgcgca gtgcgtcctg gccctgggcg gacaggacga ccggcacggg  33420
gcgctcggcc accgggggtt cgtcgctccc gtcggcggcg gcgacggggg cgggcggctc  33480
ctcgatgatg acgtgggcgt tggtgccact cgcgccgaac gaggagattc cggcacggcg  33540
```

cggtgtgtcc gcggcttccc aggggacggg ctcggtgagg agctggacgg tgccgtccga 33600
ccagtcgacg tgcgtggtcg gcgcgtccac gtgcagggtg cgcggcagcg tgctgtgacg 33660
catcgcctgc accatcttga tgattccggc ggcgcccgcc gccgctccgg tgtggccgat 33720
gttggacttc accgacccca gccacagggg cttctcgggt gagcgtccgc gtccgtaggc 33780
ggcgaccagg gcctggccct cgatggggtc gccgagtgtg gtgccggtgc cgtgcgcctc 33840
gaccgcgtcg acctcgtcgg cggtcagacg ggcgtcggtg agcgcgcggc ggatgacgcg 33900
ctgctgcgcg aggccgttgg gggcggacag gccgttggtc gcgccgtcct ggttgatggc 33960
ggtgccgcgg atcacggcca gtacggggtg cccatcgcgc agcgcgtcgg acaggcgggc 34020
gaggacgaac acgccgacgc cttcggcgaa cgaggtgccg tccgccgcgg cggcgaacgc 34080
cttgatgcgt ccgtcggggg ccagaccgcg ttggcggctg aaggtggtga acgtgccggg 34140
gctggatatc acggtgacgc cgccggccag cgccagcccg cactccccgc cctggagcga 34200
gcgcacggcc aggtggaggg ccgtgagcga gcccgagcac gcggtgtcga cggtgagtgt 34260
ggggccttcg aagccgaggg tgtaggcgac gcggccggac acgacgctgg gcaggttgcc 34320
gcccaggacg tagccgtcga gaccgtcggg ggcctcgtgc gtccggggcc cgtactcgtg 34380
cggctccacg ccgatgaaca cgcccgaggg tgtgccgcgc aggcggcccg ggtcgatgcc 34440
cgcgtgttcg agcgcttccc aggaggtctc cagcagcagc cgctgctggg ggtccatggc 34500
cagcgcttcc ttgggactga tctggaagaa gtcggcgtcg aagtcggcgg cgtccgggag 34560
gaatccgccg cgccgcacat aactggcgcc ggtgacggac gggtccgggt tgtagatgcg 34620
gtcgagatcc cagccccggt cggagggaaa gtccgtgagc acatgggtgt cgtcggcgac 34680
gatccgccac aggtcctcgg gcgtgctcac accaccgggg aagcggcagc cgattccgac 34740
gatcgcgatc ggctcgccga acgccgacgg cagggcgggc gccgccgtct cgtcgggtgc 34800
gtccgctccg gcggtgccgt gcagcaggtc ggccaggtgg ccggcgaggg cgatcggtgt 34860
cgggtggtcg aaggcaaggg tgacgggcag gtccgccccc acctcggcgg cgagccgccg 34920
ctgcaaccgg accaggccca gcgagtccag gccccccgcc aggaacgggc ggtcggcggc 34980
caggtcgacg gccccttccc cgtaggcgtc cgggtcggcg gtccgcaaca ccgctgcggc 35040
ttgcgccagc accagttcca gcatcgcggc ccttgactgc tcggtcatgt gcatactccg 35100
caacgaagaa gaggcatgga aacgaagaag acgcttggag tcgatcgagc gggtcaggac 35160
gccacgtggg cggccagggc ggtgcggtcg accttgccgt tgacggtcac ggggaactcg 35220
ttcaccacgc tcagaccgtg cgggaccatg taggcgggca gcgcggcgcg acagaacgcg 35280
aggacttctc tggtgtccgg cgcgggaccc gcgggggcgc aggtgacgaa cgcgtgcagc 35340
agtgggtcgc cgtcctcgcg cggcaggacc atcgcgaccg cgccggtgac accggcgaac 35400
tggccgatac ggcgctccac ctcgccgagt tcgacgcggt tgccgcggat ctgcacctgg 35460
gagtcgacgc gaccgcggaa gtacagctcg ccctcgggcc ccatatgggc caggtcgccg 35520
gtcttgaaca ccacctgtcc cgatccgggg tgcagcgggt ccgggaggac gacggcgcgg 35580
gtggcctccg ggtcgcgcca gtagccggag aagagcgagg ggctgcgcag gtagatctcg 35640
ccgatggtgc cgggctcgtc gacggggctg ccgtcggacc cgaggagcat catctcggcg 35700
ccggcgacgg cgtaaccgat ggagaggcgt tcggtgccgg gcggcagcgg gttgggcacc 35760
tcggtgatgg acgcggccat cgtctcggtg gccccgtaac cgttggtgaa gcgcgccttc 35820
ggcagcagtt cctggaggcg ccgcagctcg tccaggggga agtcctcccc ggagaaggtg 35880
atgcggctga ggacgccctc ctggcccatc tcggccagca ggtcggattc gtggcgcagt 35940

-continued

```
accgggcgcc agacggacgg gacaccgtcg acctgtgtga cccccgcatc gcgcaggtac  36000
gaaaggaagc ggcggggcca gttgagccgg gcgcgcggca cgggcaccag cgtggcgccg  36060
tggccgaggg cgaggccgat gtcgaacagc gcgaagtcga actggagcgg agaggtgttc  36120
gccacccggt cctcggccgt gacgagccgt gcggcctcag cgccccgcag gaacgcgatg  36180
accccgcggt ggctcatgac cacgcccttg ggccggccgg tcgtgcccga cgtgaaggtg  36240
atgtacgcgg tgtcgatggg cgtcaccacg cggcggcggc ggacgcgcgg cgcgggcgcc  36300
cgctccacgg tgaggccgcc ggggccgaag cgggcggtgc cgaccgtctc gggaatgccg  36360
gtgcgctgcc cgtggtcgga ctggatgtgc agcgcgggct ccgcgctgtc gatgatcgtc  36420
agcagccgct cgtccgggac ctcggggctg gtcggggtga acggcagccc cagcgtggcg  36480
caggccagca gggtcgccac cgcgtcggcg ttggtgtcgg attccaggat gacgcggtcg  36540
cccacatcca ggccgagcgc gtcgagcgcg tcgacgaggc ggtcgacgcg ccgctccagt  36600
tcgccgtagg tgacggtctc cagaccaccg tccgccgccg cctggatcac ggcgggccgg  36660
tcggggtccc tccgggcggc ggccagcaga tacgtccgca ggttgtccac cgacgcgtgc  36720
gcccggaccg gacgggctcc attcgggctc atgcgccacc ttcccgattc agcgtttccg  36780
agtaatgccc gcccatttct aacaggtggg cttttcaact cgcaagaacc cctggccacc  36840
ggcgcccgaa ctagggggca ttaggggtta tgcggccagt agggacgcaa gaacactgac  36900
cgtacaacag gtgggatcga agtgccgggc tttcggaacg catccgatga gcccgacaaa  36960
tagggagagc gagaatatgt cggcgattat ctttcccgga atcggcccgg tccggctcgc  37020
cgactcggcg cggttcctgg tgacccatcc catagcccgc cgactcgtcg ctgagacgga  37080
ccgaatactg ggctattccc ttctcgacag ctatcgcgag gccgaagacc gcgacgacca  37140
gggggcgttc cccgagccgg cccggatcgc gttcctggtc cagtgcctgg cgctggccga  37200
gtgggccgtc aaggagaacg acctggaccc ggtcgtctgc gccggcgcca gcttcggcgg  37260
cacggcggca gcggtgcact ccggcgcgct gtcgttcccc gaagccgtgg agatgaccgc  37320
cgcgtggggc cgccgagtcg acgactactt cacccgtgag caccgcgaca tcgtcaccca  37380
gtcattcgcc cgcgtcgcgc ccgacccgct cgcggagatc caggccgagc tggacgcacg  37440
gggcgactgg aacgaggtgg cctgccaggt cgacaacgac ttccacatgc tgtcggtgcg  37500
cgaggacgtg gtcgagtggt tgcagggacg gctccgcgcg gcgggcggcc tgccgctgta  37560
cgtcatgcgg ccgccgatgc actcgacgct gttcgaggcg ctgcgggaag agatcgcgaa  37620
cgggatcacc acggacatca cgttctccga tccccggatc cccgtggtgt ccgaccacga  37680
cgggtcgctg gtacggacgg gggccggggt gcgggagttg ctgctgaacg ccgtgacgca  37740
caccgtgcgg tggccggccg tcgtcgacac gatcaagggg ctcggcgtcg agcgggtgca  37800
tgtcaccggg caggacgccc tgtggggacg ggtggatgtc atgaccaacg cgttccaggt  37860
ggtggcggtg cgtccggaca cagctatgcg accgcgccgt cgcagcgcga tcgcatagcg  37920
gaaaagaatc cggtcagcgc atggcgtcca gggttttcca gagagccccg ggagtcgcga  37980
agttatccat gttgagcgca tcgtcgacga aacggactcc atatgcgtcc tccatcgagg  38040
acagcagtga gaccattccc atggagtcga gaccgcaatc gcgcaggctc aattcggcgg  38100
tcaactcctc atccggttcc agcaaaggaa tctgtttgcg gagaagttgc tcgaatgatt  38160
cgtcccacat acgggctcct gtgttttccc gacgtttacc gaatagccgg cgtcgctgcc  38220
aacctaagcc ccgcgcccta ccggtcggca cccctactca cccctttccc tcttcggagc  38280
```

gaggacaatg aatcagacac ccgtccccgg acacggcctg cacgaacggt tcctgaccgg 38340
cctggcgctg tcgcccggcc ggaccgcgat ccgcgtgcac gccaccgaga gcctgacgta 38400
cgagcagatg cacgaactgg cgatgcgccg ggccgcggca ctgcgggcca tggctccgca 38460
agggccgcac aacgtcgccg tgctggcgga caagagcctg accgcttatg tcgggatcat 38520
cgccgcgctg tacgcgggcg ccaccgtcgt accgctcaac ccgcggttcc cggccgagcg 38580
cacccgctcc atgctcatcg ccgccaacgt ctccaccgtc atcgctgatc cgatcggccg 38640
ctcctcactc gcggagaccg agctggatct gcccgtcctg gacgagggca ggacggggcc 38700
ctcgctggac acgccggtgg ccgtcaaccc ttccgatgtc gcgtacgtcc tgttcacctc 38760
gggctcgacg ggccgcccca agggggtgcc gatcacccac ggggccaacc accactactt 38820
cgacctgctg gaccggcgct acgacttcag ccccgacgac gtgttctgcc agaacgtcgg 38880
actcaacttc gactgcgcca tgttcgagat gttctgcgcg tggggcaacg gggcgcaggt 38940
gcaccccgtc ccgcccgccg cccaccggga cctgccggcg ttcttggccg agcggaagat 39000
gaccgtgtgg ttctccaccc cgagcggcat cacgttcatc cggcggatgg gcggcctgac 39060
ccccggatcg atgcccacac tgcgctggac cttcttcgcc ggtgaggcgc tgctgcacga 39120
ggacgccgcc gactggcacg tcgccgcacc ccagtcgaag atcgagaatc tgtacgggcc 39180
gaccgagctg accgtgacca tcaccgggca ccgctggtcg ccgaagacca ccgaggagca 39240
gaccgtgaac ggcggcgtgc cgatcggaaa ggtgcacccc ggccacgacc acctgctgct 39300
ggacgacgac ggcgagtcgg cggtggaggg cgaactgtgc gtcgccggac cgcagatgac 39360
acccggttac ctggacggcg acgacaaccg gggccgcttc ctcgagcacg ccggccgtcg 39420
ctggtaccgg accggcgacc gggtgcggcg gctggacgac gacgagctga tctacctcgg 39480
ccggatggac gcccaggtgc agatccaggg attccgggtc gaactggccg aggtcgacca 39540
tgtcgtccgg cagtgcaccg gtgtgcagaa cgcggccacc gtcacccggc cggcaccgaa 39600
cggcggactg gaactcgtcc tctactacac gggcgagcgc attccgtcgg cgacgctgcg 39660
ccgcgagctg gccgcgcacc tgcccgatcc gatggtgccc aagaccttcc ggcacgtgcc 39720
ggagttcccg ctcaattcca accgcaaggt cgaccgggcg cagttggccc gggaggccgc 39780
cgcgctgtca gacggtcgtg cctgacccga agtgacgggc gttctccgcg accgtccgta 39840
gcgcctcggc gagcgactcg cccgtcgagg cgtgctccgg gtcgacgacc cactgcatca 39900
tcacgccgct gagcagcgcg tggtagaact gcccgaccgc ggtcgcggtg gggcccggca 39960
gctcttcgcc gccccacagg agccggacca ggccgttctg tgcctgctgc tgcgcctcta 40020
tgaagaagct gccgacctcg ggcacatggt cgcgctggga gatcgcgtcg aactgggccc 40080
cccacaccgg gcggtggcgc tcgaacagct cgatcacgcg cgtccaggcc acctcgaacc 40140
gcttgatcgg atcgtcgggg aggtctccca cgtctgccag agcactcttc agctcctggg 40200
cccactcctc cagcgcctcc atgatggcgg cgttgaggag tgcttccttg gtgccgtagt 40260
ggtagccgat cgaggcgaga ttcgtaccgg aagcctcgac gatgtcgcgc gcggtggtac 40320
gcgcgtaccc cttctcgtag aggcattgct tcgctccggc cagcagatcc tctcggtgtc 40380
ccatgccgag agtctagcca ccccccctcag acatctgtct tgaacagatg tcctgaacag 40440
aatctgaatt agacgaacct cttatacaga tctagagtcg aggccatgag tccgcaacgt 40500
gcaaccttga gggactgggt cggcctcgcc gtccttgtcg tccctgtcct catgatgtcg 40560
atggacatga cggtgctgta cttcgcgctg ccgttcctca gcgcgaccct ggaaccgagc 40620
gccaccgagc aactgtggat cgtggacatc tacgcgttca tgctcgccgg gctgctcatc 40680
gcgatgggca cactcggtga ccacatcggc cgccggcggc tgctgatcat cggcgcggtg 40740
gtgttcggcg cgtcgtcact ggcctccgcc tacgcgacca gcgccgagct tctgatcctc 40800
gcccgcgccg tgctcggtat gtccggcgcc gtactcgcgc cgtccacgct ctcgctgatc 40860
cgcaacatgt tccaggatcc cggccagcgc cgtaccgcca tcgcggtatg gaccgccggt 40920
ctctccggcg gcgccgccct cggtccgatc gtgtcgggag tgctgctgga gcactactgg 40980
tggggctcgg tcttcctgat caacatcccg gtgacgatcc tgatcgtggt gctcggcccc 41040
atcctcctgc cggagcaccg cgaccccgag cccggccgtt tcgacttcct cggtgccgtg 41100
ctgtcgctgg ccgcgatgct tcccgtcatc tacggcatca aggaactcgc cgacgacggc 41160
ttcgactgga agtacgtggc ggtcaccgcc gccggcctgg tcatcggggt gctcttcgtc 41220
ctgcgccagc gcgcggcccc caatccgctg atcgacctga gcctcttccg cgaccggggg 41280
ttcaccgcgt ccatcggagt caacctggtg gccctgttcg cgatgatcgg gttcctgctc 41340
ttcgcgaccc agtggatcca gctggtccac gggctgaatc cgctggaggc gggcctctgg 41400
acactgcccg cgccgttggc ggtggcggtc acgacatcgg tcgccgtcgg gctggcgaag 41460
aagatccgcc ccggctacat catggccatc ggcatggtca tcgcgtcggc gggattcgcc 41520
atcatgacgc aactgcgcgc cgattcgagc ctggccatgg cggtgatcgg cgcgagcgtg 41580
ctgtcggccg gcgtcggcat ggcgatcccc ctgaccgccg acctgatcgt ctccgcggct 41640
ccggaggacc gcgtgggcgc tgccgccgcg ctgcccgaga ccgccaacca gctcggcgga 41700
gcgctgggcg tagcgatcct cggcagcatc ggtgccgccg tgtacacccg tgacgtcgcc 41760
gacgtgacga cggggctgcc acccgaggcc gcggaggcag cggagggttc gctcggcggc 41820
gcgacggaag tggccaaaca cctgcccggt gacacgggcg acgccctcgt cacgtccgcc 41880
ggggaggcct tcacccgcgg catgaacctc agcgccgcgg tgggcggcgt cgtcatgctg 41940
ctcggtgccg cgggcgcggc gctgctcctg cgccatgtca agactcccac cgtcacgtcc 42000
gcgccggcgg acgagacgaa gggcgagacg gcggacgagc cctcacccgt ccccaagtag 42060
tgaccgccgc ccggtagcgg cgcccaacca gaaggggtcc ccgcgcgaag attcgcgcgg 42120
ggaccccttc tggcgtttct ggtacggggc tgtcagcggc cgagagtcac cggaagcgag 42180
gtgtaaccgg tcaggcccat gatggcgcgg cgcccggggg tgcccgccag ctcgatgttc 42240
gtgaacgtgt cgatcagctt cgggaagagg tcggcggcct ccatacgggc gaggctgccg 42300
ccgaagcaga agtggccgcc ggcgctgaag ctcaggtggg cgccgttgtc gcggctcagg 42360
tccagacggt gcgggtcggg gaagcgcgcc gggtcccggt tggcggcgga gagcagggcc 42420
aggacgagaa cgccctcggg aatgtcggtg ccgccgatgg tgatggggcg cgtcgtcaga 42480
cggctcgacg ccgtggtgtg ggcggtgtga cgcagcagct cctcgacggc cgtcggggtg 42540
atgctcttgt ccgcgcgcca gcgcttcagc tcgtcggggt gctcgatgag cgcgagcacg 42600
ccggtcgcga tgaggttggt ggtggccgcg aagcccgccg tgaacaggaa gaggatgagc 42660
gccatcagct cctcctcgtc gagcttcccg ttggccgcct cctggacgag ggcggacatc 42720
aggtcgtcct tgggttcggc gcggaccgcc ttgatcacgt cattgaagta cccggtcagc 42780
tcctcggcgg cggcgtcggc cgccgccagg tcctcatcgg tgtagacacc ggagaagacc 42840
cgtgaccagt cgtcggccag ctcccaggtg cgcttgccgt cctcgtacgg aaggccgagc 42900
atgtcgctga tgaccgcgac ggggaagggc atggccagca gctcgacgat gtcgaccggc 42960
tcgccgccgg cggacctctc gacgagttcg ttgatcagct cgtcggtccg cttctccacc 43020

-continued gcgggctgca tcttcttgat cttgctgggg gtgaacaccc gggcggccag gccgcgaacc 43080
cgtccgtggt cgggcgcgtt gagtgtgacc atcgagttca ggtacatacg cagggagatg 43140
tgctcggccc agtcctcgcg catctgagcg gcggcacggg ccccactgtg gacatcgggc 43200
atcttcagga gctcggtcac ctcctcgtac ccggagagcg cgtagatacc gagcgcggac 43260
ttgtggaccc ggttcaccga ctgcaaggtc tcgtagatcg ggaaggggtc gtcggggaag 43320
ggcggcgaca gcagcttcat cagcgcttcg tcggcctgct gggtggtggg cgtcgcttcg 43380
gtggtcacgt ggtcgttctc ctcgttatgg gtggtggttc cggtccggca ggttctacga 43440
cgcggaccgc gtatcgagct cgtcgtcgag gacgtcgaac agctcatcgg ccgagagcga 43500
cccgagttcg gcctcgtcgc tctcgtcccg cctgtgggtc tcggtccagc cggccgccag 43560
ggcgcgcagc cggtcggcga cgcggccgaa cgtctcctcg tcgggcgtca ccgacgccaa 43620
cgccgcttcc agacgggcca gttccgcctc cagcggtgac ccggcgggct cctggtcgcc 43680
ggtcagctgt tcgcgcaggg actcggcgac ggcggaaggg gtgggatggt cgaagaccag 43740
ggtggccggc agcttcagcc ccgtggccga acgcagcgtg ttgcgcagtt ccacggcggt 43800
gagcgagtcg aatccgaggt ccttgaacgc ccggtcggag cggaccgcgt ccacgccgtc 43860
gtgaccgagc accgccgcca cgtgggtacg gaccaactcg accaggatgc tgtcgcgcgc 43920
ggcttcgtcg gccgccgccg ccagggtccg tcgcagtccc gcgccgccgt ccccgccgcc 43980
ggccgcgccc gcgcccccgg cgcgacggcg cgatgtgggc accagaccac gcagcagcga 44040
cggcagttgg tcgacggcgc gggtccgcag ggcccctgtg tccaggcgga acggcgccag 44100
cgcgggctcc cccgtacgca acgcgtcgtc cagcagcgcc aggccctcct tctgcgacag 44160
ggcgggcagg cccatgcgga gcatgcgctt gcggtcggcg tcggtcagct caccgagccc 44220
ggtctcggct tcccacagac cgaacgccag tgaggtcacc ggcaggccgg cctggtggcg 44280
gtggtgggcg agcgcgtcca ggaaaacgtt cgccgcggcg tagttgccct ggcccgccgc 44340
cagcagcagg ccgcccatcg aggagaacag gacgaacgcg gacaggtcgc ggtcggcagt 44400
cagctcgtgc agatgccagg cgccgtccac cttgggccgc aggaccgtgt ccatacgctc 44460
cggcgtcagc ccgcggacca gcccgttgtc cacgacaccg gccgcgtgga cgaccgcccc 44520
gacgggatgc cggtcgagca ccgcggccag cgcggcgcgg tcggccacgt cgcacgcctc 44580
gatgtccacc cgcgcgccgt ggccggtcag ttcggcgcgc agttccgccg cgcccggtgc 44640
gctcccgccc cgacggctgg tcaggaccag atgccggatg ccgtgctccg tcaccaggtg 44700
gcgggcgacc agggcaccga gaccgctggt gccgccggtg atcagcacgg tcggcgacga 44760
ctcccacggg tcgcgtccgg cgtccaccgc cgaggcgggt acgcgggtga gggcgggtac 44820
gagaagttcg ccgcctcgaa ccgccacctc gggtgcgtcg acgaagggcg gaacggtggc 44880
cccgtcgccc aggtcgagca gaaggaaccg gccgggattc tccgccgccg ccgcccggac 44940
cagcccccac acgggtgcct ggctcagatc gacgtcctcg ccctcgatcg gcaccgcgcg 45000
acgggtgacg acggcgagct tctcatcgct cctgcccttg tccgccagcc attcctggac 45060
gcgcgccagc acctcgtcgg cgaccgcgtg cgcggcctcg gatgtgtcac cttcggcgcg 45120
cgggacctcg tacaccacga cgggtgtctc cagtacgggc acgtcgccgg ccttggtcca 45180
ggtgagggcg aacagcgact cgcggtggtc gccgtcggcc cgtagctgct cggccgacac 45240
gggccgcgag gtcaggctcg cgacggagag cacgggcgcg ccggttccgt cggcgaccag 45300
aacctccgtg ccgtcgccgc cctccgggtt cgacagacgg acgcgcagcg cggaggcgcc 45360
ggcgcggtgg agcgtgacac cgttccagga gaacggcagc tccggcgcgt cggtggcggc 45420
gccttcctcg atgagaccca cgtgcatcgc cgcgtccagc aacgccggat gcaggccgaa 45480
cctggcagcc tccgttccct ccgggagcga gacctcggcg aacacgacgc cgtcaccgtc 45540
ccgccaggcc gctttcagcc cctggaacgt ggggccgtag tcgtaaccgc gggcgaggag 45600
ccgctcgtag gcgccgtcca ccgggagcgg cgtggcgccg atcggcggcc actggatcag 45660
gtcggacgag ggagatacgg ccgacgggag gagggcaccg gccgcgttgc gggtccagat 45720
ctcgtcgtcc agggacgagt agatctcgac ggtgcgtgac tcggagtcgt cggggccgcc 45780
cacgagaacg cgcacggcga ccgcgccctt ctcgggaacg acgagcggcg cctccagggt 45840
cagctcgtcg accgtgccgc agtccacctg tgcggcggct tgcagcgcga gttcgaccag 45900
cccggtgcca ggcagcagca gggtacccag tacgtcgtgg tcggcgagcc aggggtgggt 45960
gtcgagggag agacgtccgg tgaacaccac accgccggtg tcgggcagcc cgatgcccga 46020
ggtgagcagg gggtgatcga ccgcgtcggc accggctgcc gccgtcgact gctcgatcag 46080
ccagtaacgc ttgcgctgga agggatacgt gggcagatcg acccgccgcg caccacgccc 46140
gtcgaacacc gcgtcccagt ccaccgccac accggccgcg aacaaccggc ccacaccggc 46200
gaacacactc tccacctcgg ggcggtcacg ccgcagcgtg ggcgccaggg tgccgtcggc 46260
actctgtccc gccatcgccg tcagcacacc atccggaccg atctccagga accgcgtcac 46320
accctcgtcc tgcaaatagc gcacatcgtc cgcgaaacgc accgcgtccc gcacatgccc 46380
cacccagtac tcggccgaac cgacgtcctt ggtcagccgg atggtcggct cccggtaggt 46440
ggcgctctcc gcgaccttgc ggaagtcgtc cagcatcggg tccatcagcg gcgagtggaa 46500
cgcgtgcgac accttcagcc gagtcgtctt gcggtcggtg aaccgctccg cgaccgccgt 46560
caccgccttc tcctcgcccg aaatcaccac cgaagaaagg ctgttgaccg cggcaacact 46620
caccaggccg ctgagatgcg gaaccacctc ctcctccgtg gcctggatcg cgaccatcgc 46680
cccacccgcc ggcaacgcct gcatcaaccg cccacgcgcc gagatcaacc ggcccgcatc 46740
ctccagaccg aacacccccg ccacatgcgc cgccgccaac tcaccgatcg aatggcccac 46800
caggaagtcc ggcttgaccc cccacgactc caccaaccgg aacaacgcca cctcaagagc 46860
gaagatcgcg ggctgggtga actccgtacg gcccagagcc tcctcatcac cccacatcac 46920
ctcacgcaca gcgggatcga gcacgccaca cacctcgtcg aacgccgatg cgaaggcggg 46980
gaacgtctcg tacaactccc gccccatacc aaggcgttga ctcccctgcc cggtgaacag 47040
gaacgccacc ttgcccacac cggtctcgcc cgtgaccgtc tccgacccga tgagcaccgc 47100
gcggtgttcc agcgcggccc ggcctgtcgc ggccgagtac gcgacgtcca gcgggtcgcc 47160
gttcgcggcc agttcgccga agcggccgat ctgcgcctcc agcgccgccg gggtcttccc 47220
cgacaccacc accggcgcca ccggcaactc ccgccgctcc accaccactt cagcaaccgg 47280
cacgacttcc tcgacgatca cgtgggcgtt cgtgccactg attccgaagg aggacacggc 47340
tgcccggcgc ggacggccct cgctcggcca ctcacgcgcc tccgtcagca gccgcacctc 47400
acccgcgtcc cagtccacct gcttcgtcgg ctcatccaca tgcagcgtct tgggcagcct 47460
gccgtggcgc atcgcctcga ccatcttgat gatccccgcc acacccgccg ccgcctgcgt 47520
atgaccgatg ttcgacttga tcgaacccag ccacaacggc cgcccttcgg ggcgatcctg 47580
accgtacgtc tccaacaggg cctgggcctc gatcgggtcg cccagcgtcg tgcccgtgcc 47640
atgcgcctcg accgcgtcca catccgccgt cgacagaccc gccttcgcca gcgcctgctt 47700
gatcacgcga cgctgggagg ggccgttcgg cgcggtgatg ccgttgctgg cgccgtcctg 47760

-continued

```
gttgagcgcg ctcccgcgca ccaccgcgag caccggatgc cccagccgac gcgcctccga  47820
cagacgctcc accaccagga cgcccgcgcc ctcgccccac ccggtgccgt cggtggagga  47880
cgagaaggac ttgcagcggc cgtccgcggc caggccgcgc tgctcgctga agtcgatgaa  47940
cgaccgcggt gttcccatga cggtcacgcc gccgacgagg gcgagcgagc actcgccgga  48000
acgcagtgcc tgcgccgccc agtgcagggc caccagggac gacgagcatg ccgtgtccac  48060
gctcaccgcg gggccttcga gaccgagggt gtaggccacc cggcccgaca cgaggctgcc  48120
gccgccggtg ccgccggggt agtcgtggta catcaccccg gcgaacacac cggtcgggct  48180
gcccttcagc gtggtgggtg cgatcccggc acgctccagc gcctcccacg aggtctccag  48240
cagcaaccgc tgctgcgggt ccatgtccag ggcctcgcgc gggctgatgc cgaagaaatc  48300
ggcgtcgaac tgtgtggcgt cgtgcaggaa tccgccgtcg cgcacatagg tcttccccgg  48360
aattccgggc tcggggtcgt agatgtcctc cacgccccag ccacggtcgg ccgggaactc  48420
cgatatcgcg tcgacaccct cgtcgacgag ccgccacaac ccctcgggcg agtccacgcc  48480
acccgggtag cggcacgcca tcgagacaat ggcgatcggc tcgtcgtccg ccgggcgcac  48540
gacggacgcg accggagccg actccacggc tccggagagc tcccgcagca ggtggcccgc  48600
caggacgacg gggtggggt agtcgaagac gagggtggcg ggcaggcgca gtccggtggc  48660
ggcacccagc aggttgcgca gttcgatcgc cgtgagggag tcgaatccga ggtcgcggaa  48720
ggcccgctcc gggtcgaccg cctcggctcc ggcatggcgc aggaccatcg ccgcctggga  48780
gcgtacgaga gcgaggagtt cgtcggcgcg ttccgcgtcg ccgagtcccg ccaggcgctg  48840
ccgcaggacg ccggtcgcgg acgcgtcgtt gtcgaggaca cggcgcgacc ggccgcggac  48900
gaggccgcgc atgatgggcg gcggcgagtc gaaggcagcg aggtcgaacc ggacgggcac  48960
cagtacgggc tccgccacgc cggcggcggc gtcgagcagg gcgaggccct cctccggtgc  49020
cagggagcgc atgccgaccg aggcgagacc gtccgccatg ccctctccgg cccacggacc  49080
ccaggccagt gacagcgccg gcagtccggc ggcgtgccga tgccgcgcga ggccgtcgag  49140
cagggtgctg gcggcggcgt agttgccctg tccgggggca ccgagtacgc ccgcgacgga  49200
cgagaacagc acgaaagcgg tcagccccat gtcgcgggtg agttcgtgca gatgccaggc  49260
cgcgtccgcc ttcggacgga gcacgtggtc gacgcgctcg ggcgtcatcg agaggatcac  49320
gccgtcatcc aggacgcccg cggcgtgtac gaccccgccg atggtccggc cgtcgagcag  49380
cgtggccagg gcgtcgcggt cggcggcgtc gcacgcggcc acctcgacct cggcgccgag  49440
cccggtcagt tcctcggcga gctcggcggc tcccggcgcc tgcgggcccc gtcggctggt  49500
cagcagcagc cgccgtacct cgtggcgggt gacgaggtgc cgggcgacgg cggccccgag  49560
ggcaccggtc ccgccggtga tcaggacggt gcgttcggtg tcccaggtgg aggcggtcga  49620
atcgagcggt acgccgacca gccggggcac ccgtgtctcg ccgccgctca cgcgcagttc  49680
gggttcgccg atcgcgacga cgcgggcggg gtcgaccggg gcgtcggtgt cgacgaggaa  49740
gaagcggccg ggatgctcgc cctcggcggc gcgtaccagc ccccaggcgg cggcgtggcc  49800
gaggtcggag ccgtcggtgg cgccgtcggt gacgacgacg agggcggtgc cgccgtcgac  49860
tgcgccctgg acggcggcca gtacgccggt ggtcaccgcg cgtacggcgg ccggtgtgcc  49920
gccggtcgtc ggcgggcagt ggtgaacgct cacctcggtg ttctcagccg gtgaccggac  49980
ctcgccggcc gggacccagt ccacccggaa gagggcgttc gcgacccggg ccgcggccgg  50040
cgcgaggccg tccgccgtga cggggcgcag cgtcagcgat ccgaccgagg cgaccggccg  50100
tcccatggcg tcggccagct ccagggacac ggacttgtct ccccggacac gcaggctcac  50160
```

-continued ccgcgcggtc gtggcgccct ccgcgtgcag ggtgacgtcc gaccaggtga acggaagtac 50220
cttcgcgtcc tcgccggcca ggtcgagcac gtgcaacgcc gcgtcgaaca gggcgggatg 50280
gaggccgaag ccgccggcgt ccgcaccctc gggcagagct gtctcggcga acagctcgtc 50340
gccgcgccgc catcccgcgc gcagtccctg gaacgtcggc ccgtactcca gccgttcgta 50400
gagtccttcg accgcgaggg gctcggcgtc gcgcggaggc cacaccgtga ggtcggtggc 50460
cggctcaccg gcgtcgggcg ccaggaagcc ctcggcgtgc aggatccatt cgcggtcgag 50520
cggggcgtcg tcggctcggg agaacaccct cacagggcgg agtcccgacg cgtcgggcgc 50580
gtcgacggcg acctggatgt ggacgccgcc gtgctcgggc aggaacagcg gcgccgcgac 50640
gttgagttcc tcgacgcggt tccatcccac ctggtccccc gcgcgcaccg cgagttccac 50700
gtacgcggtg ccgggcagca ggacggagcc catcacggtg tggtcggaca gccaggggtg 50760
ggccccggtg gacagccgtc cggtgaacac cacaccgtcg gagccgggca ggtgcaccat 50820
cgcaccgagc agcgggtggt cgggccggtc gagaccggcg gaggtgacgt cgccgcccag 50880
gccgcgcttg tcgaaccagt aacgggcgcg ctggaagggg taggtgggca ggtcgacgcg 50940
ccgggcgccg cggccgtcga agacacccgc ccagtcgact ttcaggcccg cggtgtgcag 51000
gccgccgagg gcggtgagga cggcgacggg tccggtttcg ttacggcgca gggccgggac 51060
gagtacggcg gtgtcggcgg tggtcgtgag gcactggcgg gccatcgcgg tgaggatgcc 51120
gtcggggccc agttcgacgt accgggtgac gccttcggat tccagccggg tcacggcgtc 51180
ggcgaagcgg acggtgtcac ggacatgccc cacccagtac gcggcggtgg tgacatcgcc 51240
gttggccacg acgggaaggc cggctccgc gtaggcgacg cgctccgcga cacggcggaa 51300
gtcgtcgagc atcgggtcca tcagcgtcga gtggaacgcg tgcgacacct tcagccggtt 51360
ggtcctgcgc gcgccgagct gttcgacgac cgcgtccacg gcctcctcgg tgcccgagag 51420
caccacggag gcggggccgt tgacggcggc gattcccacg ccgtcccgaa gcagcgggac 51480
gacctcctcc tcggcggcct cgaccgccac catcgccccg cccgggggca gcgcctgcat 51540
cagccgtgcc cgcgcggtga tcagcgaggc ggcgtcgggc agggagaaca cgccggccac 51600
atgggcggcg gcgagttcgc cgatggagtg tcccgcgacg aagtcgggcc gtacacccca 51660
cgattcgagc agccggaaca gggcgatctg gagtgcgaag atcgcgggct gggtgaactc 51720
ggtacgccgc agggcctctt cgtcgcccca catcacctcg cgcacggcgg ggtcgagcgc 51780
ggagcacacc tcgtcgaagg cgcgtgcgaa cacggggaac gccgcgtgca ggtcgcggcc 51840
catgccgagg cgctggctgc cctggccggt gaagaggaag gcggtcagcc cggtcgaccg 51900
cgcggcgccg ccgaggggag cgccgtccgc caacgcggtc agcgcgccga ggatctcgtc 51960
gcggtcgtgg ccgaccacga cggcgcggcg ggtgagcgcg gcgcgggcgg tggcgaggga 52020
gtacgccatg tccacagggt cgaggtcagg cgtggtccgc aagtggtcgg ccaactgccg 52080
ggcctgggcg cgcatcgcgg tctcggtgcc ggccgacagc ggcagcggca gcggcacggt 52140
caggggtacg tcggtggacg ggcgcggtgc ggcgggctcc ggctcggagt cggacgcggg 52200
gtcgggctgc gcctgctcga tgatcacatg ggcgttggtg ccgctgacgc cgaacgagga 52260
caccgcggcg cggcgcggcc ggtcggcgtc gggccaggca cgcgcctcgg tgagcaggcg 52320
gacgtttccg gcctcccagt ccacctgggg cgacgcctcg tcgacgtgca gtgtcttcgg 52380
cagcgtgccg cgtcggatgg cctcgaccat cttgatgacg cccgcgacac cggcggcggc 52440
ctgcgtgtga ccgatgttgg acttgatcga acccagccac agcggttctt cgcggccctg 52500
tccgtacgtg gcgagcagtg cctgcgcctc gatggggtcg ccgagcgagg tgccggtgcc 52560
gtggccctcc atgacgtcga catcggcggt cgtcagtccg gccgcggtga gcgcctgctg 52620
gatgacacgg cgctgcgagg ggccgttggg ggcgctgaag ccgttggacg cgccgtcctg 52680
gttgaccgcc gagccgcgca cgacggccag tacggggtgc ccgttgcggc gggcgtcgga 52740
cagcttctcc agcagcagga cgccggcgcc ctcggcccag cccgtcccgt cggcggaggc 52800
ggcgaacgag cggcagcggc cgtcggccga gagtccgcgc tgctcgctga actcgatgaa 52860
cgtctcgggc gtggccatga cgctgacgcc gccggccagc gccagggtgc actctcccga 52920
gcgcagggcc tgcgacgccc actggagtgc gaccagcgac gacgagcagg ccgtgtcgac 52980
ggtgaccgcc gggccttcca gcccgagggt gtacgcgacg cgtccggaga cgaggctgcc 53040
gtcgctgctg gtgatgccgt agtcgtggta catcgcgccg gcgaagacac cggtgcggct 53100
gccgcgcagc gacgccgggt cgagtccggc gcgctccatc gactcccagg tgatctccag 53160
caggagccgc tgctggggt ccatggtgag ggcctcgcgc gggctgatcc cgaagaactc 53220
ggggtcgaac tgcgcggcgt cgtgcaggaa tccgccctcg cgcgcgtacg tcttgccggg 53280
ctttccgggc tcggggtcgt acagcgcgct catgtcccag ccgcggtcgt ccgggaacgg 53340
gctgatcgcg tcacggcctt cctcgaccag cgcccacagc tcctcggggg atccgacgcc 53400
accggggtac cggcaggcca tgccgatgat cgcgatgggt tcggtggtta cgctcgcggc 53460
ggcgcgcagg ctgtcgttgt cctgccgcag cctctcgttc tcgaccagcg agccacgcag 53520
tgcctcgacg atctcctcga cttcggcgtt catcgtcgtc tcagcctccg ctcacggtcg 53580
tggtccgcgt gtcgctcacg cgtaccgagt caaggaatcc gccgagcacc tcgtagaaca 53640
gctccggctc ctccaggtgc gggttgtggc tggagttctc aaggatttcc cagcgggcgc 53700
ccggaatgag ttcctggtag gggcgcaccg tgaccggggt ggcctcgtcg tggcggcccg 53760
acatgatgag ggtgggcgcg ctgatgtcgg gcaggcagtc gatcaccgac cagtcgcgga 53820
tgctgccgat gacatggaac tcgttgggac cgttcatcgt gcggtagacc gtcgggtcgg 53880
tgacggcttc caggtaggag gccatgagtt cgctgggcca cggctcgacg cggcagacgt 53940
ggcggctgta gaagaccagc atcgcctcca ggtactcgtc gctgtcggtg gtgccggcgg 54000
cctcgtgccg ccgcagtgtc tcgtcgacgc cgggcggcag ttgggcgcgc aggacgtcca 54060
tctccgacag ccacagaggg taggaggccg gtgcgttggc gatgaccagg ccgcgcagcc 54120
cggcgggttc ggccgaggcg tgccaggcgg cgagcagtcc gccccacgac tgtccgaaca 54180
ggacgtagtc gtcggcgatg tcgagccggc gcagcaggtt ctccagctcg tcgcggaaga 54240 gctgggggt ccagaagccg gggtcggcgt cgggaaggtg ggtggagccg ccgttcccga 54300
tctggtcgta gtgcaccacc gaccagccct gttcggcgta gacggacagc cctgtcaggt 54360
agtcgtgggt ggagccgggg cctccgtgca cgacgacgag ggccgggcgg ccctcagcgg 54420
gctgcccggt gacgcggtac caggtcttgt actccccgaa gggaacagtt cctttggccg 54480
tggccgtggg cgtggacgcc atttctcaaa ccacctaagt tcgggtcgtt ctcagcagcg 54540
gttgccgcgt cccccgcacg cggcgtgcac ttcttccgag gggaagcctg gcgtcggcca 54600
cggctcagtc gagcgtctcc agccattcct cgatgactcg ggcggtcgcc ggggcgtggt 54660
cctgcccgag cgagaaatgg ttgccttcga cggtgcgcag ggtgtgctcg gagtcccacg 54720
ggcgggcccg catctccgcc acgtcgaccc cctcgggggg ctgaacgaac ggctcggacg 54780
cctggacgaa cagggtcggt gtgtccagcc gtacggggtc gaagcccgcc agtacctgga 54840
agtagtgcgg catcgcggac agtcgcgccg cgtcgtagtt gccgagggtc gtctccaccg 54900

-continued

```
tcagcagttc gcccatgagg tggtcgaacc cgacgttcat cgccgtgtcc tcgaccctga  54960
aggtgtcgat caggacgagt ccggcgggcg ggaccttgag cgtctccttc aggtgacggg  55020
cgatgatgtg gccgatgatg ccgccggagg agtagccgag cagtacgaac ggctcaccgt  55080
ccgccgccgc cagcacggcg tcgcccagca cctgtgtcag cacctcgacg gagtcgggca  55140
gtggctcgtc ccggtggaat ccgggcagtg ccaccgccga cacgtgccgc acgtcccgga  55200
attcggaacc gagccgggcg tgctggtgca cgccgccgcc cgccatgggt gtggccaggc  55260
agatcagccg gggcggccg gggccgtccg ccaaccgcac cgtcttcggg gtcctcgcga  55320
ggtcggcggg tgtgacgaac cggggtcgca gcgccgcgac cgccgacatc aggcccagtg  55380
cccctgtcgt gtcaccggcc cggaccgccc gccggaacat ctcggtcacc gtctcgtcgt  55440
cctcttccga gggctcggcg gcggactcgg cgccggcggc ggccgtcccg gactccatct  55500
cgtcggcgag gagacgggcc aggttggccg gggtcttgct gtcgaacacc gccatcgtgg  55560
gcagcttcgc cccggtggcg gcgatcagcg cggtgcgcag ttccatcgcg gtgagcgagt  55620
cgaacccgga ctccaggaag tcgcggctgg ggtcgacggc ttcggcgtcg gcgtgtccga  55680
gcacggaggc ggcgaggctc agcaccagat cgctgagcgc ccgctcccgc tgctgcgcgg  55740
gcatcgcggc cagctctcgc cgcagcgccg acgggtcggt ggtcgcggag cggcgccgta  55800
cggcggggac caggccgcgc aggacgacgg ggagttcgcc tccggccccg ttccgcagcg  55860
cccgcaggtc caggctcatc ggcacgagcg ccggctcggg cctcacggac gcggcgtcga  55920
acagcgcgag gccgtcctgg gacgacagcg cgggcatgcc ctggcggcgc agccgccgca  55980
ggtctgcctc gctcaggtgg cccgccattc cgccggtgtc cgcccacagc ccccaggcga  56040
gggactgcgc gggcagtccc tcggcgtggc gccgcgcggc gagggcgtcg aggaaggtgt  56100
tggcggcggc gtagttgccc tggccgggcg agccgagcac gcccgccgcg gacgagaaca  56160
ggacgaaggc gcccagctcc tggtcgcggg tgaggtcgtg caggttgagt gcgccgtcca  56220
ccttggggcg caggacctgg tcgaggccgt gcgccgtcag gttggcgatc atgctgtcgg  56280
ccagtacccc ggcggtgtgg acgacggagc cgagggagcg gccggccagc agcgcctcga  56340
cggcgtcccg gtcggccacg tcgcaggcgg cgatctcgac cgtcgcaccg agggcggtca  56400
gctcctggtg gaggtcggcc gcgccctgcg cgtcgatgcc gcgacggctg gtcagcagca  56460
ggtcccggac gccgcgttcg gcgaccaagt ggcgggcgac gagcgcgccg agaccgcctg  56520
tgccgccggt gatcagtacg gctccgggcc ggtcccaggg cgagcgcgag ggtgcgtcct  56580
cctccggtgc ggccgggacg cgcgcgagcc gggggaccag gatctcctgg ccccgtacgc  56640
gcaggtcggg ctcgcccgac gcgacggccc ggccgatcgt ctccgggtcg tcgccgtcgg  56700
tgtcgagcag cgcgaagcgc tccgggtcct ccgaacgggc ggcgcgtacc aggccccagg  56760
cggaggcgtg tgccaggtcg tcaccgcggg tgaccaccag gagcctgctg ccggcgaacc  56820
gttcgtccgt gagccaggtc tggagggtcc ggagcgtctg ggcggtgacc gtcctgacgt  56880
cgtcggcgat ccggccggtg cctgccgggg gtgtccaggc gaccgtcgag ggcaccgggc  56940
cggagagttc ggccagttcg gtgaccgtcg tccagtccgc ctcggcggcg gtggcggtgg  57000
cggcgggtgt ccacgcgagg tggaagaggg agtcgcccgg cccggcgggc gccggtgcga  57060
gctgctcggc ggagacctcc cgggagatca gcgactccac gtacgcgacg ggacggccct  57120
gggggtcggc gacgcggatc gtcgtgccgc cctcggcgtt gggggtgaac cggacgcgcg  57180
cggccctggc gccgaaggcg tgcagccgca cacccttcca ggcgaaaggc agtgaggtgg  57240
```

```
cttcgtcctc gcccgcgccg agtatcaccg cgtgcagagc ggagtcgagc agcgccgggt  57300
gcagtacgaa cctctcggcg tcggccacgt cgtcggcgag cgccacctcg gcgaatgtct  57360
cgtcaccgac gcgccacgcc gccttgagcg cctggaacgc ggggccgtag acgtatccga  57420
ggtccgcgaa cctttcgtac gcgccctcgg tggtgatcct cgtcgcctcg tcgggcggcc  57480
agcgcgacag gtcgaaggag gtcgcctcgt tggactcctc ggccaccagg gcgccttcgg  57540
cgtgcaggac ccatggcgcg tcgtcgtcgg cgtcctcggc gagcgagtgg atgctcaggg  57600
ggcgccggcc ggtgtcctcg accggttcac cgaccgtcag ccgcagttgt acgccgccgc  57660
cctcgggcag gaccagcggc gcgcgcagcg tcagttcttc gaggacgccg tggccgacct  57720
ggtcgcccac gcgtaccgcc agttcgacga acgccgtgcc gggcagcagc gtcgcgccca  57780
gtacctcgtg gtcggcgagc caggggtggg tgtcggtcga cagacggccc gtgcagatca  57840
ccgtccgtga gccgggaacg gcgatctcgg cgctcagcag gggggtggtcg agcgcgctga  57900
ggcccatgga cgccgcgctg ccgcctcctg cgtccaccgg ctcctggagc cagtaacggg  57960
tgcgctggaa ggagtaggtg ggcagatcga cccggtgtgc ccgccggccc gcgaagaagg  58020
cggtccagtc gggagagacg cccgtggtgt gcagatgggc gacggcggtc agcagtgtcg  58080
tggcctcggg ccggtcgcgg cgcagggcgg cggcggtggt ggcctccggc gcggtctggc  58140
gggccatggc ggcgagggcc ccgtcgggtc cgagctccag gaaccgggtg acgccctcgg  58200
cctccaggcg tcgtacgtcg tcggcgaacc gcaccgcgtc gcgcacatgc cgtacccagt  58260
agtcggcgga cgccatgtcc ttcaccagcc ggatgcgcgg ccgttcgtag gtgagggact  58320
cggcgacctt gcggaagtcc tccagcatcg gttccatcag cggcgagtgg aacgcgtgag  58380
agacggtcag ccgtcgcgtc ctgcggtcgg cgaagtgctc ggtgaccgcc tccacagcgt  58440
cctcgctgcc cgaaacgacc acggaggacg ggctgttgag ggcggcgatc cccacctcct  58500
ccgtgagcag cggcgcgact tcctcctcgg tggcctcgat ggccgtcatg gccccgcccg  58560
ccgggagcgc ctgcatcagc cgcccgcgtt cggcgaccag ccgcgcggcg tcctcaaggc  58620
cgagaacgcc cgcgacatgg gccgccgcca gctcgccgat ggagtgcccg gcgaggtagt  58680
cgggcttgat tccccaggac tccaccagcc ggaacagggc gacttccaga gcgaagatcg  58740
cgggctgggc gtactcggtg cggtgcaacg ccgactcgtc gccccacacc acgtccttga  58800
gcgacaggcc cgtggcctcg cacacctcgt cgagcgcggc ggtgaagacc gggaaggtct  58860
cgtacaactc ccgtcccatg ccgaggcgct ggctgccctg gccggtgaag aggaacgcca  58920
ccttgccctc gcgccgcttg ccggtgacga cggacggcga gggggttccc gcggccagcg  58980
cggtgagccc cgcgagaagg ccctgacggt cgtcggcgac gatcgccgca cggtgttcga  59040
gagccgcgcg gcccctcgcc agggacaggc ccacgtccgc aggcgtcagg tcgggccgct  59100
cgcgcagatg ggagtgaagg ctttcggcct gcgcggacag cgcctgctgg gtcctgccgg  59160
acagggtcca cagcaccggg cccccggtgg tcgccgcgac cgggggcgcg tgctcctcgg  59220
cgggcggtgc ctcctcgatg atgacgtggg cgttggtccc gctgatgccg aaggacgaca  59280
cccccgcgcg gcgcgggtgc tcctggtcgg gccaccgccg cgcctcggtg agcagccgga  59340
cgtcgccggc ctcccagtcc acctggggtg tcggggcatc gacgtgcagc gtgggcggca  59400
tgacaccgtg ccggatggcc tcgaccacct tgatgatgcc cgccacgccc gccgcggcct  59460
gggtgtgacc gatgttcgac ttgatcgaac ccagccacag cggtcggtcc ccggggcggt  59520
cctgcccgta ggcggcgagc agggcctgcg cctcgatcgg gtcgccgagc gtcgtgccgg  59580
tgccgtggcc ctcgatcagg tcgaccccgt cggcggacac ccgggcgttg gccagcgcct  59640
```

-continued gcctgatcac ccgctgctgg gccgggccgt tgggggctgt gatgccgttg ctggcgccgt 59700
cctggttgat cgccgtaccg cgcacgatcc ccagcaccgg gtggtcgttg cggcgggcgt 59760
ccgacagccg ctccaccagg atcatgccga cgccctcacc ccagccggtg ccgtcggccg 59820
ccgcggcgta cgacttgcag cggccgtcgg tcgccagccc gcgctggtgg ctgaactcga 59880
tgaaggtctc gggtgtcgcc atcacggtga caccgccggc gagggcgagc gagcactccc 59940
ccgaccgcag ggcctggacc gcccagtgca gggcgaccag cgaggacgag caggcggtgt 60000
cgatcgtcac cgcggggccc tcaagaccca gggtgtaggc gacccggccg gaggccatgg 60060
cgccccgtgct gctgttgtac gtgtagtcgt ggtacatcat cccggcgaac acaccggtcg 60120
ggctgccctt gagagtcgtc gggtcgatgc ccgcccgctc gagcacttcc cacgacgcct 60180
ccagcagcaa tcgctgctga gggtccatca ccagcgcctc gttcggcgcg atcccgaaga 60240
aaccgggatc gaactcggcc gcgtcgtaca ggaacccgcc ttcgcgcgag tacgtcttgc 60300
cgggctttcc cggctcgggg tcgtagatgc cctcctcgtc ccagccgcgg tcggcgggga 60360
accgcgagac ggcgtccgtc ccgtcggcga ccagccgcca cagctcctcg ggagaagtcg 60420
cgccggggta gcggcagctc atcgccacga tcgcgatcgg ttcgcgggag gcggcctgca 60480
gggcgcggtt gcgcgtacgc aggctctcgg actccttgag cgacgcgcgc agcgccgcca 60540
cgagtttctg gtcggtgtcg gccatcgtgt cctcagactt cccgcgtcgc ttcgtccgga 60600
tcggtgtcct gcagggccat gctgatcagg gcttcggcgt ccatcgcgtc gatcgagtcc 60660
tcctcgggca cggctgccgc catgccggag gcggcgccgg atccggcgag ttcgagcagg 60720
gcctccatca gccccgcgtc gtgcagccgg gtgagcggaa tcgacccgag caggcggcgg 60780
accgtctcct cgtcggcggc ggcgccggcg tcaccgtcgg gtgccagctc cgcgccgatg 60840
tgctcggcga gcacccgggc ggtcggatgg tcgaagatca tggtggcgga cagtcgcagc 60900
ccggccgcgg cgttgagggt gttgcggaac tcgacagcgc ccagcgagtc gaagcccaga 60960
tcgccgaagg cccgctccgg ttcgacggcc tcgggacccg cgtgacccag taccgccgcc 61020
gcgtgggtac ggacgaggtc gaggacttcg tcgtaccgat cgtcggcggg cagtgccgcc 61080
aggcgcttgc gcagcgcggc cccgccgccc gtggattgcg ccgacacggc acgccgcgag 61140
gagccgcgta ccagtccgcg cagcatcaaa ggcacgtcgg ccgcgttcag cgtcctggtg 61200
tccaggttca tgggcaccag cgccggtgtg gccagcgcgc ccgccacgtc gaggagttcg 61260
agaccctgct cgggcgagag tcccacgagg cccgcgcggt cgatccgctg ccggtcggtg 61320
tccgccaggt caccggccat gccggcgtcg gtcgtccaca ggccccaggc cagggactgg 61380
gcgggcaggc cgtcggcgcg ccggtgcgcg gccagtgcgt ccagaagcgc gttggccgcg 61440
gcgtagttgc cctgccccgg tgtgccgatc acgccggcca ccgaggagaa gagtacgaac 61500
gcggtcaggt ccatgtcgcg tgtcagctcg tgcagatgca gggcggccac cgccttgggt 61560
gtgacgacct tgtccaggcg ttcgggggtc agcgacgcga tcacgccgtc gtccagaacg 61620
cccgccgcgt gcaccacacc ggtgagcgaa cgcccggcca gcagcgccgc gagcgcctca 61680
cggtcgccga cgtcgcaggc ggcgacctcg acctcggccc ccagcccggc cagctcctcc 61740
accaactccg ccgcgccggg cgccgccagg ccccggcggc tggtcagcag cagtcgccgt 61800
acgccgtgcc cggtgacgag atggcgcgcg accagtccgc ccagggcgcc ggacgcgccc 61860
gtgatcagta cctcgtcgcc gaagaccgag gacggctcgg actccgcgac cgaggccgcc 61920
ctcagcctcg gtacgtagac cttcccgtcc cggacggcca cctggggctc tcccgccgcc 61980

-continued agcgccaggg cgatgtccgc cttctcgtcc tcaccggcca cgtcgaccag gacgaaccgg 62040
cccggatcct ccgactgggc gctgcgcacc agtccccacg ccgaggcgcc ggccaggtcg 62100
ctcacccgct caccggccac ggacaccgcg ccgcgcgtga cgaccgcgag ggtctcggtc 62160
tccgcctgga tcgccttgag cagcggatgc agtgtggaga gcacgtcgtc gccctcggtc 62220
cgccacacct tcgcgtcacc ggccgcgtcg tcgcgtacgg cgacgggcgt ccactcgacc 62280
tggaagagcg agtcgacgcg cgtgagcgca ccggcggcca tcggacgcag ggtcagggcg 62340
tccacggaga cgaccggctg cccggcgccg tcgacggcgt ggagggccac ccggtcctgg 62400
ccgcggagcg tcatccggac acggagcgcg gtggcgccgg aggcgtgcag ttccactccc 62460
gcccaggaga acggcaggac gacgcggtcg tcgcccgaca gcaacgggac cgtgtgcagg 62520
gccgcgtcca ggagtgccgg gtggatcccg aagcggtccg ccgccccgga caggacgacg 62580
tcggcgtaga ccgtcccctc ttcgcgccag gcggacttga gtccctggaa cgccggcccg 62640
tactcgactc cggcttccgc caggctctcg tacagccccg ccagttccac gggctctgca 62700
ccgggcggtg gccactgggt catcgcctcg gccgcggggc cgccggtggc cggggccagg 62760
gttccggcgg cgtggcgggt ccagggcaga tggggatcgt ccgcgcctcg ggcgtacacc 62820
tcgacagccc ggtggcccgc tccgtcgtcc accccgacca cgacctgtac ggccgtggcg 62880
gtgtgttcgg caaggaccag cggtgcctcg atcgtcagtt cctcgatccg gccgcagccg 62940
acctcgtcgc ccgcgcggac ggccagttcg acgaagcccg taccggggaa gagcagggtg 63000
ccggcgaccg cgtgttcggc gagccagggc tgggtaccga gcgacagacg cccggtcagc 63060
acggtccggt ccgcccccgc gacagcgacc gtctggtcca gcagcgggtg gtcggacgcg 63120
tccgcgccgc gccccgactc gatccagaac ggctgccgct ggaaggggta cgtcggcagc 63180
tcgacccgcc gcgccccgcg cccgtcgaac acggcgttcc agtcgacccg cacaccggcg 63240
gcgaacagcc ggccgacgcc ggtgaagagg gtttccacgc ccggacggtc gtttcgctgg 63300
gtggccgcga ccgtcccgtc ggcggtctgc cgcaccatcg cggtgagcac actgtccggt 63360
ccgacctcca tgaaccgggt gatgccccgg tcctgcaggt ggcgtacgtc gtcggcgaac 63420
cgcaccgcgt cgcgcacgtg ccgtacccag tactccgccg acgccacgtc cttggtcagc 63480
tggatgaccg gctcgcggta ggtgacgctc tcggcgacct tccggaactc ttcgagcatc 63540
gggtccatca gcggcgagtg gaacgcgtgc gacaccttca gccgagtcgt cttgcggtcg 63600
gcgaaccgct cggcgaccgc ggtgacggcc tcctcggcgc ccgagatcac caccgagccg 63660
ggggtgttga ccgccgcgac gctcacctgc tcggtgaggt gcggcgtgac ctcctcctcg 63720
gtggcccgga tcgccaccat cgccccgccg ggcgggagtt cctggatcag ccgtccgcgc 63780
gccgtgatca gccgggcggc atcagccaga tcgaacaccc cggccgtatg ggcggcggcg 63840
agttccccga tggagtggcc ggtcatgagg tccggcttga tcccccacga ctccaccagc 63900
cggaacaggg cgacctggag agcgaagatc gcgggctggg tgaactcggt gcggcccagg 63960
gcctcctcgt cgccccacat cacctcgcgc agcgcggggt cgagcacggc gcacacctcg 64020
tcgaacgccg tggcgaaagc ggggaacgtc tcgtacagct cctggcccat cccggcccac 64080
tgactgccct gtccggtgaa caggaacgcc agcccgccct cggtgaccga gtcgatcacg 64140
gtctcggagc cgatccgcac cgcgcggtgt tccagggcgg cccggccggt cgcggccgag 64200
tacgccacgt ccagctcgtc cgcgtcgacg gaggtgatcc ggtcgagctg ggcctggagc 64260
gcggtacggg tccgggccga cagcaccagg gggacgacgg gcaactcccg ccgctccacc 64320
ggcgcttcct cgaccgggac ggcctcctcg atgatgacgt gggcgttggt gccgctgatg 64380

-continued ccgaaggagg acacgcccgc gcggcgcggg cggccgtcgt tcggccactc cctcgtctcg 64440
gtgagcagct ggacctggcc ggcctcccag tccacctggg gtgtgggcgc gtccacgtgc 64500
agcgtccgtg gcagcgtgcc ctgccgcatc gcctcgacca tcttgatgat gcccgccaca 64560
cccgcggcgg cctgggtgtg accgatgttc gacttgatcg accccagcca cagcggtcgg 64620
tcctcggggc ggccctggcc gtaggtggcc agcagcgcct gcgcctcgat cggatcaccc 64680
agggtggtgc ccgtgccgtg cgcctcgacc gcgtccacat cggcgcccgc caggcccgcg 64740
ttggccagcg cctgcttgat cacccgctgc tgggacggcc cgttgggggc ggtcaggccg 64800
ttgctcgcgc cgtcctggtt ggtcgccgtg ccccgtacga gggccagcac cgggtggccg 64860
ttgcggcggg cgtccgacag ccgctccacc aggagcatgc cgacaccctc actccagccg 64920
gcgccgtcgg cggcggccgc gaaggacttg cagcggccgt cggtcgccag accccgctgc 64980
tcgctgaact cgatgaagtt gtccgccgcg gccatcacgg tgacgccgcc ggccagggcg 65040
agcgagcact cccccgaccg cagggcctgc gccgccaggt gcagggcgac cagcgaggac 65100
gagcaggcgg tgtcgacggt caccgcgggg ccttcgagcc ccagggtgta ggagacgcgg 65160
ccggaggcga tggcgcccgt gctgctgttg tgggtgtagt cgtggtacat catcccggcg 65220
aagacaccgg tcaggctgcc cttgagagtc gtcgggtcga tgcccgcgcg ctcaagaacc 65280
tcccacgacg cctccagcag cagccgctgc tgagggtcca tcaccagcgc ctcgttcggc 65340
gcgatcccga agaagccggg atcgaactgg gccgcgtcgt aaaggaatcc gcccttgtcg 65400
acgtagctgg tgcgggggcg ggtggccgtg gggtcgtaga tccgctccag gtcccagccg 65460
cggtcggtgg ggaagtgtga gatggcgtcc gtgccgctgt cgaccagccg ccacaggtcc 65520
tccggcgagg acacgcctcc cgggtagcgg cacgccatcg cgacgatcgc gatcgggtcg 65580
tcgccgaccg gggccgcgac gggggtgaga cggccctcgt gcaccgttcc cgagacctcg 65640
tccagcagat gacgcgcgag aacggtgggg ttcgggtagt cgaacaccag cgtggccgga 65700
agccgcaggc cggtcgcgcc gccgagaccg ttgcgcagtt ccatcgccgc cagcgagtcg 65760
acacccagat cgcggaacgc gcgctccggg tcgacggccc ccggtccggc gtagccgagc 65820
gtggtggcgg cctgcgcgcg gaccaggttc agcagcatgt cgaagcgctg gtcgtcggac 65880
atgcccacga gccgctcgcg gagcccgtcc gcgtcggcgc gggtgcgggc ggtgccacgg 65940
gtgacgaccg ggaccaggcc gcgcagcagc tccggcaccg cgccgccggc gcggacggcc 66000
gggaggtcga gcttgacggg gacgagtacg gcgggtccgt ccgccgccgt cgcagcgtcg 66060
aagagcgcca gcccctcgct gtgggacagc gacaggatgc cgccgcgttc catacgggac 66120
cggtcggtgt ccgtcagttc actggccata ccggtgctgg tccgccacag gccccacgcc 66180
agggactggg cgggcaggcc acccgcacgg cggcgctcgg ccagggcgtc cagataggcg 66240
ttggccgccg cgtagttgcc ctgccccggc gagccgatca cgccggccgc ggaggagaag 66300
agtacgaacg cggtcaggtc catgtcgcgt gtcagctcgt gcagatacag ggcggcgtcc 66360
accttggggc gcatcaccag gtccacccgc tcgggcgtca gggacccgat cacaccgtcg 66420
tccaggacac ccgccgcgtg caccacaccg gtgagcgaac gcccggccag cagcgccgcg 66480
agcgcctcac ggtcgccgac gtcgcaggcg gcgacctcga cctcggcccc cagcccgctc 66540
aactcctcca ccaactccgc cgcgccgggc gtgtccacgc cccggcgacc ggtcagcagg 66600
agccgtgaca ccccgtactc ggtgacgaga tgccgggcca gcagagcacc caggacaccc 66660
actccaccgg tgatcagcac ctcgtcgccg aacgccggcg ccaggtcgtc cgtcgtctcc 66720

-continued

```
ggcaccgcgg acacgcgggc cagccggggc acgtgggcga caccgtcgcg taccaccacc  66780
cggggctcac cggtcgacag cgcaggcgcg aggtcggcgt tgtccgcgct cggcgcctcg  66840
tcggtgtcac cgtccaggtc gatcaggaag aaccggccgg ggtcttcggt ctgggcggta  66900
cgcaccagac cccagacggc cgccgcggcc aggtcgtcga cgtccccgcc gttcaccgag  66960
accgcgccgc gcgtgacgac caccagacgg gagccggcgg actgcagtgc ctccagcgcc  67020
aggttcaccg ccgcgcgtac gtccagtccg ccggggaggc ggaacacctc ctcgtcgttg  67080
ggcggctgcc ccccggtgga ggcggtaccg gcggcgaccg gggccagggc gacgtggtac  67140
agcggctccg tacgggcctt ggtcgccatg tccgtgaggg gccgcaggac caacgagtcg  67200
accgtggcga cgggccggcc ggtcgcgtcg gcgatggtca gggccgccac gccgtcctgt  67260
acgggcgtga cgcgcacccg cagcgcgccc gcgccggagg cgtgcagttc cactcccgac  67320
caggcgaacg gcagcatcgc cacatcgccg gttcccgccg gggagagtcc gatggcgtgc  67380
aggcccgcgt cgaagagggc cgggtgcaga ccaaaggcgt ccgccaccgc gttgtccggc  67440
agggcgatct cggcgaacac ctcgtcgccg gcccgccagg cggcccgaag cccccggaag  67500
gtcggcccgt acgccaaacc cgtgccgacc aactcctcgt agagggtgtc gacatcgagg  67560
tccagcggct cggcgccggg cgggggccac tcggccagtt cccctccccc ggcggaggtg  67620
gcggtggcga gcagaccggt ggcgtgccgg ttccagggca ggtcggtcgc gtcctggtcg  67680
cgggagtaca cctggacctc gcggcggccc tcttcgtccg ccgctccgac gacgacctgg  67740
acggcgaccc cgccgcgttc ggcgaggacc agcggcgcct cgatcgtcag ctcctcgaca  67800
cggccgcagc cgacctcgtc gccggcccgg atcaccagct ccacgaatcc ggtgccgggg  67860
aagaggatcg agccgccgat gacatggtcg gtgagccagg gcagcgtccc ggtcgacagc  67920
cgtccggtga gcacgacctc ctccgagccc gcgagcatga ccatcgcccc gagcagcggg  67980
tggcccagcg agcccaggcc catggaggcc gcgtcggcgt tcgccgtctc gtcgttcagc  68040
cagtagcggt tgtgctggaa ggcgtacgtg ggcagttccg tctgccccgc cccggtcgcg  68100
tcgtacacct tctcccagtc gacgtccacg ccgcgggtgt gtgcctgggc cagcacgctc  68160
aggaaacggt cgaggccgcc gtcgttgcgg cgcagcgtgc cgatcgtggt ctgttccatg  68220
ctcggcgcca gcaccgggtg cgggctggcc tcgatgaaca cccccacgcc ctgctcggtc  68280
agccggcgga tggtccggtc gaactccacg gtctggcgca gattccggta ccagtagccg  68340
gcgtcgagag cggtggtgtc cagcagcccg ccggtcacgg tggagtagaa ggggatccgc  68400
gcggcgcggg gcttgatggg cgccagcacg tcgagcagtt cccgctctat gcgctccacc  68460
tgtgccgagt gcgaggcgta gtccacctgg atccggcgcg cccgtacgcc gtcggcctcg  68520
caggaggcca tcagttcgtc cagcgcgtcg acctcgcccg agaccacggt ggcggcgttg  68580
ccgttgacca ccgcgatgcc cgtccgggtg ccccagcgct cgatcagccg ctcggtctcc  68640
tcccggggga gggcgaccga caccatcccg ccctggccgg agagggccag cagcgccttg  68700
ctgcgcaggg cgaccacccg ggcgccgtcc tgcaacgaca gcgctccggc cacgctcgcc  68760
gcggcgatct cgccctggga gtggcccacc acgccgacgg gctcgactcc gtagtgccgc  68820
cacagaccgg ccagtgacac catgaccgcc cacaggacgg gctgcacgac gtctacacgt  68880
tccagcaggg cctcgtcacc gagcgcctcg ctcaacgacc agtccacgaa cggcgccagt  68940
gcctcctcgc acgcggacat ctgctccgtg aacacggcgg acgacgccat cagctcggtc  69000
gccatgccca cccactggga gccctgtccg gggaacacca tgaccgcgcc ggcgccgggc  69060
cgggccgctg tcaccggtgc ttccccctgc accagagcgg cgagcccctg ggagaagccc  69120
```

-continued

```
tcttcgtcgg cggccagtac ggcggcccgg tagtcgtacg acgcccgccg cgtggccagg  69180
gaccatccca cgtccaccgg ccgtaggtcg tgcgtggcga cggcctggag ccgctccgcg  69240
taggcgcgta cggcggcctc ggtcttcccg gagatcagcc agggcaccac cggaagttcc  69300
cggtgctcac gcggctccgg cgactccggc gactcttcgg ccggtacgtc ctcggcctgc  69360
ggagcctcct ccaggacgat gtgggcgttg gtcccgctgg ccccgaacga ggacacggcg  69420
gcgcggcgcg ggccgccctc cggccaggcg cgggcctcgg tgagcagccg gacgcttccc  69480
gccgtccagt ccacctgcgg ggacggttcg tccacgtgca gtgtcttggg cagggagccg  69540
tggcgtatcg cctggaccat cttgatgatg cccgccacac cggcggcggc ctgtgtgtgc  69600
ccgatgttcg acttgaccga cccgagccag agcgggcggt cctcggggcg gtcctgcccg  69660
taggtggcca gcagcgcctg cgcctcgatc gggtcgccca gggtggtccc ggtaccgtgg  69720
gcctccacga cgtccacatc ggaccccacc aggcccgcgt tggccagggc ctgctggatc  69780
acccggcgct gggacgggcc gttcggggcg gtgatgccgt tgctggcgcc gtcctggttg  69840
acggcgctgc cgcgcacgac cgccagaatc gggtggccgt tgcggcgggc gtccgacagc  69900
cgctccacca ccagcatgcc gacaccctca ccccacccgg tgccgtcggc cgccgaggcg  69960
aacgccttgc agcggccgtc cgtcgacaga ccccgctgcc ggctgaactc cacgaaggtg  70020
accggcgtcg acatgatcgt cacgccgccg gccagggcga gggaacattc cccactgcgc  70080
agggccttga ccgccatgtc cagtgcgacc agcgaggacg agcaggcggt gtcgacggtc  70140
accgccggac cctccagccc cagcgtgtag gccacccggc cggaaaccag cgcaccggtc  70200
acactgctgc tcggatagtc gtggtacacg agcccggcga agactccggt ggcggtgccc  70260
ttcagcgacg gcgggtcgat cccggcccgc tccacggcct cccaggaggt ttccagcagc  70320
agccgctgct gcgggtccat cgccatcgcc tcaagggggc tgatgccgaa gaactcgggg  70380
tcgaagtcgc ccgcgccgtc caggaagctg cccttgttga cgtagctggt gttctcgccc  70440
gtcccgtcag ggtcgtacag cgagtccagg ttccagcccc ggtcggtggg gaactcgccc  70500
accgtttcca gaccgtcggc gacgaggtcc cagagtcctt ccggcgagga cgcgccaccg  70560
gggaagcggc atgccattcc cacgatcgcg atcggctccc gctcccgatc ctccgcctca  70620
cgcagacggc gccgagtctg ctgcaactca ccggtggcaa gccgcagata ctcgcgaagc  70680
cgttcgtcgt tggagtcctt cgacatcgtc atcaaccaat ccgtgaaagt tcacaaagca  70740
gaggcgggag ccgtcaggac agtccgagtt ccttgttcag caccgcgaac aactcgtcat  70800
cggattcggt cacgaggccg ccgacgggct cgtccgtcac gccgctcccg gcgtctcgcg  70860
cccgtcgcga catggtttcg aggcgggccg tgaccttggc gtgggcttcg cggtcgcccg  70920
atgccagctc ggtcagcacg gcttccagcc ggttcagttc ggccagcagc gcggccgccc  70980
cgtcggcctc ctccgggcgc agcccgtcgt gcacgagctc ggcgatggcc agggggggtcg  71040
ggtagtcgaa ggccagggtc gggggcagtg acagccctgt ctcggtgttg agggcgttgc  71100
gcagttccac cgcgcccagc gaggtgaggc cgagttcgtt gaaagcgcgg tccgggggca  71160
cctcgtcggc gccgccgtgt ccgagcacct gggcgacgtg gccccgtacc aactccagga  71220
ggaacttctc gcgttccggc acggtcagtc cggacagccg ctcccacgac gcccggcctg  71280
ccggcgcgcg acggttctgg ccgcgtacca gtccgccgaa tatcgcgggc agtgtccccg  71340
tctcggcgag ggaccgcatc accgccaggt cgaaccggac cggcagcgtc atcggcggcc  71400
ggccgcgcag ggtcgcggca tccatcagcg ccagcccctc gtccggggac agcggcggca  71460
```

-continued

```
ttcccgagcg cctgagccgc gccagctcgg cgtcgtccag acggtcggcc atgcccccga  71520
cctcggtcca gggtccccag ccgagggtca gcgcgggcag ccccttggtc gcgcgatgcc  71580
tggcgagcgc gtccagccag gcgttcgcgg cggcgtagtt gccctgtccc gcgccgccga  71640
gcgtgccggc gacggaggag aagatcacga acgacgagag atcgtggtcc agggtgagtt  71700
cgtgcagatg ccaggcggcg tcgaccttcg gcctcatgac cgtgtccagc cgctcgggcg  71760
tcaacgctcc catgagtccg tcgtccagca caccggccga gtgcacgagg cccgtcaggg  71820
gccgctcggc cagcagggcg gccagcgcgt cccggtcggt gacgtcgcag acgacgacct  71880
ccacctcggc gcccgatccg gtcagctccg ccaccagttc ggccgcgccc ggcgtgtcca  71940
tgccccggcg gctggtcagc agcaggctct tcgcgccgtg ctccgcggcc aggtgccggg  72000
cggccagggc gccgagcccg ttcaggccac cggtgatcag gatcgtgccg tgcgtgcccc  72060
acgactggac gcggccttcg accgcgggga cgcgggccag cctcgccacc cggatctcgc  72120
cgtcccgtac ggcgatctcg ggctcggcga ggcgcagcac ctcgtcgggg agttcggctt  72180
cggcgtccag gtccaccagg acgaaccggc ccgggtgctc cgactccgcc gaacgcacca  72240
ggccccagac cgccgcgtgc ccgaggtcgc ttccgtcggt cgcgccgcgc gtgacgacga  72300
cgagcttggc ggatgccgcc tgctcgtcgt ccagccaccg ctggatgacg gggagcacct  72360
gatgggtgat cgtccggaag ccttcgggcg cgggctcgtc cagtggcggg cactcgtaga  72420
cgacatgagc accggtctcg gagccgacgg gtgcgggggc tgcgacccag tcgacgtgga  72480
acagcgattc acggccgccg gtgtgtgccc gtacctcgtc cgtggtgatc gagcgggtct  72540
cgaccgaggc caccgacaga acgggctgtc cgtcctggcc gacgctcacc gaggcgccgc  72600
gccacacatg ggcgagcgtc ggctcgccgt cggggtggag tccggcggtg tgcgcggcgg  72660
cttcgagcac cgtggcgtac gtctcgtcgt cacgtgtcca cgaggactcg gtggcctcgg  72720
aggtcaggac gccggtggcg tgcttgaccc aggccgccgt ccggtcgcca cggcgcgcgt  72780
acacgctgaa cgccccggcc tcgtcgacca tcgcgcgcag tgtcgtgtcg tcctcggtgc  72840
cggccatgac cagcggcgcg tggaggtcga gcgcttcgac gcgcccgcga cccgtctgct  72900
ccgctgccgt cagggcgagt tccaggaaca cttccccggg cacgaccacg gcgccgaagg  72960
cgtcgtggtc ggcgagccag gggtgggtgt cgagggagag acgtccggtg aacaccacac  73020
cgccggtgtc cgggagcacc atgccggagg tcagcagggg gtggtcgacg gcgtccgcgc  73080
cggccgtgga cttggactgc tcgatcagcc agtaacgctt gcgctggaag gcgtacgtgg  73140
gcagatccac ccgccgcgca ccacgcccgt cgaacaccgc gtcccagtcg accggaacac  73200
cggccgcgaa caaccggccc accccggcga acacactctc cacctcgggg cggtcgcgtc  73260
gcagcgtggg cgccagggtg ccgtcggcac tctgtcccgc catcgccgtc agcacaccat  73320
ccggaccgat ctccaggaac cgcgtcacac cctcgtcctg caaatgccgg acatcatcgg  73380
cgaaccgcac cgcgtcgcgt acgtgcccga cccagtactc cgccgaaccg acgtccttgg  73440
tcagccggat ggccggttcg ctgtacgtga cgctctcggc gatctcgcgg aagtcgtcca  73500
gcatcgggtc catcagcggt gagtggaagg cgtgcgagac cgtcagacgg ttgcgcttgc  73560
ggtcggtgaa ccgctccgcg accgccgtca ccgccttctc ctcgcccgaa atcaccaccg  73620
aggacgggct gttgaccgcc gcgacactca cctcgtccgt gagcagcggg agtacttctt  73680
cttcggtggc ctggatcgcg accatcgccc cacccgccgg caacgcctgc atcaaccgcc  73740
cacgcgccga gatcaaccgg cccgcatcct ccagaccgaa cacccccgcc acatgcgccg  73800
ccgccagctc accgatcgaa tgccccacca ggaagtccgg cttgaccccc cacgactcca  73860
```

-continued ccaaccggaa caacgccacc tcaagagcga agatcgcagg ctgggtgaac tccgtacggc 73920
tcagtacttc ttcgtcgccc cacatcacct cacgcacagc ggggtcgagc accgcacaca 73980
cctcgtcgaa cgccgacgcg aaggcgggga acgtctcgta caactcccgt cccataccca 74040
ggcgttgact cccctgcccg gtgaacagga acgccacctt gccctcggcg accgagccgg 74100
tcacggtctc ggggcccacc agcaccgccc ggtgctccag aacagcgcgc cctgtcgcgg 74160
ccgagtacgc cacgtcgagc gcgttcccgt tcgcggccag ttcgccgaag cggccgatct 74220
gcgcctccag cgccgccggg gtcttccccg acaccaccac cggcgccacc ggcaactccc 74280
gccgctccac caccacttcc tcgacgggga cggcctcttc gacgatgacg tgggcgttgg 74340
ttccgctgag cccgaacgac gacactcccg cgcggcgcgg acggccttcg ctcggccact 74400
cacgcgcctc cgtcagcagc cgcacctcac ccgcgtccca gtccacctgc ttcgtcggct 74460
catccacatg cagcgtcttg ggcagcctgc cgtggcgcat cgcctcgacc atcttgatga 74520
tccccgccac acccgccgcc gcctgcgtat gaccgatgtt cgacttgatc gaacccagcc 74580
acaacggccg cccctccgga cggccctgac cgtacgtctc cagcagcgcc tgcgcctcga 74640
tcgggtcacc cagcgtcgta cccgtgccgt gtgcctcgac cgcgtccaca tccgccgtcg 74700
acagacccgc cttcgccagc gcctgcttga tcacccggcg ctgcgccggg ccgttggggg 74760
cggtcagacc gttgctggcc ccgtcctggt tcagcgcgct cccgcgcacc accgccagca 74820
ccggatgccc caggcgacgc gcgtccgaca gccgctccag aaggagtact ccgacacctt 74880
cggagcagct catgccgttg gcggcgtcgc tgaacgactt gcagcggccg tcgatcgaca 74940
ggccgcgctg ctcgctgaag tagaggaaca tctcgggcgt ggacatcacc gtcacaccac 75000
ccgcgagagc gagcgagcac tcaccggaac gcagcgactg gatcgccgtg tgcagcgcga 75060
ccagcgagga cgagcacgcg gtgtccatgg tgaccgcggg acccaccagg cccaacgtgt 75120
aggcgacgcg cccggagacg atgctgccgc cgctgctgcc gccggcgtag tcgtggtaca 75180
tcaccccggc gaacacaccg gtcgggctgc ccttcagcga ggcggggtcg atcccggcgc 75240
gctccagcac ctcccaggac gcctccagca gcagccgctg ctgcgggtcg gtctccaggg 75300
cctcgcgcgg actgataccg aagaactcgg cgtcgaactc cgctgcgtcg tgcaggaatc 75360
cgccctcgcg ggacgttgtc tttccgggct tgccgacctc ggggtcgtag atgtcctcca 75420
ctccccagcc gcggtctgcc gggaactcgg agatcgcgtc gacgccctcg tcgacgagcc 75480
gccacaagtc ctcgggcgag ttcacaccgc ccgggtagcg gcacgccatc gagacaatgg 75540
cgatcggctc ctggtcacgc tgctcaagct cggcgacgcg tctgcgcgct gtgcgcagat 75600
ccgtggtcgc gcgcttgagg tagtcaagaa gcttctcctg gtcgctcacc aaagccaccc 75660
cgggtcgaaa gggcgtcgac acttacgacg cgcgcttgcc gggaacgtta cgcagggtga 75720
aaagaccccc caacccctga tcgcccctaa cgtggcccga cccctttcgcc cggcgcgacc 75780 atcggtttcc gaccccggcg tccggaccac gtgcagccca caccgaccgc gcccgatcgt 75840
ggcaggggtt cgccctgtca cgcgcggtag tcgggtcttg gggacgtacg gggtcggtgc 75900
gccgccgcgc ggcgacgcac ccgggcaccg gtggttcggc gggacggcgc gggtcagtgc 75960
cgccactctc tgtcctggcc gcccgtccag gcgcccggcg gtgtgtacca ggcaccgggt 76020
gaggcgtaac ggaccgcgcc ccaggcggag ttgcgccgct gtcgggccgc ggaggacgcg 76080
acggcctgct cccgggtacc ggtcagggcg ctcaacaccg cgagcagcgc cgccagttcc 76140
atctctcccg gagcgcccct gacgacgcgc acgaggtgct cggcaggtgt gacggcgacg 76200

-continued

```
ggttcccgtg ttcgcgggcc ggccacgtag tcagggtgca tgatttccct ccggtactct  76260
tcggtgctct tcgaaagact ccgcccgtgc tttctccgtg ctttctctcc ttcattgaaa  76320
ggtccctccg ccccgcactt ccagcggatc gaccccctaa ttccccgctt cgtcccccta  76380
ttcgaaagcc gtggtagtcc gtcctcacaa caacgggccg ccattccgga ccgagcgcga  76440
cccgcgaagc gggtacggtt cgataggggt catgaggggt cgccacgcgc ccgtacacac  76500
atgaacgctg aacacagcct gccgcagcgg cttcagccgg atcgatccaa ggaacttgat  76560
tgatgaccgc catatcgagc gacaacgcgt ccaattggat tcgagaattt catccggcgg  76620
accggacatc cccgaggatg atctgcttcc cccacgcggg cggtgcggcg agctactact  76680
tccccgtctc ccgggcgctg gccgggaaga tcgaagtcct cgccatccag tacccggggc  76740
gccaggaccg ttacacggaa ccggccatcg gcaacgtcga ggccctcgcc gccgcggtct  76800
tccgtgagct tccgacggag gacctggacc ggacctggct cttcgggcac agcatggggg  76860
ccgccgtcgc cttcgaggtg gcccggctga tggaacggga gttgaaccag tcgcctgtcg  76920
ggatcatcct ctccggccgg cgcgcaccgt cccggttccg tcccgagacc ctccacctgc  76980
agggcgacgc ggcgatcatc gccaacgtgc agtcgctcag cggtaccgac gcgatcctct  77040
tcgaggaccc cgacacccag cggctgatca tgccggcgct gcgagccgac taccgggcca  77100
tcgagaccta ccggccgccc ggcactccac gcgtcgcgtg cccgatccac accttcgtgg  77160
gcgacgccga cccgttggcc acgctggacg aggtcggcag ctggcgcgac cacacctcgg  77220
ccgagtacac cctgcgcgtt ttcccgggtg accacttcta tctgacggcg cgtgccgtcg  77280
aggtcatctc cgcgatctcc cagctgatcg tggagcccac ccagacccgc ggctgatcgc  77340
ggcgcgggtg ccgccaccgc cgccggaggc ggtgggatcg gcgtcgggcc ggaacgcgac  77400
cgggcccacg gatcgactgg actctcgcct gtgtgttgtg atcaggcgaa cagcgaggca  77460
gccggtccgg cagagtggga gaaacgccgt gttctactac gtactgaagt acgtgctgtt  77520
ggggcccgtg ctgcggttgc tcttccggcc ccggatcgag ggctcgaac acatcccggc  77580
ggacggcgcc gcgatcgtcg cgggcaatca tctctccttc tccgaccact tcctgatgcc  77640
cgcgatcatc cggcggcgga tcacgtttct cgcgaaggcc gagtacttca ccggtcccgg  77700
cgtcaaggga cgcctcaccg cctccttctt ccgcggcgtc ggccagatcc cggtcgaccg  77760
gtccggcaag gaggccggga aggccgcgat ccgggaaggg ctcggggtgc tcggcaaggg  77820
tgagttgctg gggatctacc cggagggcac gcgctcgcac gacggacggc tctacaaggg  77880
caaggtcggg gtggcggtga tggccatcag ggcgcaggtc ccggtggtgc cgtgcgcgat  77940
ggtgggtacg ttcgagatcc agccgcccgg tcagaagatc ccgaacatcc ggcgggtcac  78000
gatccggttc ggtgagccgc tggacttctc gcgctacgcg ggtctggaga accagaaggc  78060
ggcggtccgc gcggtcaccg acgagatcat gtacgcgatc ctcggtctgt ccgggcagga  78120
gtacgtggac cggtacgccg ccgaggtgaa ggccgaggag gcgcagcagg cgccgaagaa  78180
gttcccgcgc ctgcgacgct gagcaccgcg gggccgcccg gcagccggac ggcgaaggag  78240
gggcggctgc cgtctccggc cgccgcccct cccccggttc accggtgctg cccgtgcctt  78300
acggcttggg tgtggcgtgc ggtgcgcacg tcacgtcgcg gcggtccagc tcgccgctga  78360
gcagatacga ctcgacccgg tcgttgatgc acgcgttcgc gacattggtg atgccgtgcg  78420
aaccggcgtc ccgctcggtg atcaggcgtg agcccttgaa gcgcttgtgc agctcgacgg  78480
cgcccccgta cggggtggcg gcgtcacgcg tggactgcgc gatcagtacg ggcggcaggc  78540
cgcggcccgt accgacctcg atcggtgtct gctgctctac gccccaggtc gaacagggca  78600
```

```
ggttcatcca ggcgttggcc caggtgagga acgggtggtc gcggtggagc cgggtgttgt  78660
cccggtccca ggtgcgccag ctcgtgggcc acttggcgtc ggcgcactcg acggcggtgt  78720
agaccgcgtt gctgttctcg gcgcgggtgt tgcccaccgt gtcggacagg tccggcgcgg  78780
cggcgtcgac gagcgcctgg gtgtctccgg ccaggtactt gctccaggtg tcggcgaccg  78840
gcacccagct ggagtcgtag tagggcgcgc tctggaacag cccgatgagt tcggccggtc  78900
ccacgacgcc gccgatcggg ttcttcttgg cggtggcgcg gagcttgtcc cactgcttct  78960
cgaccttggc gacggtgtcg ccgatgtgga acgccgcgtc gttctcggcg acccacttct  79020
tccagtcgtc gaagcgtgtc tcgaaggcga cgtcctggtc caggttggcc tggtaccaga  79080
tcttctcctt cgacgggttg accacgctgt ccagcaccat gcgccgtaca tgggacggga  79140
agagcgtgcc gtagacggcg cccaggtagg tgccgtagga gacacccacg tagttgagct  79200
tcttgtcgcc gagcgcggcc cgcaggacgt ccaggtcgcg cgcgctgttg ggcgtcgtca  79260
tgtgcggcag catccagccg ctgcgctcct tgcagccgtc cgcgtactcg gccgcgagct  79320
tgcgctgggc gcgcttgtcg gcctcggtgt cggggacggg gtcggccttg ggagccttga  79380
cgaactcctg cgggtcgacg caggagatgg gcgtcgagcg cccgacgccg cgcgggtcga  79440
agccgacgaa gtcgtacgcc ttggcggcgt ccgcccagat ggcgttcttg gtcacgacgc  79500
ggcgcgggaa cgccatgccg gacgcgccgg ggccaccggg gttgtagacg agggagccct  79560
gacgctcacc cgccgtcccg gtgttgccga tccggtcgac ggctatcttg atctgcttgc  79620
cgttcggacg ggcgtagtcg agcgggacac tgatgtagcc gcactggatc ggcttctcca  79680
gggcccagtc ggccgggcag tccgcccagt cgatgccctt cttcgcggcc cgctcggcgg  79740
cgatctcggc gccggccgcc tgggcgttca gcgtcttctg ttccttgccc gacgcggccg  79800
ggccactgtc ggcgcggccg tcggcgctcg ccgacgaggc ggcgagcgtg gtcgctatga  79860
gcgtgcccgc gagcagagtg ccggccgagc caagcactgc tgtgcgtctc aagtggtacc  79920
tccccctggc tgacgcgccg cacgctgcgg cgctgttcgt agggttaccg agaggatcct  79980
tatctctgtg ggccggttga gaacaggcca tacggcatat tctttgccga accgatagcc  80040
ggtgagtccg gttccgctca                                              80060
```

<210> SEQ ID NO 2
<211> LENGTH: 2856
<212> TYPE: DNA
<213> ORGANISM: Streptomyces sp. MP28-13

<400> SEQUENCE: 2

```
gtgttgaagg aacgggacaa gatactcgaa cagctcgatg ccctactgat ccagtccacg    60
cggggcaggg gggccatcgc cgcgatcagc ggttcgaccg cgatcggcaa gaccacgaca   120
ctcaacgccc tggccgaacg ggcgacttcg gcggacatca cggtgctcag cgtggtgagt   180
tcgccgcacg agcgcgaggt tccctacagc gccctcgccc agctgctgca ttcgatcgaa   240
gcccagtgca ccaccgccga cgttccgcgc gccgggggcg ccgggaccgt ccatgccggc   300
aggcaggcgg acgaggccgc cgccctcgcc ccgccgttgg cccaggacga cccgatgaca   360
gtcgcacggc ggacctacca gatcatcgcc gagctgaccg ccctgcggcc tctgctgatc   420
acggtggacg acatccagca caccgacacg gccaccctca cgtgcctgcg ctacctggcg   480
cagcgtctga cccagctctc actcgcgctg gtgttcacgc acgggatctc cgtcgacgag   540
cagccggctc gtgtcctgga cgacctcctc taccgcacga gcgcgcgcca cttccacctg   600
```

-continued

```
gagccgctct cgcgggtgga catcatgggg ctggccgcga accggctccc ggtcctcccg    660
tcggaccggc tcatcgtcga gatccaccgg ctgagcgggg gcaatccgct gctcgcccag    720
gcactcatcg aggagcacag gctgcgtctc gcgtccgatt ccgtcgcggg gccgatgccg    780
ccgcagagcg acggcatcgg ccgccggtcg accaccgagg gcggggcgtc gatcggcccc    840
gccttctacc aggccgtcct cgcctacctg caccggctcg gcccgcgcgc ggtccgtctc    900
gcccggtgcg tcgccctcct ggacgaggcg acgactcccc ttctgttgag tcggctcagc    960
ggtatcgaca cggaactgtc gaaacgttac ttacggttgt tcaccggctt gggcgtgctg   1020
gagggcgcgc ggttgcggca cgcgggcgta cggcaggccg tactgggtga gatgcctcac   1080
ggcgaggcga cccagcagcg ctaccgcgcc gctcgcctcc tgaacgaggg aggagcgccg   1140
ccgcaagccg tcgccatgca tctgctcggc gtcggtccgc tccacgacgg atgggtgctg   1200
cccgtactcc aggaggccgc ggcccacgcc atggaggacg gtgacgtacc gcagggcatc   1260
cgttatctgg agctggcctg cgaatgctcc ctggacgagg gacagcggct ctcggcgaag   1320
tcgctgtacg ccttcggcca gtggcagctc aggcccgccg agtccgcccc gcacttccgc   1380
gcgctcaagg gccccatcct tgaggggaag ctcacgggca ccgacgccct gtgggtcgcc   1440
gagggcatgc tcttccacct cgacttcgac gaggccgtcg aggttgtcga ccatgtcaac   1500
agcggcgagg cggacatgtc caccgcgctg cacagcaccc ggatgctcat ggccgcggag   1560
gtcccgggcc tgctcgaacg gctggagcac ccactgccgg ccacaaccgc cccggcgacg   1620
tcccattcgg agttaagagc ccgtcacgcc ctcgccctca tccttgagaa cggagcggac   1680
aagtacgcca tcgccctggc cgaccaggtg ttccagggca gccagaactg gccgacgtcg   1740
aagctcagcg gcctgccgaa ggcgctgctg gccctgtgct acgcggatca actcgacacc   1800
gccgccgcgt ggtacgacct gctcgcggcc gaggtggaac gacacgacgc ccctggctgg   1860
tgggcccaga tcgaaagcgt cggcgcgctc ctggcgctgc ggcgcgggcg gctggcggac   1920
gccgtacgcc aggcggagac ggcccacgcc cggctgtccg ggccgaggtg gaacgtcagc   1980
agcgcgcttg cgctgaccgt gctcatcgag gcccacaccg ccatgggcaa ccatcagacc   2040
gcggccaagt atctggagac gtccgagccg ccgcccgcgc tgttcctcac ccgcgcgggg   2100
ctgcactacc tgtacgcgcg cggccgtcat cacctcgcga ccggcaacac ctacctggct   2160
ctgtccgact tccaggagtg cggcacgctg atgcgtcgct ggaacatcga cacaccctcc   2220
ctggcgccct ggcggctggg agaggcggag gtgtggctgc gcctgggcga ccagaaacag   2280
gcggcccggc tcgtcgagaa gcagctggcc aacccggacg ccgggctcac ccggtcgcgc   2340
ggtatgaccc tgcacgccct ggccctggtc caggcaaccg ccaagcagcc cccgatcctg   2400
cgggacgcgt tccgtctgct ggaggccgcg ggcgcgcgtt acgaggctgc ccgtgtcctg   2460
gccgatctca gccgcgccta ccagcagttg ggcgacaaac aggcccggcc gaccgcacgg   2520
cgggcctggc ggctcgccaa gagctgccag gcggagtccc tctgccaggc tctgctcccg   2580
acatccatac cccagaacat ggacacaaag ccgagcgagg ggtcctgcgg cgccgaccgc   2640
gcgggccagg acagcttcgg cacactcagt gaatccgaac ggcgcgtcgc cacactggcc   2700
gcccaggggt acgccaaccg tgagatcgcc gagaggctgt tcatcacggt cagcaccgtg   2760
gagcagcatc tgacccgcgt ctaccgcaag atgggcatca ggaaccgcga gcagctcctg   2820
cagagagccc acgcggtcag ctacgagtcc gtctga                             2856
```

<210> SEQ ID NO 3
<211> LENGTH: 951

<212> TYPE: PRT
<213> ORGANISM: Streptomyces sp. MP28-13

<400> SEQUENCE: 3

```
Met Leu Lys Glu Arg Asp Lys Ile Leu Glu Gln Leu Asp Ala Leu Leu
1               5                   10                  15

Ile Gln Ser Thr Arg Gly Arg Gly Ala Ile Ala Ala Ile Ser Gly Ser
            20                  25                  30

Thr Ala Ile Gly Lys Thr Thr Thr Leu Asn Ala Leu Ala Glu Arg Ala
        35                  40                  45

Thr Ser Ala Asp Ile Thr Val Leu Ser Val Val Ser Ser Pro His Glu
    50                  55                  60

Arg Glu Val Pro Tyr Ser Ala Leu Ala Gln Leu Leu His Ser Ile Glu
65                  70                  75                  80

Ala Gln Cys Thr Thr Ala Asp Val Pro Arg Ala Gly Gly Ala Gly Thr
                85                  90                  95

Val His Ala Gly Arg Gln Ala Asp Glu Ala Ala Ala Leu Ala Pro Pro
            100                 105                 110

Leu Ala Gln Asp Asp Pro Met Thr Val Ala Arg Arg Thr Tyr Gln Ile
        115                 120                 125

Ile Ala Glu Leu Thr Ala Leu Arg Pro Leu Leu Ile Thr Val Asp Asp
    130                 135                 140

Ile Gln His Thr Asp Thr Ala Thr Leu Thr Cys Leu Arg Tyr Leu Ala
145                 150                 155                 160

Gln Arg Leu Thr Gln Leu Ser Leu Ala Leu Val Phe Thr His Gly Ile
                165                 170                 175

Ser Val Asp Glu Gln Pro Ala Arg Val Leu Asp Asp Leu Leu Tyr Arg
            180                 185                 190

Thr Ser Ala Arg His Phe His Leu Glu Pro Leu Ser Arg Val Asp Ile
        195                 200                 205

Met Gly Leu Ala Ala Asn Arg Leu Pro Val Leu Pro Ser Asp Arg Leu
    210                 215                 220

Ile Val Glu Ile His Arg Leu Ser Gly Gly Asn Pro Leu Leu Ala Gln
225                 230                 235                 240

Ala Leu Ile Glu Glu His Arg Leu Arg Leu Ala Ser Asp Ser Val Ala
                245                 250                 255

Gly Pro Met Pro Pro Gln Ser Asp Gly Ile Gly Arg Arg Ser Thr Thr
            260                 265                 270

Glu Gly Gly Ala Ser Ile Gly Pro Ala Phe Tyr Gln Ala Val Leu Ala
        275                 280                 285

Tyr Leu His Arg Leu Gly Pro Arg Ala Val Arg Leu Ala Arg Cys Val
    290                 295                 300

Ala Leu Leu Asp Glu Ala Thr Thr Pro Leu Leu Leu Ser Arg Leu Ser
305                 310                 315                 320

Gly Ile Asp Thr Glu Leu Ser Lys Arg Tyr Leu Arg Leu Phe Thr Gly
                325                 330                 335

Leu Gly Val Leu Glu Gly Ala Arg Leu Arg His Ala Gly Val Arg Gln
            340                 345                 350

Ala Val Leu Gly Glu Met Pro His Gly Glu Ala Thr Gln Gln Arg Tyr
        355                 360                 365

Arg Ala Ala Arg Leu Leu Asn Glu Gly Gly Ala Pro Pro Gln Ala Val
    370                 375                 380

Ala Met His Leu Leu Gly Val Gly Pro Leu His Asp Gly Trp Val Leu
385                 390                 395                 400
```

-continued

```
Pro Val Leu Gln Glu Ala Ala Ala His Ala Met Glu Asp Gly Asp Val
                405                 410                 415

Pro Gln Gly Ile Arg Tyr Leu Glu Leu Ala Cys Glu Cys Ser Leu Asp
            420                 425                 430

Glu Gly Gln Arg Leu Ser Ala Lys Ser Leu Tyr Ala Phe Gly Gln Trp
        435                 440                 445

Gln Leu Arg Pro Ala Glu Ser Ala Pro His Phe Arg Ala Leu Lys Gly
    450                 455                 460

Pro Ile Leu Glu Gly Lys Leu Thr Gly Thr Asp Ala Leu Trp Val Ala
465                 470                 475                 480

Glu Gly Met Leu Phe His Leu Asp Phe Asp Glu Ala Val Glu Val Val
                485                 490                 495

Asp His Val Asn Ser Gly Glu Ala Asp Met Ser Thr Ala Leu His Ser
            500                 505                 510

Thr Arg Met Leu Met Ala Ala Glu Val Pro Gly Leu Leu Glu Arg Leu
        515                 520                 525

Glu His Pro Leu Pro Ala Thr Thr Ala Pro Ala Thr Ser His Ser Glu
    530                 535                 540

Leu Arg Ala Arg His Ala Leu Ala Leu Ile Leu Glu Asn Gly Ala Asp
545                 550                 555                 560

Lys Tyr Ala Ile Ala Leu Ala Asp Gln Val Phe Gln Gly Ser Gln Asn
                565                 570                 575

Trp Pro Thr Ser Lys Leu Ser Gly Leu Pro Lys Ala Leu Leu Ala Leu
            580                 585                 590

Cys Tyr Ala Asp Gln Leu Asp Thr Ala Ala Ala Trp Tyr Asp Leu Leu
        595                 600                 605

Ala Ala Glu Val Glu Arg His Asp Ala Pro Gly Trp Trp Ala Gln Ile
    610                 615                 620

Glu Ser Val Gly Ala Leu Leu Ala Leu Arg Arg Gly Arg Leu Ala Asp
625                 630                 635                 640

Ala Val Arg Gln Ala Glu Thr Ala His Ala Arg Leu Ser Gly Pro Arg
                645                 650                 655

Trp Asn Val Ser Ser Ala Leu Ala Leu Thr Val Leu Ile Glu Ala His
            660                 665                 670

Thr Ala Met Gly Asn His Gln Thr Ala Ala Lys Tyr Leu Glu Thr Ser
        675                 680                 685

Glu Pro Pro Pro Ala Leu Phe Leu Thr Arg Ala Gly Leu His Tyr Leu
    690                 695                 700

Tyr Ala Arg Gly Arg His His Leu Ala Thr Gly Asn Thr Tyr Leu Ala
705                 710                 715                 720

Leu Ser Asp Phe Gln Glu Cys Gly Thr Leu Met Arg Arg Trp Asn Ile
                725                 730                 735

Asp Thr Pro Ser Leu Ala Pro Trp Arg Leu Gly Glu Ala Glu Val Trp
            740                 745                 750

Leu Arg Leu Gly Asp Gln Lys Gln Ala Ala Arg Leu Val Glu Lys Gln
        755                 760                 765

Leu Ala Asn Pro Asp Ala Gly Leu Thr Arg Ser Arg Gly Met Thr Leu
    770                 775                 780

His Ala Leu Ala Leu Val Gln Ala Thr Ala Lys Gln Pro Pro Ile Leu
785                 790                 795                 800

Arg Asp Ala Phe Arg Leu Leu Glu Ala Ala Gly Ala Arg Tyr Glu Ala
                805                 810                 815
```

-continued

```
Ala Arg Val Leu Ala Asp Leu Ser Arg Ala Tyr Gln Gln Leu Gly Asp
            820                 825                 830

Lys Gln Ala Arg Pro Thr Ala Arg Arg Ala Trp Arg Leu Ala Lys Ser
        835                 840                 845

Cys Gln Ala Glu Ser Leu Cys Gln Ala Leu Leu Pro Thr Ser Ile Pro
    850                 855                 860

Gln Asn Met Asp Thr Lys Pro Ser Glu Gly Ser Cys Gly Ala Asp Arg
865                 870                 875                 880

Ala Gly Gln Asp Ser Phe Gly Thr Leu Ser Glu Ser Glu Arg Arg Val
                885                 890                 895

Ala Thr Leu Ala Ala Gln Gly Tyr Ala Asn Arg Glu Ile Ala Glu Arg
            900                 905                 910

Leu Phe Ile Thr Val Ser Thr Val Glu Gln His Leu Thr Arg Val Tyr
        915                 920                 925

Arg Lys Met Gly Ile Arg Asn Arg Glu Gln Leu Leu Gln Arg Ala His
    930                 935                 940

Ala Val Ser Tyr Glu Ser Val
945                 950


<210> SEQ ID NO 4
<211> LENGTH: 16749
<212> TYPE: DNA
<213> ORGANISM: Streptomyces sp. MP28-13

<400> SEQUENCE: 4

atgagggagg cactcgccat catgtcgagt gatcttgttc acggcacgga cgcaatcgca     60

atcaccggca tgtcatgccg cctcccccag gcacccgacg ccaactcctt ctgggagttg    120

ctgcggtcgg gccgtagtgc gatcaccgag gtgccgccgg accgctggga cccggacgag    180

gtgctgccgg actcaccgga gcggcaccgc gcagcgctgc gccacggcgg gttcctcgac    240

cgagtggacc agttcgacgc ggccttcttc gggatctcgc cgcgcgaggc cgtggcgatc    300

gacccgcagc agcggctctt cgccgagctg gcctgggagg cgctggagga cgcgggaatc    360

gtccccgaga cgctgcggtc caccgcgacc gccgtcatcg tgggagcgat cgccggggac    420

tacgcggcgc tggcacaccg cggcggtgcg atcacacagc actcgctgcc ggggctgaac    480

cgcggtgtca tcgccaaccg ggtgtcctac gcgctgggac tgaacggccc gagcatggcg    540

gtcgactcgg cgcagtcgtc gtcgctcgtg gcggtgcatc tggccgtgga gagtctgcgc    600

aagggtgagt gcaccctggc cctggcgggc ggtgtggcgc tcaacttcgc gcccgagagc    660

gccgaagtcg ccggaatgtt cggcgggttg tcgccggacg gacgctgctt caccttcgac    720

gcgcgggcca acggctacgt gcgcggtgag ggcggcggcg tcgtcgtact gaagccgctg    780

gcacacgcgg tgcgcgacgg cgacacggtg tacggggtca tccgtggcac cgcggtcaac    840

aacgacggct ccaccgacgg gctcacggtg cccagcgccg aggcccaggc gaccgtgctg    900

cgccaggcgt gcgaggacgc cggcgtggac ccggccgagg tccgttacgt ggaactccac    960

ggcacgggca ctccgacggg cgatccgctg gaggcggcgg gtgtgggcgc cgcgtacggc   1020

agcgcgcgtc ctgcgggctc accggtactc gtcggctcgg ccaagaccaa cgtcgggcac   1080

ctggagggcg cggcgggcat cgtcgggctg atcaagacgg cgctgagcat ccggcaccgg   1140

gagatcccgg ccagcctcaa ctacgagacg cccaacccgc ggatcgaccc cgaggcgctg   1200

aatctgcgcg tccagaccgc gtccggcccg tggccggacg cgccgctgct ggccggggtc   1260

agctccttcg gtgtgggcgg aacgaactgc catgtcgtac tggccgaggc gcccgagcgg   1320
```

-continued

```
gccgcgtccg aggaggacgc gccgcagggc gacgagccgg agatcccgct ggctccgtgg   1380
ctggtgtccg ggcgtaccga ggcggctctg cgcgcccagg ccgggcggct gctggagcgg   1440
cggacggcgg acgccgacgc gttcgacatc ggccgctcgc tcgcgggcac ccgtacccac   1500
ttcgagcacc gcgccgtcgc gctcgggctc ggacacgacg cgcagcttga ggcgttgcgg   1560
tccggcgccg acgtaccggg gctcgtcacg gggtcaccg gcgaccacgg gaagatcgcg   1620
ctggtgttcc cggggcaggg ctcgcagtgg gagggcatgg cgcgcgagtt gatgcgcacg   1680
tcggcggtct tccgcgcgtc gatcgaggcg tgccacgaag ccctcgcgcc gtacgtcgac   1740
tggtcgctgc tggacacgct caccgatgag tccggcgcga cgtccctcga ccgcgcggac   1800
gtcgtccagc ccgtgctgtt cgcggtgatg gtctcgctcg ccagggtgtg ggagtcgctg   1860
ggtgtacggc ccgacgcggt catcgggcac tcgcagggcg agatcgcggc ggcgcacatc   1920
gcgggagcgc tcgacctggc ggacgccgcc aggatcgtgg ccctgcgcag ccagacgatc   1980
atgacgctgg cgggtaccgg ggccatggcg tcggtgccgc tggcggccga ccgggtcacc   2040
gagtacatcg ccccttcgg cgacgggctg agcatcgccg cggtcaacgg gccgaccacc   2100
actgtcgtgg ccggaaaccc cgacgccatc gccgagttgc tggcccgctg cgaggcggag   2160
gggattcgcg cgagggccgt ctcggccgtg gacttcgcct cccactcttc gcacatggag   2220
gcggtcaagg accggttgct ggagcagttc gccgaggtga cgccgcgttc gtgcgacatc   2280
gcgttctact ccacggtcac cgcgagcgcc atcgacacgg ccggtctcga cgccggctac   2340
tggtactcca accttcgccg gcccgtcctc ttcgaggcga cgctcagggc catggcggag   2400
gacggcttcg gcacgttcgt cgagtcgagt ccgcaccccg ttctcacgct cggattgcgg   2460
gcgacgctgc cggacgcgct ggtcgcggac tcgctgcgcc gtaacgaggc tccgtggccg   2520
cagctgctga cctccctggc ggaactgcac gtatccggcc tgcccgtgga ctggtccgcc   2580
gtcttcaagg ggcgtacacc gggtcgcgtg gcgctgccca cgtacgcctt ccagcgcgag   2640
cgctactggc ccgaggtctc gaccgcgttc gagcccggga cgcgcggcgc cgtccagcac   2700
caggaagccg cgcgcgagga gatccccgcg gcgagctcca cctggtcgga tcggctggcc   2760
ggactgccgg cggacgagcg ctcccgtgag gcgctggagc tggtgcggct gcgcacggcg   2820
atcgtgctcg gtcatctgag cacggacggg gtcgatgtcg gccaggcgtt ccgcgagctg   2880
ggcatggact ccacgatggc cgtccagctc cgtcagaacc tcgtggacat caccgggctg   2940
gcgctgccgg agaccgtcgt cttcgactac gcgagcccgt cccggctggc cagccggctc   3000
tgcgaactgg ccctgggcga ggacacgtcg tcggccgcgt ccgcgctgtc gcggtcggcg   3060
tcggtgctgg acgccgacga tccgatcgtg atcgtcggca tggcctgccg ttaccccggc   3120
ggcgccagca ccccggacga gctgtggcag ctcgtcgacg acggcgtgag cgcgatctcg   3180
ggcttcccca ccgatcgcgg gtgggacctg gacgccctgt acgaccccga gcccggggtg   3240
cgcggcaaga cctacacacg gcacggcggg ttcctcgacg aggccgccga gttcgacacc   3300
gagttcttcg ggatcagccc gcgcgaggcc accgcgatgg acccgcagca gcggctgctc   3360
ctccaggtca cctgggaggc gctggaacgc gccgggatcg acccggacgg cctccagggc   3420
agcagcaccg gtgtgttcgt gggcgcgatg tcgcaggagt acggcccccg gctgcacgag   3480
ggcgacgacg gactgggcgg ctatctgctc accggcacca ccgcgagtgt cgtctccggg   3540
cggatctcgt acaccttcgg tcttgagggc ccggcggtca ccgtcgacac ggcctgctcg   3600
tcgtcgctcg tcgcgatgca ccaggcggcg caggcgctgc gcgtcgggga gtgctcgctg   3660
gccctggcgg gcggcgtcgc ggtcatggcg acgcccggca tgttcgtgga gttcggacag   3720
```

-continued

```
cagcgtggtc tggctcccga cggccggtgc aagtcgttcg ccggtgcggc ggacggcacc   3780
atctgggccg agggcgcggg catggtcctc ctggagcgtc tgtccgacgc gaaggccaac   3840
ggacacacgg tcctggccgt catccgcggc tccgcggtca accaggacgg cgccagcaac   3900
ggcctcaccg cccccaacgg gccctcgcag cagcgggtca tcaccgccgc tctggccggc   3960
gcgggcctca cgcccgacca ggtcgacgcg gtcgaggcac acggcaccgg aaccccgttg   4020
ggcgacccga tcgaggccca ggcgctcctg gccacctacg gccagaaccg tgaagaaccg   4080
ctgtggctcg ggtcgttgaa gtcgaacatc ggccacacgc aggccgccgc cggtatcggc   4140
ggggtcatca agatgatcca ggccatgcgc cacggcaccc tgccccggac cctgcacgtc   4200
gacgagccca gcccgcacat cgactgggac tccggcaacg tgcggctcct caccgaggcc   4260
cgggcctggc ccgagaccga ccacccgcgc cgctccgccg tctcctcctt cggcatcagc   4320
ggcaccaacg cccacctcat cctcgaacag gcccccgcga cgccggagcc cgtggacggc   4380
gacgacgagc aggagacccc gcaggggggcc ctcgttccct ggttcctgtc cgccaagagc   4440
gcccccgcgc tccgcgacca ggcccagcgc ctcctcgacc atgtcatcgc gcgccccggg   4500
gtcgacccgg cgcacatcgg ccgtgccctg acagccaccc gcgcccgttt ccagcaccgt   4560
gcggtggtgg tgggagaggg ccgtgacgaa ctactcgcgg gtcttcgggc gctgagcaac   4620
gacgagtcat cccgcgcggt cgtcaccggc acggcacggg aaggcaccac cgcgttcctg   4680
ttcacgggac agggcgcgca gcgggccggc atgggccgcg agctctacga cacgtacccg   4740
gtcttccggg acagcttcga cgaggtctgc gccaccctcg accggcatct gaacgccgaa   4800
cagccggtca aggacgtcgt cttcgccgac gacgccaccc tgctcaacca gacccgctac   4860
acccaggccg ctctcttcgc gatcgagacc tcgctctacc gcctggtcga atcattcggg   4920
atcaccccgc agcacctgac cggccactcc atcggtgaac tcaccgccgc ccatatcgcg   4980
ggcgtcttca ccctgaacga cgcctgccgg ctcgtcgccg cgcgcggctc actgatgcag   5040
gccctgcccg ccaacggcgc gatgatctcc ctgcgcgcca ccgaggagca gatccttccg   5100
ttcctcgaag gccacgagca ccacgtcgcc atcgcggcgg tcaacgggcc caactcgatc   5160
gtcatatcgg gcgaccagga agccaccacc gccatcgcgg aagccctggc cgagacaggt   5220
gtcaagacgc ggcgcctcac ggtctcccac gcgttccact ccccccacat ggaccccatg   5280
ctggaggagt tcgagcgtac ggcggcggac ctgacgtacc acgccccgac gagcccgatc   5340
gtctccaacc tcaccggcca actcgccgac caccgcatca ccaccccgca gtactgggtc   5400
cagcacgtcc gggacgccgt gcgcttcgcc gacaccatca ccaccctcga tcagctcggc   5460
acccggcact acctcgaact cggacccgac cccgtcctca ccactctcgt caacgagacc   5520
ctcggcaaga cccggggcac catccccacc gccgtcctgc gcaaggggca ctccgaagcc   5580
gccacgcttc tcacggcgct cgccaccgcg tacaccgccg gcgcgcccgt caacctcagc   5640
agccacctcc cggcccccca cacccacccc gacctgccca cgtacccctt ccagcgccag   5700
cgttactggc acgcggccac caccgccacg ggagacgtgt cgtcggccgg gctgaccgcc   5760
acgggacacc cggtgctgac cacggccgcc gagcttcccg atccgggcgg gttgctgctg   5820
accggccggg tgaacgcggc gtcacccgcc tgggcggcgg accacgccgt cttcggcacc   5880
ccggtcatgc cgggcgtggc gttcgtcgac atgctgctgc acgccgcggc gctggtcggg   5940
cgccctcgta tcgaggaact cacccaccat gtcttcctgg ccctgccgga acacggcgcc   6000
ctccagctga gggtggtcgt ccgcccggcg gacgactccg ggcggcggtc cttcgccgtc   6060
```

-continued

```
cactcgcggc ccgaggacgc cccgctgggc gccgactgga cctgccacgc caccggtgcg   6120
ctgggcgtcg ccccggccgt accgccggcc cttccgcccg tggacgcggc ctggcccccg   6180
gcctccgccg cggtcctcga caccgacggc ttctaccggc ggatcgccga ggccgggttc   6240
ggctacgggc cggtcttcca ggggctcgcc gccgcctggg aggacggaga cacgctgtac   6300
gccgaggtcg ccctgcccgc ggggacctcc ccgggctcgt acggcgtcca ccccggcctg   6360
ctcgactccg cgctgcaccc gatcgccctg gccgcgaccg gtgccgagac ggacggcaca   6420
ctccatgtgc cgttctcctg gagcggtgtg acgctccacg cgtccggcgc gcacaccctg   6480
cgcgtccggc tcgtgcgctc cacgccggag acggtcgcgc tgaccgtcac ggacccgtcc   6540
ggcgcgccgg tgctgaccgt cgactccctc gccatgcgcg gggtccgtgc cgagcagctc   6600
gaagccgcca ggcccgaccg cgacggtgcg ctgcacgacg tcgcctggcg cgcggtgccc   6660
gcgccgccac gcgccaactc gcgccccgac ggcgtcggct gggccgtggt gggagacacc   6720
cgtgacccgc gagtcgccgc cgtgctggca tcgctcggtg cggccgccga gtcgtacccg   6780
gacgccgaag cgctgcgcgc ctcgttgcgg gccggcgcgg tccggccctc gacgatcgtc   6840
gcccgcttcg ccaccgggac cgccgaagac ggcgccgacc cggtcgcggc ggcacacacc   6900
gggacacgcc acgccatgca cctgctccag gccgtcctgg ccgacggggc accggactcc   6960
cggctggtga tcctcaccga gaacgcgaga tacaccggaa ccggcgacgc ggcggccgac   7020
atggccggtg cggcggtctg gggcctgatc cgttcggccc agtccgagca ccccgaccgg   7080
ttcacgctcc tcgacgtcga cggctcgcgg gcctccgacg aggccgtcgt cgcggcgctc   7140
tccgccggtg agccccaact ggccgtacgc gaaggccggc tgttcgttcc ccgcctcgcc   7200
cgtctgaccc cgggcgcgat tcccgccacg ttcgacgcgc ggcgtacggt gctcatcacc   7260
ggcggcaccg gcgcgctggg ctcgattctc gcgcgccacc tggtcacccg gcacggcgtc   7320
aggaagctgc tgctgaccag caggagcggt cgtacggcgg acagcaccgt cgtcgcggaa   7380
ctcgccggac tcggcgccga ggtcaccgtc gcggcctgcg acgtcaccga ccggctgtcg   7440
ctggagaccc tgctcgcggg cctgccgacg gagcatccgc tcggcgcggt cgtgcactgc   7500
gcgggcgtcc tggacgacgg tgtggtcacg gagctgaccg aggaccggct ggacgcggtg   7560
ctccgcccga aggtggacgg cgcgtggaac ctgcaccagg tgacccgtga catgggcctg   7620
gacctggacg ccttcgtgct gttctcgtcc gtggtcggtg tcctcggctc gcccggacag   7680
gccaactacg ccgccgccaa ctccttcctc gacgaactcg ccgagcaccg ccgtacggcc   7740
gggctccccg ccaagtccct cgcctgggga ctgtgggaga gcggcatggc cgacaccctc   7800
gacgagcagg accgggcgcg gatgagccgc ggcggactct cgccgatgcc cgccgagcgg   7860
gcgctcgcgc tcttcgactc ggcactcgcg acggcgcggg cggtgctcgt gcccgccggg   7920
gtcgatgtct cccacgcgcg cacgcagcgg gcgtcgatgc tctcccctct gctcgccgaa   7980
ctgctcccgg cccaggcggc gcccgccgaa cgaggcggtg aagcggtcga cgagtcctcg   8040
ctgcgccagc agttggccct cctgcccgag cccgaacagc gcgaactcct cctggaggtc   8100
ctgcgcaagc atgtcgcggc ggttctgggc cacagctctc cgctcgtcat cgaccccgag   8160
agctcgttca aggacctcgg tttcgactcg ctcgccggca tcgaactcct catggtgctg   8220
ggcgagtcca tggggctgca cctgccgtcc acgatgctgt tcgaccaccc gacgcccgag   8280
ttgctgatca cccacctcag ggacgaactg gtcgacgacg aggccgtacc tgtcaccgcc   8340
gcggacaccg cggccgtcgc cgtggcacca cgcgacgacg acgaacccat cgccgtgatc   8400
ggcatggggt gccgctaccc gggcggcgcc accacgccgg acgagctgtg gcgactggtc   8460
```

-continued

```
accgaggggg tggacgccat cggctccttc cccaccaacc gcggctggga tctggaggag   8520
ctgttcgatc ccgaccccga catgcgcggg aagacctatg cccgcaaggg cgggttcctc   8580
tacgacgccg accgtttcga ccccgagttc ttcggcatca gcccccgcga ggccctggcg   8640
ctcgacccgc agcagcgact cctcctggag accacctggg agacgttcga gaacgcgggc   8700
atccgccccg acaccctgcg cggcaagccc gtcggcgtct tcgccggcgt cgtcacccag   8760
gagtacggct ccctcgtcca ccggggcacc gagccggtcg acggcttcct gctgacgggt   8820
acgacggcga gtgtcgcctc cgggcgactg gcctacacgc tgggtcttga gggcccggcg   8880
gtcaccgtcg acaccgcgtg ctcctcctcg ctggtcgcga tgcacctggc ctgccagtcg   8940
ctgcggaaca acgagtccac gatggccctg gccggtggcg ccacggtgat ggccaacccc   9000
ggaatgttcc tggagttcag ccgccagcgc ggtctggctc ccgacggccg gtgcaagtcg   9060
ttcgccggtg gcgccgacgg caccatctgg gccgagggcg cgggcatggt cctcctggag   9120
cgtctgtcgg acgccaaggc caacggacac accgttctcg ccgtgatccg cggctcggcc   9180
gtcaaccagg acggcgccag caacggactg accgctccga gcggcccgtc ccagcagcgg   9240
gtcatcaccg ccgctctggc cggcgcgggc ctcacctccg accaggtcga cgcggtcgaa   9300
ggacacggca ccggaacccc gttgggcgac ccgatcgagg cccaggcgct cctggcgacg   9360
tacggccagg gccgtgaagc cgaccagccg ctgtggctcg ggtcgttcaa gtcgaacatc   9420
ggccacgcgc aggccgccgc cggtatcggc ggggtcatca agatgatcca ggccatgcgc   9480
cacggcactc tcccccggac cctgcacgtc gacgagccca gcccgcacat caactgggcc   9540
tcgggcaacg tgcggctcct caccgaggag cgcgcctggc ccgagaccga ccacccgcgc   9600
cgctccgccg tctcctcctt cggcatcagc ggcaccaacg cccatgtcat cctcgaacag   9660
gcccccgcga cgccggagcc cgccgaggat gaccacgagc aggacgcgcc gcaggcgacc   9720
ctggtcccgt gggtcctgtc cggcaagacg gagcaggccc tccgcgacca ggcgcagcag   9780
ctgcgcacgt acctcgaact caaccccggg ctgcgcacgg accgagtcgc tcacgcgctc   9840
gccaccaccc gcgcccagtt ccagtaccgg gccgtggtgc tcggcaccga ccaccaggcg   9900
ttcgaccgtg ccctgggcac gctcaccctc ggcgagccgt ccccggcgct ggtacgcggg   9960
acgccgcacc ccggcaagac agccttcatg ttcacgggac agggcgcgca gcgggccggc  10020
atgggccgcg agctctacga cacgtacccg gtcttccggg acacgttcga cgaggtctgc  10080
gccaccctcg accggcatct gaacgccgaa cagccggtca aggacgtcgt cttcgccgac  10140
gacgccatcc tgctcaacca gacccgctac acccaggccg ctctcttcgc gatcgagacc  10200
tcgctctacc gcctggtcga atcattcggg atcaccccgc actacctgac cggccactcg  10260
atcggtgaga tcacggccgc ccacgtggcc gggatcttca ccctcgacga cgcctgccga  10320
ctggtcgccg cgcgcggctc actgatgcag gctctgcccg ccaacggcgt catgatctcg  10380
ctgcgggcca ccgaggagca gatcgtcccg ttcctcgaag gccacgagca ccacgtcagc  10440
gtcgcggcgg tcaacgggcc cagctcgatc gtcatctcgg gcgaccagga agccaccacc  10500
gccatcgccg gcgctctcgc cgagacgggt gtcaagacgc ggcgcctcac ggtctcccac  10560
gcgttccact ccccccacat ggaccccatg ctggacgagt tcgaactcgt ggccggagag  10620
ctgacctacc acgccccgac gatcccgatc gtctccaacc tcaccggcca actcgccgac  10680
cactacatca ccaccccgca gtactgggtc cagcacgtcc gggaggccgt ccgcttctcc  10740
gacggcatca ccaccctcga ccggctcggc acccggcact acctcgaact cggacccgac  10800
```

-continued cccgtcctca ccaccatggc gcaggacagc gtggccgatg acagcgacgc cgccctcgtc 10860
gccaccctgt accgcgaccg ggacgagaac cacagcttcc tcaccgccct ggccacggca 10920
cacgcccatg gcatccaggt cggctggacc cccgtggtcg gtgagacctc ggtccccgcc 10980
ctcggcctcc ccacctaccc cttccagcgc cagcactact ggctggaggc ggcgaagccc 11040
acctcgggtg ccgacggtct ggggctgacg gcgaccgacc atccggtgct gaccaccttg 11100
gccgaactcc cggacggagg cgggcacctg ttcaccggcc gcgtctccgg gaacgatccg 11160
gactgggtgg ccgagcacat catcttcggg acaatgatcg ttccgggtgt ggccttcgtc 11220
gacctcctgc tccacgcggc acgccatgtg gactgcgagc acatcgagga actcacccac 11280
cacgtgttcc tcgccgtgcc ggagcgcgcc gccctccagc tgcggctcct gatcgagccg 11340
gcggacagct ccggaagccg ggccttcgcg ttctactcgc ggccggagga cgtcccggtc 11400
gaaaccgact ggaccctcca cgccacgggc gcgctcggag ccgaacgcag ggaagtcccc 11460
gcgggcgccg actcgctcag gaacgaggtc tggccgcctg acatctcgga caccatggac 11520
gtgggggagt tctaccgccg ggtcacggac ggtggcttcg gctacggacc gctgttccga 11580
gggctcaaga aggcctggca ggacgggaac acgacgtacg cggaagtctc cttgcccgcc 11640
ggctccgatc ccggcgacta cggcatccac cccggtctgc tcgactcggc gctccagccg 11700
gccgcgctca tcatgggaga gaccgaggcg gccgactcga tccgggtgcc gttctcctgg 11760
gccggtgtgt ccctccacgc gacgggggcc gactccctgc gtatccgcca cacgtggacc 11820
acaccggaca ccgcgtcgct ggtcatcgcc gaccagacgg ggacaccggt catgacgatc 11880
gactccctcg ccatgcggac ggtcggcgcc gaccaactcg ccgccacccg tgcggcggac 11940
gccggagagc tgtacaaggt cgactggttc gacgtccaga ccgtggagga caagacccag 12000
ggcgcgggca ccgccaagtg ggcggtggtc gccgacccgg ggaacaccca ggtcgccgcg 12060
gcactctccc cgctcggcgc cgcggtcgag gtggagccgg acgcggtgac gctcccgacg 12120
acaccggggg acgacaccac ccggccggac gtggtcttca catggtgcgt ctccgagccc 12180
ggcgccgacc cggcacaggc cgcgcgctcc ttcacccacc gcgtgctcgg cctcgtccag 12240
gcggtcctct ccgacgatcg gccggactcc cgcctggtga tcctcaccaa gggcgcgatg 12300
tccgccggta gcggcggcgc ggccgacctg gccggagccg cggtctgggg gctgatccgc 12360
accgctcaga ccgaacaccc cgatcggttc atcctgatgg acctcgacgg ttcggatgcg 12420
tcgctgcggg ccgtgggcgc tgccctgaac gccggcgaac cccaactcgc cgttcgcgac 12480
ggccggctcc tcgcccctcg cctcgcccgt atcggcaccg ccgactccga gccgaccgcc 12540
gcaccggcgt cgttcgaccc ggacaagacg gtgctcatca ccggcggcac cggcgccctg 12600
ggcacgctcc tcgcccgtca cctggtcacc cgccacggtg tgaagaagct gctcctgacc 12660
agccggcgcg gccgtccggc aggcagcacc atcaccgcgg aactcgccga actcggcgcc 12720
gaggtcacca tcgtggcctg cgacgcggcg gaccgggagt cgctggaagc cctgctcgcg 12780
agcctgccgg acgagcatcc gctcggagcg gtggtgcact gcgcgggaac gctcgacgac 12840
ggcatcgtca cggcgctgac acctgaccgg ttcgacgagg tgctccggcc gaaggtggac 12900
ggcgcgtgga acctgcacga gctgacccgt gacctggacc tggacgcctt cgtgacgttc 12960
tcgtccgtgg tcggtgtcct cggctcgccg ggacagtcca actacgccgc cgcgaacgtc 13020
ttcctcgacg agctggccga acaccgccgt acggccggac tgcccgccaa gtccctcgcc 13080
tggggactgt gggagagcgg catggccgac accctcgacg agcaggacca ggcgcggatg 13140
aaccgcggcg gcctcctgcc gatgcccgcc gaacaggcac tcgggcactt cgactcggcg 13200

-continued

```
ctcgcgaccg accagaccgt cgtggtcccg gccaagctcg acctcgccgg gctccgtgcc  13260
cgcgccgcga cggtcccggt ggcgccgatc ttccgtgggc tggtccgtac gccgctgcgc  13320
agcgccgccc aggcgggcgg cgcgggagcg gaggtcggag ccctggggca gtcgatcgcg  13380
ggccgcccgg aggccgagca ggaccagatc atcctggact tcctgcgcaa tcacgtggcc  13440
accgtcctcg gacacggctc ggcgaacgcg atcgaccccg cgcactcctt caaggagctg  13500
ggcttcgact cgctcagctc ggtggaactg cgcaactcgc tcaacaaggc gtccgggatg  13560
cgactcccgt ccaccctgtt gttcgactac cccacccct cggtactggc cggctacatc  13620
cgcaaccaac tggcgggcgg caagcaggcg gaggcaggcg cgcaagtggc ccgccgcacc  13680
gttcgcccgg cgtcctcgcg gagcgacgcg gccgacccga tcgtgatcgt gggcatgggg  13740
tgccgcttcc ccggtggcgc cgacacgccc gaggcgctgt ggaagctggt cgcggacgag  13800
cgtgacgcgg tgggggcctt ccccgacaac cgcggctggg acatcgagaa cctcttcgac  13860
gacgaccccg acgtacgggg gaagtcgtac gccagtgagg gcgggttcct ctacgacgcc  13920
gaccgtttcg accccgagtt cttcggcatc agccctcgcg aggccctggc gctcgacccg  13980
cagcagcggc tgctgctcga aaccacctgg gaagcgttcg agaacgcggg catccgcccc  14040
gacactctgc gcggcaagcc cgtcggcgtc ttcgccggcg tcgcggccgg ggagtacgtc  14100
tcgctcaccc accacggcgg cgagcccgtc gagggttacc tgctgacggg tacgacggcg  14160
agtgtcgcct ccgggcgcat ctcgtacacg ctgggtcttg agggccccgc ggtcaccgtc  14220
gacacggcct gctcgtcgtc gctcgtcgcg atgcacctgg cgtgccagtc actgcggaac  14280
aacgagtcca cgatggccct ggccggcggc gccacgatca tgtccaacgc gggcatgttc  14340
atggagttca gccgccagcg tggtctggct cccgacagcc gtgccaagtc ctacgcgggc  14400
gccgccgacg gcaccatctg ggccgagggc gcgggcatgg tcctcctgga gcgtctgtcg  14460
gacgccaagg ccaacggaca cacggtcctg gccgtcatcc gcggctcggc cgtcaaccag  14520
gacggcgcca gcaacggcct caccgccccc aacgggccct cgcagcagcg ggtcatcaac  14580
acggcgctcg ccagcgcggg tctcaccccc gaccaggtcg acgccgtcga aggacacggc  14640
accggaacgc cgctgggtga cccgatcgag gcccaggccc tgctctccac ctacggccag  14700
aaccgtgaag agccgctgtg gctcggatcg ttcaagtcca acatcggcca cgcgcaggcc  14760
gccgccggcg tcggcggggt catcaagatg atccaggcca tgcgccacgg caccctgccc  14820
cggacgctcc acgtcgacga gcccagcccg aacatcgact gggactccgg caatgtgcgg  14880
ctcctgaccg aggcccgggc ctggcccgag accgaccgcc cgcgccgctc cgccgtctcg  14940
tccttcggca tcagcggcac caacgcccac ctcatcctgg aggaagcgcc cactcccacc  15000
caccctgagc cggcccccga gagcgcaccg caggcaacca cggtgccctg gatactctcg  15060
ggcaagagtg aacaggccgt gcgggaccag gcccagcgct tgctcgacca cgtcagcgag  15120
taccccgagc tccagccggt cgacatcgcg tactcgctgg ccaccgcccg tacctccttc  15180
gagcgccagg ccgtcgcgat cggcgccacc catgacgaac tcgtcgacca cctccgctcg  15240
ctgacccagg accccggcac cgccctcctg cacggccagt cccactccaa gaaggtggcc  15300
ctcctcttca ccggtcaggg ctcccagcac ccgggcatgg gccgtcagct ctacgacacg  15360
caccccgtct accgggacgc gttcgacgag gtgaccgcca ccctggacca gcacctccag  15420
gccgaacagc cggtcaagga cgtcgtcttc gccgacgacc ccaccctgct caaccagacc  15480
cggtacaccc agcccgccat cttcgccctc caggtggccc tcacccggct cctcgtcgac  15540
```

-continued

```
gagttcggcg tctcccccac ccatctcatc ggccactcga tcggcgagat ctcggcggcc    15600

cacacggcgg ggatcctcac cctcgacgac gcctgccggc tggtcgccgc ccgcggcact    15660

ctcatgcaga ccctccccgc caccggcgcg atgacggccg tcgaggcgac cgaggaagag    15720

gtgctcccgc acctcacgga gcgggtcggt atcgccgcgg tgaacggccc gcgttcggtg    15780

gtcgtctccg gggacgaagc cgctgtcatc gccgtcggcg aggagttcgc cggtcaggga    15840

cgacgcatcc gccgtctcac cgtcagccac gccttccact cgcaccacat ggacccgatg    15900

ctcggcgagc tccacgcggt ggccgacacg ctgacctacc acgtgccacg caccccgctc    15960

gtctccaccg tcaccggccg cctggccggc tccgagatca ccagcgccac ctactggagc    16020

gatcacgccc gcaacgccac ccgcttccac gacggcctca acacgcttca cgagcagggc    16080

gtcaccacgt acatcgaggt cggccccgac gccgtactcg ccgcgctgac ccgtgaagcg    16140

ctgcccgacg ccaccgccgt accgctgatc cgggccaagg cctccgagcc ggccactctg    16200

ctcgacgggc tcgtccgggc tcacgtgtcc ggcgccacgg tcgactgggc agggttcctc    16260

gcacgacgcg ggggcaggag cgtcgaccTt cccacgtacg ccttccagcg tcggcgccac    16320

tggctggaga ccgccgaccc cgtcggtacg gccgccggcc tcggtctgga gtccgcctcc    16380

cacccgctgc tggccacgac caccgaactc ccggacggaa ccgccctgtt cacggggcgg    16440

gtgacgctgg ccgaccaccc gtggctcagc gaccacaccg tcatgggaac ggtcatcctc    16500

ccgggcacgg ccttcgtgga gctcgcgctc cacgcggccg agacggtggg tctcgacgag    16560

atagcggaac tcgtcctgca cgcgccggtc accttcgggt cccagtccgc ggcccttctc    16620

caggtgatcg tcggacctga cgacccgtcg gcgggccgga ccctcaccat caggtcccgt    16680

tcggaagagg accagtcctg gaccgagaac gcgaccggca cgctcggcgc actggtgggg    16740

gtctcctga                                                            16749
```

<210> SEQ ID NO 5
<211> LENGTH: 5582
<212> TYPE: PRT
<213> ORGANISM: Streptomyces sp. MP28-13

<400> SEQUENCE: 5

```
Met Arg Glu Ala Leu Ala Ile Met Ser Ser Asp Leu Val His Gly Thr
1               5                   10                  15

Asp Ala Ile Ala Ile Thr Gly Met Ser Cys Arg Leu Pro Gln Ala Pro
            20                  25                  30

Asp Ala Asn Ser Phe Trp Glu Leu Leu Arg Ser Gly Arg Ser Ala Ile
        35                  40                  45

Thr Glu Val Pro Pro Asp Arg Trp Asp Pro Asp Glu Val Leu Pro Asp
    50                  55                  60

Ser Pro Glu Arg His Arg Ala Ala Leu Arg His Gly Gly Phe Leu Asp
65                  70                  75                  80

Arg Val Asp Gln Phe Asp Ala Ala Phe Phe Gly Ile Ser Pro Arg Glu
                85                  90                  95

Ala Val Ala Ile Asp Pro Gln Gln Arg Leu Phe Ala Glu Leu Ala Trp
            100                 105                 110

Glu Ala Leu Glu Asp Ala Gly Ile Val Pro Glu Thr Leu Arg Ser Thr
        115                 120                 125

Ala Thr Ala Val Ile Val Gly Ala Ile Ala Gly Asp Tyr Ala Ala Leu
    130                 135                 140

Ala His Arg Gly Gly Ala Ile Thr Gln His Ser Leu Pro Gly Leu Asn
145                 150                 155                 160
```

-continued

```
Arg Gly Val Ile Ala Asn Arg Val Ser Tyr Ala Leu Gly Leu Asn Gly
                165                 170                 175

Pro Ser Met Ala Val Asp Ser Ala Gln Ser Ser Ser Leu Val Ala Val
            180                 185                 190

His Leu Ala Val Glu Ser Leu Arg Lys Gly Glu Cys Thr Leu Ala Leu
        195                 200                 205

Ala Gly Gly Val Ala Leu Asn Phe Ala Pro Glu Ser Ala Glu Val Ala
    210                 215                 220

Gly Met Phe Gly Gly Leu Ser Pro Asp Gly Arg Cys Phe Thr Phe Asp
225                 230                 235                 240

Ala Arg Ala Asn Gly Tyr Val Arg Gly Glu Gly Gly Gly Val Val Val
                245                 250                 255

Leu Lys Pro Leu Ala His Ala Val Arg Asp Gly Asp Thr Val Tyr Gly
            260                 265                 270

Val Ile Arg Gly Thr Ala Val Asn Asn Asp Gly Ser Thr Asp Gly Leu
        275                 280                 285

Thr Val Pro Ser Ala Glu Ala Gln Ala Thr Val Leu Arg Gln Ala Cys
    290                 295                 300

Glu Asp Ala Gly Val Asp Pro Ala Glu Val Arg Tyr Val Glu Leu His
305                 310                 315                 320

Gly Thr Gly Thr Pro Thr Gly Asp Pro Leu Glu Ala Ala Gly Val Gly
                325                 330                 335

Ala Ala Tyr Gly Ser Ala Arg Pro Ala Gly Ser Pro Val Leu Val Gly
            340                 345                 350

Ser Ala Lys Thr Asn Val Gly His Leu Glu Gly Ala Ala Gly Ile Val
        355                 360                 365

Gly Leu Ile Lys Thr Ala Leu Ser Ile Arg His Arg Glu Ile Pro Ala
    370                 375                 380

Ser Leu Asn Tyr Glu Thr Pro Asn Pro Arg Ile Asp Pro Glu Ala Leu
385                 390                 395                 400

Asn Leu Arg Val Gln Thr Ala Ser Gly Pro Trp Pro Asp Ala Pro Leu
                405                 410                 415

Leu Ala Gly Val Ser Ser Phe Gly Val Gly Gly Thr Asn Cys His Val
            420                 425                 430

Val Leu Ala Glu Ala Pro Glu Arg Ala Ala Ser Glu Glu Asp Ala Pro
        435                 440                 445

Gln Gly Asp Glu Pro Glu Ile Pro Leu Ala Pro Trp Leu Val Ser Gly
    450                 455                 460

Arg Thr Glu Ala Ala Leu Arg Ala Gln Ala Gly Arg Leu Leu Glu Arg
465                 470                 475                 480

Arg Thr Ala Asp Ala Asp Ala Phe Asp Ile Gly Arg Ser Leu Ala Gly
                485                 490                 495

Thr Arg Thr His Phe Glu His Arg Ala Val Ala Leu Gly Leu Gly His
            500                 505                 510

Asp Ala Gln Leu Glu Ala Leu Arg Ser Gly Ala Asp Val Pro Gly Leu
        515                 520                 525

Val Thr Gly Val Thr Gly Asp His Gly Lys Ile Ala Leu Val Phe Pro
    530                 535                 540

Gly Gln Gly Ser Gln Trp Glu Gly Met Ala Arg Glu Leu Met Arg Thr
545                 550                 555                 560

Ser Ala Val Phe Arg Ala Ser Ile Glu Ala Cys His Glu Ala Leu Ala
                565                 570                 575
```

-continued

```
Pro Tyr Val Asp Trp Ser Leu Leu Asp Thr Leu Thr Asp Glu Ser Gly
            580                 585                 590

Ala Thr Ser Leu Asp Arg Ala Asp Val Val Gln Pro Val Leu Phe Ala
        595                 600                 605

Val Met Val Ser Leu Ala Arg Val Trp Glu Ser Leu Gly Val Arg Pro
    610                 615                 620

Asp Ala Val Ile Gly His Ser Gln Gly Glu Ile Ala Ala Ala His Ile
625                 630                 635                 640

Ala Gly Ala Leu Asp Leu Ala Asp Ala Ala Arg Ile Val Ala Leu Arg
                645                 650                 655

Ser Gln Thr Ile Met Thr Leu Ala Gly Thr Gly Ala Met Ala Ser Val
            660                 665                 670

Pro Leu Ala Ala Asp Arg Val Thr Glu Tyr Ile Ala Pro Phe Gly Asp
        675                 680                 685

Gly Leu Ser Ile Ala Ala Val Asn Gly Pro Thr Thr Thr Val Val Ala
    690                 695                 700

Gly Asn Pro Asp Ala Ile Ala Glu Leu Leu Ala Arg Cys Glu Ala Glu
705                 710                 715                 720

Gly Ile Arg Ala Arg Ala Val Ser Ala Val Asp Phe Ala Ser His Ser
                725                 730                 735

Ser His Met Glu Ala Val Lys Asp Arg Leu Leu Glu Gln Phe Ala Glu
            740                 745                 750

Val Thr Pro Arg Ser Cys Asp Ile Ala Phe Tyr Ser Thr Val Thr Ala
        755                 760                 765

Ser Ala Ile Asp Thr Ala Gly Leu Asp Ala Gly Tyr Trp Tyr Ser Asn
    770                 775                 780

Leu Arg Arg Pro Val Leu Phe Glu Ala Thr Leu Arg Ala Met Ala Glu
785                 790                 795                 800

Asp Gly Phe Gly Thr Phe Val Glu Ser Ser Pro His Pro Val Leu Thr
                805                 810                 815

Leu Gly Leu Arg Ala Thr Leu Pro Asp Ala Leu Val Ala Asp Ser Leu
            820                 825                 830

Arg Arg Asn Glu Ala Pro Trp Pro Gln Leu Leu Thr Ser Leu Ala Glu
        835                 840                 845

Leu His Val Ser Gly Leu Pro Val Asp Trp Ser Ala Val Phe Lys Gly
    850                 855                 860

Arg Thr Pro Gly Arg Val Ala Leu Pro Thr Tyr Ala Phe Gln Arg Glu
865                 870                 875                 880

Arg Tyr Trp Pro Glu Val Ser Thr Ala Phe Glu Pro Gly Thr Arg Gly
                885                 890                 895

Ala Val Gln His Gln Glu Ala Ala Arg Glu Glu Ile Pro Ala Ala Ser
            900                 905                 910

Ser Thr Trp Ser Asp Arg Leu Ala Gly Leu Pro Ala Asp Glu Arg Ser
        915                 920                 925

Arg Glu Ala Leu Glu Leu Val Arg Leu Arg Thr Ala Ile Val Leu Gly
    930                 935                 940

His Leu Ser Thr Asp Gly Val Asp Val Gly Gln Ala Phe Arg Glu Leu
945                 950                 955                 960

Gly Met Asp Ser Thr Met Ala Val Gln Leu Arg Gln Asn Leu Val Asp
                965                 970                 975

Ile Thr Gly Leu Ala Leu Pro Glu Thr Val Val Phe Asp Tyr Ala Ser
            980                 985                 990

Pro Ser Arg Leu Ala Ser Arg Leu  Cys Glu Leu Ala Leu  Gly Glu Asp
```

```
        995                 1000                1005

Thr Ser  Ser Ala Ala Ser Ala  Leu Ser Arg Ser Ala  Ser Val Leu
    1010                 1015                 1020

Asp Ala  Asp Asp Pro Ile Val  Ile Val Gly Met Ala  Cys Arg Tyr
    1025                 1030                 1035

Pro Gly  Gly Ala Ser Thr Pro  Asp Glu Leu Trp Gln  Leu Val Asp
    1040                 1045                 1050

Asp Gly  Val Ser Ala Ile Ser  Gly Phe Pro Thr Asp  Arg Gly Trp
    1055                 1060                 1065

Asp Leu  Asp Ala Leu Tyr Asp  Pro Glu Pro Gly Val  Arg Gly Lys
    1070                 1075                 1080

Thr Tyr  Thr Arg His Gly Gly  Phe Leu Asp Glu Ala  Ala Glu Phe
    1085                 1090                 1095

Asp Thr  Glu Phe Phe Gly Ile  Ser Pro Arg Glu Ala  Thr Ala Met
    1100                 1105                 1110

Asp Pro  Gln Gln Arg Leu Leu  Leu Gln Val Thr Trp  Glu Ala Leu
    1115                 1120                 1125

Glu Arg  Ala Gly Ile Asp Pro  Asp Gly Leu Gln Gly  Ser Ser Thr
    1130                 1135                 1140

Gly Val  Phe Val Gly Ala Met  Ser Gln Glu Tyr Gly  Pro Arg Leu
    1145                 1150                 1155

His Glu  Gly Asp Asp Gly Leu  Gly Gly Tyr Leu Leu  Thr Gly Thr
    1160                 1165                 1170

Thr Ala  Ser Val Val Ser Gly  Arg Ile Ser Tyr Thr  Phe Gly Leu
    1175                 1180                 1185

Glu Gly  Pro Ala Val Thr Val  Asp Thr Ala Cys Ser  Ser Ser Leu
    1190                 1195                 1200

Val Ala  Met His Gln Ala Ala  Gln Ala Leu Arg Val  Gly Glu Cys
    1205                 1210                 1215

Ser Leu  Ala Leu Ala Gly Gly  Val Ala Val Met Ala  Thr Pro Gly
    1220                 1225                 1230

Met Phe  Val Glu Phe Gly Gln  Gln Arg Gly Leu Ala  Pro Asp Gly
    1235                 1240                 1245

Arg Cys  Lys Ser Phe Ala Gly  Ala Ala Asp Gly Thr  Ile Trp Ala
    1250                 1255                 1260

Glu Gly  Ala Gly Met Val Leu  Leu Glu Arg Leu Ser  Asp Ala Lys
    1265                 1270                 1275

Ala Asn  Gly His Thr Val Leu  Ala Val Ile Arg Gly  Ser Ala Val
    1280                 1285                 1290

Asn Gln  Asp Gly Ala Ser Asn  Gly Leu Thr Ala Pro  Asn Gly Pro
    1295                 1300                 1305

Ser Gln  Gln Arg Val Ile Thr  Ala Ala Leu Ala Gly  Ala Gly Leu
    1310                 1315                 1320

Thr Pro  Asp Gln Val Asp Ala  Val Glu Ala His Gly  Thr Gly Thr
    1325                 1330                 1335

Pro Leu  Gly Asp Pro Ile Glu  Ala Gln Ala Leu Leu  Ala Thr Tyr
    1340                 1345                 1350

Gly Gln  Asn Arg Glu Glu Pro  Leu Trp Leu Gly Ser  Leu Lys Ser
    1355                 1360                 1365

Asn Ile  Gly His Thr Gln Ala  Ala Ala Gly Ile Gly  Gly Val Ile
    1370                 1375                 1380

Lys Met  Ile Gln Ala Met Arg  His Gly Thr Leu Pro  Arg Thr Leu
    1385                 1390                 1395
```

```
His Val  Asp Glu Pro Ser Pro  His Ile Asp Trp Asp  Ser Gly Asn
    1400                 1405                 1410

Val Arg  Leu Leu Thr Glu Ala  Arg Ala Trp Pro Glu  Thr Asp His
    1415                 1420                 1425

Pro Arg  Arg Ser Ala Val Ser  Ser Phe Gly Ile Ser  Gly Thr Asn
    1430                 1435                 1440

Ala His  Leu Ile Leu Glu Gln  Ala Pro Ala Thr Pro  Glu Pro Val
    1445                 1450                 1455

Asp Gly  Asp Asp Glu Gln Glu  Thr Pro Gln Gly Ala  Leu Val Pro
    1460                 1465                 1470

Trp Phe  Leu Ser Ala Lys Ser  Ala Pro Ala Leu Arg  Asp Gln Ala
    1475                 1480                 1485

Gln Arg  Leu Leu Asp His Val  Ile Ala Arg Pro Gly  Val Asp Pro
    1490                 1495                 1500

Ala His  Ile Gly Arg Ala Leu  Thr Ala Thr Arg Ala  Arg Phe Gln
    1505                 1510                 1515

His Arg  Ala Val Val Val Gly  Glu Gly Arg Asp Glu  Leu Leu Ala
    1520                 1525                 1530

Gly Leu  Arg Ala Leu Ser Asn  Asp Glu Ser Ser Arg  Ala Val Val
    1535                 1540                 1545

Thr Gly  Thr Ala Arg Glu Gly  Thr Thr Ala Phe Leu  Phe Thr Gly
    1550                 1555                 1560

Gln Gly  Ala Gln Arg Ala Gly  Met Gly Arg Glu Leu  Tyr Asp Thr
    1565                 1570                 1575

Tyr Pro  Val Phe Arg Asp Ser  Phe Asp Glu Val Cys  Ala Thr Leu
    1580                 1585                 1590

Asp Arg  His Leu Asn Ala Glu  Gln Pro Val Lys Asp  Val Val Phe
    1595                 1600                 1605

Ala Asp  Asp Ala Thr Leu Leu  Asn Gln Thr Arg Tyr  Thr Gln Ala
    1610                 1615                 1620

Ala Leu  Phe Ala Ile Glu Thr  Ser Leu Tyr Arg Leu  Val Glu Ser
    1625                 1630                 1635

Phe Gly  Ile Thr Pro Gln His  Leu Thr Gly His Ser  Ile Gly Glu
    1640                 1645                 1650

Leu Thr  Ala Ala His Ile Ala  Gly Val Phe Thr Leu  Asn Asp Ala
    1655                 1660                 1665

Cys Arg  Leu Val Ala Ala Arg  Gly Ser Leu Met Gln  Ala Leu Pro
    1670                 1675                 1680

Ala Asn  Gly Ala Met Ile Ser  Leu Arg Ala Thr Glu  Glu Gln Ile
    1685                 1690                 1695

Leu Pro  Phe Leu Glu Gly His  Glu His His Val Ala  Ile Ala Ala
    1700                 1705                 1710

Val Asn  Gly Pro Asn Ser Ile  Val Ile Ser Gly Asp  Gln Glu Ala
    1715                 1720                 1725

Thr Thr  Ala Ile Ala Glu Ala  Leu Ala Glu Thr Gly  Val Lys Thr
    1730                 1735                 1740

Arg Arg  Leu Thr Val Ser His  Ala Phe His Ser Pro  His Met Asp
    1745                 1750                 1755

Pro Met  Leu Glu Glu Phe Glu  Arg Thr Ala Ala Asp  Leu Thr Tyr
    1760                 1765                 1770

His Ala  Pro Thr Ser Pro Ile  Val Ser Asn Leu Thr  Gly Gln Leu
    1775                 1780                 1785
```

-continued

```
Ala Asp His Arg Ile Thr Thr Pro Gln Tyr Trp Val Gln His Val
    1790                1795                1800

Arg Asp Ala Val Arg Phe Ala Asp Thr Ile Thr Thr Leu Asp Gln
    1805                1810                1815

Leu Gly Thr Arg His Tyr Leu Glu Leu Gly Pro Asp Pro Val Leu
    1820                1825                1830

Thr Thr Leu Val Asn Glu Thr Leu Gly Lys Thr Arg Gly Thr Ile
    1835                1840                1845

Pro Thr Ala Val Leu Arg Lys Gly His Ser Glu Ala Ala Thr Leu
    1850                1855                1860

Leu Thr Ala Leu Ala Thr Ala Tyr Thr Ala Gly Ala Pro Val Asn
    1865                1870                1875

Leu Ser Ser His Leu Pro Ala Pro His Thr His Pro Asp Leu Pro
    1880                1885                1890

Thr Tyr Pro Phe Gln Arg Gln Arg Tyr Trp His Ala Ala Thr Thr
    1895                1900                1905

Ala Thr Gly Asp Val Ser Ser Ala Gly Leu Thr Ala Thr Gly His
    1910                1915                1920

Pro Val Leu Thr Thr Ala Ala Glu Leu Pro Asp Pro Gly Gly Leu
    1925                1930                1935

Leu Leu Thr Gly Arg Val Asn Ala Ala Ser Pro Ala Trp Ala Ala
    1940                1945                1950

Asp His Ala Val Phe Gly Thr Pro Val Met Pro Gly Val Ala Phe
    1955                1960                1965

Val Asp Met Leu Leu His Ala Ala Ala Leu Val Gly Arg Pro Arg
    1970                1975                1980

Ile Glu Glu Leu Thr His His Val Phe Leu Ala Leu Pro Glu His
    1985                1990                1995

Gly Ala Leu Gln Leu Arg Val Val Val Arg Pro Ala Asp Asp Ser
    2000                2005                2010

Gly Arg Arg Ser Phe Ala Val His Ser Arg Pro Glu Asp Ala Pro
    2015                2020                2025

Leu Gly Ala Asp Trp Thr Cys His Ala Thr Gly Ala Leu Gly Val
    2030                2035                2040

Ala Pro Ala Val Pro Pro Ala Leu Pro Pro Val Asp Ala Ala Trp
    2045                2050                2055

Pro Pro Ala Ser Ala Ala Val Leu Asp Thr Asp Gly Phe Tyr Arg
    2060                2065                2070

Arg Ile Ala Glu Ala Gly Phe Gly Tyr Gly Pro Val Phe Gln Gly
    2075                2080                2085

Leu Ala Ala Ala Trp Glu Asp Gly Asp Thr Leu Tyr Ala Glu Val
    2090                2095                2100

Ala Leu Pro Ala Gly Thr Ser Pro Gly Ser Tyr Gly Val His Pro
    2105                2110                2115

Gly Leu Leu Asp Ser Ala Leu His Pro Ile Ala Leu Ala Ala Thr
    2120                2125                2130

Gly Ala Glu Thr Asp Gly Thr Leu His Val Pro Phe Ser Trp Ser
    2135                2140                2145

Gly Val Thr Leu His Ala Ser Gly Ala His Thr Leu Arg Val Arg
    2150                2155                2160

Leu Val Arg Ser Thr Pro Glu Thr Val Ala Leu Thr Val Thr Asp
    2165                2170                2175

Pro Ser Gly Ala Pro Val Leu Thr Val Asp Ser Leu Ala Met Arg
```

```
    2180                2185                2190

Gly Val  Arg Ala Glu Gln Leu  Glu Ala Ala Arg Pro  Asp Arg Asp
    2195                2200                2205

Gly Ala  Leu His Asp Val Ala  Trp Arg Ala Val Pro  Ala Pro Pro
    2210                2215                2220

Arg Ala  Asn Ser Arg Pro Asp  Gly Val Gly Trp Ala  Val Val Gly
    2225                2230                2235

Asp Thr  Arg Asp Pro Arg Val  Ala Ala Val Leu Ala  Ser Leu Gly
    2240                2245                2250

Ala Ala  Ala Glu Ser Tyr Pro  Asp Ala Glu Ala Leu  Arg Ala Ser
    2255                2260                2265

Leu Arg  Ala Gly Ala Val Arg  Pro Ser Thr Ile Val  Ala Arg Phe
    2270                2275                2280

Ala Thr  Gly Thr Ala Glu Asp  Gly Ala Asp Pro Val  Ala Ala Ala
    2285                2290                2295

His Thr  Gly Thr Arg His Ala  Met His Leu Leu Gln  Ala Val Leu
    2300                2305                2310

Ala Asp  Gly Ala Pro Asp Ser  Arg Leu Val Ile Leu  Thr Glu Asn
    2315                2320                2325

Ala Arg  Tyr Thr Gly Thr Gly  Asp Ala Ala Ala Asp  Met Ala Gly
    2330                2335                2340

Ala Ala  Val Trp Gly Leu Ile  Arg Ser Ala Gln Ser  Glu His Pro
    2345                2350                2355

Asp Arg  Phe Thr Leu Leu Asp  Val Asp Gly Ser Arg  Ala Ser Asp
    2360                2365                2370

Glu Ala  Val Val Ala Ala Leu  Ser Ala Gly Glu Pro  Gln Leu Ala
    2375                2380                2385

Val Arg  Glu Gly Arg Leu Phe  Val Pro Arg Leu Ala  Arg Leu Thr
    2390                2395                2400

Pro Gly  Ala Ile Pro Ala Thr  Phe Asp Ala Arg Arg  Thr Val Leu
    2405                2410                2415

Ile Thr  Gly Gly Thr Gly Ala  Leu Gly Ser Ile Leu  Ala Arg His
    2420                2425                2430

Leu Val  Thr Arg His Gly Val  Arg Lys Leu Leu Leu  Thr Ser Arg
    2435                2440                2445

Ser Gly  Arg Thr Ala Asp Ser  Thr Val Val Ala Glu  Leu Ala Gly
    2450                2455                2460

Leu Gly  Ala Glu Val Thr Val  Ala Ala Cys Asp Val  Thr Asp Arg
    2465                2470                2475

Leu Ser  Leu Glu Thr Leu Leu  Ala Gly Leu Pro Thr  Glu His Pro
    2480                2485                2490

Leu Gly  Ala Val Val His Cys  Ala Gly Val Leu Asp  Asp Gly Val
    2495                2500                2505

Val Thr  Glu Leu Thr Glu Asp  Arg Leu Asp Ala Val  Leu Arg Pro
    2510                2515                2520

Lys Val  Asp Gly Ala Trp Asn  Leu His Gln Val Thr  Arg Asp Met
    2525                2530                2535

Gly Leu  Asp Leu Asp Ala Phe  Val Leu Phe Ser Ser  Val Val Gly
    2540                2545                2550

Val Leu  Gly Ser Pro Gly Gln  Ala Asn Tyr Ala Ala  Ala Asn Ser
    2555                2560                2565

Phe Leu  Asp Glu Leu Ala Glu  His Arg Arg Thr Ala  Gly Leu Pro
    2570                2575                2580
```

-continued

```
Ala Lys Ser Leu Ala Trp Gly Leu Trp Glu Ser Gly Met Ala Asp
    2585                2590                2595

Thr Leu Asp Glu Gln Asp Arg Ala Arg Met Ser Arg Gly Gly Leu
    2600                2605                2610

Ser Pro Met Pro Ala Glu Arg Ala Leu Ala Leu Phe Asp Ser Ala
    2615                2620                2625

Leu Ala Thr Ala Arg Ala Val Leu Val Pro Ala Gly Val Asp Val
    2630                2635                2640

Ser His Ala Arg Thr Gln Arg Ala Ser Met Leu Ser Pro Leu Leu
    2645                2650                2655

Ala Glu Leu Leu Pro Ala Gln Ala Ala Pro Ala Glu Arg Gly Gly
    2660                2665                2670

Glu Ala Val Asp Glu Ser Ser Leu Arg Gln Gln Leu Ala Leu Leu
    2675                2680                2685

Pro Glu Pro Glu Gln Arg Glu Leu Leu Leu Glu Val Leu Arg Lys
    2690                2695                2700

His Val Ala Ala Val Leu Gly His Ser Ser Pro Leu Val Ile Asp
    2705                2710                2715

Pro Glu Ser Ser Phe Lys Asp Leu Gly Phe Asp Ser Leu Ala Gly
    2720                2725                2730

Ile Glu Leu Leu Met Val Leu Gly Glu Ser Met Gly Leu His Leu
    2735                2740                2745

Pro Ser Thr Met Leu Phe Asp His Pro Thr Pro Glu Leu Leu Ile
    2750                2755                2760

Thr His Leu Arg Asp Glu Leu Val Asp Asp Glu Ala Val Pro Val
    2765                2770                2775

Thr Ala Ala Asp Thr Ala Ala Val Ala Val Ala Pro Arg Asp Asp
    2780                2785                2790

Asp Glu Pro Ile Ala Val Ile Gly Met Gly Cys Arg Tyr Pro Gly
    2795                2800                2805

Gly Ala Thr Thr Pro Asp Glu Leu Trp Arg Leu Val Thr Glu Gly
    2810                2815                2820

Val Asp Ala Ile Gly Ser Phe Pro Thr Asn Arg Gly Trp Asp Leu
    2825                2830                2835

Glu Glu Leu Phe Asp Pro Asp Pro Asp Met Arg Gly Lys Thr Tyr
    2840                2845                2850

Ala Arg Lys Gly Gly Phe Leu Tyr Asp Ala Asp Arg Phe Asp Pro
    2855                2860                2865

Glu Phe Phe Gly Ile Ser Pro Arg Glu Ala Leu Ala Leu Asp Pro
    2870                2875                2880

Gln Gln Arg Leu Leu Leu Glu Thr Thr Trp Glu Thr Phe Glu Asn
    2885                2890                2895

Ala Gly Ile Arg Pro Asp Thr Leu Arg Gly Lys Pro Val Gly Val
    2900                2905                2910

Phe Ala Gly Val Val Thr Gln Glu Tyr Gly Ser Leu Val His Arg
    2915                2920                2925

Gly Thr Glu Pro Val Asp Gly Phe Leu Leu Thr Gly Thr Thr Ala
    2930                2935                2940

Ser Val Ala Ser Gly Arg Leu Ala Tyr Thr Leu Gly Leu Glu Gly
    2945                2950                2955

Pro Ala Val Thr Val Asp Thr Ala Cys Ser Ser Ser Leu Val Ala
    2960                2965                2970
```

Met His Leu Ala Cys Gln Ser Leu Arg Asn Asn Glu Ser Thr Met
2975 2980 2985

Ala Leu Ala Gly Gly Ala Thr Val Met Ala Asn Pro Gly Met Phe
2990 2995 3000

Leu Glu Phe Ser Arg Gln Arg Gly Leu Ala Pro Asp Gly Arg Cys
3005 3010 3015

Lys Ser Phe Ala Gly Gly Ala Asp Gly Thr Ile Trp Ala Glu Gly
3020 3025 3030

Ala Gly Met Val Leu Leu Glu Arg Leu Ser Asp Ala Lys Ala Asn
3035 3040 3045

Gly His Thr Val Leu Ala Val Ile Arg Gly Ser Ala Val Asn Gln
3050 3055 3060

Asp Gly Ala Ser Asn Gly Leu Thr Ala Pro Ser Gly Pro Ser Gln
3065 3070 3075

Gln Arg Val Ile Thr Ala Ala Leu Ala Gly Ala Gly Leu Thr Ser
3080 3085 3090

Asp Gln Val Asp Ala Val Glu Gly His Gly Thr Gly Thr Pro Leu
3095 3100 3105

Gly Asp Pro Ile Glu Ala Gln Ala Leu Leu Ala Thr Tyr Gly Gln
3110 3115 3120

Gly Arg Glu Ala Asp Gln Pro Leu Trp Leu Gly Ser Phe Lys Ser
3125 3130 3135

Asn Ile Gly His Ala Gln Ala Ala Ala Gly Ile Gly Gly Val Ile
3140 3145 3150

Lys Met Ile Gln Ala Met Arg His Gly Thr Leu Pro Arg Thr Leu
3155 3160 3165

His Val Asp Glu Pro Ser Pro His Ile Asn Trp Ala Ser Gly Asn
3170 3175 3180

Val Arg Leu Leu Thr Glu Glu Arg Ala Trp Pro Glu Thr Asp His
3185 3190 3195

Pro Arg Arg Ser Ala Val Ser Ser Phe Gly Ile Ser Gly Thr Asn
3200 3205 3210

Ala His Val Ile Leu Glu Gln Ala Pro Ala Thr Pro Glu Pro Ala
3215 3220 3225

Glu Asp Asp His Glu Gln Asp Ala Pro Gln Ala Thr Leu Val Pro
3230 3235 3240

Trp Val Leu Ser Gly Lys Thr Glu Gln Ala Leu Arg Asp Gln Ala
3245 3250 3255

Gln Gln Leu Arg Thr Tyr Leu Glu Leu Asn Pro Gly Leu Arg Thr
3260 3265 3270

Asp Arg Val Ala His Ala Leu Ala Thr Thr Arg Ala Gln Phe Gln
3275 3280 3285

Tyr Arg Ala Val Val Leu Gly Thr Asp His Gln Ala Phe Asp Arg
3290 3295 3300

Ala Leu Gly Thr Leu Thr Leu Gly Glu Pro Ser Pro Ala Leu Val
3305 3310 3315

Arg Gly Thr Pro His Pro Gly Lys Thr Ala Phe Met Phe Thr Gly
3320 3325 3330

Gln Gly Ala Gln Arg Ala Gly Met Gly Arg Glu Leu Tyr Asp Thr
3335 3340 3345

Tyr Pro Val Phe Arg Asp Thr Phe Asp Glu Val Cys Ala Thr Leu
3350 3355 3360

Asp Arg His Leu Asn Ala Glu Gln Pro Val Lys Asp Val Val Phe

-continued

```
    3365                3370                3375

Ala Asp  Asp Ala Ile Leu Leu  Asn Gln Thr Arg Tyr  Thr Gln Ala
    3380                3385                3390

Ala Leu  Phe Ala Ile Glu Thr  Ser Leu Tyr Arg Leu  Val Glu Ser
    3395                3400                3405

Phe Gly  Ile Thr Pro His Tyr  Leu Thr Gly His Ser  Ile Gly Glu
    3410                3415                3420

Ile Thr  Ala Ala His Val Ala  Gly Ile Phe Thr Leu  Asp Asp Ala
    3425                3430                3435

Cys Arg  Leu Val Ala Ala Arg  Gly Ser Leu Met Gln  Ala Leu Pro
    3440                3445                3450

Ala Asn  Gly Val Met Ile Ser  Leu Arg Ala Thr Glu  Glu Gln Ile
    3455                3460                3465

Val Pro  Phe Leu Glu Gly His  Glu His His Val Ser  Val Ala Ala
    3470                3475                3480

Val Asn  Gly Pro Ser Ser Ile  Val Ile Ser Gly Asp  Gln Glu Ala
    3485                3490                3495

Thr Thr  Ala Ile Ala Gly Ala  Leu Ala Glu Thr Gly  Val Lys Thr
    3500                3505                3510

Arg Arg  Leu Thr Val Ser His  Ala Phe His Ser Pro  His Met Asp
    3515                3520                3525

Pro Met  Leu Asp Glu Phe Glu  Leu Val Ala Gly Glu  Leu Thr Tyr
    3530                3535                3540

His Ala  Pro Thr Ile Pro Ile  Val Ser Asn Leu Thr  Gly Gln Leu
    3545                3550                3555

Ala Asp  His Tyr Ile Thr Thr  Pro Gln Tyr Trp Val  Gln His Val
    3560                3565                3570

Arg Glu  Ala Val Arg Phe Ser  Asp Gly Ile Thr Thr  Leu Asp Arg
    3575                3580                3585

Leu Gly  Thr Arg His Tyr Leu  Glu Leu Gly Pro Asp  Pro Val Leu
    3590                3595                3600

Thr Thr  Met Ala Gln Asp Ser  Val Ala Asp Asp Ser  Asp Ala Ala
    3605                3610                3615

Leu Val  Ala Thr Leu Tyr Arg  Asp Arg Asp Glu Asn  His Ser Phe
    3620                3625                3630

Leu Thr  Ala Leu Ala Thr Ala  His Ala His Gly Ile  Gln Val Gly
    3635                3640                3645

Trp Thr  Pro Val Val Gly Glu  Thr Ser Val Pro Ala  Leu Gly Leu
    3650                3655                3660

Pro Thr  Tyr Pro Phe Gln Arg  Gln His Tyr Trp Leu  Glu Ala Ala
    3665                3670                3675

Lys Pro  Thr Ser Gly Ala Asp  Gly Leu Gly Leu Thr  Ala Thr Asp
    3680                3685                3690

His Pro  Val Leu Thr Thr Leu  Ala Glu Leu Pro Asp  Gly Gly Gly
    3695                3700                3705

His Leu  Phe Thr Gly Arg Val  Ser Gly Asn Asp Pro  Asp Trp Val
    3710                3715                3720

Ala Glu  His Ile Ile Phe Gly  Thr Met Ile Val Pro  Gly Val Ala
    3725                3730                3735

Phe Val  Asp Leu Leu Leu His  Ala Ala Arg His Val  Asp Cys Glu
    3740                3745                3750

His Ile  Glu Glu Leu Thr His  His Val Phe Leu Ala  Val Pro Glu
    3755                3760                3765
```

Arg Ala Ala Leu Gln Leu Arg Leu Leu Ile Glu Pro Ala Asp Ser
3770 3775 3780

Ser Gly Ser Arg Ala Phe Ala Phe Tyr Ser Arg Pro Glu Asp Val
3785 3790 3795

Pro Val Glu Thr Asp Trp Thr Leu His Ala Thr Gly Ala Leu Gly
3800 3805 3810

Ala Glu Arg Arg Glu Val Pro Ala Gly Ala Asp Ser Leu Arg Asn
3815 3820 3825

Glu Val Trp Pro Pro Asp Ile Ser Asp Thr Met Asp Val Gly Glu
3830 3835 3840

Phe Tyr Arg Arg Val Thr Asp Gly Gly Phe Gly Tyr Gly Pro Leu
3845 3850 3855

Phe Arg Gly Leu Lys Lys Ala Trp Gln Asp Gly Asn Thr Thr Tyr
3860 3865 3870

Ala Glu Val Ser Leu Pro Ala Gly Ser Asp Pro Gly Asp Tyr Gly
3875 3880 3885

Ile His Pro Gly Leu Leu Asp Ser Ala Leu Gln Pro Ala Ala Leu
3890 3895 3900

Ile Met Gly Glu Thr Glu Ala Ala Asp Ser Ile Arg Val Pro Phe
3905 3910 3915

Ser Trp Ala Gly Val Ser Leu His Ala Thr Gly Ala Asp Ser Leu
3920 3925 3930

Arg Ile Arg His Thr Trp Thr Thr Pro Asp Thr Ala Ser Leu Val
3935 3940 3945

Ile Ala Asp Gln Thr Gly Thr Pro Val Met Thr Ile Asp Ser Leu
3950 3955 3960

Ala Met Arg Thr Val Gly Ala Asp Gln Leu Ala Ala Thr Arg Ala
3965 3970 3975

Ala Asp Ala Gly Glu Leu Tyr Lys Val Asp Trp Phe Asp Val Gln
3980 3985 3990

Thr Val Glu Asp Lys Thr Gln Gly Ala Gly Thr Ala Lys Trp Ala
3995 4000 4005

Val Val Ala Asp Pro Gly Asn Thr Gln Val Ala Ala Ala Leu Ser
4010 4015 4020

Pro Leu Gly Ala Ala Val Glu Val Glu Pro Asp Ala Val Thr Leu
4025 4030 4035

Pro Thr Thr Pro Gly Asp Asp Thr Thr Arg Pro Asp Val Val Phe
4040 4045 4050

Thr Trp Cys Val Ser Glu Pro Gly Ala Asp Pro Ala Gln Ala Ala
4055 4060 4065

Arg Ser Phe Thr His Arg Val Leu Gly Leu Val Gln Ala Val Leu
4070 4075 4080

Ser Asp Asp Arg Pro Asp Ser Arg Leu Val Ile Leu Thr Lys Gly
4085 4090 4095

Ala Met Ser Ala Gly Ser Gly Gly Ala Ala Asp Leu Ala Gly Ala
4100 4105 4110

Ala Val Trp Gly Leu Ile Arg Thr Ala Gln Thr Glu His Pro Asp
4115 4120 4125

Arg Phe Ile Leu Met Asp Leu Asp Gly Ser Asp Ala Ser Leu Arg
4130 4135 4140

Ala Val Gly Ala Ala Leu Asn Ala Gly Glu Pro Gln Leu Ala Val
4145 4150 4155

-continued

```
Arg Asp  Gly Arg Leu Leu Ala  Pro Arg Leu Ala Arg  Ile Gly Thr
    4160                 4165                 4170

Ala Asp  Ser Glu Pro Thr Ala  Ala Pro Ala Ser Phe  Asp Pro Asp
    4175                 4180                 4185

Lys Thr  Val Leu Ile Thr Gly  Gly Thr Gly Ala Leu  Gly Thr Leu
    4190                 4195                 4200

Leu Ala  Arg His Leu Val Thr  Arg His Gly Val Lys  Lys Leu Leu
    4205                 4210                 4215

Leu Thr  Ser Arg Arg Gly Arg  Pro Ala Gly Ser Thr  Ile Thr Ala
    4220                 4225                 4230

Glu Leu  Ala Glu Leu Gly Ala  Glu Val Thr Ile Val  Ala Cys Asp
    4235                 4240                 4245

Ala Ala  Asp Arg Glu Ser Leu  Glu Ala Leu Leu Ala  Ser Leu Pro
    4250                 4255                 4260

Asp Glu  His Pro Leu Gly Ala  Val Val His Cys Ala  Gly Thr Leu
    4265                 4270                 4275

Asp Asp  Gly Ile Val Thr Ala  Leu Thr Pro Asp Arg  Phe Asp Glu
    4280                 4285                 4290

Val Leu  Arg Pro Lys Val Asp  Gly Ala Trp Asn Leu  His Glu Leu
    4295                 4300                 4305

Thr Arg  Asp Leu Asp Leu Asp  Ala Phe Val Thr Phe  Ser Ser Val
    4310                 4315                 4320

Val Gly  Val Leu Gly Ser Pro  Gly Gln Ser Asn Tyr  Ala Ala Ala
    4325                 4330                 4335

Asn Val  Phe Leu Asp Glu Leu  Ala Glu His Arg Arg  Thr Ala Gly
    4340                 4345                 4350

Leu Pro  Ala Lys Ser Leu Ala  Trp Gly Leu Trp Glu  Ser Gly Met
    4355                 4360                 4365

Ala Asp  Thr Leu Asp Glu Gln  Asp Gln Ala Arg Met  Asn Arg Gly
    4370                 4375                 4380

Gly Leu  Leu Pro Met Pro Ala  Glu Gln Ala Leu Gly  His Phe Asp
    4385                 4390                 4395

Ser Ala  Leu Ala Thr Asp Gln  Thr Val Val Val Pro  Ala Lys Leu
    4400                 4405                 4410

Asp Leu  Ala Gly Leu Arg Ala  Arg Ala Ala Thr Val  Pro Val Ala
    4415                 4420                 4425

Pro Ile  Phe Arg Gly Leu Val  Arg Thr Pro Leu Arg  Ser Ala Ala
    4430                 4435                 4440

Gln Ala  Gly Gly Ala Gly Ala  Glu Val Gly Ala Leu  Gly Gln Ser
    4445                 4450                 4455

Ile Ala  Gly Arg Pro Glu Ala  Glu Gln Asp Gln Ile  Ile Leu Asp
    4460                 4465                 4470

Phe Leu  Arg Asn His Val Ala  Thr Val Leu Gly His  Gly Ser Ala
    4475                 4480                 4485

Asn Ala  Ile Asp Pro Ala His  Ser Phe Lys Glu Leu  Gly Phe Asp
    4490                 4495                 4500

Ser Leu  Ser Ser Val Glu Leu  Arg Asn Ser Leu Asn  Lys Ala Ser
    4505                 4510                 4515

Gly Met  Arg Leu Pro Ser Thr  Leu Leu Phe Asp Tyr  Pro Thr Pro
    4520                 4525                 4530

Ser Val  Leu Ala Gly Tyr Ile  Arg Asn Gln Leu Ala  Gly Gly Lys
    4535                 4540                 4545

Gln Ala  Glu Ala Gly Ala Gln  Val Ala Arg Arg Thr  Val Arg Pro
```

```
    4550                4555                4560

Ala Ser  Ser Arg Ser Asp Ala  Ala Asp Pro Ile Val  Ile Val Gly
    4565                4570                4575

Met Gly  Cys Arg Phe Pro Gly  Gly Ala Asp Thr Pro  Glu Ala Leu
    4580                4585                4590

Trp Lys  Leu Val Ala Asp Glu  Arg Asp Ala Val Gly  Ala Phe Pro
    4595                4600                4605

Asp Asn  Arg Gly Trp Asp Ile  Glu Asn Leu Phe Asp  Asp Asp Pro
    4610                4615                4620

Asp Val  Arg Gly Lys Ser Tyr  Ala Ser Glu Gly Gly  Phe Leu Tyr
    4625                4630                4635

Asp Ala  Asp Arg Phe Asp Pro  Glu Phe Phe Gly Ile  Ser Pro Arg
    4640                4645                4650

Glu Ala  Leu Ala Leu Asp Pro  Gln Gln Arg Leu Leu  Leu Glu Thr
    4655                4660                4665

Thr Trp  Glu Ala Phe Glu Asn  Ala Gly Ile Arg Pro  Asp Thr Leu
    4670                4675                4680

Arg Gly  Lys Pro Val Gly Val  Phe Ala Gly Val Ala  Ala Gly Glu
    4685                4690                4695

Tyr Val  Ser Leu Thr His His  Gly Gly Glu Pro Val  Glu Gly Tyr
    4700                4705                4710

Leu Leu  Thr Gly Thr Thr Ala  Ser Val Ala Ser Gly  Arg Ile Ser
    4715                4720                4725

Tyr Thr  Leu Gly Leu Glu Gly  Pro Ala Val Thr Val  Asp Thr Ala
    4730                4735                4740

Cys Ser  Ser Ser Leu Val Ala  Met His Leu Ala Cys  Gln Ser Leu
    4745                4750                4755

Arg Asn  Asn Glu Ser Thr Met  Ala Leu Ala Gly Gly  Ala Thr Ile
    4760                4765                4770

Met Ser  Asn Ala Gly Met Phe  Met Glu Phe Ser Arg  Gln Arg Gly
    4775                4780                4785

Leu Ala  Pro Asp Ser Arg Ala  Lys Ser Tyr Ala Gly  Ala Ala Asp
    4790                4795                4800

Gly Thr  Ile Trp Ala Glu Gly  Ala Gly Met Val Leu  Leu Glu Arg
    4805                4810                4815

Leu Ser  Asp Ala Lys Ala Asn  Gly His Thr Val Leu  Ala Val Ile
    4820                4825                4830

Arg Gly  Ser Ala Val Asn Gln  Asp Gly Ala Ser Asn  Gly Leu Thr
    4835                4840                4845

Ala Pro  Asn Gly Pro Ser Gln  Gln Arg Val Ile Asn  Thr Ala Leu
    4850                4855                4860

Ala Ser  Ala Gly Leu Thr Pro  Asp Gln Val Asp Ala  Val Glu Gly
    4865                4870                4875

His Gly  Thr Gly Thr Pro Leu  Gly Asp Pro Ile Glu  Ala Gln Ala
    4880                4885                4890

Leu Leu  Ser Thr Tyr Gly Gln  Asn Arg Glu Glu Pro  Leu Trp Leu
    4895                4900                4905

Gly Ser  Phe Lys Ser Asn Ile  Gly His Ala Gln Ala  Ala Ala Gly
    4910                4915                4920

Val Gly  Gly Val Ile Lys Met  Ile Gln Ala Met Arg  His Gly Thr
    4925                4930                4935

Leu Pro  Arg Thr Leu His Val  Asp Glu Pro Ser Pro  Asn Ile Asp
    4940                4945                4950
```

```
Trp Asp  Ser Gly Asn Val Arg  Leu Leu Thr Glu Ala  Arg Ala Trp
    4955                 4960                 4965

Pro Glu  Thr Asp Arg Pro Arg  Arg Ser Ala Val Ser  Ser Phe Gly
    4970                 4975                 4980

Ile Ser  Gly Thr Asn Ala His  Leu Ile Leu Glu Glu  Ala Pro Thr
    4985                 4990                 4995

Pro Thr  His Pro Glu Pro Ala  Pro Glu Ser Ala Pro  Gln Ala Thr
    5000                 5005                 5010

Thr Val  Pro Trp Ile Leu Ser  Gly Lys Ser Glu Gln  Ala Val Arg
    5015                 5020                 5025

Asp Gln  Ala Gln Arg Leu Leu  Asp His Val Ser Glu  Tyr Pro Glu
    5030                 5035                 5040

Leu Gln  Pro Val Asp Ile Ala  Tyr Ser Leu Ala Thr  Ala Arg Thr
    5045                 5050                 5055

Ser Phe  Glu Arg Gln Ala Val  Ala Ile Gly Ala Thr  His Asp Glu
    5060                 5065                 5070

Leu Val  Asp His Leu Arg Ser  Leu Thr Gln Asp Pro  Gly Thr Ala
    5075                 5080                 5085

Leu Leu  His Gly Gln Ser His  Ser Lys Lys Val Ala  Leu Leu Phe
    5090                 5095                 5100

Thr Gly  Gln Gly Ser Gln His  Pro Gly Met Gly Arg  Gln Leu Tyr
    5105                 5110                 5115

Asp Thr  His Pro Val Tyr Arg  Asp Ala Phe Asp Glu  Val Thr Ala
    5120                 5125                 5130

Thr Leu  Asp Gln His Leu Gln  Ala Glu Gln Pro Val  Lys Asp Val
    5135                 5140                 5145

Val Phe  Ala Asp Asp Pro Thr  Leu Leu Asn Gln Thr  Arg Tyr Thr
    5150                 5155                 5160

Gln Pro  Ala Ile Phe Ala Leu  Gln Val Ala Leu Thr  Arg Leu Leu
    5165                 5170                 5175

Val Asp  Glu Phe Gly Val Ser  Pro Thr His Leu Ile  Gly His Ser
    5180                 5185                 5190

Ile Gly  Glu Ile Ser Ala Ala  His Thr Ala Gly Ile  Leu Thr Leu
    5195                 5200                 5205

Asp Asp  Ala Cys Arg Leu Val  Ala Ala Arg Gly Thr  Leu Met Gln
    5210                 5215                 5220

Thr Leu  Pro Ala Thr Gly Ala  Met Thr Ala Val Glu  Ala Thr Glu
    5225                 5230                 5235

Glu Glu  Val Leu Pro His Leu  Thr Glu Arg Val Gly  Ile Ala Ala
    5240                 5245                 5250

Val Asn  Gly Pro Arg Ser Val  Val Val Ser Gly Asp  Glu Ala Ala
    5255                 5260                 5265

Val Ile  Ala Val Gly Glu Glu  Phe Ala Gly Gln Gly  Arg Arg Ile
    5270                 5275                 5280

Arg Arg  Leu Thr Val Ser His  Ala Phe His Ser His  His Met Asp
    5285                 5290                 5295

Pro Met  Leu Gly Glu Leu His  Ala Val Ala Asp Thr  Leu Thr Tyr
    5300                 5305                 5310

His Val  Pro Arg Thr Pro Leu  Val Ser Thr Val Thr  Gly Arg Leu
    5315                 5320                 5325

Ala Gly  Ser Glu Ile Thr Ser  Ala Thr Tyr Trp Ser  Asp His Ala
    5330                 5335                 5340
```

Arg Asn Ala Thr Arg Phe His Asp Gly Leu Asn Thr Leu His Glu
5345 5350 5355

Gln Gly Val Thr Thr Tyr Ile Glu Val Gly Pro Asp Ala Val Leu
5360 5365 5370

Ala Ala Leu Thr Arg Glu Ala Leu Pro Asp Ala Thr Ala Val Pro
5375 5380 5385

Leu Ile Arg Ala Lys Ala Ser Glu Pro Ala Thr Leu Leu Asp Gly
5390 5395 5400

Leu Val Arg Ala His Val Ser Gly Ala Thr Val Asp Trp Ala Gly
5405 5410 5415

Phe Leu Ala Arg Arg Gly Gly Arg Ser Val Asp Leu Pro Thr Tyr
5420 5425 5430

Ala Phe Gln Arg Arg Arg His Trp Leu Glu Thr Ala Asp Pro Val
5435 5440 5445

Gly Thr Ala Ala Gly Leu Gly Leu Glu Ser Ala Ser His Pro Leu
5450 5455 5460

Leu Ala Thr Thr Thr Glu Leu Pro Asp Gly Thr Ala Leu Phe Thr
5465 5470 5475

Gly Arg Val Thr Leu Ala Asp His Pro Trp Leu Ser Asp His Thr
5480 5485 5490

Val Met Gly Thr Val Ile Leu Pro Gly Thr Ala Phe Val Glu Leu
5495 5500 5505

Ala Leu His Ala Ala Glu Thr Val Gly Leu Asp Glu Ile Ala Glu
5510 5515 5520

Leu Val Leu His Ala Pro Val Thr Phe Gly Ser Gln Ser Ala Ala
5525 5530 5535

Leu Leu Gln Val Ile Val Gly Pro Asp Asp Pro Ser Ala Gly Arg
5540 5545 5550

Thr Leu Thr Ile Arg Ser Arg Ser Glu Glu Asp Gln Ser Trp Thr
5555 5560 5565

Glu Asn Ala Thr Gly Thr Leu Gly Ala Leu Val Gly Val Ser
5570 5575 5580

<210> SEQ ID NO 6
<211> LENGTH: 1089
<212> TYPE: DNA
<213> ORGANISM: Streptomyces sp. MP28-13

<400> SEQUENCE: 6
atgagaactg ttgtcgtcgg cggtggtgtc atcggcctgg ccaccgcatg gcgggccgcg 60
cgcgaaggcg tctccgtcac ggtgatcgac cctgccccgg gcagcaaggc gtcccacgcc 120
tcggcgggac tgctcccggc catcaacgac cagctgtacg accagccgga actcctgcgc 180
ctgtgcctgg cctcccgtga gctgtacccg tccttcgtcg aggaactgga ggagttcgct 240
ccggccggct tccggcgcga cggcgtcctg gacgcggcgt tcgacgagga atccctgccg 300
atcctcgacc gccaactggc cttccagaag tccatcggtg tgcgcaccga acggctgacc 360
gccgaggagt gcgccaagct ccagccggcc ttcgcccccg tggtcggcgg cctgctgtcc 420
ccggacgacg gcgccatcga cccgcgcgtt ctcgacgcgg cgctgatcac cgccatcgaa 480
gccctgggcg gcagcgtcgt acgcagggga gccacccgga tcgaggacca caccgtcgtc 540
ctcgacaccg gtgacaaggt gcccttcgac cgtctcgtcc tggccgccgg ctgctggacc 600
caccagatcg aggggctgcc cgcgggcgcg atcccggaga tccgtcccgt caagggccag 660
atcctccgcc tgcgctccga cgtgccactg ctcaacgtga cggcccgcgc catctccaag 720

-continued ggcaagtccc tctacctggc tccccgcctg gacggtgaac tcgtcgtcgg cgccacctac 780
gaggagcgcg gctacgacga gaccgtcacc gccgagggca ccggcagcct gctgcgccgc 840
gccgccgagg tcattcccga ggtgggcgcc ctgcgtttcg ccgagatcac cgcggggctc 900
cgtcccgcct cgcccgacga cctccccgtc atgggtccga ccacggttcc cgatgtctac 960
ctggcgagcg gtcacttccg gatgggagtc cagctggctc ccgtcacggc cgtggccatg 1020
gcggcctacc tgaccgacac cgtcccgcac gccgcgacgg cgccgttcac cccgctccgc 1080
ttctcctga 1089

<210> SEQ ID NO 7
<211> LENGTH: 362
<212> TYPE: PRT
<213> ORGANISM: Streptomyces sp. MP28-13

<400> SEQUENCE: 7

Met Arg Thr Val Val Val Gly Gly Gly Val Ile Gly Leu Ala Thr Ala
1 5 10 15

Trp Arg Ala Ala Arg Glu Gly Val Ser Val Thr Val Ile Asp Pro Ala
20 25 30

Pro Gly Ser Lys Ala Ser His Ala Ser Ala Gly Leu Leu Pro Ala Ile
35 40 45

Asn Asp Gln Leu Tyr Asp Gln Pro Glu Leu Leu Arg Leu Cys Leu Ala
50 55 60

Ser Arg Glu Leu Tyr Pro Ser Phe Val Glu Glu Leu Glu Glu Phe Ala
65 70 75 80

Pro Ala Gly Phe Arg Arg Asp Gly Val Leu Asp Ala Ala Phe Asp Glu
85 90 95

Glu Ser Leu Pro Ile Leu Asp Arg Gln Leu Ala Phe Gln Lys Ser Ile
100 105 110

Gly Val Arg Thr Glu Arg Leu Thr Ala Glu Glu Cys Ala Lys Leu Gln
115 120 125

Pro Ala Phe Ala Pro Val Val Gly Gly Leu Leu Ser Pro Asp Asp Gly
130 135 140

Ala Ile Asp Pro Arg Val Leu Asp Ala Ala Leu Ile Thr Ala Ile Glu
145 150 155 160

Ala Leu Gly Gly Ser Val Val Arg Arg Gly Ala Thr Arg Ile Glu Asp
165 170 175

His Thr Val Val Leu Asp Thr Gly Asp Lys Val Pro Phe Asp Arg Leu
180 185 190

Val Leu Ala Ala Gly Cys Trp Thr His Gln Ile Glu Gly Leu Pro Ala
195 200 205

Gly Ala Ile Pro Glu Ile Arg Pro Val Lys Gly Gln Ile Leu Arg Leu
210 215 220

Arg Ser Asp Val Pro Leu Leu Asn Val Thr Ala Arg Ala Ile Ser Lys
225 230 235 240

Gly Lys Ser Leu Tyr Leu Ala Pro Arg Leu Asp Gly Glu Leu Val Val
245 250 255

Gly Ala Thr Tyr Glu Glu Arg Gly Tyr Asp Glu Thr Val Thr Ala Glu
260 265 270

Gly Thr Gly Ser Leu Leu Arg Arg Ala Ala Glu Val Ile Pro Glu Val
275 280 285

Gly Ala Leu Arg Phe Ala Glu Ile Thr Ala Gly Leu Arg Pro Ala Ser
290 295 300

```
Pro Asp Asp Leu Pro Val Met Gly Pro Thr Thr Val Pro Asp Val Tyr
305                 310                 315                 320

Leu Ala Ser Gly His Phe Arg Met Gly Val Gln Leu Ala Pro Val Thr
                325                 330                 335

Ala Val Ala Met Ala Ala Tyr Leu Thr Asp Thr Val Pro His Ala Ala
            340                 345                 350

Thr Ala Pro Phe Thr Pro Leu Arg Phe Ser
        355                 360


<210> SEQ ID NO 8
<211> LENGTH: 2085
<212> TYPE: DNA
<213> ORGANISM: Streptomyces sp. MP28-13

<400> SEQUENCE: 8

atgagtaaag cagaacggcc cgggcttcct gacggagtcc gcgaggtcga catcgagcac     60

ctctacagcc gcttcgccga ccgcggtctc cagtacgggc cggccttccg gggcctgcgc    120

gccgtgtggt cgcacggcga ggaggtctac gccgactcag cgctcgacac cgcgaccggc    180

ggcgactacc tcctgcaccc ggccctgctc gacaccgcgc tccaagcggc actggtcccc    240

gacatcgacc gcgacgaccg gacgttcctg ccgttcgcgc tgcgcgggat acgggtgcac    300

aagggcggcg cccgcgccgt ccgcatccac accgtcccgg gcgacgacgg cttctccctg    360

gcgctcaccg gcgacgacgg cgagccgatc gccacgatcg gttccgtcgt cagccggccc    420

gtcacggccg agcagctcga cgccgcggcg cagcgcaccc aactgctgcg cgtcgtatgg    480

aagtccgtcg tacagcagtc ggacaactcc gaccagcagc gctggggatt cctcggaacc    540

gaccgcatcg gcctcaccgg cgcgctgaag gccacccgcc ccttgttcga ctcctacccc    600

acgctgcgcg aactcgactc cgtgctccgg gccgccacag ccgtcccgga cgtgatcgtc    660

gtctcctgca cggacgagga ctcgccggta cgctcggcgg cgcaacgcgc cctcatggtc    720

gtacaggagt gcctggccga ccaccgcctc gccaagaccc gcctggtgct ggtcagtagc    780

ggagccgtcg ccgcccgcgc cggggaggac ctgtccgacg tgtcgggcgc cgccgtctgg    840

ggactgctcc gcagcgtcca gtccgaacac cccgaccgct tcgtcctggt cgacgtcgac    900

gaccccggga actcgggccg ctccctcgcc gccgccgtcg cctccggcga accccaactc    960

gccgtgcgca acggcgcgct gctcaggccg cgtctcgtac gcagcccacc gccgccgcgg   1020

cgcaggagcc tcacgggtac cgtcgtgatc accggcggca ccggagaact gggccgcctg   1080

ctcgcccggc acctcgtcac cggccatgac gtccggcacc tcgtgctgct cagccgccgc   1140

ggtcccggct cgcccggcgc cgccgagctg gatgccgaac tcaccgcgct cggcgcccgt   1200

gtcgacgtgg tcgcctgcga cgtcgccgac cgctcgtcgc tggagagcgc actggccggc   1260

atccccgccc cgtccgccgt catccacacc gcgggtgtgc tgtccgacgg cgcgatcggc   1320

accctcacgc cacgcggact cgacaaggtt ctgcgtccca aggtcgacgc cgcgctccac   1380

ctgcacgacc tgatccagga cccggactgc gcgttcgtgg tgttctcgtc cgtcgcgggg   1440

ctggtcggca acgcggggca gggcaactac gcagccgcca acgccgtcct cgacgcgctc   1500

gcccaccacc gccgtgcccg cagactgcag ggcctctcgc tcgcctgggg tctgtgggag   1560

agcgagaacg gcatgggctc cgacctgtcc gccgccgacc acaaccgcat caagcggtcc   1620

ggcttcgccc ccctggggca cgaccagggc ctggctctct tcgacgccac gctcggcagc   1680

gacgaggcgg tcctggcgcc cgtccggctc aacgaggcgg gcctcaccgg ggacatcccg   1740
```

-continued cccgtcctgg aggagctggc gcccacccgt accggcaagc ccgccgtgac cgacaccctg 1800
gtcagccggc tggccgagct gcccgaggcc gaacgcgacg ccgccgccct ggagttcgtc 1860
cgctcggtgt ccgccttggt cttcggctac gagagcggcg acgagatcga cccgcagcgg 1920
gagttcagcg ccgccgggct cgactccatc ggcaacctcg aactcagccg ccacctggcg 1980
gccgccaccg gcctgcggct cccggcgacc ctcgtcttcg accatcccac ccccgcagaa 2040
ctcgcctccc acctgcgtcg actcctccag gagagcaatt catga 2085

<210> SEQ ID NO 9
<211> LENGTH: 694
<212> TYPE: PRT
<213> ORGANISM: Streptomyces sp. MP28-13

<400> SEQUENCE: 9

Met Ser Lys Ala Glu Arg Pro Gly Leu Pro Asp Gly Val Arg Glu Val
1 5 10 15

Asp Ile Glu His Leu Tyr Ser Arg Phe Ala Asp Arg Gly Leu Gln Tyr
20 25 30

Gly Pro Ala Phe Arg Gly Leu Arg Ala Val Trp Ser His Gly Glu Glu
35 40 45

Val Tyr Ala Asp Ser Ala Leu Asp Thr Ala Thr Gly Gly Asp Tyr Leu
50 55 60

Leu His Pro Ala Leu Leu Asp Thr Ala Leu Gln Ala Ala Leu Val Pro
65 70 75 80

Asp Ile Asp Arg Asp Asp Arg Thr Phe Leu Pro Phe Ala Leu Arg Gly
85 90 95

Ile Arg Val His Lys Gly Gly Ala Arg Ala Val Arg Ile His Thr Val
100 105 110

Pro Gly Asp Asp Gly Phe Ser Leu Ala Leu Thr Gly Asp Asp Gly Glu
115 120 125

Pro Ile Ala Thr Ile Gly Ser Val Val Ser Arg Pro Val Thr Ala Glu
130 135 140

Gln Leu Asp Ala Ala Ala Gln Arg Thr Gln Leu Leu Arg Val Val Trp
145 150 155 160

Lys Ser Val Val Gln Gln Ser Asp Asn Ser Asp Gln Gln Arg Trp Gly
165 170 175

Phe Leu Gly Thr Asp Arg Ile Gly Leu Thr Gly Ala Leu Lys Ala Thr
180 185 190

Arg Pro Leu Phe Asp Ser Tyr Pro Thr Leu Arg Glu Leu Asp Ser Val
195 200 205

Leu Arg Ala Ala Thr Ala Val Pro Asp Val Ile Val Val Ser Cys Thr
210 215 220

Asp Glu Asp Ser Pro Val Arg Ser Ala Ala Gln Arg Ala Leu Met Val
225 230 235 240

Val Gln Glu Cys Leu Ala Asp His Arg Leu Ala Lys Thr Arg Leu Val
245 250 255

Leu Val Ser Ser Gly Ala Val Ala Ala Arg Ala Gly Glu Asp Leu Ser
260 265 270

Asp Val Ser Gly Ala Ala Val Trp Gly Leu Leu Arg Ser Val Gln Ser
275 280 285

Glu His Pro Asp Arg Phe Val Leu Val Asp Val Asp Asp Pro Gly Asn
290 295 300

Ser Gly Arg Ser Leu Ala Ala Ala Val Ala Ser Gly Glu Pro Gln Leu
305 310 315 320

-continued

```
Ala Val Arg Asn Gly Ala Leu Leu Arg Pro Arg Leu Val Arg Ser Pro
                325                 330                 335

Pro Pro Pro Arg Arg Arg Ser Leu Thr Gly Thr Val Val Ile Thr Gly
            340                 345                 350

Gly Thr Gly Glu Leu Gly Arg Leu Leu Ala Arg His Leu Val Thr Gly
        355                 360                 365

His Asp Val Arg His Leu Val Leu Leu Ser Arg Arg Gly Pro Gly Ser
    370                 375                 380

Pro Gly Ala Ala Glu Leu Asp Ala Glu Leu Thr Ala Leu Gly Ala Arg
385                 390                 395                 400

Val Asp Val Val Ala Cys Asp Val Ala Asp Arg Ser Ser Leu Glu Ser
                405                 410                 415

Ala Leu Ala Gly Ile Pro Ala Pro Ser Ala Val Ile His Thr Ala Gly
            420                 425                 430

Val Leu Ser Asp Gly Ala Ile Gly Thr Leu Thr Pro Arg Gly Leu Asp
        435                 440                 445

Lys Val Leu Arg Pro Lys Val Asp Ala Ala Leu His Leu His Asp Leu
    450                 455                 460

Ile Gln Asp Pro Asp Cys Ala Phe Val Val Phe Ser Ser Val Ala Gly
465                 470                 475                 480

Leu Val Gly Asn Ala Gly Gln Gly Asn Tyr Ala Ala Ala Asn Ala Val
                485                 490                 495

Leu Asp Ala Leu Ala His His Arg Arg Ala Arg Arg Leu Gln Gly Leu
            500                 505                 510

Ser Leu Ala Trp Gly Leu Trp Glu Ser Glu Asn Gly Met Gly Ser Asp
        515                 520                 525

Leu Ser Ala Ala Asp His Asn Arg Ile Lys Arg Ser Gly Phe Ala Pro
    530                 535                 540

Leu Gly His Asp Gln Gly Leu Ala Leu Phe Asp Ala Thr Leu Gly Ser
545                 550                 555                 560

Asp Glu Ala Val Leu Ala Pro Val Arg Leu Asn Glu Ala Gly Leu Thr
                565                 570                 575

Gly Asp Ile Pro Pro Val Leu Glu Glu Leu Ala Pro Thr Arg Thr Gly
            580                 585                 590

Lys Pro Ala Val Thr Asp Thr Leu Val Ser Arg Leu Ala Glu Leu Pro
        595                 600                 605

Glu Ala Glu Arg Asp Ala Ala Ala Leu Glu Phe Val Arg Ser Val Ser
    610                 615                 620

Ala Leu Val Phe Gly Tyr Glu Ser Gly Asp Glu Ile Asp Pro Gln Arg
625                 630                 635                 640

Glu Phe Ser Ala Ala Gly Leu Asp Ser Ile Gly Asn Leu Glu Leu Ser
                645                 650                 655

Arg His Leu Ala Ala Ala Thr Gly Leu Arg Leu Pro Ala Thr Leu Val
            660                 665                 670

Phe Asp His Pro Thr Pro Ala Glu Leu Ala Ser His Leu Arg Arg Leu
        675                 680                 685

Leu Gln Glu Ser Asn Ser
    690
```

<210> SEQ ID NO 10
<211> LENGTH: 564
<212> TYPE: DNA
<213> ORGANISM: Streptomyces sp. MP28-13

<400> SEQUENCE: 10
atgacccagc ttctcgaaga caccgaccgg cgcgtcttcc ccaccgacga cgaactgctg 60
caccgggtgc tgacccccta ccgggccaag cggtgcgagt acctcacctc ggccacggtc 120
acctcggagg gcgacccccg cgacggcgga cgactcatcg ccacctgcac cttcgagatc 180
cccgagtcct gctacatcga cgacaccggg cacttcaact cggtcgagtt caacatctgc 240
ttcaaccaga tggcctacta cctgctggcc atgtcggtac gggagtcact cgtcgagccg 300
ttctccggct ggacgatcga gcagttctgg acccggcagc tcgccgacgt gttcatcacc 360
gacttcaaga gcagcttccg cagcgcgatg cagggccgcc gcttcaccgg cgagatcgag 420
atcatcgaca tcgccgaatg ggacgccaac gacctgcgcg acgccctggt gatcctgcgg 480
accaagtgcc actacgccga cgagcaaggt ggcgagagcc acggcgagat caccgccgcc 540
gtcaccaacc cgcccgtgat ctga 564

<210> SEQ ID NO 11
<211> LENGTH: 187
<212> TYPE: PRT
<213> ORGANISM: Streptomyces sp. MP28-13

<400> SEQUENCE: 11

Met Thr Gln Leu Leu Glu Asp Thr Asp Arg Arg Val Phe Pro Thr Asp
1 5 10 15

Asp Glu Leu Leu His Arg Val Leu Thr Pro Tyr Arg Ala Lys Arg Cys
20 25 30

Glu Tyr Leu Thr Ser Ala Thr Val Thr Ser Glu Gly Asp Pro Arg Asp
35 40 45

Gly Gly Arg Leu Ile Ala Thr Cys Thr Phe Glu Ile Pro Glu Ser Cys
50 55 60

Tyr Ile Asp Asp Thr Gly His Phe Asn Ser Val Glu Phe Asn Ile Cys
65 70 75 80

Phe Asn Gln Met Ala Tyr Tyr Leu Leu Ala Met Ser Val Arg Glu Ser
85 90 95

Leu Val Glu Pro Phe Ser Gly Trp Thr Ile Glu Gln Phe Trp Thr Arg
100 105 110

Gln Leu Ala Asp Val Phe Ile Thr Asp Phe Lys Ser Ser Phe Arg Ser
115 120 125

Ala Met Gln Gly Arg Arg Phe Thr Gly Glu Ile Glu Ile Ile Asp Ile
130 135 140

Ala Glu Trp Asp Ala Asn Asp Leu Arg Asp Ala Leu Val Ile Leu Arg
145 150 155 160

Thr Lys Cys His Tyr Ala Asp Glu Gln Gly Gly Glu Ser His Gly Glu
165 170 175

Ile Thr Ala Ala Val Thr Asn Pro Pro Val Ile
180 185

<210> SEQ ID NO 12
<211> LENGTH: 10584
<212> TYPE: DNA
<213> ORGANISM: Streptomyces sp. MP28-13

<400> SEQUENCE: 12
atgaccgagc agtcaagggc cgcgatgctg gaactggtgc tggcgcaagc cgcagcggtg 60
ttgcggaccg ccgacccgga cgcctacggg gaaggggccg tcgacctggc cgccgaccgc 120
ccgttcctgg cggggggcct ggactcgctg ggcctggtcc ggttgcagcg gcggctcgcc 180
gccgaggtgg gggcggacct gcccgtcacc cttgccttcg accacccgac accgatcgcc 240
ctcgccggcc acctggccga cctgctgcac ggcaccgccg gagcggacgc acccgacgag 300
acggcggcgc ccgccctgcc gtcggcgttc ggcgagccga tcgcgatcgt cggaatcggc 360
tgccgcttcc ccggtggtgt gagcacgccc gaggacctgt ggcggatcgt cgccgacgac 420
acccatgtgc tcacggactt tccctccgac cggggctggg atctcgaccg catctacaac 480
ccggacccgt ccgtcaccgg cgccagttat gtgcggcgcg gcggattcct cccggacgcc 540
gccgacttcg acgccgactt cttccagatc agtcccaagg aagcgctggc catggacccc 600
cagcagcggc tgctgctgga gacctcctgg gaagcgctcg aacacgcggg catcgacccg 660
ggccgcctgc gcggcacacc ctcgggcgtg ttcatcggcg tggagccgca cgagtacggg 720
ccccggacgc acgaggcccc cgacggtctc gacggctacg tcctgggcgg caacctgccc 780
agcgtcgtgt ccggccgcgt cgcctacacc ctcggcttcg aaggccccac actcaccgtc 840
gacaccgcgt gctcgggctc gctcacggcc ctccacctgg ccgtgcgctc gctccagggc 900
ggggagtgcg ggctggcgct ggccggcggc gtcaccgtga tatccagccc cggcacgttc 960
accaccttca gccgccaacg cggtctggcc cccgacggac gcatcaaggc gttcgccgcc 1020
gcggcggacg gcacctcgtt cgccgaaggc gtcggcgtgt tcgtcctcgc ccgcctgtcc 1080
gacgcgctgc gcgatgggca ccccgtactg gccgtgatcc gcggcaccgc catcaaccag 1140
gacggcgcga ccaacggcct gtccgccccc aacggcctcg cgcagcagcg cgtcatccgc 1200
cgcgcgctca ccgacgcccg tctgaccgcc gacgaggtcg acgcggtcga ggcgcacggc 1260
accggcacca cactcggcga ccccatcgag ggccaggccc tggtcgccgc ctacggacgc 1320
ggacgctcac ccgagaagcc cctgtggctg gggtcggtga agtccaacat cggccacacc 1380
ggagcggcgg cgggcgccgc cggaatcatc aagatggtgc aggcgatgcg tcacagcacg 1440
ctgccgcgca ccctgcacgt ggacgcgccg accacgcacg tcgactggtc ggacggcacc 1500
gtccagctcc tcaccgagcc cgtcccctgg gaagccgcgg acacaccgcg ccgtgccgga 1560
atctcctcgt tcggcgcgag tggcaccaac gcccacgtca tcatcgagga gccgcccgcc 1620
cccgtcgccg ccgccgacgg gagcgacgaa cccccggtgg ccgagcgccc cgtgccggtc 1680
gtcctgtccg cccagggcca ggacgcactg cgcggccagg ccgaacggct cctgacggcg 1740
gtcgacgacg cctcgccgct ggacctcgcc tactcggccg ccaccacgcg cgccgcgctg 1800
cgcgaccgcg ccaccgtcgt ggccgccgac cgtgccgaac tgcgccgcgc cctgaccgcc 1860
ctcgccgcgg gcgagagcgc gcccggactg ctcaccggta cgacgccggc cgcgggccgt 1920
accgcgttcc tcttcaccgg ccagggcagc cagcgtcttg gcatgggccg cgaactggtg 1980
cgcgccttcc cggtgttcgc gcgggcgctc caggacgccg ccgaccacct cgacctccac 2040
ctcgacgagc ccctgggcga ggtgctgttc gccgagcccg gttcggcgca ggccgaactg 2100
ctccagcaga cccgctacgc gcaggccgcc ctcttcgccg tcgagaccgc catgttccgg 2160
ctgctggagt cgtggggcgt cacgcccgga ctcctcaccg gacactccat cggcgagatc 2220
gccgccgcgc acgtcgccgg cgtcatgaac ctggccgacg cggcgctgct ggtcggcgcg 2280
cgcggcacgc tgatgcagga gcttcccgcc ggcggcgcca tggtcgccgt ccaggcggcg 2340
gaggccgaag tcgccccgta tctcaccgag aaggtgggca tcgccgccgt caacggcccg 2400
ctggcggtcg tgctgtccgg tgagaccgac gccgtactcg ccgtcgccgc ccgcttcacc 2460
gaggagggac gcaagacgcg gcggctgcgc gtctcgcacg cgttccactc gccgctgatg 2520

-continued gaaccgatgc tcgacgactt ccgccgcgtc gccgagaccc tgacctacca gccgccgcgt 2580
atccccgtgg tgtccaacct gaccggcgag cccgtcgccg cgttcgacgc cgactactgg 2640
gtacgccacg tgcgcgagcc ggtccggttc gccgacgcca tgagctggct cgaatcccag 2700
ggcgtcacca cctacctgga actgggcccc gacgccgtcc tgtcggcaat gggccgcgac 2760
tgcctgaccg acggcggcgc cgacgccgcg ttcgccgccc tgctgcgcga cgggcacgac 2820
gaggagcgcc agagtctcac cgcgctcggc ctggcgcacg cccacggtct cgcggtcgac 2880
tgggaccgct tcttcgccgg ccgcggcgcc caccgcaccg cgctgcccac ctactcgttc 2940
cagcgcaggc gctactggct ggacgccgga agcagccacc ccggcacgat cgggcacccg 3000
atgctggaca gcgccgtcag cctcgcgggc gccgacggag tgatcctgac gggccggatg 3060
tccacccggg cacagccctg gctggccgac catgtcatcg cgggtgtcgt cctcgtaccc 3120
ggcaccgccc tcgtcgaact ggccgtccgc gccggcgacg aggcgggctg cgccgcggtg 3180
gaggaactca ccctggagac accgctggcg gtcaccaccg acgccggagt cgagatccag 3240
gtcgtcgtcg gcgcgctcga cgcctcgggc cgccgctcgg tcgacatcta ctcgcgcccc 3300
gcgcggagcg aggacaactg gacccgccac gccagcgggg tgctgaccga gcacggcgag 3360
ggcgcgacgg ccgacccggc cgtgttcgcc cagtggccgc cggccgacgc cgagccgatc 3420
gacgtcgacg gcctctacga gcgccaggcc gcgcaggggt acggctacgg gcccgcgttc 3480
cgacgcgtgc gcgccgcgtg gcgccgcggg gacgacgtgt tcgccgaggt cgccctcgac 3540
gacgccggag gcgaccggtt cggactgcac cccgcgctgc tggactcctc actgcacgcc 3600
gccgaaggcc cggaggacga cggccaggtg cggctgccgt tcgcctggcg cggtgtcgaa 3660
ctccacgcca ccggcgccac cgccgtacgc gtccacgtcg tccagaccgc cccggacgag 3720
gtcacggtcg aactcgccga cgcgaacggg gcacccgtcg ccaccgtccg ctcgctcgtc 3780
cagcgccccg tgccgatcaa cggcgtacgg ccgtccgcct cgggcggcgg ctcgctgctg 3840
cgcgtcgaat ggaccgccgt ccaggccccg tccgagccgg acgccgcgtc gcacgagttc 3900
caactggcgt acgtccccga gaccttcccc ggcgaacccg ccgacgcggc ccgggcggcg 3960
acactgcacg ccctcaccct catccaggac gcgctgcgcg acgacacccg cctcgcgatc 4020
gtcacccgcg gcgagccgta cgacttcacc ctcgcgtccc cgtgggcgct cgtgcgctcc 4080
gcccaggccg agaaccccgg ccgcttcgtc ctcgtcggca ccgaccacga cgtgcccgaa 4140
cacgaactgc gcgccgccct ggccaccggc gaaccccaac tcgccctgcg cgacggcaag 4200
gtactcgtgc cccgcctggc caggacgccc gcacccgagg acccgcgccc cgtcgcgtgg 4260
gacccggacg gcacggtgct gatcaccggc ggcaccggcg gtctgggcgg cgtggtcgcc 4320
cgccacctcg tacaacagca cggcgtgcgg cacctgctgc tcaccgggcg acgcggcccc 4380
gacagccccg gcgccgccga actcgtcgcc gaactggccg gcttgggcgc ccacgccacg 4440
gtcgccgcct gtgatgtcgc cgaccgcgcc gccctggccg cgctgctgga gacggtcccc 4500
ggcgagcacc cgctgacggg tgtcgtccac agcgccggag tcgtcgacga cgggctcgcc 4560
ggatcgctca cgcccgagca ggtccacacc gtcttccacg gcaaggccga cggcgcctgg 4620
catctgcacg agctgacccg cggcctcccg ctcgccgcct tcgtcctgtt ctcctccgcg 4680
gccgggacca tggaggcggc cgggcagggc aactacgccg ccgccaacgc cttcctggac 4740
gccctcgccg cgcaccgcgt cacccagggc ctccccgcga cctccctcgc gtggaacctg 4800
tgggcgggcg acgcgggaat gggcgcccgc ctggacgagg tcaccctccg ccgggccgag 4860
cgttccgggc tccccgccct ggacgccgag gagaacctcg ccctgctgga ccaggcgctc 4920

-continued

```
gtcaccggtg cgccggcact cgtcccgctg cgcgtcgacg cccgcgcgct gcgggcccgc   4980
tccgaaggca tcccgccgat gctgcggggg ctggtccgcc cgcccgcccg ccggaacacc   5040
gccgcggcgg ccgcgaccgg ccccggcggc gcactggccg accggctcgc cggaaagccg   5100
gacgccgaac gcgaacgcat cgtcctcgac ctggtccgga cccagatcgc cgccgtactc   5160
ggacacgaca gcggcaccgc gatcgacccc cgccgcgcct tcaccgagct gggcttcgac   5220
tcactggccg ccatcgaact gcgcaacgcg ctcggtacgg ccaccgggct gcggctcacc   5280
tccacgctga tcttcgacca cccgaccccg cgcgccctgg tcgaccacgt gctcgaaacc   5340
gtacgcggag ccgtacccgt caccgcggcg ccgcggccca ccgtgcggac cgcgaccgac   5400
gagcccatcg cgatcgtggc gatgggctgc cgctacccgg gcggcgtgac ctccgccgag   5460
gaactgtggc ggctggtcgc cggcggcacc gacgccatca ccgagttccc ggacgaccgg   5520
gactggcaca ccgacgacat ctacgacccc gagcccggca agcacggcac cacgtacacc   5580
cgtgagggcg gcttcctgca cgacgtcgcc gagttcgacc ccgccttctt cggcatcagc   5640
ccgaaggagg cccaggcgat ggacccccag caccgcatgc tcctcgaagt cgcctgggag   5700
gccctcgaac agggcggcat cgatccgcac tccctgcacg gcaccgccgc cggtgtgttc   5760
gccggtgtca tgaaccacga ctggacgacc cgctccggcg ccgtccccga ggacctcgcg   5820
ggcttcaccg ccgggggcgg cctcggcagc atcgcctccg gacgcatcgc ctacaccctg   5880
ggtctccagg gccctgcggt caccatcgac accgcctgct cctcctccct ggtggccatg   5940
cactgggcga tgcagtcgct gcggcagggc gagtgcacgc tcgccctggc cggcggcgtc   6000
accgtgatgg ccacgcccga gacgttcgtc gggatgagcc tgcagagcgg cctcgccgcc   6060
gacggccgct gcaaggcgta cggcgccggc gccgacggca ccggctgggg cgagggcgcc   6120
ggactcctgg tgctcgaacg cctgtcggac gcccgccgca acggtcaccc ggtggtcgcg   6180
gtgatccgcg gctcggcgat caaccaggac ggcgcgtcca acggcatcgc ggccccccaac   6240
ggccccgccc agcagcgggt gatccggcag gccgtggcct ccgccggtct gacactcgcc   6300
gacatcgacg cggtcgaggg ccacggcacc ggcaccaccc tcggcgaccc gatcgaggca   6360
caggcgctga tggccaccta cggccaggag cgccgcgacg atccgctgtg gctcggctcg   6420
gtcaagtcca acctcgggca cacccaggcc gccgccggcg tcgccggcgt catcaagatg   6480
gtgatggcga tgcgccacgg cgtactgccg cgcaccctgc atgccgagac cccctctccg   6540
cacatcgact ggaccgaggg cgccgtcgaa ctgctcaccg agcccaggga ctggacggcc   6600
gacggccgcc cgcgccgcgc cgccgtctcc tccttcggcg tcagcggcac caacgcccac   6660
gtgatcatcg agcaggcgcc gccggccggc ccgggcgaac cgcgcggcga gcggcctccg   6720
gtcgtcccgc tgaccgtgtc gggctcgacc cccgaggcga tgcgcgccca ggcggcgcgc   6780
atcgccgccc acctgcgcga gaacggcgac gtcgacgaac tggacgccgc cgccacgctt   6840
gcccgaggcc gcgccgccct ggaacaccgg gccgtgatcg tggacgccga ccgcgacggc   6900
ctgctcgccg gactcgacgc gctggccgcc gggaactcgt ccgccgccgt ggtccagggc   6960
ctgcaacgcg gcgactcgcg cgccgtgctg gtcttcccag gacagggctc gcagtggcag   7020
ggcatgggcg tcgaactgct ggagcactca ccggcgttcg cgacacgcct gggcgaatgc   7080
gccaaggcac tcgaatcgta cgtcgactgg aacctgctcg acgtggtcca cggcgcgccc   7140
ggcgcaccgg ccctggacgc cgtcgacgtc gtccagccca cgctgtgggc gctgatggtg   7200
tcgctggccg aggcctggcg cgcggccggt gtcgaaccgg ccgccgtcgt cggccactcc   7260
```

-continued

```
cagggcgaga tcgccgccgc ctgtgtcgcc ggcgcgctgt cgctggagga cggcgcacgc   7320
gtggtcgccc tgcgcagccg cgtcatccgg caggacctgg cgggccgggg cggcatgatg   7380
tcggtcgccc tgtccgccga ccgcgcgagt gagtacctgg ccgactggga cggccgcctg   7440
caactcgccg tcgtcaacgg cccgagctcc gtcgtcgtgt gcggcggccc ggaggccctc   7500
gacgaactgc ggggccggct ggacaccgac gaggtccagt cccgccgtat cccggtggac   7560
tacgcctccc actcgatgtt cgtggaggag atccgcgacc ggctgctcac cgaactgagc   7620
ggcctgacac cccgtacctc gtccatcccg ttctactcca ccgtcaccgc gggaaccctg   7680
gacaccgccg gtctcgacgc cgagtactgg tacaccaacc tgcgccagac cgtccggttc   7740
gaggacacga cgcgggcact gctcgccgac ggcttcgaga ccttcatcga ggccagcccg   7800
cacccgggcc tgctgaccgg actcgacgag accgccgagt cggccggggt ggccgccaca   7860
ctcgtcggca cactgcgccg cgactccggc agcccgcgcc agttcgtcac ctcgctggcc   7920
gaggcgtacg tgcggggcgc gaccgtcgac tgggacaccc agttcgtcgg aaccggggcc   7980
cagcacgtcg aactgcccac ctaccccttc cagcgcaagc ggtactggct gcacctgtcc   8040
gagcacaccg gcgacgccgt gggcatcggc cagataccca ccgaccaccc gctgctcggg   8100
gcggccgtgc cggtcgccgg ggccgggggga gtactgctca ccggacgcct ctcgctctcc   8160
ggccagccat ggctcgccga ccacgtcgtc ggcggcaccg tcctgttccc cgggtcaggc   8220
ttcgtggaac tggccgtccg ggccggtgac gaggtcggcc ggggccgcgt ggaagaactg   8280
acactcgaag caccgctggc tctccccgag cgcggcggcg tggccatcca ggtcgtggtc   8340
gacgccgatc tgcgtaccgt gtcgatccac tcgcggcccg acaacgcccc cgccgacacc   8400
ctctggacac gccacgccca gggcacgctc accgacgccg cgcccgaacc ggcccacgag   8460
ccggcggcct ggccgccgcc gggcgccgag cccgtcgacc tcaccggctt ctacgagccg   8520
gccgccgacg gcggcctcgc ctacgggccg gtgttccagg gtttgcgtgc cgcctggcgc   8580
tccggcgacg aggtgttcgc ggagatcacg ctccccgagc aggccgccgc cgaggcccag   8640
cggttcgggc tgcacccggc cgcactcgac gccgctctcc acgcgaccgg actgctcgcc   8700
accgacgccc aaagggtcac cctgccgttc gcctggacac gggtcgacct gcacgcctcg   8760
ggagccgccg cgctcagact gcggatgacc agcctgggtg atgacgaggt ggcgctgcgc   8820
ctcaccgaca ccgcgggccg ccccgtcgcc tccgtcgagt cgctcgtact gcgtccggtg   8880
gccccgggcg ggccgatccg caccggcgcg tacgacgact cgctgttcga gctggtctgg   8940
gcacccgccg cacccgtacc tggcggcacc gccccccgga ccgtcgtgca ccactgcacg   9000
ggcggcacca ccgccgcgtc ggcccacgcc gagaccgcca cgacactcgc cgtcctccag   9060
tcctggctgg agagcggcgc cgacgacgcc gtgctcgccg tcgtcacccg cggcgccctg   9120
tccgtgaacg gcgaggacgt caccgacctc gccggagcgg ccgtctgggg actcgtacgc   9180
agcgctcaga cggagaaccc cggacgcgtc gtcctgatcg acctggacgc cgtcgacgac   9240
cgcgccgacc acacggacgc cgacatcgac gcggcggtgg ccacgggcga ggcccagatc   9300
gccatacgct ccggcaccct ccaccgcccg cgactggccc gcgtcaccgg ggacctgagc   9360
ggcaccgccg ccaccgtctt cggcgaccgg cccggcaccg tactgatcac cggcggcacc   9420
ggcaccctgg gcagcctcgt cgccaggcac ctggtcacca cccacggcgt caccgacctg   9480
ctgctcacca gccgccgcgg ccccgccgca cccggtgccg ccgaactgga cgccgaactc   9540
accgcgctcg gcgcccgtgt cgaggtggtc gcctgcgaca ccgccgaccg cgacgcgctg   9600
gcggccgtgc tggcggaccg caccctcacc ggaatcgtcc acaccgcggg cgtcctcgac   9660
```

```
gacgggatcc tctcctcgct gacaccggag agaatggccg cggtgatgcg ccccaaggtc   9720
gacgcggcgc tgaacctgca cgaactcacc gccggtcaag acctctcggc gttcgtgatg   9780
ttctcgtccg ccgcgggcgt gaccggcggc gccggacagg gcaactacgc cgccgccaac   9840
accttcctcg acggcctcgc cgcgcaccgg cgcgcgaacg ggctctcggc acagtccctg   9900
gcctggggac tgtgggaaga ggccagcggc atgaccggcg aactggccga cgccgacgtg   9960
gccggcatgg tgcgcgacgg tgtcctgccc atcggctccg acgagggcct ggcgatgctg  10020
gacgccgccg gcgcgctcga ccgggcgttc ctggcgcccg tccggctcga cctgagcggg  10080
cagagccggt ccgacgtgcc ctatctgatg cgcgatctcg tacgcggccc gtcccgccgc  10140
gtagtcgatc ccgccgcacg ggccgccgaa ccggccgaga gcctgcgcga ccggctggca  10200
cggctgactc cgtcccgccg cgaacagaca ctgctcgaca tcgtccgggc gcaggccgcc  10260
accaccctcg gcttcggcga cgccgacgag gtcgacgccg accggtcgtt ccgcgacatg  10320
ggcttcgact ccctcgccgc cgtgcggttc cgcaacgccc tcggcgaggt catcggggaa  10380
cgcctgcccg cgacgctcgt cttcgaccac ccgacctcgc tcgtcctcac tcggcacctg  10440
cttgaggaaa tggcgatcga cgtacccgag aacgaaccgg agcccgagtc ggccgagggt  10500
gccgcggacc gcaccgccgc gatccagaac atgagcctgg ccgaccttct ccgcaccgcg  10560
cgacgatcag gagacccgac atga                                          10584
```

<210> SEQ ID NO 13
<211> LENGTH: 3527
<212> TYPE: PRT
<213> ORGANISM: Streptomyces sp. MP28-13

<400> SEQUENCE: 13

```
Met Thr Glu Gln Ser Arg Ala Ala Met Leu Glu Leu Val Leu Ala Gln
1               5                   10                  15

Ala Ala Ala Val Leu Arg Thr Ala Asp Pro Asp Ala Tyr Gly Glu Gly
            20                  25                  30

Ala Val Asp Leu Ala Ala Asp Arg Pro Phe Leu Ala Gly Gly Leu Asp
        35                  40                  45

Ser Leu Gly Leu Val Arg Leu Gln Arg Arg Leu Ala Ala Glu Val Gly
    50                  55                  60

Ala Asp Leu Pro Val Thr Leu Ala Phe Asp His Pro Thr Pro Ile Ala
65                  70                  75                  80

Leu Ala Gly His Leu Ala Asp Leu Leu His Gly Thr Ala Gly Ala Asp
                85                  90                  95

Ala Pro Asp Glu Thr Ala Ala Pro Ala Leu Pro Ser Ala Phe Gly Glu
            100                 105                 110

Pro Ile Ala Ile Val Gly Ile Gly Cys Arg Phe Pro Gly Gly Val Ser
        115                 120                 125

Thr Pro Glu Asp Leu Trp Arg Ile Val Ala Asp Asp Thr His Val Leu
    130                 135                 140

Thr Asp Phe Pro Ser Asp Arg Gly Trp Asp Leu Asp Arg Ile Tyr Asn
145                 150                 155                 160

Pro Asp Pro Ser Val Thr Gly Ala Ser Tyr Val Arg Arg Gly Gly Phe
                165                 170                 175

Leu Pro Asp Ala Ala Asp Phe Asp Ala Asp Phe Phe Gln Ile Ser Pro
            180                 185                 190

Lys Glu Ala Leu Ala Met Asp Pro Gln Gln Arg Leu Leu Leu Glu Thr
        195                 200                 205
```

-continued

```
Ser Trp Glu Ala Leu Glu His Ala Gly Ile Asp Pro Gly Arg Leu Arg
    210                 215                 220

Gly Thr Pro Ser Gly Val Phe Ile Gly Val Glu Pro His Glu Tyr Gly
225                 230                 235                 240

Pro Arg Thr His Glu Ala Pro Asp Gly Leu Asp Gly Tyr Val Leu Gly
                245                 250                 255

Gly Asn Leu Pro Ser Val Val Ser Gly Arg Val Ala Tyr Thr Leu Gly
            260                 265                 270

Phe Glu Gly Pro Thr Leu Thr Val Asp Thr Ala Cys Ser Gly Ser Leu
        275                 280                 285

Thr Ala Leu His Leu Ala Val Arg Ser Leu Gln Gly Gly Glu Cys Gly
    290                 295                 300

Leu Ala Leu Ala Gly Gly Val Thr Val Ile Ser Ser Pro Gly Thr Phe
305                 310                 315                 320

Thr Thr Phe Ser Arg Gln Arg Gly Leu Ala Pro Asp Gly Arg Ile Lys
                325                 330                 335

Ala Phe Ala Ala Ala Ala Asp Gly Thr Ser Phe Ala Glu Gly Val Gly
            340                 345                 350

Val Phe Val Leu Ala Arg Leu Ser Asp Ala Leu Arg Asp Gly His Pro
        355                 360                 365

Val Leu Ala Val Ile Arg Gly Thr Ala Ile Asn Gln Asp Gly Ala Thr
    370                 375                 380

Asn Gly Leu Ser Ala Pro Asn Gly Leu Ala Gln Gln Arg Val Ile Arg
385                 390                 395                 400

Arg Ala Leu Thr Asp Ala Arg Leu Thr Ala Asp Glu Val Asp Ala Val
                405                 410                 415

Glu Ala His Gly Thr Gly Thr Thr Leu Gly Asp Pro Ile Glu Gly Gln
            420                 425                 430

Ala Leu Val Ala Ala Tyr Gly Arg Gly Arg Ser Pro Glu Lys Pro Leu
        435                 440                 445

Trp Leu Gly Ser Val Lys Ser Asn Ile Gly His Thr Gly Ala Ala Ala
    450                 455                 460

Gly Ala Ala Gly Ile Ile Lys Met Val Gln Ala Met Arg His Ser Thr
465                 470                 475                 480

Leu Pro Arg Thr Leu His Val Asp Ala Pro Thr Thr His Val Asp Trp
                485                 490                 495

Ser Asp Gly Thr Val Gln Leu Leu Thr Glu Pro Val Pro Trp Glu Ala
            500                 505                 510

Ala Asp Thr Pro Arg Arg Ala Gly Ile Ser Ser Phe Gly Ala Ser Gly
        515                 520                 525

Thr Asn Ala His Val Ile Ile Glu Glu Pro Pro Ala Pro Val Ala Ala
    530                 535                 540

Ala Asp Gly Ser Asp Glu Pro Pro Val Ala Glu Arg Pro Val Pro Val
545                 550                 555                 560

Val Leu Ser Ala Gln Gly Gln Asp Ala Leu Arg Gly Gln Ala Glu Arg
                565                 570                 575

Leu Leu Thr Ala Val Asp Asp Ala Ser Pro Leu Asp Leu Ala Tyr Ser
            580                 585                 590

Ala Ala Thr Thr Arg Ala Ala Leu Arg Asp Arg Ala Thr Val Val Ala
        595                 600                 605

Ala Asp Arg Ala Glu Leu Arg Arg Ala Leu Thr Ala Leu Ala Ala Gly
    610                 615                 620
```

-continued

```
Glu Ser Ala Pro Gly Leu Leu Thr Gly Thr Thr Pro Ala Ala Gly Arg
625                 630                 635                 640

Thr Ala Phe Leu Phe Thr Gly Gln Gly Ser Gln Arg Leu Gly Met Gly
                645                 650                 655

Arg Glu Leu Val Arg Ala Phe Pro Val Phe Ala Arg Ala Leu Gln Asp
            660                 665                 670

Ala Ala Asp His Leu Asp Leu His Leu Asp Glu Pro Leu Gly Glu Val
        675                 680                 685

Leu Phe Ala Glu Pro Gly Ser Ala Gln Ala Glu Leu Leu Gln Gln Thr
    690                 695                 700

Arg Tyr Ala Gln Ala Ala Leu Phe Ala Val Glu Thr Ala Met Phe Arg
705                 710                 715                 720

Leu Leu Glu Ser Trp Gly Val Thr Pro Gly Leu Leu Thr Gly His Ser
                725                 730                 735

Ile Gly Glu Ile Ala Ala Ala His Val Ala Gly Val Met Asn Leu Ala
            740                 745                 750

Asp Ala Ala Leu Leu Val Gly Ala Arg Gly Thr Leu Met Gln Glu Leu
        755                 760                 765

Pro Ala Gly Gly Ala Met Val Ala Val Gln Ala Ala Glu Ala Glu Val
    770                 775                 780

Ala Pro Tyr Leu Thr Glu Lys Val Gly Ile Ala Ala Val Asn Gly Pro
785                 790                 795                 800

Leu Ala Val Val Leu Ser Gly Glu Thr Asp Ala Val Leu Ala Val Ala
                805                 810                 815

Ala Arg Phe Thr Glu Glu Gly Arg Lys Thr Arg Arg Leu Arg Val Ser
            820                 825                 830

His Ala Phe His Ser Pro Leu Met Glu Pro Met Leu Asp Asp Phe Arg
        835                 840                 845

Arg Val Ala Glu Thr Leu Thr Tyr Gln Pro Pro Arg Ile Pro Val Val
    850                 855                 860

Ser Asn Leu Thr Gly Glu Pro Val Ala Ala Phe Asp Ala Asp Tyr Trp
865                 870                 875                 880

Val Arg His Val Arg Glu Pro Val Arg Phe Ala Asp Ala Met Ser Trp
                885                 890                 895

Leu Glu Ser Gln Gly Val Thr Thr Tyr Leu Glu Leu Gly Pro Asp Ala
            900                 905                 910

Val Leu Ser Ala Met Gly Arg Asp Cys Leu Thr Asp Gly Gly Ala Asp
        915                 920                 925

Ala Ala Phe Ala Ala Leu Leu Arg Asp Gly His Asp Glu Glu Arg Gln
    930                 935                 940

Ser Leu Thr Ala Leu Gly Leu Ala His Ala His Gly Leu Ala Val Asp
945                 950                 955                 960

Trp Asp Arg Phe Phe Ala Gly Arg Gly Ala His Arg Thr Ala Leu Pro
                965                 970                 975

Thr Tyr Ser Phe Gln Arg Arg Arg Tyr Trp Leu Asp Ala Gly Ser Ser
            980                 985                 990

His Pro Gly Thr Ile Gly His Pro  Met Leu Asp Ser Ala  Val Ser Leu
        995                 1000                 1005

Ala Gly  Ala Asp Gly Val Ile  Leu Thr Gly Arg Met  Ser Thr Arg
    1010                 1015                 1020

Ala Gln  Pro Trp Leu Ala Asp  His Val Ile Ala Gly  Val Val Leu
    1025                 1030                 1035

Val Pro  Gly Thr Ala Leu Val  Glu Leu Ala Val Arg  Ala Gly Asp
```

```
    1040                1045                1050

Glu Ala  Gly Cys Ala Ala Val  Glu Glu Leu Thr Leu  Glu Thr Pro
    1055                1060                1065

Leu Ala  Val Thr Thr Asp Ala  Gly Val Glu Ile Gln  Val Val Val
    1070                1075                1080

Gly Ala  Leu Asp Ala Ser Gly  Arg Arg Ser Val Asp  Ile Tyr Ser
    1085                1090                1095

Arg Pro  Ala Arg Ser Glu Asp  Asn Trp Thr Arg His  Ala Ser Gly
    1100                1105                1110

Val Leu  Thr Glu His Gly Glu  Gly Ala Thr Ala Asp  Pro Ala Val
    1115                1120                1125

Phe Ala  Gln Trp Pro Pro Ala  Asp Ala Glu Pro Ile  Asp Val Asp
    1130                1135                1140

Gly Leu  Tyr Glu Arg Gln Ala  Ala Gln Gly Tyr Gly  Tyr Gly Pro
    1145                1150                1155

Ala Phe  Arg Arg Val Arg Ala  Ala Trp Arg Arg Gly  Asp Asp Val
    1160                1165                1170

Phe Ala  Glu Val Ala Leu Asp  Asp Ala Gly Gly Asp  Arg Phe Gly
    1175                1180                1185

Leu His  Pro Ala Leu Leu Asp  Ser Ser Leu His Ala  Ala Glu Gly
    1190                1195                1200

Pro Glu  Asp Asp Gly Gln Val  Arg Leu Pro Phe Ala  Trp Arg Gly
    1205                1210                1215

Val Glu  Leu His Ala Thr Gly  Ala Thr Ala Val Arg  Val His Val
    1220                1225                1230

Val Gln  Thr Ala Pro Asp Glu  Val Thr Val Glu Leu  Ala Asp Ala
    1235                1240                1245

Asn Gly  Ala Pro Val Ala Thr  Val Arg Ser Leu Val  Gln Arg Pro
    1250                1255                1260

Val Pro  Ile Asn Gly Val Arg  Pro Ser Ala Ser Gly  Gly Gly Ser
    1265                1270                1275

Leu Leu  Arg Val Glu Trp Thr  Ala Val Gln Ala Pro  Ser Glu Pro
    1280                1285                1290

Asp Ala  Ala Ser His Glu Phe  Gln Leu Ala Tyr Val  Pro Glu Thr
    1295                1300                1305

Phe Pro  Gly Glu Pro Ala Asp  Ala Ala Arg Ala Ala  Thr Leu His
    1310                1315                1320

Ala Leu  Thr Leu Ile Gln Asp  Ala Leu Arg Asp Asp  Thr Arg Leu
    1325                1330                1335

Ala Ile  Val Thr Arg Gly Glu  Pro Tyr Asp Phe Thr  Leu Ala Ser
    1340                1345                1350

Pro Trp  Ala Leu Val Arg Ser  Ala Gln Ala Glu Asn  Pro Gly Arg
    1355                1360                1365

Phe Val  Leu Val Gly Thr Asp  His Asp Val Pro Glu  His Glu Leu
    1370                1375                1380

Arg Ala  Ala Leu Ala Thr Gly  Glu Pro Gln Leu Ala  Leu Arg Asp
    1385                1390                1395

Gly Lys  Val Leu Val Pro Arg  Leu Ala Arg Thr Pro  Ala Pro Glu
    1400                1405                1410

Asp Pro  Arg Pro Val Ala Trp  Asp Pro Asp Gly Thr  Val Leu Ile
    1415                1420                1425

Thr Gly  Gly Thr Gly Gly Leu  Gly Gly Val Val Ala  Arg His Leu
    1430                1435                1440
```

-continued

Val Gln Gln His Gly Val Arg His Leu Leu Leu Thr Gly Arg Arg
1445 1450 1455

Gly Pro Asp Ser Pro Gly Ala Ala Glu Leu Val Ala Glu Leu Ala
1460 1465 1470

Gly Leu Gly Ala His Ala Thr Val Ala Ala Cys Asp Val Ala Asp
1475 1480 1485

Arg Ala Ala Leu Ala Ala Leu Leu Glu Thr Val Pro Gly Glu His
1490 1495 1500

Pro Leu Thr Gly Val Val His Ser Ala Gly Val Val Asp Asp Gly
1505 1510 1515

Leu Ala Gly Ser Leu Thr Pro Glu Gln Val His Thr Val Phe His
1520 1525 1530

Gly Lys Ala Asp Gly Ala Trp His Leu His Glu Leu Thr Arg Gly
1535 1540 1545

Leu Pro Leu Ala Ala Phe Val Leu Phe Ser Ser Ala Ala Gly Thr
1550 1555 1560

Met Glu Ala Ala Gly Gln Gly Asn Tyr Ala Ala Ala Asn Ala Phe
1565 1570 1575

Leu Asp Ala Leu Ala Ala His Arg Val Thr Gln Gly Leu Pro Ala
1580 1585 1590

Thr Ser Leu Ala Trp Asn Leu Trp Ala Gly Asp Ala Gly Met Gly
1595 1600 1605

Ala Arg Leu Asp Glu Val Thr Leu Arg Arg Ala Glu Arg Ser Gly
1610 1615 1620

Leu Pro Ala Leu Asp Ala Glu Glu Asn Leu Ala Leu Leu Asp Gln
1625 1630 1635

Ala Leu Val Thr Gly Ala Pro Ala Leu Val Pro Leu Arg Val Asp
1640 1645 1650

Ala Arg Ala Leu Arg Ala Arg Ser Glu Gly Ile Pro Pro Met Leu
1655 1660 1665

Arg Gly Leu Val Arg Pro Pro Ala Arg Arg Asn Thr Ala Ala Ala
1670 1675 1680

Ala Ala Thr Gly Pro Gly Gly Ala Leu Ala Asp Arg Leu Ala Gly
1685 1690 1695

Lys Pro Asp Ala Glu Arg Glu Arg Ile Val Leu Asp Leu Val Arg
1700 1705 1710

Thr Gln Ile Ala Ala Val Leu Gly His Asp Ser Gly Thr Ala Ile
1715 1720 1725

Asp Pro Arg Arg Ala Phe Thr Glu Leu Gly Phe Asp Ser Leu Ala
1730 1735 1740

Ala Ile Glu Leu Arg Asn Ala Leu Gly Thr Ala Thr Gly Leu Arg
1745 1750 1755

Leu Thr Ser Thr Leu Ile Phe Asp His Pro Thr Pro Arg Ala Leu
1760 1765 1770

Val Asp His Val Leu Glu Thr Val Arg Gly Ala Val Pro Val Thr
1775 1780 1785

Ala Ala Pro Arg Pro Thr Val Arg Thr Ala Thr Asp Glu Pro Ile
1790 1795 1800

Ala Ile Val Ala Met Gly Cys Arg Tyr Pro Gly Gly Val Thr Ser
1805 1810 1815

Ala Glu Glu Leu Trp Arg Leu Val Ala Gly Gly Thr Asp Ala Ile
1820 1825 1830

```
Thr Glu  Phe Pro Asp Asp Arg  Asp Trp His Thr Asp  Asp Ile Tyr
    1835                 1840                 1845

Asp Pro  Glu Pro Gly Lys His  Gly Thr Thr Tyr Thr  Arg Glu Gly
    1850                 1855                 1860

Gly Phe  Leu His Asp Val Ala  Glu Phe Asp Pro Ala  Phe Phe Gly
    1865                 1870                 1875

Ile Ser  Pro Lys Glu Ala Gln  Ala Met Asp Pro Gln  His Arg Met
    1880                 1885                 1890

Leu Leu  Glu Val Ala Trp Glu  Ala Leu Glu Gln Gly  Gly Ile Asp
    1895                 1900                 1905

Pro His  Ser Leu His Gly Thr  Ala Ala Gly Val Phe  Ala Gly Val
    1910                 1915                 1920

Met Asn  His Asp Trp Thr Thr  Arg Ser Gly Ala Val  Pro Glu Asp
    1925                 1930                 1935

Leu Ala  Gly Phe Thr Ala Gly  Gly Gly Leu Gly Ser  Ile Ala Ser
    1940                 1945                 1950

Gly Arg  Ile Ala Tyr Thr Leu  Gly Leu Gln Gly Pro  Ala Val Thr
    1955                 1960                 1965

Ile Asp  Thr Ala Cys Ser Ser  Ser Leu Val Ala Met  His Trp Ala
    1970                 1975                 1980

Met Gln  Ser Leu Arg Gln Gly  Glu Cys Thr Leu Ala  Leu Ala Gly
    1985                 1990                 1995

Gly Val  Thr Val Met Ala Thr  Pro Glu Thr Phe Val  Gly Met Ser
    2000                 2005                 2010

Leu Gln  Ser Gly Leu Ala Ala  Asp Gly Arg Cys Lys  Ala Tyr Gly
    2015                 2020                 2025

Ala Gly  Ala Asp Gly Thr Gly  Trp Gly Glu Gly Ala  Gly Leu Leu
    2030                 2035                 2040

Val Leu  Glu Arg Leu Ser Asp  Ala Arg Arg Asn Gly  His Pro Val
    2045                 2050                 2055

Val Ala  Val Ile Arg Gly Ser  Ala Ile Asn Gln Asp  Gly Ala Ser
    2060                 2065                 2070

Asn Gly  Ile Ala Ala Pro Asn  Gly Pro Ala Gln Gln  Arg Val Ile
    2075                 2080                 2085

Arg Gln  Ala Val Ala Ser Ala  Gly Leu Thr Leu Ala  Asp Ile Asp
    2090                 2095                 2100

Ala Val  Glu Gly His Gly Thr  Gly Thr Thr Leu Gly  Asp Pro Ile
    2105                 2110                 2115

Glu Ala  Gln Ala Leu Met Ala  Thr Tyr Gly Gln Glu  Arg Arg Asp
    2120                 2125                 2130

Asp Pro  Leu Trp Leu Gly Ser  Val Lys Ser Asn Leu  Gly His Thr
    2135                 2140                 2145

Gln Ala  Ala Ala Gly Val Ala  Gly Val Ile Lys Met  Val Met Ala
    2150                 2155                 2160

Met Arg  His Gly Val Leu Pro  Arg Thr Leu His Ala  Glu Thr Pro
    2165                 2170                 2175

Ser Pro  His Ile Asp Trp Thr  Glu Gly Ala Val Glu  Leu Leu Thr
    2180                 2185                 2190

Glu Pro  Arg Asp Trp Thr Ala  Asp Gly Arg Pro Arg  Arg Ala Ala
    2195                 2200                 2205

Val Ser  Ser Phe Gly Val Ser  Gly Thr Asn Ala His  Val Ile Ile
    2210                 2215                 2220

Glu Gln  Ala Pro Pro Ala Gly  Pro Gly Glu Pro Arg  Gly Glu Arg
```

```
    2225                2230                2235

Pro Pro  Val Val Pro Leu Thr  Val Ser Gly Ser Thr  Pro Glu Ala
    2240                2245                2250

Met Arg  Ala Gln Ala Ala Arg  Ile Ala Ala His Leu  Arg Glu Asn
    2255                2260                2265

Gly Asp  Val Asp Glu Leu Asp  Ala Ala Ala Thr Leu  Ala Arg Gly
    2270                2275                2280

Arg Ala  Ala Leu Glu His Arg  Ala Val Ile Val Asp  Ala Asp Arg
    2285                2290                2295

Asp Gly  Leu Leu Ala Gly Leu  Asp Ala Leu Ala Ala  Gly Asn Ser
    2300                2305                2310

Ser Ala  Ala Val Val Gln Gly  Leu Gln Arg Gly Asp  Ser Arg Ala
    2315                2320                2325

Val Leu  Val Phe Pro Gly Gln  Gly Ser Gln Trp Gln  Gly Met Gly
    2330                2335                2340

Val Glu  Leu Leu Glu His Ser  Pro Ala Phe Ala Thr  Arg Leu Gly
    2345                2350                2355

Glu Cys  Ala Lys Ala Leu Glu  Ser Tyr Val Asp Trp  Asn Leu Leu
    2360                2365                2370

Asp Val  Val His Gly Ala Pro  Gly Ala Pro Ala Leu  Asp Ala Val
    2375                2380                2385

Asp Val  Val Gln Pro Thr Leu  Trp Ala Leu Met Val  Ser Leu Ala
    2390                2395                2400

Glu Ala  Trp Arg Ala Ala Gly  Val Glu Pro Ala Ala  Val Val Gly
    2405                2410                2415

His Ser  Gln Gly Glu Ile Ala  Ala Ala Cys Val Ala  Gly Ala Leu
    2420                2425                2430

Ser Leu  Glu Asp Gly Ala Arg  Val Val Ala Leu Arg  Ser Arg Val
    2435                2440                2445

Ile Arg  Gln Asp Leu Ala Gly  Arg Gly Gly Met Met  Ser Val Ala
    2450                2455                2460

Leu Ser  Ala Asp Arg Ala Ser  Glu Tyr Leu Ala Asp  Trp Asp Gly
    2465                2470                2475

Arg Leu  Gln Leu Ala Val Val  Asn Gly Pro Ser Ser  Val Val Val
    2480                2485                2490

Cys Gly  Gly Pro Glu Ala Leu  Asp Glu Leu Arg Gly  Arg Leu Asp
    2495                2500                2505

Thr Asp  Glu Val Gln Ser Arg  Arg Ile Pro Val Asp  Tyr Ala Ser
    2510                2515                2520

His Ser  Met Phe Val Glu Glu  Ile Arg Asp Arg Leu  Leu Thr Glu
    2525                2530                2535

Leu Ser  Gly Leu Thr Pro Arg  Thr Ser Ser Ile Pro  Phe Tyr Ser
    2540                2545                2550

Thr Val  Thr Ala Gly Thr Leu  Asp Thr Ala Gly Leu  Asp Ala Glu
    2555                2560                2565

Tyr Trp  Tyr Thr Asn Leu Arg  Gln Thr Val Arg Phe  Glu Asp Thr
    2570                2575                2580

Thr Arg  Ala Leu Leu Ala Asp  Gly Phe Glu Thr Phe  Ile Glu Ala
    2585                2590                2595

Ser Pro  His Pro Gly Leu Leu  Thr Gly Leu Asp Glu  Thr Ala Glu
    2600                2605                2610

Ser Ala  Gly Val Ala Ala Thr  Leu Val Gly Thr Leu  Arg Arg Asp
    2615                2620                2625
```

-continued

```
Ser Gly  Ser Pro Arg Gln Phe  Val Thr Ser Leu Ala  Glu Ala Tyr
    2630                 2635                 2640

Val Arg  Gly Ala Thr Val Asp  Trp Asp Thr Gln Phe  Val Gly Thr
    2645                 2650                 2655

Gly Ala  Gln His Val Glu Leu  Pro Thr Tyr Pro Phe  Gln Arg Lys
    2660                 2665                 2670

Arg Tyr  Trp Leu His Leu Ser  Glu His Thr Gly Asp  Ala Val Gly
    2675                 2680                 2685

Ile Gly  Gln Ile Pro Thr Asp  His Pro Leu Leu Gly  Ala Ala Val
    2690                 2695                 2700

Pro Val  Ala Gly Ala Gly Gly  Val Leu Leu Thr Gly  Arg Leu Ser
    2705                 2710                 2715

Leu Ser  Gly Gln Pro Trp Leu  Ala Asp His Val Val  Gly Gly Thr
    2720                 2725                 2730

Val Leu  Phe Pro Gly Ser Gly  Phe Val Glu Leu Ala  Val Arg Ala
    2735                 2740                 2745

Gly Asp  Glu Val Gly Arg Gly  Arg Val Glu Glu Leu  Thr Leu Glu
    2750                 2755                 2760

Ala Pro  Leu Ala Leu Pro Glu  Arg Gly Gly Val Ala  Ile Gln Val
    2765                 2770                 2775

Val Val  Asp Ala Asp Leu Arg  Thr Val Ser Ile His  Ser Arg Pro
    2780                 2785                 2790

Asp Asn  Ala Pro Ala Asp Thr  Leu Trp Thr Arg His  Ala Gln Gly
    2795                 2800                 2805

Thr Leu  Thr Asp Ala Ala Pro  Glu Pro Ala His Glu  Pro Ala Ala
    2810                 2815                 2820

Trp Pro  Pro Pro Gly Ala Glu  Pro Val Asp Leu Thr  Gly Phe Tyr
    2825                 2830                 2835

Glu Pro  Ala Ala Asp Gly Gly  Leu Ala Tyr Gly Pro  Val Phe Gln
    2840                 2845                 2850

Gly Leu  Arg Ala Ala Trp Arg  Ser Gly Asp Glu Val  Phe Ala Glu
    2855                 2860                 2865

Ile Thr  Leu Pro Glu Gln Ala  Ala Ala Glu Ala Gln  Arg Phe Gly
    2870                 2875                 2880

Leu His  Pro Ala Ala Leu Asp  Ala Ala Leu His Ala  Thr Gly Leu
    2885                 2890                 2895

Leu Ala  Thr Asp Ala Gln Arg  Val Thr Leu Pro Phe  Ala Trp Thr
    2900                 2905                 2910

Arg Val  Asp Leu His Ala Ser  Gly Ala Ala Ala Leu  Arg Leu Arg
    2915                 2920                 2925

Met Thr  Ser Leu Gly Asp Asp  Glu Val Ala Leu Arg  Leu Thr Asp
    2930                 2935                 2940

Thr Ala  Gly Arg Pro Val Ala  Ser Val Glu Ser Leu  Val Leu Arg
    2945                 2950                 2955

Pro Val  Ala Pro Gly Gly Pro  Ile Arg Thr Gly Ala  Tyr Asp Asp
    2960                 2965                 2970

Ser Leu  Phe Glu Leu Val Trp  Ala Pro Ala Ala Pro  Val Pro Gly
    2975                 2980                 2985

Gly Thr  Ala Pro Arg Thr Val  Val His His Cys Thr  Gly Gly Thr
    2990                 2995                 3000

Thr Ala  Ala Ser Ala His Ala  Glu Thr Ala Thr Thr  Leu Ala Val
    3005                 3010                 3015
```

```
Leu Gln  Ser Trp Leu Glu Ser  Gly Ala Asp Asp Ala  Val Leu Ala
    3020                 3025                 3030

Val Val  Thr Arg Gly Ala Leu  Ser Val Asn Gly Glu  Asp Val Thr
    3035                 3040                 3045

Asp Leu  Ala Gly Ala Ala Val  Trp Gly Leu Val Arg  Ser Ala Gln
    3050                 3055                 3060

Thr Glu  Asn Pro Gly Arg Val  Val Leu Ile Asp Leu  Asp Ala Val
    3065                 3070                 3075

Asp Asp  Arg Ala Asp His Thr  Asp Ala Asp Ile Asp  Ala Ala Val
    3080                 3085                 3090

Ala Thr  Gly Glu Ala Gln Ile  Ala Ile Arg Ser Gly  Thr Leu His
    3095                 3100                 3105

Arg Pro  Arg Leu Ala Arg Val  Thr Gly Asp Leu Ser  Gly Thr Ala
    3110                 3115                 3120

Ala Thr  Val Phe Gly Asp Arg  Pro Gly Thr Val Leu  Ile Thr Gly
    3125                 3130                 3135

Gly Thr  Gly Thr Leu Gly Ser  Leu Val Ala Arg His  Leu Val Thr
    3140                 3145                 3150

Thr His  Gly Val Thr Asp Leu  Leu Leu Thr Ser Arg  Arg Gly Pro
    3155                 3160                 3165

Ala Ala  Pro Gly Ala Ala Glu  Leu Asp Ala Glu Leu  Thr Ala Leu
    3170                 3175                 3180

Gly Ala  Arg Val Glu Val Val  Ala Cys Asp Thr Ala  Asp Arg Asp
    3185                 3190                 3195

Ala Leu  Ala Ala Val Leu Ala  Asp Arg Thr Leu Thr  Gly Ile Val
    3200                 3205                 3210

His Thr  Ala Gly Val Leu Asp  Asp Gly Ile Leu Ser  Ser Leu Thr
    3215                 3220                 3225

Pro Glu  Arg Met Ala Ala Val  Met Arg Pro Lys Val  Asp Ala Ala
    3230                 3235                 3240

Leu Asn  Leu His Glu Leu Thr  Ala Gly Gln Asp Leu  Ser Ala Phe
    3245                 3250                 3255

Val Met  Phe Ser Ser Ala Ala  Gly Val Thr Gly Gly  Ala Gly Gln
    3260                 3265                 3270

Gly Asn  Tyr Ala Ala Ala Asn  Thr Phe Leu Asp Gly  Leu Ala Ala
    3275                 3280                 3285

His Arg  Arg Ala Asn Gly Leu  Ser Ala Gln Ser Leu  Ala Trp Gly
    3290                 3295                 3300

Leu Trp  Glu Glu Ala Ser Gly  Met Thr Gly Glu Leu  Ala Asp Ala
    3305                 3310                 3315

Asp Val  Ala Gly Met Val Arg  Asp Gly Val Leu Pro  Ile Gly Ser
    3320                 3325                 3330

Asp Glu  Gly Leu Ala Met Leu  Asp Ala Ala Gly Ala  Leu Asp Arg
    3335                 3340                 3345

Ala Phe  Leu Ala Pro Val Arg  Leu Asp Leu Ser Gly  Gln Ser Arg
    3350                 3355                 3360

Ser Asp  Val Pro Tyr Leu Met  Arg Asp Leu Val Arg  Gly Pro Ser
    3365                 3370                 3375

Arg Arg  Val Val Asp Pro Ala  Ala Arg Ala Ala Glu  Pro Ala Glu
    3380                 3385                 3390

Ser Leu  Arg Asp Arg Leu Ala  Arg Leu Thr Pro Ser  Arg Arg Glu
    3395                 3400                 3405

Gln Thr  Leu Leu Asp Ile Val  Arg Ala Gln Ala Ala  Thr Thr Leu
```

```
    3410                3415                3420

Gly Phe  Gly Asp Ala Asp Glu  Val Asp Ala Asp Arg  Ser Phe Arg
    3425                3430                3435

Asp Met  Gly Phe Asp Ser Leu  Ala Ala Val Arg Phe  Arg Asn Ala
    3440                3445                3450

Leu Gly  Glu Val Ile Gly Glu  Arg Leu Pro Ala Thr  Leu Val Phe
    3455                3460                3465

Asp His  Pro Thr Ser Leu Val  Leu Thr Arg His Leu  Leu Glu Glu
    3470                3475                3480

Met Ala  Ile Asp Val Pro Glu  Asn Glu Pro Glu Pro  Glu Ser Ala
    3485                3490                3495

Glu Gly  Ala Ala Asp Arg Thr  Ala Ala Ile Gln Asn  Met Ser Leu
    3500                3505                3510

Ala Asp  Leu Leu Arg Thr Ala  Arg Arg Ser Gly Asp  Pro Thr
    3515                3520                3525


<210> SEQ ID NO 14
<211> LENGTH: 1599
<212> TYPE: DNA
<213> ORGANISM: Streptomyces sp. MP28-13

<400> SEQUENCE: 14

atgagcccga atggagcccg tccggtccgg gcgcacgcgt cggtggacaa cctgcggacg     60

tatctgctgg ccgccgcccg gagggacccc gaccggcccg ccgtgatcca ggcggcggcg    120

gacggtggtc tggagaccgt cacctacggc gaactggagc ggcgcgtcga ccgcctcgtc    180

gacgcgctcg acgcgctcgg cctggatgtg ggcgaccgcg tcatcctgga atccgacacc    240

aacgccgacg cggtggcgac cctgctggcc tgcgccacgc tggggctgcc gttcaccccg    300

accagccccg aggtcccgga cgagcggctg ctgacgatca tcgacagcgc ggagcccgcg    360

ctgcacatcc agtccgacca cgggcagcgc accggcattc ccgagacggt cggcaccgcc    420

cgcttcggcc ccggcggcct caccgtggag cgggcgcccg cgccgcgcgt ccgccgccgc    480

cgcgtggtga cgcccatcga caccgcgtac atcaccttca cgtcgggcac gaccggccgg    540

cccaagggcg tggtcatgag ccaccgcggg gtcatcgcgt tcctgcgggg cgctgaggcc    600

gcacggctcg tcacggccga ggaccgggtg gcgaacacct ctccgctcca gttcgacttc    660

gcgctgttcg acatcggcct cgccctcggc cacggcgcca cgctggtgcc cgtgccgcgc    720

gcccggctca actggccccg ccgcttcctt tcgtacctgc gcgatgcggg ggtcacacag    780

gtcgacggtg tcccgtccgt ctggcgcccg gtactgcgcc acgaatccga cctgctggcc    840

gagatgggcc aggagggcgt cctcagccgc atcaccttct ccggggagga cttccccctg    900

gacgagctgc ggcgcctcca ggaactgctg ccgaaggcgc gcttcaccaa cggttacggg    960

gccaccgaga cgatggccgc gtccatcacc gaggtgccca acccgctgcc gcccggcacc   1020

gaacgcctct ccatcggtta cgccgtcgcc ggcgccgaga tgatgctcct cgggtccgac   1080

ggcagccccg tcgacgagcc cggcaccatc ggcgagatct acctgcgcag cccctcgctc   1140

ttctccggct actggcgcga cccggaggcc acccgcgccg tcgtcctccc ggacccgctg   1200

caccccggat cgggacaggt ggtgttcaag accggcgacc tggcccatat ggggcccgag   1260

ggcgagctgt acttccgcgg tcgcgtcgac tcccaggtgc agatccgcgg caaccgcgtc   1320

gaactcggcg aggtggagcg ccgtatcggc cagttcgccg gtgtcaccgg cgcggtcgcg   1380

atggtcctgc cgcgcgagga cggcgaccca ctgctgcacg cgttcgtcac ctgcgccccc   1440
```

-continued

```
gcgggtcccg cgccggacac cagagaagtc ctcgcgttct gtcgcgccgc gctgcccgcc   1500

tacatggtcc cgcacggtct gagcgtggtg aacgagttcc ccgtgaccgt caacggcaag   1560

gtcgaccgca ccgccctggc cgcccacgtg gcgtcctga                          1599


<210> SEQ ID NO 15
<211> LENGTH: 532
<212> TYPE: PRT
<213> ORGANISM: Streptomyces sp. MP28-13

<400> SEQUENCE: 15

Met Ser Pro Asn Gly Ala Arg Pro Val Arg Ala His Ala Ser Val Asp
1               5                   10                  15

Asn Leu Arg Thr Tyr Leu Leu Ala Ala Ala Arg Arg Asp Pro Asp Arg
            20                  25                  30

Pro Ala Val Ile Gln Ala Ala Ala Asp Gly Gly Leu Glu Thr Val Thr
        35                  40                  45

Tyr Gly Glu Leu Glu Arg Arg Val Asp Arg Leu Val Asp Ala Leu Asp
    50                  55                  60

Ala Leu Gly Leu Asp Val Gly Asp Arg Val Ile Leu Glu Ser Asp Thr
65                  70                  75                  80

Asn Ala Asp Ala Val Ala Thr Leu Leu Ala Cys Ala Thr Leu Gly Leu
                85                  90                  95

Pro Phe Thr Pro Thr Ser Pro Glu Val Pro Asp Glu Arg Leu Leu Thr
            100                 105                 110

Ile Ile Asp Ser Ala Glu Pro Ala Leu His Ile Gln Ser Asp His Gly
        115                 120                 125

Gln Arg Thr Gly Ile Pro Glu Thr Val Gly Thr Ala Arg Phe Gly Pro
    130                 135                 140

Gly Gly Leu Thr Val Glu Arg Ala Pro Ala Pro Arg Val Arg Arg Arg
145                 150                 155                 160

Arg Val Val Thr Pro Ile Asp Thr Ala Tyr Ile Thr Phe Thr Ser Gly
                165                 170                 175

Thr Thr Gly Arg Pro Lys Gly Val Val Met Ser His Arg Gly Val Ile
            180                 185                 190

Ala Phe Leu Arg Gly Ala Glu Ala Ala Arg Leu Val Thr Ala Glu Asp
        195                 200                 205

Arg Val Ala Asn Thr Ser Pro Leu Gln Phe Asp Phe Ala Leu Phe Asp
    210                 215                 220

Ile Gly Leu Ala Leu Gly His Gly Ala Thr Leu Val Pro Val Pro Arg
225                 230                 235                 240

Ala Arg Leu Asn Trp Pro Arg Arg Phe Leu Ser Tyr Leu Arg Asp Ala
                245                 250                 255

Gly Val Thr Gln Val Asp Gly Val Pro Ser Val Trp Arg Pro Val Leu
            260                 265                 270

Arg His Glu Ser Asp Leu Leu Ala Glu Met Gly Gln Glu Gly Val Leu
        275                 280                 285

Ser Arg Ile Thr Phe Ser Gly Glu Asp Phe Pro Leu Asp Glu Leu Arg
    290                 295                 300

Arg Leu Gln Glu Leu Leu Pro Lys Ala Arg Phe Thr Asn Gly Tyr Gly
305                 310                 315                 320

Ala Thr Glu Thr Met Ala Ala Ser Ile Thr Glu Val Pro Asn Pro Leu
                325                 330                 335

Pro Pro Gly Thr Glu Arg Leu Ser Ile Gly Tyr Ala Val Ala Gly Ala
            340                 345                 350
```

```
Glu Met Met Leu Leu Gly Ser Asp Gly Ser Pro Val Asp Glu Pro Gly
        355                 360                 365

Thr Ile Gly Glu Ile Tyr Leu Arg Ser Pro Ser Leu Phe Ser Gly Tyr
    370                 375                 380

Trp Arg Asp Pro Glu Ala Thr Arg Ala Val Val Leu Pro Asp Pro Leu
385                 390                 395                 400

His Pro Gly Ser Gly Gln Val Val Phe Lys Thr Gly Asp Leu Ala His
                405                 410                 415

Met Gly Pro Glu Gly Glu Leu Tyr Phe Arg Gly Arg Val Asp Ser Gln
            420                 425                 430

Val Gln Ile Arg Gly Asn Arg Val Glu Leu Gly Glu Val Glu Arg Arg
        435                 440                 445

Ile Gly Gln Phe Ala Gly Val Thr Gly Ala Val Ala Met Val Leu Pro
    450                 455                 460

Arg Glu Asp Gly Asp Pro Leu Leu His Ala Phe Val Thr Cys Ala Pro
465                 470                 475                 480

Ala Gly Pro Ala Pro Asp Thr Arg Glu Val Leu Ala Phe Cys Arg Ala
                485                 490                 495

Ala Leu Pro Ala Tyr Met Val Pro His Gly Leu Ser Val Val Asn Glu
            500                 505                 510

Phe Pro Val Thr Val Asn Gly Lys Val Asp Arg Thr Ala Leu Ala Ala
        515                 520                 525

His Val Ala Ser
    530
```

<210> SEQ ID NO 16
<211> LENGTH: 972
<212> TYPE: DNA
<213> ORGANISM: Streptomyces sp. MP28-13

<400> SEQUENCE: 16

```
atgagcccga caaataggga gagcgagaat atgtcggcga ttatctttcc cggaatcggc      60

ccggtccggc tcgccgactc ggcgcggttc ctggtgaccc atcccatagc ccgccgactc     120

gtcgctgaga cggaccgaat actgggctat tcccttctcg acagctatcg cgaggccgaa     180

gaccgcgacg accagggggc gttccccgag ccggcccgga tcgcgttcct ggtccagtgc     240

ctggcgctgg ccgagtgggc cgtcaaggag aacgacctgg acccggtcgt ctgcgccggc     300

gccagcttcg gcggcacggc ggcagcggtg cactccggcg cgctgtcgtt ccccgaagcc     360

gtggagatga ccgccgcgtg ggccgccgca gtcgacgact acttcacccg tgagcaccgc     420

gacatcgtca cccagtcatt cgcccgcgtc gcgcccgacc cgctcgcgga gatccaggcc     480

gagctggacg cacggggcga ctggaacgag gtggcctgcc aggtcgacaa cgacttccac     540

atgctgtcgg tgcgcgagga cgtggtcgag tggttgcagg gacggctccg cgcggcgggc     600

ggcctgccgc tgtacgtcat gcggccgccg atgcactcga cgctgttcga ggcgctgcgg     660

gaagagatcg cgaacgggat caccacggac atcacgttct ccgatccccg gatccccgtg     720

gtgtccgacc acgacgggtc gctggtacgg acgggggccg gggtgcggga gttgctgctg     780

aacgccgtga cgcacaccgt gcggtggccg gccgtcgtcg acacgatcaa ggggctcggc     840

gtcgagcggg tgcatgtcac cgggcaggac gccctgtggg gacgggtgga tgtcatgacc     900

aacgcgttcc aggtggtggc ggtgcgtccg gacacagcta tgcgaccgcg ccgtcgcagc     960

gcgatcgcat ag                                                         972
```

<210> SEQ ID NO 17
<211> LENGTH: 323
<212> TYPE: PRT
<213> ORGANISM: Streptomyces sp. MP28-13

<400> SEQUENCE: 17

```
Met Ser Pro Thr Asn Arg Glu Ser Glu Asn Met Ser Ala Ile Ile Phe
1               5                   10                  15

Pro Gly Ile Gly Pro Val Arg Leu Ala Asp Ser Ala Arg Phe Leu Val
            20                  25                  30

Thr His Pro Ile Ala Arg Arg Leu Val Ala Glu Thr Asp Arg Ile Leu
        35                  40                  45

Gly Tyr Ser Leu Leu Asp Ser Tyr Arg Glu Ala Glu Asp Arg Asp Asp
    50                  55                  60

Gln Gly Ala Phe Pro Glu Pro Ala Arg Ile Ala Phe Leu Val Gln Cys
65                  70                  75                  80

Leu Ala Leu Ala Glu Trp Ala Val Lys Glu Asn Asp Leu Asp Pro Val
                85                  90                  95

Val Cys Ala Gly Ala Ser Phe Gly Gly Thr Ala Ala Ala Val His Ser
            100                 105                 110

Gly Ala Leu Ser Phe Pro Glu Ala Val Glu Met Thr Ala Ala Trp Gly
        115                 120                 125

Arg Arg Val Asp Asp Tyr Phe Thr Arg Glu His Arg Asp Ile Val Thr
    130                 135                 140

Gln Ser Phe Ala Arg Val Ala Pro Asp Pro Leu Ala Glu Ile Gln Ala
145                 150                 155                 160

Glu Leu Asp Ala Arg Gly Asp Trp Asn Glu Val Ala Cys Gln Val Asp
                165                 170                 175

Asn Asp Phe His Met Leu Ser Val Arg Glu Asp Val Val Glu Trp Leu
            180                 185                 190

Gln Gly Arg Leu Arg Ala Ala Gly Gly Leu Pro Leu Tyr Val Met Arg
        195                 200                 205

Pro Pro Met His Ser Thr Leu Phe Glu Ala Leu Arg Glu Glu Ile Ala
    210                 215                 220

Asn Gly Ile Thr Thr Asp Ile Thr Phe Ser Asp Pro Arg Ile Pro Val
225                 230                 235                 240

Val Ser Asp His Asp Gly Ser Leu Val Arg Thr Gly Ala Gly Val Arg
                245                 250                 255

Glu Leu Leu Leu Asn Ala Val Thr His Thr Val Arg Trp Pro Ala Val
            260                 265                 270

Val Asp Thr Ile Lys Gly Leu Gly Val Glu Arg Val His Val Thr Gly
        275                 280                 285

Gln Asp Ala Leu Trp Gly Arg Val Asp Val Met Thr Asn Ala Phe Gln
    290                 295                 300

Val Val Ala Val Arg Pro Asp Thr Ala Met Arg Pro Arg Arg Arg Ser
305                 310                 315                 320

Ala Ile Ala
```

<210> SEQ ID NO 18
<211> LENGTH: 237
<212> TYPE: DNA
<213> ORGANISM: Streptomyces sp. MP28-13

<400> SEQUENCE: 18

```
atgtgggacg aatcattcga gcaacttctc cgcaaacaga ttcctttgct ggaaccggat      60
```

gaggagttga ccgccgaatt gagcctgcgc gattgcggtc tcgactccat gggaatggtc 120
tcactgctgt cctcgatgga ggacgcatat ggagtccgtt tcgtcgacga tgcgctcaac 180
atggataact tcgcgactcc cggggctctc tggaaaaccc tggacgccat gcgctga 237

<210> SEQ ID NO 19
<211> LENGTH: 78
<212> TYPE: PRT
<213> ORGANISM: Streptomyces sp. MP28-13

<400> SEQUENCE: 19

Met Trp Asp Glu Ser Phe Glu Gln Leu Leu Arg Lys Gln Ile Pro Leu
1 5 10 15

Leu Glu Pro Asp Glu Glu Leu Thr Ala Glu Leu Ser Leu Arg Asp Cys
20 25 30

Gly Leu Asp Ser Met Gly Met Val Ser Leu Leu Ser Ser Met Glu Asp
35 40 45

Ala Tyr Gly Val Arg Phe Val Asp Asp Ala Leu Asn Met Asp Asn Phe
50 55 60

Ala Thr Pro Gly Ala Leu Trp Lys Thr Leu Asp Ala Met Arg
65 70 75

<210> SEQ ID NO 20
<211> LENGTH: 1518
<212> TYPE: DNA
<213> ORGANISM: Streptomyces sp. MP28-13

<400> SEQUENCE: 20
atgaatcaga cacccgtccc cggacacggc ctgcacgaac ggttcctgac cggcctggcg 60
ctgtcgcccg gccggaccgc gatccgcgtg cacgccaccg agagcctgac gtacgagcag 120
atgcacgaac tggcgatgcg ccgggccgcg gcactgcggg ccatggctcc gcaagggccg 180
cacaacgtcg ccgtgctggc ggacaagagc ctgaccgctt atgtcgggat catcgccgcg 240
ctgtacgcgg gcgccaccgt cgtaccgctc aacccgcggt tcccggccga gcgcacccgc 300
tccatgctca tcgccgccaa cgtctccacc gtcatcgctg atccgatcgg ccgctcctca 360
ctcgcggaga ccgagctgga tctgcccgtc ctggacgagg gcaggacggg gccctcgctg 420
gacacgccgg tggccgtcaa cccttccgat gtcgcgtacg tcctgttcac ctcgggctcg 480
acgggccgcc ccaagggggt gccgatcacc cacggggcca accaccacta cttcgacctg 540
ctggaccggc gctacgactt cagccccgac gacgtgttct gccagaacgt cggactcaac 600
ttcgactgcg ccatgttcga gatgttctgc gcgtggggca acggggcgca ggtgcacccc 660
gtcccgcccg ccgcccaccg ggacctgccg gcgttcttgg ccgagcggaa gatgaccgtg 720
tggttctcca ccccgagcgg catcacgttc atccggcgga tgggcggcct gacccccgga 780
tcgatgccca cactgcgctg gaccttcttc gccggtgagg cgctgctgca cgaggacgcc 840
gccgactggc acgtcgccgc accccagtcg aagatcgaga atctgtacgg gccgaccgag 900
ctgaccgtga ccatcaccgg gcaccgctgg tcgccgaaga ccaccgagga gcagaccgtg 960
aacggcggcg tgccgatcgg aaaggtgcac cccggccacg accacctgct gctggacgac 1020
gacggcgagt cggcggtgga gggcgaactg tgcgtcgccg gaccgcagat gacacccggt 1080
tacctggacg gcgacgacaa ccggggccgc ttcctcgagc acgccggccg tcgctggtac 1140
cggaccggcg accgggtgcg gcggctggac gacgacgagc tgatctacct cggccggatg 1200
gacgcccagg tgcagatcca gggattccgg gtcgaactgg ccgaggtcga ccatgtcgtc 1260

-continued

```
cggcagtgca ccggtgtgca gaacgcggcc accgtcaccc ggccggcacc gaacggcgga   1320

ctggaactcg tcctctacta cacgggcgag cgcattccgt cggcgacgct gcgccgcgag   1380

ctggccgcgc acctgcccga tccgatggtg cccaagacct tccggcacgt gccggagttc   1440

ccgctcaatt ccaaccgcaa ggtcgaccgg gcgcagttgg cccgggaggc cgccgcgctg   1500

tcagacggtc gtgcctga                                                  1518
```

<210> SEQ ID NO 21
<211> LENGTH: 505
<212> TYPE: PRT
<213> ORGANISM: Streptomyces sp. MP28-13

<400> SEQUENCE: 21

```
Met Asn Gln Thr Pro Val Pro Gly His Gly Leu His Glu Arg Phe Leu
1               5                   10                  15

Thr Gly Leu Ala Leu Ser Pro Gly Arg Thr Ala Ile Arg Val His Ala
            20                  25                  30

Thr Glu Ser Leu Thr Tyr Glu Gln Met His Glu Leu Ala Met Arg Arg
        35                  40                  45

Ala Ala Ala Leu Arg Ala Met Ala Pro Gln Gly Pro His Asn Val Ala
    50                  55                  60

Val Leu Ala Asp Lys Ser Leu Thr Ala Tyr Val Gly Ile Ile Ala Ala
65                  70                  75                  80

Leu Tyr Ala Gly Ala Thr Val Val Pro Leu Asn Pro Arg Phe Pro Ala
                85                  90                  95

Glu Arg Thr Arg Ser Met Leu Ile Ala Ala Asn Val Ser Thr Val Ile
            100                 105                 110

Ala Asp Pro Ile Gly Arg Ser Ser Leu Ala Glu Thr Glu Leu Asp Leu
        115                 120                 125

Pro Val Leu Asp Glu Gly Arg Thr Gly Pro Ser Leu Asp Thr Pro Val
    130                 135                 140

Ala Val Asn Pro Ser Asp Val Ala Tyr Val Leu Phe Thr Ser Gly Ser
145                 150                 155                 160

Thr Gly Arg Pro Lys Gly Val Pro Ile Thr His Gly Ala Asn His His
                165                 170                 175

Tyr Phe Asp Leu Leu Asp Arg Arg Tyr Asp Phe Ser Pro Asp Asp Val
            180                 185                 190

Phe Cys Gln Asn Val Gly Leu Asn Phe Asp Cys Ala Met Phe Glu Met
        195                 200                 205

Phe Cys Ala Trp Gly Asn Gly Ala Gln Val His Pro Val Pro Pro Ala
    210                 215                 220

Ala His Arg Asp Leu Pro Ala Phe Leu Ala Glu Arg Lys Met Thr Val
225                 230                 235                 240

Trp Phe Ser Thr Pro Ser Gly Ile Thr Phe Ile Arg Arg Met Gly Gly
                245                 250                 255

Leu Thr Pro Gly Ser Met Pro Thr Leu Arg Trp Thr Phe Phe Ala Gly
            260                 265                 270

Glu Ala Leu Leu His Glu Asp Ala Ala Asp Trp His Val Ala Ala Pro
        275                 280                 285

Gln Ser Lys Ile Glu Asn Leu Tyr Gly Pro Thr Glu Leu Thr Val Thr
    290                 295                 300

Ile Thr Gly His Arg Trp Ser Pro Lys Thr Thr Glu Glu Gln Thr Val
305                 310                 315                 320
```

-continued

```
Asn Gly Gly Val Pro Ile Gly Lys Val His Pro Gly His Asp His Leu
                325                 330                 335

Leu Leu Asp Asp Asp Gly Glu Ser Ala Val Glu Gly Glu Leu Cys Val
            340                 345                 350

Ala Gly Pro Gln Met Thr Pro Gly Tyr Leu Asp Gly Asp Asp Asn Arg
        355                 360                 365

Gly Arg Phe Leu Glu His Ala Gly Arg Arg Trp Tyr Arg Thr Gly Asp
    370                 375                 380

Arg Val Arg Arg Leu Asp Asp Asp Glu Leu Ile Tyr Leu Gly Arg Met
385                 390                 395                 400

Asp Ala Gln Val Gln Ile Gln Gly Phe Arg Val Glu Leu Ala Glu Val
                405                 410                 415

Asp His Val Val Arg Gln Cys Thr Gly Val Gln Asn Ala Ala Thr Val
            420                 425                 430

Thr Arg Pro Ala Pro Asn Gly Gly Leu Glu Leu Val Leu Tyr Tyr Thr
        435                 440                 445

Gly Glu Arg Ile Pro Ser Ala Thr Leu Arg Arg Glu Leu Ala Ala His
    450                 455                 460

Leu Pro Asp Pro Met Val Pro Lys Thr Phe Arg His Val Pro Glu Phe
465                 470                 475                 480

Pro Leu Asn Ser Asn Arg Lys Val Asp Arg Ala Gln Leu Ala Arg Glu
                485                 490                 495

Ala Ala Ala Leu Ser Asp Gly Arg Ala
            500                 505


<210> SEQ ID NO 22
<211> LENGTH: 597
<212> TYPE: DNA
<213> ORGANISM: Streptomyces sp. MP28-13

<400> SEQUENCE: 22

atgggacacc gagaggatct gctggccgga gcgaagcaat gcctctacga gaaggggtac      60

gcgcgtacca ccgcgcgcga catcgtcgag gcttccggta cgaatctcgc ctcgatcggc     120

taccactacg gcaccaagga agcactcctc aacgccgcca tcatggaggc gctggaggag     180

tgggcccagg agctgaagag tgctctggca gacgtgggag acctccccga cgatccgatc     240

aagcggttcg aggtggcctg gacgcgcgtg atcgagctgt tcgagcgcca ccgcccggtg     300

tggggggccc agttcgacgc gatctcccag cgcgaccatg tgcccgaggt cggcagcttc     360

ttcatagagg cgcagcagca ggcacagaac ggcctggtcc ggctcctgtg ggcggcgaa      420

gagctgccgg gccccaccgc gaccgcggtc gggcagttct accacgcgct gctcagcggc     480

gtgatgatgc agtgggtcgt cgacccggag cacgcctcga cgggcgagtc gctcgccgag     540

gcgctacgga cggtcgcgga gaacgcccgt cacttcgggt caggcacgac cgtctga        597


<210> SEQ ID NO 23
<211> LENGTH: 198
<212> TYPE: PRT
<213> ORGANISM: Streptomyces sp. MP28-13

<400> SEQUENCE: 23

Met Gly His Arg Glu Asp Leu Leu Ala Gly Ala Lys Gln Cys Leu Tyr
1               5                   10                  15

Glu Lys Gly Tyr Ala Arg Thr Thr Ala Arg Asp Ile Val Glu Ala Ser
            20                  25                  30

Gly Thr Asn Leu Ala Ser Ile Gly Tyr His Tyr Gly Thr Lys Glu Ala
```

```
        35                  40                  45

Leu Leu Asn Ala Ala Ile Met Glu Ala Leu Glu Glu Trp Ala Gln Glu
    50                  55                  60

Leu Lys Ser Ala Leu Ala Asp Val Gly Asp Leu Pro Asp Asp Pro Ile
65                  70                  75                  80

Lys Arg Phe Glu Val Ala Trp Thr Arg Val Ile Glu Leu Phe Glu Arg
                85                  90                  95

His Arg Pro Val Trp Gly Ala Gln Phe Asp Ala Ile Ser Gln Arg Asp
            100                 105                 110

His Val Pro Glu Val Gly Ser Phe Phe Ile Glu Ala Gln Gln Gln Ala
        115                 120                 125

Gln Asn Gly Leu Val Arg Leu Leu Trp Gly Gly Glu Glu Leu Pro Gly
    130                 135                 140

Pro Thr Ala Thr Ala Val Gly Gln Phe Tyr His Ala Leu Leu Ser Gly
145                 150                 155                 160

Val Met Met Gln Trp Val Val Asp Pro Glu His Ala Ser Thr Gly Glu
                165                 170                 175

Ser Leu Ala Glu Ala Leu Arg Thr Val Ala Glu Asn Ala Arg His Phe
            180                 185                 190

Gly Ser Gly Thr Thr Val
        195
```

<210> SEQ ID NO 24
<211> LENGTH: 1575
<212> TYPE: DNA
<213> ORGANISM: Streptomyces sp. MP28-13

<400> SEQUENCE: 24

```
atgagtccgc aacgtgcaac cttgagggac tgggtcggcc tcgccgtcct tgtcgtccct     60

gtcctcatga tgtcgatgga catgacggtg ctgtacttcg cgctgccgtt cctcagcgcg    120

accctggaac cgagcgccac cgagcaactg tggatcgtgg acatctacgc gttcatgctc    180

gccgggctgc tcatcgcgat gggcacactc ggtgaccaca tcggccgccg gcggctgctg    240

atcatcggcg cggtggtgtt cggcgcgtcg tcactggcct ccgcctacgc gaccagcgcc    300

gagcttctga tcctcgcccg cgccgtgctc ggtatgtccg gcgccgtact cgcgccgtcc    360

acgctctcgc tgatccgcaa catgttccag gatcccggcc agcgccgtac cgccatcgcg    420

gtatggaccg ccggtctctc cggcggcgcc gccctcggtc cgatcgtgtc gggagtgctg    480

ctggagcact actggtgggg ctcggtcttc ctgatcaaca tcccggtgac gatcctgatc    540

gtggtgctcg gccccatcct cctgccggag caccgcgacc ccgagcccgg ccgtttcgac    600

ttcctcggtg ccgtgctgtc gctggccgcg atgcttcccg tcatctacgg catcaaggaa    660

ctcgccgacg acggcttcga ctggaagtac gtggcggtca ccgccgccgg cctggtcatc    720

ggggtgctct tcgtcctgcg ccagcgcgcg gcccccaatc cgctgatcga cctgagcctc    780

ttccgcgacc gggggttcac cgcgtccatc ggagtcaacc tggtggccct gttcgcgatg    840

atcgggttcc tgctcttcgc gacccagtgg atccagctgg tccacgggct gaatccgctg    900

gaggcgggcc tctggacact gcccgcgccg ttggcggtgg cggtcacgac atcggtcgcc    960

gtcgggctgg cgaagaagat ccgcccccggc tacatcatgg ccatcggcat ggtcatcgcg   1020

tcggcgggat tcgccatcat gacgcaactg cgcgccgatt cgagcctggc catggcggtg   1080

atcggcgcga gcgtgctgtc ggccggcgtc ggcatggcga tccccctgac cgccgacctg   1140

atcgtctccg cggctccgga ggaccgcgtg ggcgctgccg ccgcgctgcc cgagaccgcc   1200
```

```
aaccagctcg gcggagcgct gggcgtagcg atcctcggca gcatcggtgc cgccgtgtac   1260

acccgtgacg tcgccgacgt gacgacgggg ctgccacccg aggccgcgga ggcagcggag   1320

ggttcgctcg gcggcgcgac ggaagtggcc aaacacctgc ccggtgacac gggcgacgcc   1380

ctcgtcacgt ccgccgggga ggccttcacc cgcggcatga acctcagcgc cgcggtgggc   1440

ggcgtcgtca tgctgctcgg tgccgcgggc gcggcgctgc tcctgcgcca tgtcaagact   1500

cccaccgtca cgtccgcgcc ggcggacgag acgaagggcg agacggcgga cgagccctca   1560

cccgtcccca agtag                                                    1575

<210> SEQ ID NO 25
<211> LENGTH: 524
<212> TYPE: PRT
<213> ORGANISM: Streptomyces sp. MP28-13

<400> SEQUENCE: 25

Met Ser Pro Gln Arg Ala Thr Leu Arg Asp Trp Val Gly Leu Ala Val
1               5                   10                  15

Leu Val Val Pro Val Leu Met Met Ser Met Asp Met Thr Val Leu Tyr
            20                  25                  30

Phe Ala Leu Pro Phe Leu Ser Ala Thr Leu Glu Pro Ser Ala Thr Glu
        35                  40                  45

Gln Leu Trp Ile Val Asp Ile Tyr Ala Phe Met Leu Ala Gly Leu Leu
    50                  55                  60

Ile Ala Met Gly Thr Leu Gly Asp His Ile Gly Arg Arg Arg Leu Leu
65                  70                  75                  80

Ile Ile Gly Ala Val Val Phe Gly Ala Ser Ser Leu Ala Ser Ala Tyr
                85                  90                  95

Ala Thr Ser Ala Glu Leu Leu Ile Leu Ala Arg Ala Val Leu Gly Met
            100                 105                 110

Ser Gly Ala Val Leu Ala Pro Ser Thr Leu Ser Leu Ile Arg Asn Met
        115                 120                 125

Phe Gln Asp Pro Gly Gln Arg Arg Thr Ala Ile Ala Val Trp Thr Ala
    130                 135                 140

Gly Leu Ser Gly Gly Ala Ala Leu Gly Pro Ile Val Ser Gly Val Leu
145                 150                 155                 160

Leu Glu His Tyr Trp Trp Gly Ser Val Phe Leu Ile Asn Ile Pro Val
                165                 170                 175

Thr Ile Leu Ile Val Val Leu Gly Pro Ile Leu Leu Pro Glu His Arg
            180                 185                 190

Asp Pro Glu Pro Gly Arg Phe Asp Phe Leu Gly Ala Val Leu Ser Leu
        195                 200                 205

Ala Ala Met Leu Pro Val Ile Tyr Gly Ile Lys Glu Leu Ala Asp Asp
    210                 215                 220

Gly Phe Asp Trp Lys Tyr Val Ala Val Thr Ala Ala Gly Leu Val Ile
225                 230                 235                 240

Gly Val Leu Phe Val Leu Arg Gln Arg Ala Ala Pro Asn Pro Leu Ile
                245                 250                 255

Asp Leu Ser Leu Phe Arg Asp Arg Gly Phe Thr Ala Ser Ile Gly Val
            260                 265                 270

Asn Leu Val Ala Leu Phe Ala Met Ile Gly Phe Leu Leu Phe Ala Thr
        275                 280                 285

Gln Trp Ile Gln Leu Val His Gly Leu Asn Pro Leu Glu Ala Gly Leu
    290                 295                 300
```

```
Trp Thr Leu Pro Ala Pro Leu Ala Val Ala Val Thr Thr Ser Val Ala
305                 310                 315                 320

Val Gly Leu Ala Lys Lys Ile Arg Pro Gly Tyr Ile Met Ala Ile Gly
                325                 330                 335

Met Val Ile Ala Ser Ala Gly Phe Ala Ile Met Thr Gln Leu Arg Ala
            340                 345                 350

Asp Ser Ser Leu Ala Met Ala Val Ile Gly Ala Ser Val Leu Ser Ala
        355                 360                 365

Gly Val Gly Met Ala Ile Pro Leu Thr Ala Asp Leu Ile Val Ser Ala
    370                 375                 380

Ala Pro Glu Asp Arg Val Gly Ala Ala Ala Ala Leu Pro Glu Thr Ala
385                 390                 395                 400

Asn Gln Leu Gly Gly Ala Leu Gly Val Ala Ile Leu Gly Ser Ile Gly
                405                 410                 415

Ala Ala Val Tyr Thr Arg Asp Val Ala Asp Val Thr Thr Gly Leu Pro
            420                 425                 430

Pro Glu Ala Ala Glu Ala Ala Glu Gly Ser Leu Gly Gly Ala Thr Glu
        435                 440                 445

Val Ala Lys His Leu Pro Gly Asp Thr Gly Asp Ala Leu Val Thr Ser
    450                 455                 460

Ala Gly Glu Ala Phe Thr Arg Gly Met Asn Leu Ser Ala Ala Val Gly
465                 470                 475                 480

Gly Val Val Met Leu Leu Gly Ala Ala Gly Ala Ala Leu Leu Leu Arg
                485                 490                 495

His Val Lys Thr Pro Thr Val Thr Ser Ala Pro Ala Asp Glu Thr Lys
            500                 505                 510

Gly Glu Thr Ala Asp Glu Pro Ser Pro Val Pro Lys
        515                 520
```

<210> SEQ ID NO 26
<211> LENGTH: 1236
<212> TYPE: DNA
<213> ORGANISM: Streptomyces sp. MP28-13

<400> SEQUENCE: 26

```
gtgaccaccg aagcgacgcc caccacccag caggccgacg aagcgctgat gaagctgctg     60

tcgccgccct tccccgacga ccccttcccg atctacgaga ccttgcagtc ggtgaaccgg    120

gtccacaagt ccgcgctcgg tatctacgcg ctctccgggt acgaggaggt gaccgagctc    180

ctgaagatgc ccgatgtcca cagtggggcc cgtgccgccg ctcagatgcg cgaggactgg    240

gccgagcaca tctccctgcg tatgtacctg aactcgatgg tcacactcaa cgcgcccgac    300

cacggacggg ttcgcggcct ggccgcccgg gtgttcaccc ccagcaagat caagaagatg    360

cagcccgcgg tggagaagcg gaccgacgag ctgatcaacg aactcgtcga gaggtccgcc    420

ggcggcgagc cggtcgacat cgtcgagctg ctggccatgc ccttccccgt cgcggtcatc    480

agcgacatgc tcggccttcc gtacgaggac ggcaagcgca cctgggagct ggccgacgac    540

tggtcacggg tcttctccgg tgtctacacc gatgaggacc tggcggcggc cgacgccgcc    600

gccgaggagc tgaccgggta cttcaatgac gtgatcaagg cggtccgcgc cgaacccaag    660

gacgacctga tgtccgccct cgtccaggag gcggccaacg ggaagctcga cgaggaggag    720

ctgatggcgc tcatcctctt cctgttcacg gcgggcttcg cggccaccac caacctcatc    780

gcgaccggcg tgctcgcgct catcgagcac cccgacgagc tgaagcgctg gcgcgcggac    840
```

-continued

```
aagagcatca ccccgacggc cgtcgaggag ctgctgcgtc acaccgccca caccacggcg    900

tcgagccgtc tgacgacgcg ccccatcacc atcggcggca ccgacattcc cgagggcgtt    960

ctcgtcctgg ccctgctctc cgccgccaac cgggacccgg cgcgcttccc cgacccgcac   1020

cgtctggacc tgagccgcga caacggcgcc cacctgagct tcagcgccgg cggccacttc   1080

tgcttcggcg gcagcctcgc ccgtatggag gccgccgacc tcttcccgaa gctgatcgac   1140

acgttcacga acatcgagct ggcgggcacc cccgggcgcc gcgccatcat gggcctgacc   1200

ggttacacct cgcttccggt gactctcggc cgctga                             1236


<210> SEQ ID NO 27
<211> LENGTH: 411
<212> TYPE: PRT
<213> ORGANISM: Streptomyces sp. MP28-13

<400> SEQUENCE: 27

Met Thr Thr Glu Ala Thr Pro Thr Thr Gln Gln Ala Asp Glu Ala Leu
1               5                   10                  15

Met Lys Leu Leu Ser Pro Pro Phe Pro Asp Asp Pro Phe Pro Ile Tyr
            20                  25                  30

Glu Thr Leu Gln Ser Val Asn Arg Val His Lys Ser Ala Leu Gly Ile
        35                  40                  45

Tyr Ala Leu Ser Gly Tyr Glu Glu Val Thr Glu Leu Leu Lys Met Pro
    50                  55                  60

Asp Val His Ser Gly Ala Arg Ala Ala Ala Gln Met Arg Glu Asp Trp
65                  70                  75                  80

Ala Glu His Ile Ser Leu Arg Met Tyr Leu Asn Ser Met Val Thr Leu
                85                  90                  95

Asn Ala Pro Asp His Gly Arg Val Arg Gly Leu Ala Ala Arg Val Phe
            100                 105                 110

Thr Pro Ser Lys Ile Lys Lys Met Gln Pro Ala Val Glu Lys Arg Thr
        115                 120                 125

Asp Glu Leu Ile Asn Glu Leu Val Glu Arg Ser Ala Gly Gly Glu Pro
    130                 135                 140

Val Asp Ile Val Glu Leu Leu Ala Met Pro Phe Pro Val Ala Val Ile
145                 150                 155                 160

Ser Asp Met Leu Gly Leu Pro Tyr Glu Asp Gly Lys Arg Thr Trp Glu
                165                 170                 175

Leu Ala Asp Asp Trp Ser Arg Val Phe Ser Gly Val Tyr Thr Asp Glu
            180                 185                 190

Asp Leu Ala Ala Ala Asp Ala Ala Ala Glu Glu Leu Thr Gly Tyr Phe
        195                 200                 205

Asn Asp Val Ile Lys Ala Val Arg Ala Glu Pro Lys Asp Asp Leu Met
    210                 215                 220

Ser Ala Leu Val Gln Glu Ala Ala Asn Gly Lys Leu Asp Glu Glu Glu
225                 230                 235                 240

Leu Met Ala Leu Ile Leu Phe Leu Phe Thr Ala Gly Phe Ala Ala Thr
                245                 250                 255

Thr Asn Leu Ile Ala Thr Gly Val Leu Ala Leu Ile Glu His Pro Asp
            260                 265                 270

Glu Leu Lys Arg Trp Arg Ala Asp Lys Ser Ile Thr Pro Thr Ala Val
        275                 280                 285

Glu Glu Leu Leu Arg His Thr Ala His Thr Thr Ala Ser Ser Arg Leu
    290                 295                 300
```

-continued

```
Thr Thr Arg Pro Ile Thr Ile Gly Gly Thr Asp Ile Pro Glu Gly Val
305                 310                 315                 320

Leu Val Leu Ala Leu Leu Ser Ala Ala Asn Arg Asp Pro Ala Arg Phe
                325                 330                 335

Pro Asp Pro His Arg Leu Asp Leu Ser Arg Asp Asn Gly Ala His Leu
            340                 345                 350

Ser Phe Ser Ala Gly Gly His Phe Cys Phe Gly Gly Ser Leu Ala Arg
        355                 360                 365

Met Glu Ala Ala Asp Leu Phe Pro Lys Leu Ile Asp Thr Phe Thr Asn
    370                 375                 380

Ile Glu Leu Ala Gly Thr Pro Gly Arg Arg Ala Ile Met Gly Leu Thr
385                 390                 395                 400

Gly Tyr Thr Ser Leu Pro Val Thr Leu Gly Arg
                405                 410
```

<210> SEQ ID NO 28
<211> LENGTH: 10119
<212> TYPE: DNA
<213> ORGANISM: Streptomyces sp. MP28-13

<400> SEQUENCE: 28

```
atgaacgccg aagtcgagga gatcgtcgag gcactgcgtg gctcgctggt cgagaacgag      60

aggctgcggc aggacaacga cagcctgcgc gccgccgcga gcgtaaccac cgaacccatc     120

gcgatcatcg gcatggcctg ccggtacccc ggtggcgtcg gatcccccga ggagctgtgg     180

gcgctggtcg aggaaggccg tgacgcgatc agcccgttcc cggacgaccg cggctgggac     240

atgagcgcgc tgtacgaccc cgagcccgga aagcccggca agacgtacgc gcgcgagggc     300

ggattcctgc acgacgccgc gcagttcgac cccgagttct tcgggatcag cccgcgcgag     360

gccctcacca tggaccccca gcagcggctc ctgctggaga tcacctggga gtcgatggag     420

cgcgccggac tcgacccggc gtcgctgcgc ggcagccgca ccggtgtctt cgccggcgcg     480

atgtaccacg actacggcat caccagcagc gacggcagcc tcgtctccgg acgcgtcgcg     540

tacaccctcg ggctggaagg cccggcggtc accgtcgaca cggcctgctc gtcgtcgctg     600

gtcgcactcc agtgggcgtc gcaggccctg cgctcgggag agtgcaccct ggcgctggcc     660

ggcggcgtca gcgtcatggc cacgcccgag acgttcatcg agttcagcga gcagcgcgga     720

ctctcggccg acggccgctg ccgctcgttc gccgcctccg ccgacgggac gggctgggcc     780

gagggcgccg gcgtcctgct gctggagaag ctgtccgacg cccgccgcaa cgggcacccc     840

gtactggccg tcgtgcgcgg ctcggcggtc aaccaggacg gcgcgtccaa cggcttcagc     900

gcccccaacg gcccctcgca gcgccgtgtc atccagcagg cgctcaccgc ggccggactg     960

acgaccgccg atgtcgacgt catggagggc cacggcaccg gcacctcgct cggcgacccc    1020

atcgaggcgc aggcactgct cgccacgtac ggacagggcc gcgaagaacc gctgtggctg    1080

ggttcgatca agtccaacat cggtcacacg caggccgccg ccggtgtcgc gggcgtcatc    1140

aagatggtcg aggccatccg acgcggcacg ctgccgaaga cactgcacgt cgacgaggcg    1200

tcgccccagg tggactggga ggccggaaac gtccgcctgc tcaccgaggc gcgtgcctgg    1260

cccgacgccg accggccgcg ccgcgccgcg gtgtcctcgt tcggcgtcag cggcaccaac    1320

gcccatgtga tcatcgagca ggcgcagccc gaccccgcgt ccgactccga gccggagccc    1380

gccgcaccgc gcccgtccac cgacgtaccc ctgaccgtgc cgctgccgct gccgctgtcg    1440

gccggcaccg agaccgcgat gcgcgcccag gcccggcagt tggccgacca cttgcggacc    1500
```

-continued

```
acgcctgacc tcgaccctgt ggacatggcg tactccctcg ccaccgcccg cgccgcgctc   1560
acccgccgcg ccgtcgtggt cggccacgac cgcgacgaga tcctcggcgc gctgaccgcg   1620
ttggcggacg gcgctcccct cggcggcgcc gcgcggtcga ccgggctgac cgccttcctc   1680
ttcaccggcc agggcagcca gcgcctcggc atgggccgcg acctgcacgc ggcgttcccc   1740
gtgttcgcac gcgccttcga cgaggtgtgc tccgcgctcg accccgccgt gcgcgaggtg   1800
atgtggggcg acgaagaggc cctgcggcgt accgagttca cccagcccgc gatcttcgca   1860
ctccagatcg ccctgttccg gctgctcgaa tcgtggggtg tacggcccga cttcgtcgcg   1920
ggacactcca tcggcgaact cgccgccgcc catgtggccg gcgtgttctc cctgcccgac   1980
gccgcctcgc tgatcaccgc gcgggcacgg ctgatgcagg cgctgccccc gggcggggcg   2040
atggtggcgg tcgaggccgc cgaggaggag gtcgtcccgc tgcttcggga cggcgtggga   2100
atcgccgccg tcaacggccc cgcctccgtg gtgctctcgg gcaccgagga ggccgtggac   2160
gcggtcgtcg aacagctcgg cgcgcgcagg accaaccggc tgaaggtgtc gcacgcgttc   2220
cactcgacgc tgatggaccc gatgctcgac gacttccgcc gtgtcgcgga gcgcgtcgcc   2280
tacgcggagc ccggccttcc cgtcgtggcc aacggcgatg tcaccaccgc cgcgtactgg   2340
gtggggcatg tccgtgacac cgtccgcttc gccgacgccg tgacccggct ggaatccgaa   2400
ggcgtcaccc ggtacgtcga actgggcccc gacggcatcc tcaccgcgat ggcccgccag   2460
tgcctcacga ccaccgccga caccgccgta ctcgtcccgg ccctgcgccg taacgaaacc   2520
ggacccgtcg ccgtcctcac cgccctcggc ggcctgcaca ccgcgggcct gaaagtcgac   2580
tgggcgggtg tcttcgacgg ccgcggcgcc cggcgcgtcg acctgcccac ctaccccttc   2640
cagcgcgccc gttactggtt cgacaagcgc ggcctgggcg gcgacgtcac ctccgccggt   2700
ctcgaccggc ccgaccaccc gctgctcggt gcgatggtgc acctgcccgg ctccgacggt   2760
gtggtgttca ccggacggct gtccaccggg gcccacccct ggctgtccga ccacaccgtg   2820
atgggctccg tcctgctgcc cggcaccgcg tacgtggaac tcgcggtgcg cgcgggggac   2880
caggtgggat ggaaccgcgt cgaggaactc aacgtcgcgg cgccgctgtt cctgcccgag   2940
cacggcggcg tccacatcca ggtcgccgtc gacgcgcccg acgcgtcggg actccgccct   3000
gtgagggtgt tctcccgagc cgacgacgcc ccgctcgacc gcgaatggat cctgcacgcc   3060
gagggcttcc tggcgcccga cgccggtgag ccggccaccg acctcacggt gtggcctccg   3120
cgcgacgccg agcccctcgc ggtcgaagga ctctacgaac ggctggagta cgggccgacg   3180
ttccagggac tgcgcgcggg atggcggcgc ggcgacgagc tgttcgccga gacagctctg   3240
cccgagggtg cggacgccgg cggcttcggc ctccatcccg ccctgttcga cgcggcgttg   3300
cacgtgctcg acctggccgg cgaggacgcg aaggtacttc cgttcacctg gtcggacgtc   3360
accctgcacg cggagggcgc cacgaccgcg cgggtgagcc tgcgtgtccg gggagacaag   3420
tccgtgtccc tggagctggc cgacgccatg ggacggccgg tcgcctcggt cggatcgctg   3480
acgctgcgcc ccgtcacggc ggacggcctc gcgccggccg cggcccgggt cgcgaacgcc   3540
ctcttccggg tggactgggt cccggccggc gaggtccggt caccggctga gaacaccgag   3600
gtgagcgttc accactgccc gccgacgacc ggcggcacac cggccgccgt acgcgcggtg   3660
accaccggcg tactggccgc cgtccagggc gcagtcgacg gcggcaccgc cctcgtcgtc   3720
gtcaccgacg gcgccaccga cggctccgac ctcggccacg ccgccgcctg ggggctggta   3780
cgcgccgccg agggcgagca tcccggccgc ttcttcctcg tcgacaccga cgcccggtc    3840
gaccccgccc gcgtcgtcgc gatcggcgaa cccgaactgc gcgtgagcgg cggcgagaca   3900
```

cgggtgcccc ggctggtcgg cgtaccgctc gattcgaccg cctccacctg ggacaccgaa 3960
cgcaccgtcc tgatcaccgg cgggaccggt gccctcgggg ccgccgtcgc ccggcacctc 4020
gtcacccgcc acgaggtacg gcggctgctg ctgaccagcc gacggggccc gcaggcgccg 4080
ggagccgccg agctcgccga ggaactgacc gggctcggcg ccgaggtcga ggtggccgcg 4140
tgcgacgccg ccgaccgcga cgccctggcc acgctgctcg acggccggac catcggcggg 4200
gtcgtacacg ccgcgggcgt cctggatgac ggcgtgatcc tctcgatgac gcccgagcgc 4260
gtcgaccacg tgctccgtcc gaaggcggac gcggcctggc atctgcacga actcacccgc 4320
gacatggggc tgaccgcttt cgtgctgttc tcgtccgtcg cgggcgtact cggtgccccc 4380
ggacagggca actacgccgc cgccagcacc ctgctcgacg gcctcgcgcg gcatcggcac 4440
gccgccggac tgccggcgct gtcactggcc tggggtccgt gggccggaga gggcatggcg 4500
gacggtctcg cctcggtcgg catgcgctcc ctggcaccgg aggagggcct cgccctgctc 4560
gacgccgccg ccggcgtggc ggagcccgta ctggtgcccg tccggttcga cctcgctgcc 4620
ttcgactcgc cgccgcccat catgcgcggc ctcgtccgcg gccggtcgcg ccgtgtcctc 4680
gacaacgacg cgtccgcgac cggcgtcctg cggcagcgcc tggcgggact cggcgacgcg 4740
gaacgcgccg acgaactcct cgctctcgta cgctcccagg cggcgatggt cctgcgccat 4800
gccggagccg aggcggtcga cccggagcgg gccttccgcg acctcggatt cgactccctc 4860
acggcgatcg aactgcgcaa cctgctgggt gccgccaccg gactgcgcct gcccgccacc 4920
ctcgtcttcg actaccccac ccccgtcgtc ctggcgggcc acctgctgcg ggagctctcc 4980
ggagccgtgg agtcggctcc ggtcgcgtcc gtcgtgcgcc cggcggacga cgagccgatc 5040
gccattgtct cgatggcgtg ccgctacccg ggtggcgtgg actcgcccga ggggttgtgg 5100
cggctcgtcg acgagggtgt cgacgcgata tcggagttcc cggccgaccg tggctggggc 5160
gtggaggaca tctacgaccc cgagcccgga attccgggga agacctatgt gcgcgacggc 5220
ggattcctgc acgacgccac acagttcgac gccgatttct tcggcatcag cccgcgcgag 5280
gccctggaca tggacccgca gcagcggttg ctgctggaga cctcgtggga ggcgctggag 5340
cgtgccggga tcgcacccac cacgctgaag ggcagcccga ccggtgtgtt cgccggggtg 5400
atgtaccacg actaccccgg cggcaccggc ggcggcagcc tcgtgtcggg ccgggtggcc 5460
tacaccctcg gtctcgaagg ccccgcggtg agcgtggaca cggcatgctc gtcgtccctg 5520
gtggccctgc actgggcggc gcaggcactg cgttccggcg agtgctcgct cgccctcgtc 5580
ggcggcgtga ccgtcatggg aacaccgcgg tcgttcatcg acttcagcga gcagcgcggc 5640
ctggccgcgg acggccgctg caagtccttc tcgtcctcca ccgacggcac cgggtggggc 5700
gagggcgcgg gcgtcctggt ggtggagcgt ctgtcggagg cgcgtcggct ggggcatccg 5760
gtgctcgcgg tggtgcgcgg gagcgcgctc aaccaggacg gcgccagcaa cggcatcacc 5820
gcgccgaacg gcccctccca gcgtcgcgtg atcaagcagg cgctggcgaa ggcgggtctg 5880
tcgacggcgg atgtggacgc ggtcgaggcg catggcacgg gcacgacgct gggcgacccg 5940
atcgaggccc aggccctgtt ggagacgtac ggtcaggatc gccccgaagg gcggccgttg 6000
tggctgggtt cgatcaagtc gaacatcggt catacgcagg cggcggcggg tgtggcgggg 6060
atcatcaaga tggtcgaggc gatgcgccac ggcaggctgc ccaagacgct gcatgtggat 6120
gagccgacga agcaggtgga ctgggacgcg ggtgaggtgc ggctgctgac ggaggcgcgt 6180
gagtggccga gcgagggccg tccgcgccgg gcagccgtgt cctccttcgg aatcagtggc 6240

-continued

```
acgaacgccc acgtgatcgt cgaggaagtc gtgccggttg ctgaagtggt ggtggagcgg   6300
cgggagttgc cggtggcgcc ggtggtggtg tcggggaaga ccccggcggc gctggaggcg   6360
cagatcggcc gcttcggcga actggccgcg aacggcgacc cgctggacgt cgcgtactcg   6420
gccgcgacag gccgggccgc gctggaacac cgcgcggtgc tcatcgggtc ggagacggtc   6480
acgggcgaga ccggtgtggg caaggtggcg ttcctgttca ccgggcaggg gagtcaacgc   6540
cttggtatgg ggcgggagtt gtacgagacg ttccccgcct tcgcatcggc gttcgacgag   6600
gtgtgtggcg tgctcgatcc cgctgtgcgt gaggtgatgt ggggtgatga ggaggctctg   6660
ggccgtacgg agttcaccca gcccgcgatc ttcgctcttg aggtggcgtt gttccggttg   6720
gtggagtcgt ggggggtcaa gccggacttc ctggtgggcc attcgatcgg tgagttggcg   6780
gcggcgcatg tggcgggggt gttcggtctg gaggatgcgg gccggttgat ctcggcgcgt   6840
gggcggttga tgcaggcgtt gccggcgggt ggggcgatgg tcgcgatcca ggccacggag   6900
gaggaggtgg ttccgcatct cagcggcctg gtgagtgttg ccgcggtcaa cagcctttct   6960
tcggtggtga tttcgggcga ggagaaggcg gtgacggcgg tcgcggagcg gttcaccgac   7020
cgcaagacga ctcggctgaa ggtgtcgcac gcgttccact cgccgctgat ggacccgatg   7080
ctggacgact tccgcaaggt cgcggagagc gccacctacc gggagccgac catccggctg   7140
accaaggacg tcggttcggc cgagtactgg gtggggcatg tgcgggacgc ggtgcgtttc   7200
gcggacgatg tgcgctattt gcaggacgag ggtgtgacgc ggttcctgga gatcggtccg   7260
gatggtgtgc tgacggcgat ggcgggacag agtgccgacg gcaccctggc gcccacgctg   7320
cggcgtgacc gccccgaggt ggagagtgtg ttcgccggtg tgggccggtt gttcgcggcc   7380
ggtgtggcgg tggactggga cgcggtgttc gacgggcgtg gtgcgcggcg ggtcgatctg   7440
cccacgtatc ccttccagcg caagcgttac tggctgatcg agcagtcgac ggcggcagcc   7500
ggtgccgacg cggtcgatca ccccctgctc acctcgggca tcgggctgcc cgacaccggc   7560
ggtgtggtgt tcaccggacg tctctccctc gacacccacc cctggctcgc cgaccacgac   7620
gtactgggta ccctgctgct gcctggcacc gggctggtcg aactcgcgct gcaagccgcc   7680
gcacaggtgg actgcggcac ggtcgacgag ctgaccctgg aggcgccgct cgtcgttccc   7740
gagaagggcg cggtcgccgt gcgcgttctc gtgggcggcc ccgacgactc cgagtcacgc   7800
accgtcgaga tctactcgtc cctggacgac gagatctgga cccgcaacgc ggccggtgcc   7860
ctcctcccgt cggccgtatc tccctcgtcc gacctgatcc agtggccgcc gatcggcgcc   7920
acgccgctcc cggtggacgg cgcctacgag cggctcctcg cccgcggtta cgactacggc   7980
cccacgttcc aggggctgaa agcggcctgg cgggacggtg acggcgtcgt gttcgccgag   8040
gtctcgctcc cggagggaac ggaggctgcc aggttcggcc tgcatccggc gttgctggac   8100
gcggcgatgc acgtgggtct catcgaggaa ggcgccgcca ccgacgcgcc ggagctgccg   8160
ttctcctgga acggtgtcac gctccaccgc gccggcgcct ccgcgctgcg cgtccgtctg   8220
tcgaacccgg agggcggcga cggcacggag gttctggtcg ccgacggaac cggcgcgccc   8280
gtgctctccg tcgcgagcct gacctcgcgg cccgtgtcgg ccgagcagct acgggccgac   8340
ggcgaccacc gcgagtcgct gttcgccctc acctggacca aggccggcga cgtgcccgta   8400
ctggagacac ccgtcgtggt gtacgaggtc ccgcgcgccg aaggtgacac atccgaggcc   8460
gcgcacgcgg tcgccgacga ggtgctggcg cgcgtccagg aatggctggc ggacaagggc   8520
aggagcgatg agaagctcgc cgtcgtcacc cgtcgcgcgg tgccgatcga gggcgaggac   8580
gtcgatctga gccaggcacc cgtgtggggg ctggtccggg cggcggcggc ggagaatccc   8640
```

ggccggttcc ttctgctcga cctgggcgac ggggccaccg ttccgccctt cgtcgacgca 8700
cccgaggtgg cggttcgagg cggcgaactt ctcgtacccg ccctcacccg cgtacccgcc 8760
tcggcggtgg acgccggacg cgacccgtgg gagtcgtcgc cgaccgtgct gatcaccggc 8820
ggcaccagcg gtctcggtgc cctggtcgcc cgccacctgg tgacggagca cggcatccgg 8880
catctggtcc tgaccagccg tcggggcggg agcgcaccgg gcgcggcgga actgcgcgcc 8940
gaactgaccg gccacggcgc gcgggtggac atcgaggcgt gcgacgtggc cgaccgcgcc 9000
gcgctggccg cggtgctcga ccggcatccc gtcggggcgg tcgtccacgc ggccggtgtc 9060
gtggacaacg ggctggtccg cgggctgacg ccggagcgta tggacacggt cctgcggccc 9120
aaggtggacg gcgcctggca tctgcacgag ctgactgccg accgcgacct gtccgcgttc 9180
gtcctgttct cctcgatggg cggcctgctg ctggcggcgg gccagggcaa ctacgccgcg 9240
gcgaacgttt tcctggacgc gctcgcccac caccgccacc aggccggcct gccggtgacc 9300
tcactggcgt tcggtctgtg ggaagccgag accgggctcg gtgagctgac cgacgccgac 9360
cgcaagcgca tgctccgcat gggcctgccc gccctgtcgc agaaggaggg cctggcgctg 9420
ctggacgacg cgttgcgtac gggggagccc gcgctggcgc cgttccgcct ggacacaggg 9480
gccctgcgga cccgcgccgt cgaccaactg ccgtcgctgc tgcgtggtct ggtgcccaca 9540
tcgcgccgtc gcgccggggg cgcgggcgcg gccggcggcg gggacggcgg cgcgggactg 9600
cgacggaccc tggcggcggc ggccgacgaa gccgcgcgcg acagcatcct ggtcgagttg 9660
gtccgtaccc acgtggcggc ggtgctcggt cacgacggcg tggacgcggt ccgctccgac 9720
cgggcgttca aggacctcgg attcgactcg ctcaccgccg tggaactgcg caacacgctg 9780
cgttcggcca cggggctgaa gctgccggcc accctggtct tcgaccatcc cacccccttcc 9840 gccgtcgccg agtccctgcg cgaacagctg accggcgacc aggagcccgc cgggtcaccg 9900
ctggaggcgg aactggcccg tctggaagcg gcgttggcgt cggtgacgcc cgacgaggag 9960
acgttcggcc gcgtcgccga ccggctgcgc gccctggcgg ccggctggac cgagacccac 10020
aggcgggacg agagcgacga ggccgaactc gggtcgctct cggccgatga gctgttcgac 10080
gtcctcgacg acgagctcga tacgcggtcc gcgtcgtag 10119

<210> SEQ ID NO 29
<211> LENGTH: 3372
<212> TYPE: PRT
<213> ORGANISM: Streptomyces sp. MP28-13

<400> SEQUENCE: 29

Met Asn Ala Glu Val Glu Glu Ile Val Glu Ala Leu Arg Gly Ser Leu
1 5 10 15

Val Glu Asn Glu Arg Leu Arg Gln Asp Asn Asp Ser Leu Arg Ala Ala
20 25 30

Ala Ser Val Thr Thr Glu Pro Ile Ala Ile Ile Gly Met Ala Cys Arg
35 40 45

Tyr Pro Gly Gly Val Gly Ser Pro Glu Glu Leu Trp Ala Leu Val Glu
50 55 60

Glu Gly Arg Asp Ala Ile Ser Pro Phe Pro Asp Asp Arg Gly Trp Asp
65 70 75 80

Met Ser Ala Leu Tyr Asp Pro Glu Pro Gly Lys Pro Gly Lys Thr Tyr
85 90 95

Ala Arg Glu Gly Gly Phe Leu His Asp Ala Ala Gln Phe Asp Pro Glu
100 105 110

```
Phe Phe Gly Ile Ser Pro Arg Glu Ala Leu Thr Met Asp Pro Gln Gln
        115                 120                 125

Arg Leu Leu Leu Glu Ile Thr Trp Glu Ser Met Glu Arg Ala Gly Leu
    130                 135                 140

Asp Pro Ala Ser Leu Arg Gly Ser Arg Thr Gly Val Phe Ala Gly Ala
145                 150                 155                 160

Met Tyr His Asp Tyr Gly Ile Thr Ser Ser Asp Gly Ser Leu Val Ser
                165                 170                 175

Gly Arg Val Ala Tyr Thr Leu Gly Leu Glu Gly Pro Ala Val Thr Val
            180                 185                 190

Asp Thr Ala Cys Ser Ser Ser Leu Val Ala Leu Gln Trp Ala Ser Gln
        195                 200                 205

Ala Leu Arg Ser Gly Glu Cys Thr Leu Ala Leu Ala Gly Gly Val Ser
    210                 215                 220

Val Met Ala Thr Pro Glu Thr Phe Ile Glu Phe Ser Glu Gln Arg Gly
225                 230                 235                 240

Leu Ser Ala Asp Gly Arg Cys Arg Ser Phe Ala Ala Ser Ala Asp Gly
                245                 250                 255

Thr Gly Trp Ala Glu Gly Ala Gly Val Leu Leu Leu Glu Lys Leu Ser
            260                 265                 270

Asp Ala Arg Arg Asn Gly His Pro Val Leu Ala Val Val Arg Gly Ser
        275                 280                 285

Ala Val Asn Gln Asp Gly Ala Ser Asn Gly Phe Ser Ala Pro Asn Gly
    290                 295                 300

Pro Ser Gln Arg Arg Val Ile Gln Gln Ala Leu Thr Ala Ala Gly Leu
305                 310                 315                 320

Thr Thr Ala Asp Val Asp Val Met Glu Gly His Gly Thr Gly Thr Ser
                325                 330                 335

Leu Gly Asp Pro Ile Glu Ala Gln Ala Leu Leu Ala Thr Tyr Gly Gln
            340                 345                 350

Gly Arg Glu Glu Pro Leu Trp Leu Gly Ser Ile Lys Ser Asn Ile Gly
        355                 360                 365

His Thr Gln Ala Ala Ala Gly Val Ala Gly Val Ile Lys Met Val Glu
    370                 375                 380

Ala Ile Arg Arg Gly Thr Leu Pro Lys Thr Leu His Val Asp Glu Ala
385                 390                 395                 400

Ser Pro Gln Val Asp Trp Glu Ala Gly Asn Val Arg Leu Leu Thr Glu
                405                 410                 415

Ala Arg Ala Trp Pro Asp Ala Asp Arg Pro Arg Arg Ala Ala Val Ser
            420                 425                 430

Ser Phe Gly Val Ser Gly Thr Asn Ala His Val Ile Ile Glu Gln Ala
        435                 440                 445

Gln Pro Asp Pro Ala Ser Asp Ser Glu Pro Glu Pro Ala Ala Pro Arg
    450                 455                 460

Pro Ser Thr Asp Val Pro Leu Thr Val Pro Leu Pro Leu Pro Leu Ser
465                 470                 475                 480

Ala Gly Thr Glu Thr Ala Met Arg Ala Gln Ala Arg Gln Leu Ala Asp
                485                 490                 495

His Leu Arg Thr Thr Pro Asp Leu Asp Pro Val Asp Met Ala Tyr Ser
            500                 505                 510

Leu Ala Thr Ala Arg Ala Ala Leu Thr Arg Arg Ala Val Val Val Gly
        515                 520                 525
```

```
His Asp Arg Asp Glu Ile Leu Gly Ala Leu Thr Ala Leu Ala Asp Gly
    530                 535                 540

Ala Pro Leu Gly Gly Ala Ala Arg Ser Thr Gly Leu Thr Ala Phe Leu
545                 550                 555                 560

Phe Thr Gly Gln Gly Ser Gln Arg Leu Gly Met Gly Arg Asp Leu His
                565                 570                 575

Ala Ala Phe Pro Val Phe Ala Arg Ala Phe Asp Glu Val Cys Ser Ala
            580                 585                 590

Leu Asp Pro Ala Val Arg Glu Val Met Trp Gly Asp Glu Glu Ala Leu
        595                 600                 605

Arg Arg Thr Glu Phe Thr Gln Pro Ala Ile Phe Ala Leu Gln Ile Ala
    610                 615                 620

Leu Phe Arg Leu Leu Glu Ser Trp Gly Val Arg Pro Asp Phe Val Ala
625                 630                 635                 640

Gly His Ser Ile Gly Glu Leu Ala Ala Ala His Val Ala Gly Val Phe
                645                 650                 655

Ser Leu Pro Asp Ala Ala Ser Leu Ile Thr Ala Arg Ala Arg Leu Met
            660                 665                 670

Gln Ala Leu Pro Pro Gly Gly Ala Met Val Ala Val Glu Ala Ala Glu
        675                 680                 685

Glu Glu Val Val Pro Leu Leu Arg Asp Gly Val Gly Ile Ala Ala Val
    690                 695                 700

Asn Gly Pro Ala Ser Val Val Leu Ser Gly Thr Glu Glu Ala Val Asp
705                 710                 715                 720

Ala Val Val Glu Gln Leu Gly Ala Arg Arg Thr Asn Arg Leu Lys Val
                725                 730                 735

Ser His Ala Phe His Ser Thr Leu Met Asp Pro Met Leu Asp Asp Phe
            740                 745                 750

Arg Arg Val Ala Glu Arg Val Ala Tyr Ala Glu Pro Gly Leu Pro Val
        755                 760                 765

Val Ala Asn Gly Asp Val Thr Thr Ala Ala Tyr Trp Val Gly His Val
    770                 775                 780

Arg Asp Thr Val Arg Phe Ala Asp Ala Val Thr Arg Leu Glu Ser Glu
785                 790                 795                 800

Gly Val Thr Arg Tyr Val Glu Leu Gly Pro Asp Gly Ile Leu Thr Ala
                805                 810                 815

Met Ala Arg Gln Cys Leu Thr Thr Thr Ala Asp Thr Ala Val Leu Val
            820                 825                 830

Pro Ala Leu Arg Arg Asn Glu Thr Gly Pro Val Ala Val Leu Thr Ala
        835                 840                 845

Leu Gly Gly Leu His Thr Ala Gly Leu Lys Val Asp Trp Ala Gly Val
    850                 855                 860

Phe Asp Gly Arg Gly Ala Arg Arg Val Asp Leu Pro Thr Tyr Pro Phe
865                 870                 875                 880

Gln Arg Ala Arg Tyr Trp Phe Asp Lys Arg Gly Leu Gly Gly Asp Val
                885                 890                 895

Thr Ser Ala Gly Leu Asp Arg Pro Asp His Pro Leu Leu Gly Ala Met
            900                 905                 910

Val His Leu Pro Gly Ser Asp Gly Val Val Phe Thr Gly Arg Leu Ser
        915                 920                 925

Thr Gly Ala His Pro Trp Leu Ser Asp His Thr Val Met Gly Ser Val
    930                 935                 940

Leu Leu Pro Gly Thr Ala Tyr Val Glu Leu Ala Val Arg Ala Gly Asp
```

```
945                 950                 955                 960

Gln Val Gly Trp Asn Arg Val Glu Glu Leu Asn Val Ala Ala Pro Leu
                965                 970                 975

Phe Leu Pro Glu His Gly Gly Val His Ile Gln Val Ala Val Asp Ala
            980                 985                 990

Pro Asp Ala Ser Gly Leu Arg Pro  Val Arg Val Phe Ser  Arg Ala Asp
        995                 1000                1005

Asp Ala  Pro Leu Asp Arg Glu  Trp Ile Leu His Ala  Glu Gly Phe
    1010                 1015                 1020

Leu Ala  Pro Asp Ala Gly Glu  Pro Ala Thr Asp Leu  Thr Val Trp
    1025                 1030                 1035

Pro Pro  Arg Asp Ala Glu Pro  Leu Ala Val Glu Gly  Leu Tyr Glu
    1040                 1045                 1050

Arg Leu  Glu Tyr Gly Pro Thr  Phe Gln Gly Leu Arg  Ala Gly Trp
    1055                 1060                 1065

Arg Arg  Gly Asp Glu Leu Phe  Ala Glu Thr Ala Leu  Pro Glu Gly
    1070                 1075                 1080

Ala Asp  Ala Gly Gly Phe Gly  Leu His Pro Ala Leu  Phe Asp Ala
    1085                 1090                 1095

Ala Leu  His Val Leu Asp Leu  Ala Gly Glu Asp Ala  Lys Val Leu
    1100                 1105                 1110

Pro Phe  Thr Trp Ser Asp Val  Thr Leu His Ala Glu  Gly Ala Thr
    1115                 1120                 1125

Thr Ala  Arg Val Ser Leu Arg  Val Arg Gly Asp Lys  Ser Val Ser
    1130                 1135                 1140

Leu Glu  Leu Ala Asp Ala Met  Gly Arg Pro Val Ala  Ser Val Gly
    1145                 1150                 1155

Ser Leu  Thr Leu Arg Pro Val  Thr Ala Asp Gly Leu  Ala Pro Ala
    1160                 1165                 1170

Ala Ala  Arg Val Ala Asn Ala  Leu Phe Arg Val Asp  Trp Val Pro
    1175                 1180                 1185

Ala Gly  Glu Val Arg Ser Pro  Ala Glu Asn Thr Glu  Val Ser Val
    1190                 1195                 1200

His His  Cys Pro Pro Thr Thr  Gly Gly Thr Pro Ala  Ala Val Arg
    1205                 1210                 1215

Ala Val  Thr Thr Gly Val Leu  Ala Ala Val Gln Gly  Ala Val Asp
    1220                 1225                 1230

Gly Gly  Thr Ala Leu Val Val  Val Thr Asp Gly Ala  Thr Asp Gly
    1235                 1240                 1245

Ser Asp  Leu Gly His Ala Ala  Ala Trp Gly Leu Val  Arg Ala Ala
    1250                 1255                 1260

Glu Gly  Glu His Pro Gly Arg  Phe Phe Leu Val Asp  Thr Asp Ala
    1265                 1270                 1275

Pro Val  Asp Pro Ala Arg Val  Val Ala Ile Gly Glu  Pro Glu Leu
    1280                 1285                 1290

Arg Val  Ser Gly Gly Glu Thr  Arg Val Pro Arg Leu  Val Gly Val
    1295                 1300                 1305

Pro Leu  Asp Ser Thr Ala Ser  Thr Trp Asp Thr Glu  Arg Thr Val
    1310                 1315                 1320

Leu Ile  Thr Gly Gly Thr Gly  Ala Leu Gly Ala Ala  Val Ala Arg
    1325                 1330                 1335

His Leu  Val Thr Arg His Glu  Val Arg Arg Leu Leu  Leu Thr Ser
    1340                 1345                 1350
```

```
Arg Arg  Gly Pro Gln Ala Pro  Gly Ala Ala Glu Leu  Ala Glu Glu
    1355                 1360                 1365

Leu Thr  Gly Leu Gly Ala Glu  Val Glu Val Ala Ala  Cys Asp Ala
    1370                 1375                 1380

Ala Asp  Arg Asp Ala Leu Ala  Thr Leu Leu Asp Gly  Arg Thr Ile
    1385                 1390                 1395

Gly Gly  Val Val His Ala Ala  Gly Val Leu Asp Asp  Gly Val Ile
    1400                 1405                 1410

Leu Ser  Met Thr Pro Glu Arg  Val Asp His Val Leu  Arg Pro Lys
    1415                 1420                 1425

Ala Asp  Ala Ala Trp His Leu  His Glu Leu Thr Arg  Asp Met Gly
    1430                 1435                 1440

Leu Thr  Ala Phe Val Leu Phe  Ser Ser Val Ala Gly  Val Leu Gly
    1445                 1450                 1455

Ala Pro  Gly Gln Gly Asn Tyr  Ala Ala Ala Ser Thr  Leu Leu Asp
    1460                 1465                 1470

Gly Leu  Ala Arg His Arg His  Ala Ala Gly Leu Pro  Ala Leu Ser
    1475                 1480                 1485

Leu Ala  Trp Gly Pro Trp Ala  Gly Glu Gly Met Ala  Asp Gly Leu
    1490                 1495                 1500

Ala Ser  Val Gly Met Arg Ser  Leu Ala Pro Glu Glu  Gly Leu Ala
    1505                 1510                 1515

Leu Leu  Asp Ala Ala Ala Gly  Val Ala Glu Pro Val  Leu Val Pro
    1520                 1525                 1530

Val Arg  Phe Asp Leu Ala Ala  Phe Asp Ser Pro Pro  Pro Ile Met
    1535                 1540                 1545

Arg Gly  Leu Val Arg Gly Arg  Ser Arg Arg Val Leu  Asp Asn Asp
    1550                 1555                 1560

Ala Ser  Ala Thr Gly Val Leu  Arg Gln Arg Leu Ala  Gly Leu Gly
    1565                 1570                 1575

Asp Ala  Glu Arg Ala Asp Glu  Leu Leu Ala Leu Val  Arg Ser Gln
    1580                 1585                 1590

Ala Ala  Met Val Leu Arg His  Ala Gly Ala Glu Ala  Val Asp Pro
    1595                 1600                 1605

Glu Arg  Ala Phe Arg Asp Leu  Gly Phe Asp Ser Leu  Thr Ala Ile
    1610                 1615                 1620

Glu Leu  Arg Asn Leu Leu Gly  Ala Ala Thr Gly Leu  Arg Leu Pro
    1625                 1630                 1635

Ala Thr  Leu Val Phe Asp Tyr  Pro Thr Pro Val Val  Leu Ala Gly
    1640                 1645                 1650

His Leu  Leu Arg Glu Leu Ser  Gly Ala Val Glu Ser  Ala Pro Val
    1655                 1660                 1665

Ala Ser  Val Val Arg Pro Ala  Asp Asp Glu Pro Ile  Ala Ile Val
    1670                 1675                 1680

Ser Met  Ala Cys Arg Tyr Pro  Gly Gly Val Asp Ser  Pro Glu Gly
    1685                 1690                 1695

Leu Trp  Arg Leu Val Asp Glu  Gly Val Asp Ala Ile  Ser Glu Phe
    1700                 1705                 1710

Pro Ala  Asp Arg Gly Trp Gly  Val Glu Asp Ile Tyr  Asp Pro Glu
    1715                 1720                 1725

Pro Gly  Ile Pro Gly Lys Thr  Tyr Val Arg Asp Gly  Gly Phe Leu
    1730                 1735                 1740
```

```
His Asp  Ala Thr Gln Phe Asp  Ala Asp Phe Phe Gly  Ile Ser Pro
    1745                 1750                 1755

Arg Glu  Ala Leu Asp Met Asp  Pro Gln Gln Arg Leu  Leu Leu Glu
    1760                 1765                 1770

Thr Ser  Trp Glu Ala Leu Glu  Arg Ala Gly Ile Ala  Pro Thr Thr
    1775                 1780                 1785

Leu Lys  Gly Ser Pro Thr Gly  Val Phe Ala Gly Val  Met Tyr His
    1790                 1795                 1800

Asp Tyr  Pro Gly Gly Thr Gly  Gly Gly Ser Leu Val  Ser Gly Arg
    1805                 1810                 1815

Val Ala  Tyr Thr Leu Gly Leu  Glu Gly Pro Ala Val  Ser Val Asp
    1820                 1825                 1830

Thr Ala  Cys Ser Ser Ser Leu  Val Ala Leu His Trp  Ala Ala Gln
    1835                 1840                 1845

Ala Leu  Arg Ser Gly Glu Cys  Ser Leu Ala Leu Val  Gly Gly Val
    1850                 1855                 1860

Thr Val  Met Gly Thr Pro Arg  Ser Phe Ile Asp Phe  Ser Glu Gln
    1865                 1870                 1875

Arg Gly  Leu Ala Ala Asp Gly  Arg Cys Lys Ser Phe  Ser Ser Ser
    1880                 1885                 1890

Thr Asp  Gly Thr Gly Trp Gly  Glu Gly Ala Gly Val  Leu Val Val
    1895                 1900                 1905

Glu Arg  Leu Ser Glu Ala Arg  Arg Leu Gly His Pro  Val Leu Ala
    1910                 1915                 1920

Val Val  Arg Gly Ser Ala Leu  Asn Gln Asp Gly Ala  Ser Asn Gly
    1925                 1930                 1935

Ile Thr  Ala Pro Asn Gly Pro  Ser Gln Arg Arg Val  Ile Lys Gln
    1940                 1945                 1950

Ala Leu  Ala Lys Ala Gly Leu  Ser Thr Ala Asp Val  Asp Ala Val
    1955                 1960                 1965

Glu Ala  His Gly Thr Gly Thr  Thr Leu Gly Asp Pro  Ile Glu Ala
    1970                 1975                 1980

Gln Ala  Leu Leu Glu Thr Tyr  Gly Gln Asp Arg Pro  Glu Gly Arg
    1985                 1990                 1995

Pro Leu  Trp Leu Gly Ser Ile  Lys Ser Asn Ile Gly  His Thr Gln
    2000                 2005                 2010

Ala Ala  Ala Gly Val Ala Gly  Ile Ile Lys Met Val  Glu Ala Met
    2015                 2020                 2025

Arg His  Gly Arg Leu Pro Lys  Thr Leu His Val Asp  Glu Pro Thr
    2030                 2035                 2040

Lys Gln  Val Asp Trp Asp Ala  Gly Glu Val Arg Leu  Leu Thr Glu
    2045                 2050                 2055

Ala Arg  Glu Trp Pro Ser Glu  Gly Arg Pro Arg Arg  Ala Ala Val
    2060                 2065                 2070

Ser Ser  Phe Gly Ile Ser Gly  Thr Asn Ala His Val  Ile Val Glu
    2075                 2080                 2085

Glu Val  Val Pro Val Ala Glu  Val Val Val Glu Arg  Arg Glu Leu
    2090                 2095                 2100

Pro Val  Ala Pro Val Val Val  Ser Gly Lys Thr Pro  Ala Ala Leu
    2105                 2110                 2115

Glu Ala  Gln Ile Gly Arg Phe  Gly Glu Leu Ala Ala  Asn Gly Asp
    2120                 2125                 2130

Pro Leu  Asp Val Ala Tyr Ser  Ala Ala Thr Gly Arg  Ala Ala Leu
```

```
    2135                2140                2145

Glu His  Arg Ala Val Leu Ile  Gly Ser Glu Thr Val  Thr Gly Glu
    2150                2155                2160

Thr Gly  Val Gly Lys Val Ala  Phe Leu Phe Thr Gly  Gln Gly Ser
    2165                2170                2175

Gln Arg  Leu Gly Met Gly Arg  Glu Leu Tyr Glu Thr  Phe Pro Ala
    2180                2185                2190

Phe Ala  Ser Ala Phe Asp Glu  Val Cys Gly Val Leu  Asp Pro Ala
    2195                2200                2205

Val Arg  Glu Val Met Trp Gly  Asp Glu Glu Ala Leu  Gly Arg Thr
    2210                2215                2220

Glu Phe  Thr Gln Pro Ala Ile  Phe Ala Leu Glu Val  Ala Leu Phe
    2225                2230                2235

Arg Leu  Val Glu Ser Trp Gly  Val Lys Pro Asp Phe  Leu Val Gly
    2240                2245                2250

His Ser  Ile Gly Glu Leu Ala  Ala Ala His Val Ala  Gly Val Phe
    2255                2260                2265

Gly Leu  Glu Asp Ala Gly Arg  Leu Ile Ser Ala Arg  Gly Arg Leu
    2270                2275                2280

Met Gln  Ala Leu Pro Ala Gly  Gly Ala Met Val Ala  Ile Gln Ala
    2285                2290                2295

Thr Glu  Glu Glu Val Val Pro  His Leu Ser Gly Leu  Val Ser Val
    2300                2305                2310

Ala Ala  Val Asn Ser Leu Ser  Ser Val Val Ile Ser  Gly Glu Glu
    2315                2320                2325

Lys Ala  Val Thr Ala Val Ala  Glu Arg Phe Thr Asp  Arg Lys Thr
    2330                2335                2340

Thr Arg  Leu Lys Val Ser His  Ala Phe His Ser Pro  Leu Met Asp
    2345                2350                2355

Pro Met  Leu Asp Asp Phe Arg  Lys Val Ala Glu Ser  Ala Thr Tyr
    2360                2365                2370

Arg Glu  Pro Thr Ile Arg Leu  Thr Lys Asp Val Gly  Ser Ala Glu
    2375                2380                2385

Tyr Trp  Val Gly His Val Arg  Asp Ala Val Arg Phe  Ala Asp Asp
    2390                2395                2400

Val Arg  Tyr Leu Gln Asp Glu  Gly Val Thr Arg Phe  Leu Glu Ile
    2405                2410                2415

Gly Pro  Asp Gly Val Leu Thr  Ala Met Ala Gly Gln  Ser Ala Asp
    2420                2425                2430

Gly Thr  Leu Ala Pro Thr Leu  Arg Arg Asp Arg Pro  Glu Val Glu
    2435                2440                2445

Ser Val  Phe Ala Gly Val Gly  Arg Leu Phe Ala Ala  Gly Val Ala
    2450                2455                2460

Val Asp  Trp Asp Ala Val Phe  Asp Gly Arg Gly Ala  Arg Arg Val
    2465                2470                2475

Asp Leu  Pro Thr Tyr Pro Phe  Gln Arg Lys Arg Tyr  Trp Leu Ile
    2480                2485                2490

Glu Gln  Ser Thr Ala Ala Ala  Gly Ala Asp Ala Val  Asp His Pro
    2495                2500                2505

Leu Leu  Thr Ser Gly Ile Gly  Leu Pro Asp Thr Gly  Gly Val Val
    2510                2515                2520

Phe Thr  Gly Arg Leu Ser Leu  Asp Thr His Pro Trp  Leu Ala Asp
    2525                2530                2535
```

-continued

His Asp Val Leu Gly Thr Leu Leu Leu Pro Gly Thr Gly Leu Val
2540 2545 2550

Glu Leu Ala Leu Gln Ala Ala Ala Gln Val Asp Cys Gly Thr Val
2555 2560 2565

Asp Glu Leu Thr Leu Glu Ala Pro Leu Val Val Pro Glu Lys Gly
2570 2575 2580

Ala Val Ala Val Arg Val Leu Val Gly Gly Pro Asp Asp Ser Glu
2585 2590 2595

Ser Arg Thr Val Glu Ile Tyr Ser Ser Leu Asp Asp Glu Ile Trp
2600 2605 2610

Thr Arg Asn Ala Ala Gly Ala Leu Leu Pro Ser Ala Val Ser Pro
2615 2620 2625

Ser Ser Asp Leu Ile Gln Trp Pro Pro Ile Gly Ala Thr Pro Leu
2630 2635 2640

Pro Val Asp Gly Ala Tyr Glu Arg Leu Leu Ala Arg Gly Tyr Asp
2645 2650 2655

Tyr Gly Pro Thr Phe Gln Gly Leu Lys Ala Ala Trp Arg Asp Gly
2660 2665 2670

Asp Gly Val Val Phe Ala Glu Val Ser Leu Pro Glu Gly Thr Glu
2675 2680 2685

Ala Ala Arg Phe Gly Leu His Pro Ala Leu Leu Asp Ala Ala Met
2690 2695 2700

His Val Gly Leu Ile Glu Glu Gly Ala Ala Thr Asp Ala Pro Glu
2705 2710 2715

Leu Pro Phe Ser Trp Asn Gly Val Thr Leu His Arg Ala Gly Ala
2720 2725 2730

Ser Ala Leu Arg Val Arg Leu Ser Asn Pro Glu Gly Gly Asp Gly
2735 2740 2745

Thr Glu Val Leu Val Ala Asp Gly Thr Gly Ala Pro Val Leu Ser
2750 2755 2760

Val Ala Ser Leu Thr Ser Arg Pro Val Ser Ala Glu Gln Leu Arg
2765 2770 2775

Ala Asp Gly Asp His Arg Glu Ser Leu Phe Ala Leu Thr Trp Thr
2780 2785 2790

Lys Ala Gly Asp Val Pro Val Leu Glu Thr Pro Val Val Val Tyr
2795 2800 2805

Glu Val Pro Arg Ala Glu Gly Asp Thr Ser Glu Ala Ala His Ala
2810 2815 2820

Val Ala Asp Glu Val Leu Ala Arg Val Gln Glu Trp Leu Ala Asp
2825 2830 2835

Lys Gly Arg Ser Asp Glu Lys Leu Ala Val Val Thr Arg Arg Ala
2840 2845 2850

Val Pro Ile Glu Gly Glu Asp Val Asp Leu Ser Gln Ala Pro Val
2855 2860 2865

Trp Gly Leu Val Arg Ala Ala Ala Ala Glu Asn Pro Gly Arg Phe
2870 2875 2880

Leu Leu Leu Asp Leu Gly Asp Gly Ala Thr Val Pro Pro Phe Val
2885 2890 2895

Asp Ala Pro Glu Val Ala Val Arg Gly Gly Glu Leu Leu Val Pro
2900 2905 2910

Ala Leu Thr Arg Val Pro Ala Ser Ala Val Asp Ala Gly Arg Asp
2915 2920 2925

-continued

```
Pro Trp Glu Ser Ser Pro Thr Val Leu Ile Thr Gly Gly Thr Ser
    2930                2935                2940

Gly Leu Gly Ala Leu Val Ala Arg His Leu Val Thr Glu His Gly
    2945                2950                2955

Ile Arg His Leu Val Leu Thr Ser Arg Arg Gly Gly Ser Ala Pro
    2960                2965                2970

Gly Ala Ala Glu Leu Arg Ala Glu Leu Thr Gly His Gly Ala Arg
    2975                2980                2985

Val Asp Ile Glu Ala Cys Asp Val Ala Asp Arg Ala Ala Leu Ala
    2990                2995                3000

Ala Val Leu Asp Arg His Pro Val Gly Ala Val Val His Ala Ala
    3005                3010                3015

Gly Val Val Asp Asn Gly Leu Val Arg Gly Leu Thr Pro Glu Arg
    3020                3025                3030

Met Asp Thr Val Leu Arg Pro Lys Val Asp Gly Ala Trp His Leu
    3035                3040                3045

His Glu Leu Thr Ala Asp Arg Asp Leu Ser Ala Phe Val Leu Phe
    3050                3055                3060

Ser Ser Met Gly Gly Leu Leu Leu Ala Ala Gly Gln Gly Asn Tyr
    3065                3070                3075

Ala Ala Ala Asn Val Phe Leu Asp Ala Leu Ala His His Arg His
    3080                3085                3090

Gln Ala Gly Leu Pro Val Thr Ser Leu Ala Phe Gly Leu Trp Glu
    3095                3100                3105

Ala Glu Thr Gly Leu Gly Glu Leu Thr Asp Ala Asp Arg Lys Arg
    3110                3115                3120

Met Leu Arg Met Gly Leu Pro Ala Leu Ser Gln Lys Glu Gly Leu
    3125                3130                3135

Ala Leu Leu Asp Asp Ala Leu Arg Thr Gly Glu Pro Ala Leu Ala
    3140                3145                3150

Pro Phe Arg Leu Asp Thr Gly Ala Leu Arg Thr Arg Ala Val Asp
    3155                3160                3165

Gln Leu Pro Ser Leu Leu Arg Gly Leu Val Pro Thr Ser Arg Arg
    3170                3175                3180

Arg Ala Gly Gly Ala Gly Ala Ala Gly Gly Gly Asp Gly Gly Ala
    3185                3190                3195

Gly Leu Arg Arg Thr Leu Ala Ala Ala Ala Asp Glu Ala Ala Arg
    3200                3205                3210

Asp Ser Ile Leu Val Glu Leu Val Arg Thr His Val Ala Ala Val
    3215                3220                3225

Leu Gly His Asp Gly Val Asp Ala Val Arg Ser Asp Arg Ala Phe
    3230                3235                3240

Lys Asp Leu Gly Phe Asp Ser Leu Thr Ala Val Glu Leu Arg Asn
    3245                3250                3255

Thr Leu Arg Ser Ala Thr Gly Leu Lys Leu Pro Ala Thr Leu Val
    3260                3265                3270

Phe Asp His Pro Thr Pro Ser Ala Val Ala Glu Ser Leu Arg Glu
    3275                3280                3285

Gln Leu Thr Gly Asp Gln Glu Pro Ala Gly Ser Pro Leu Glu Ala
    3290                3295                3300

Glu Leu Ala Arg Leu Glu Ala Ala Leu Ala Ser Val Thr Pro Asp
    3305                3310                3315

Glu Glu Thr Phe Gly Arg Val Ala Asp Arg Leu Arg Ala Leu Ala
```

3320 3325 3330

Ala Gly Trp Thr Glu Thr His Arg Arg Asp Glu Ser Asp Glu Ala
3335 3340 3345

Glu Leu Gly Ser Leu Ser Ala Asp Glu Leu Phe Asp Val Leu Asp
3350 3355 3360

Asp Glu Leu Asp Thr Arg Ser Ala Ser
3365 3370

<210> SEQ ID NO 30
<211> LENGTH: 942
<212> TYPE: DNA
<213> ORGANISM: Streptomyces sp. MP28-13

<400> SEQUENCE: 30
atggcgtcca cgcccacggc cacggccaaa ggaactgttc ccttcgggga gtacaagacc 60
tggtaccgcg tcaccgggca gcccgctgag ggccgcccgg ccctcgtcgt cgtgcacgga 120
ggccccggct ccacccacga ctacctgaca gggctgtccg tctacgccga acagggctgg 180
tcggtggtgc actacgacca gatcgggaac ggcggctcca cccaccttcc cgacgccgac 240
cccggcttct ggacccccca gctcttccgc gacgagctgg agaacctgct gcgccggctc 300
gacatcgccg acgactacgt cctgttcgga cagtcgtggg gcggactgct cgccgcctgg 360
cacgcctcgg ccgaacccgc cgggctgcgc ggcctggtca tcgccaacgc accggcctcc 420
taccctctgt ggctgtcgga gatggacgtc ctgcgcgccc aactgccgcc cggcgtcgac 480
gagacactgc ggcggcacga ggccgccggc accaccgaca gcgacgagta cctggaggcg 540
atgctggtct tctacagccg ccacgtctgc cgcgtcgagc cgtggcccag cgaactcatg 600
gcctcctacc tggaagccgt caccgacccg acggtctacc gcacgatgaa cggtcccaac 660
gagttccatg tcatcggcag catccgcgac tggtcggtga tcgactgcct gcccgacatc 720
agcgcgccca ccctcatcat gtcgggccgc cacgacgagg ccaccccggt cacggtgcgc 780
ccctaccagg aactcattcc gggcgcccgc tgggaaatcc ttgagaactc cagccacaac 840
ccgcacctgg aggagccgga gctgttctac gaggtgctcg gcggattcct tgactcggta 900
cgcgtgagcg acacgcggac cacgaccgtg agcggaggct ga 942

<210> SEQ ID NO 31
<211> LENGTH: 313
<212> TYPE: PRT
<213> ORGANISM: Streptomyces sp. MP28-13

<400> SEQUENCE: 31

Met Ala Ser Thr Pro Thr Ala Thr Ala Lys Gly Thr Val Pro Phe Gly
1 5 10 15

Glu Tyr Lys Thr Trp Tyr Arg Val Thr Gly Gln Pro Ala Glu Gly Arg
20 25 30

Pro Ala Leu Val Val Val His Gly Gly Pro Gly Ser Thr His Asp Tyr
35 40 45

Leu Thr Gly Leu Ser Val Tyr Ala Glu Gln Gly Trp Ser Val Val His
50 55 60

Tyr Asp Gln Ile Gly Asn Gly Gly Ser Thr His Leu Pro Asp Ala Asp
65 70 75 80

Pro Gly Phe Trp Thr Pro Gln Leu Phe Arg Asp Glu Leu Glu Asn Leu
85 90 95

Leu Arg Arg Leu Asp Ile Ala Asp Asp Tyr Val Leu Phe Gly Gln Ser
100 105 110

Trp Gly Gly Leu Leu Ala Ala Trp His Ala Ser Ala Glu Pro Ala Gly
115 120 125

Leu Arg Gly Leu Val Ile Ala Asn Ala Pro Ala Ser Tyr Pro Leu Trp
130 135 140

Leu Ser Glu Met Asp Val Leu Arg Ala Gln Leu Pro Pro Gly Val Asp
145 150 155 160

Glu Thr Leu Arg Arg His Glu Ala Ala Gly Thr Thr Asp Ser Asp Glu
165 170 175

Tyr Leu Glu Ala Met Leu Val Phe Tyr Ser Arg His Val Cys Arg Val
180 185 190

Glu Pro Trp Pro Ser Glu Leu Met Ala Ser Tyr Leu Glu Ala Val Thr
195 200 205

Asp Pro Thr Val Tyr Arg Thr Met Asn Gly Pro Asn Glu Phe His Val
210 215 220

Ile Gly Ser Ile Arg Asp Trp Ser Val Ile Asp Cys Leu Pro Asp Ile
225 230 235 240

Ser Ala Pro Thr Leu Ile Met Ser Gly Arg His Asp Glu Ala Thr Pro
245 250 255

Val Thr Val Arg Pro Tyr Gln Glu Leu Ile Pro Gly Ala Arg Trp Glu
260 265 270

Ile Leu Glu Asn Ser Ser His Asn Pro His Leu Glu Glu Pro Glu Leu
275 280 285

Phe Tyr Glu Val Leu Gly Gly Phe Leu Asp Ser Val Arg Val Ser Asp
290 295 300

Thr Arg Thr Thr Thr Val Ser Gly Gly
305 310

<210> SEQ ID NO 32
<211> LENGTH: 5961
<212> TYPE: DNA
<213> ORGANISM: Streptomyces sp. MP28-13

<400> SEQUENCE: 32
atggccgaca ccgaccagaa actcgtggcg gcgctgcgcg cgtcgctcaa ggagtccgag 60
agcctgcgta cgcgcaaccg cgccctgcag gccgcctccc gcgaaccgat cgcgatcgtg 120
gcgatgagct gccgctaccc cggcgcgact tctcccgagg agctgtggcg gctggtcgcc 180
gacgggacgg acgccgtctc gcggttcccc gccgaccgcg gctgggacga ggagggcatc 240
tacgaccccg agccgggaaa gcccggcaag acgtactcgc gcgaaggcgg gttcctgtac 300
gacgcggccg agttcgatcc cggtttcttc gggatcgcgc cgaacgaggc gctggtgatg 360
gaccctcagc agcgattgct gctggaggcg tcgtgggaag tgctcgagcg ggcgggcatc 420
gacccgacga ctctcaaggg cagcccgacc ggtgtgttcg ccgggatgat gtaccacgac 480
tacacgtaca acagcagcac gggcgccatg gcctccggcc gggtcgccta caccctgggt 540
cttgagggcc ccgcggtgac gatcgacacc gcctgctcgt cctcgctggt cgccctgcac 600
tgggcggtcc aggccctgcg gtcgggggag tgctcgctcg ccctcgccgg cggtgtcacc 660
gtgatggcga cacccgagac cttcatcgag ttcagccacc agcgcgggct ggcgaccgac 720
ggccgctgca agtcgtacgc cgcggcggcc gacggcaccg gctggggtga gggcgtcggc 780
atgatcctgg tggagcggct gtcggacgcc cgccgcaacg accacccggt gctggggatc 840
gtgcgcggta cggcgatcaa ccaggacggc gccagcaacg gcatcacagc ccccaacggc 900
ccggcccagc agcgggtgat caggcaggcg ctggccaacg cccgggtgtc cgccgacggg 960

```
gtcgacctga tcgagggcca cggcaccggc acgacgctcg gcgacccgat cgaggcgcag   1020
gccctgctcg ccgcctacgg gcaggaccgc cccggggacc gaccgctgtg gctgggttcg   1080
atcaagtcga acatcggtca cacccaggcc gcggcgggcg tggcgggcat catcaaggtg   1140
gtcgaggcca tccggcacgg tgtcatgccg cccacgctgc acgtcgatgc cccgacaccc   1200
caggtggact gggaggccgg cgacgtccgg ctgctcaccg aggcgcggcg gtggcccgac   1260
caggagcacc cgcgccgcgc gggggtgtcg tccttcggca tcagcgggac caacgcccac   1320
gtcatcatcg aggaggcacc gcccgccgag gagcacgcgc ccccggtcgc ggcgaccacc   1380
gggggcccgg tgctgtggac cctgtccggc aggacccagc aggcgctgtc cgcgcaggcc   1440
gaaagccttc actcccatct gcgcgagcgg cccgacctga cgcctgcgga cgtgggcctg   1500
tccctggcga ggggccgcgc ggctctcgaa caccgtgcgg cgatcgtcgc cgacgaccgt   1560
cagggccttc tcgcggggct caccgcgctg gccgcgggaa ccccctcgcc gtccgtcgtc   1620
accggcaagc ggcgcgaggg caaggtggcg ttcctcttca ccggccaggg cagccagcgc   1680
ctcggcatgg gacgggagtt gtacgagacc ttcccggtct tcaccgccgc gctcgacgag   1740
gtgtgcgagg ccacgggcct gtcgctcaag gacgtggtgt ggggcgacga gtcggcgttg   1800
caccgcaccg agtacgccca gcccgcgatc ttcgctctgg aagtcgccct gttccggctg   1860
gtggagtcct ggggaatcaa gcccgactac ctcgccgggc actccatcgg cgagctggcg   1920
gcggcccatg tcgcgggcgt tctcggcctt gaggacgccg cgcggctggt cgccgaacgc   1980
gggcggctga tgcaggcgct cccggcgggc ggggccatga cggccatcga ggccaccgag   2040
gaggaagtcg cgccgctgct cacggaggag gtggggatcg ccgccctcaa cagcccgtcc   2100
tccgtggtcg tttcgggcag cgaggacgct gtggaggcgg tcaccgagca cttcgccgac   2160
cgcaggacgc gacggctgac cgtctctcac gcgttccact cgccgctgat ggaaccgatg   2220
ctggaggact tccgcaaggt cgccgagtcc ctcacctacg aacggccgcg catccggctg   2280
gtgaaggaca tggcgtccgc cgactactgg gtacggcatg tgcgcgacgc ggtgcggttc   2340
gccgacgacg tacgacgcct ggaggccgag ggcgtcaccc ggttcctgga gctcggaccc   2400
gacggggccc tcgccgccat ggcccgccag accgcgccgg aggccaccac cgccgccgcc   2460
ctgcgccgcg accggcccga ggccacgaca ctgctgaccg ccgtcgccca tctgcacacc   2520
acgggcgtct ctcccgactg gaccgccttc ttcgcgggcc ggcgggcaca ccgggtcgat   2580
ctgcccacct actccttcca gcgcacccgt tactggctcc aggagccggt ggacgcagga   2640
ggcggcagcg cggcgtccat gggcctcagc gcgctcgacc acccccctgct gagcgccgag   2700
atcgccgttc ccggctcacg gacggtgatc tgcacgggcc gtctgtcgac cgacacccac   2760
ccctggctcg ccgaccacga ggtactgggc gcgacgctgc tgcccggcac ggcgttcgtc   2820
gaactggcgg tacgcgtggg cgaccaggtc ggccacggcg tcctcgaaga actgacgctg   2880
cgcgcgccgc tggtcctgcc cgagggcggc ggcgtacaac tgcggctgac ggtcggtgaa   2940
ccggtcgagg acaccggccg gcgcccccctg agcatccact cgctcgccga ggacgccgac   3000
gacgacgcgc catgggtcct gcacgccgaa ggcgccctgg tggccgagga gtccaacgag   3060
gcgacctcct tcgacctgtc gcgctggccg cccgacgagg cgacgaggat caccaccgag   3120
ggcgcgtacg aaaggttcgc ggacctcgga tacgtctacg gccccgcgtt ccaggcgctc   3180
aaggcggcgt ggcgcgtcgg tgacgagaca ttcgccgagg tggcgctcgc cgacgacgtg   3240
gccgacgccg agaggttcgt actgcacccg gcgctgctcg actccgctct gcacgcggtg   3300
```

-continued atactcggcg cgggcgagga cgaagccacc tcactgcctt tcgcctggaa gggtgtgcgg 3360
ctgcacgcct tcggcgccag ggccgcgcgc gtccggttca cccccaacgc cgagggcggc 3420
acgacgatcc gcgtcgccga cccccagggc cgtcccgtcg cgtacgtgga gtcgctgatc 3480
tcccgggagg tctccgccga gcagctcgca ccggcgcccg ccgggccggg cgactccctc 3540
ttccacctcg cgtggacacc cgccgccacc gccaccgccg ccgaggcgga ctggacgacg 3600
gtcaccgaac tggccgaact ctccggcccg gtgccctcga cggtcgcctg gacacccccg 3660
gcaggcaccg gccggatcgc cgacgacgtc aggacggtca ccgcccagac gctccggacc 3720
ctccagacct ggctcacgga cgaacggttc gccggcagca ggctcctggt ggtcacccgc 3780
ggtgacgacc tggcacacgc ctccgcctgg ggcctggtac gcgccgcccg ttcggaggac 3840
ccggagcgct tcgcgctgct cgacaccgac ggcgacgacc cggagacgat cggccgggcc 3900
gtcgcgtcgg gcgagcccga cctgcgcgta cggggccagg agatcctggt cccccggctc 3960
gcgcgcgtcc cggccgcacc ggaggaggac gcaccctcgc gctcgccctg ggaccggccc 4020
ggagccgtac tgatcaccgg cggcacaggc ggtctcggcg cgctcgtcgc ccgccacttg 4080
gtcgccgaac gcggcgtccg ggacctgctg ctgaccagcc gtcgcggcat cgacgcgcag 4140
ggcgcggccg acctccacca ggagctgacc gccctcggtg cgacggtcga gatcgccgcc 4200
tgcgacgtgg ccgaccggga cgccgtcgag gcgctgctgg ccggccgctc cctcggctcc 4260
gtcgtccaca ccgccggggt actggccgac agcatgatcg ccaacctgac ggcgcacggc 4320
ctcgaccagg tcctgcgccc caaggtggac ggcgcactca acctgcacga cctcacccgc 4380
gaccaggagc tgggcgcctt cgtcctgttc tcgtccgcgg cgggcgtgct cggctcgccc 4440
ggccagggca actacgccgc cgccaacacc ttcctcgacg ccctcgccgc gcggcgccac 4500
gccgagggac tgcccgcgca gtccctcgcc tgggggctgt gggcggacac cggcggaatg 4560
gcgggccacc tgagcgaggc agacctgcgg cggctgcgcc gccagggcat gcccgcgctg 4620
tcgtcccagg acggcctcgc gctgttcgac gccgcgtccg tgaggcccga gccggcgctc 4680
gtgccgatga gcctggacct gcgggcgctg cggaacgggg ccggaggcga actccccgtc 4740
gtcctgcgcg gcctggtccc cgccgtacgg cgccgctccg cgaccaccga cccgtcggcg 4800
ctgcggcgag agctggccgc gatgcccgcg cagcagcggg agcgggcgct cagcgatctg 4860
gtgctgagcc tcgccgcctc cgtgctcgga cacgccgacg ccgaagccgt cgaccccagc 4920
cgcgacttcc tggagtccgg gttcgactcg ctcaccgcga tggaactgcg caccgcgctg 4980
atcgccgcca ccggggcgaa gctgcccacg atggcggtgt tcgacagcaa gaccccggcc 5040
aacctggccc gtctcctcgc cgacgagatg gagtccggga cggccgccgc cggcgccgag 5100
tccgccgccg agccctcgga agaggacgac gagacggtga ccgagatgtt ccggcgggcg 5160
gtccgggccg gtgacacgac aggggcactg ggcctgatgt cggcggtcgc ggcgctgcga 5220
ccccggttcg tcacacccgc cgacctcgcg aggaccccga agacggtgcg gttggcggac 5280
ggccccggcc gcccccggct gatctgcctg gccacaccca tggcgggcgg cggcgtgcac 5340
cagcacgccc ggctcggttc cgaattccgg gacgtgcggc acgtgtcggc ggtggcactg 5400
cccggattcc accgggacga gccactgccc gactccgtcg aggtgctgac acaggtgctg 5460
ggcgacgccg tgctggcggc ggcggacggt gagccgttcg tactgctcgg ctactcctcc 5520
ggcggcatca tcggccacat catcgcccgt cacctgaagg agacgctcaa ggtcccgccc 5580
gccggactcg tcctgatcga caccttcagg gtcgaggaca cggcgatgaa cgtcgggttc 5640
gaccacctca tgggcgaact gctgacggtg gagacgaccc tcggcaacta cgacgcggcg 5700
cgactgtccg cgatgccgca ctacttccag gtactggcgg gcttcgaccc cgtacggctg 5760
gacacaccga ccctgttcgt ccaggcgtcc gagccgttcg ttcagccccc cgagggggtc 5820
gacgtggcgg agatgcgggc ccgcccgtgg gactccgagc acaccctgcg caccgtcgaa 5880
ggcaaccatt tctcgctcgg gcaggaccac gccccggcga ccgcccgagt catcgaggaa 5940
tggctggaga cgctcgactg a 5961

<210> SEQ ID NO 33
<211> LENGTH: 1986
<212> TYPE: PRT
<213> ORGANISM: Streptomyces sp. MP28-13

<400> SEQUENCE: 33

Met Ala Asp Thr Asp Gln Lys Leu Val Ala Ala Leu Arg Ala Ser Leu
1 5 10 15

Lys Glu Ser Glu Ser Leu Arg Thr Arg Asn Arg Ala Leu Gln Ala Ala
20 25 30

Ser Arg Glu Pro Ile Ala Ile Val Ala Met Ser Cys Arg Tyr Pro Gly
35 40 45

Ala Thr Ser Pro Glu Glu Leu Trp Arg Leu Val Ala Asp Gly Thr Asp
50 55 60

Ala Val Ser Arg Phe Pro Ala Asp Arg Gly Trp Asp Glu Glu Gly Ile
65 70 75 80

Tyr Asp Pro Glu Pro Gly Lys Pro Gly Lys Thr Tyr Ser Arg Glu Gly
85 90 95

Gly Phe Leu Tyr Asp Ala Ala Glu Phe Asp Pro Gly Phe Phe Gly Ile
100 105 110

Ala Pro Asn Glu Ala Leu Val Met Asp Pro Gln Gln Arg Leu Leu Leu
115 120 125

Glu Ala Ser Trp Glu Val Leu Glu Arg Ala Gly Ile Asp Pro Thr Thr
130 135 140

Leu Lys Gly Ser Pro Thr Gly Val Phe Ala Gly Met Met Tyr His Asp
145 150 155 160

Tyr Thr Tyr Asn Ser Ser Thr Gly Ala Met Ala Ser Gly Arg Val Ala
165 170 175

Tyr Thr Leu Gly Leu Glu Gly Pro Ala Val Thr Ile Asp Thr Ala Cys
180 185 190

Ser Ser Ser Leu Val Ala Leu His Trp Ala Val Gln Ala Leu Arg Ser
195 200 205

Gly Glu Cys Ser Leu Ala Leu Ala Gly Gly Val Thr Val Met Ala Thr
210 215 220

Pro Glu Thr Phe Ile Glu Phe Ser His Gln Arg Gly Leu Ala Thr Asp
225 230 235 240

Gly Arg Cys Lys Ser Tyr Ala Ala Ala Ala Asp Gly Thr Gly Trp Gly
245 250 255

Glu Gly Val Gly Met Ile Leu Val Glu Arg Leu Ser Asp Ala Arg Arg
260 265 270

Asn Asp His Pro Val Leu Gly Ile Val Arg Gly Thr Ala Ile Asn Gln
275 280 285

Asp Gly Ala Ser Asn Gly Ile Thr Ala Pro Asn Gly Pro Ala Gln Gln
290 295 300

Arg Val Ile Arg Gln Ala Leu Ala Asn Ala Arg Val Ser Ala Asp Gly
305 310 315 320

-continued

```
Val Asp Leu Ile Glu Gly His Gly Thr Gly Thr Thr Leu Gly Asp Pro
                325                 330                 335

Ile Glu Ala Gln Ala Leu Leu Ala Ala Tyr Gly Gln Asp Arg Pro Gly
            340                 345                 350

Asp Arg Pro Leu Trp Leu Gly Ser Ile Lys Ser Asn Ile Gly His Thr
        355                 360                 365

Gln Ala Ala Ala Gly Val Ala Gly Ile Ile Lys Val Val Glu Ala Ile
    370                 375                 380

Arg His Gly Val Met Pro Pro Thr Leu His Val Asp Ala Pro Thr Pro
385                 390                 395                 400

Gln Val Asp Trp Glu Ala Gly Asp Val Arg Leu Leu Thr Glu Ala Arg
                405                 410                 415

Arg Trp Pro Asp Gln Glu His Pro Arg Arg Ala Gly Val Ser Ser Phe
            420                 425                 430

Gly Ile Ser Gly Thr Asn Ala His Val Ile Ile Glu Glu Ala Pro Pro
        435                 440                 445

Ala Glu Glu His Ala Pro Pro Val Ala Ala Thr Thr Gly Gly Pro Val
    450                 455                 460

Leu Trp Thr Leu Ser Gly Arg Thr Gln Gln Ala Leu Ser Ala Gln Ala
465                 470                 475                 480

Glu Ser Leu His Ser His Leu Arg Glu Arg Pro Asp Leu Thr Pro Ala
                485                 490                 495

Asp Val Gly Leu Ser Leu Ala Arg Gly Arg Ala Ala Leu Glu His Arg
            500                 505                 510

Ala Ala Ile Val Ala Asp Asp Arg Gln Gly Leu Leu Ala Gly Leu Thr
        515                 520                 525

Ala Leu Ala Ala Gly Thr Pro Ser Pro Ser Val Val Thr Gly Lys Arg
    530                 535                 540

Arg Glu Gly Lys Val Ala Phe Leu Phe Thr Gly Gln Gly Ser Gln Arg
545                 550                 555                 560

Leu Gly Met Gly Arg Glu Leu Tyr Glu Thr Phe Pro Val Phe Thr Ala
                565                 570                 575

Ala Leu Asp Glu Val Cys Glu Ala Thr Gly Leu Ser Leu Lys Asp Val
            580                 585                 590

Val Trp Gly Asp Glu Ser Ala Leu His Arg Thr Glu Tyr Ala Gln Pro
        595                 600                 605

Ala Ile Phe Ala Leu Glu Val Ala Leu Phe Arg Leu Val Glu Ser Trp
    610                 615                 620

Gly Ile Lys Pro Asp Tyr Leu Ala Gly His Ser Ile Gly Glu Leu Ala
625                 630                 635                 640

Ala Ala His Val Ala Gly Val Leu Gly Leu Glu Asp Ala Ala Arg Leu
                645                 650                 655

Val Ala Glu Arg Gly Arg Leu Met Gln Ala Leu Pro Ala Gly Gly Ala
            660                 665                 670

Met Thr Ala Ile Glu Ala Thr Glu Glu Glu Val Ala Pro Leu Leu Thr
        675                 680                 685

Glu Glu Val Gly Ile Ala Ala Leu Asn Ser Pro Ser Ser Val Val Val
    690                 695                 700

Ser Gly Ser Glu Asp Ala Val Glu Ala Val Thr Glu His Phe Ala Asp
705                 710                 715                 720

Arg Arg Thr Arg Arg Leu Thr Val Ser His Ala Phe His Ser Pro Leu
                725                 730                 735

Met Glu Pro Met Leu Glu Asp Phe Arg Lys Val Ala Glu Ser Leu Thr
```

-continued

```
            740                 745                 750

Tyr Glu Arg Pro Arg Ile Arg Leu Val Lys Asp Met Ala Ser Ala Asp
        755                 760                 765

Tyr Trp Val Arg His Val Arg Asp Ala Val Arg Phe Ala Asp Asp Val
    770                 775                 780

Arg Arg Leu Glu Ala Glu Gly Val Thr Arg Phe Leu Glu Leu Gly Pro
785                 790                 795                 800

Asp Gly Ala Leu Ala Ala Met Ala Arg Gln Thr Ala Pro Glu Ala Thr
                805                 810                 815

Thr Ala Ala Ala Leu Arg Arg Asp Arg Pro Glu Ala Thr Thr Leu Leu
            820                 825                 830

Thr Ala Val Ala His Leu His Thr Thr Gly Val Ser Pro Asp Trp Thr
        835                 840                 845

Ala Phe Phe Ala Gly Arg Arg Ala His Arg Val Asp Leu Pro Thr Tyr
    850                 855                 860

Ser Phe Gln Arg Thr Arg Tyr Trp Leu Gln Glu Pro Val Asp Ala Gly
865                 870                 875                 880

Gly Gly Ser Ala Ala Ser Met Gly Leu Ser Ala Leu Asp His Pro Leu
                885                 890                 895

Leu Ser Ala Glu Ile Ala Val Pro Gly Ser Arg Thr Val Ile Cys Thr
            900                 905                 910

Gly Arg Leu Ser Thr Asp Thr His Pro Trp Leu Ala Asp His Glu Val
        915                 920                 925

Leu Gly Ala Thr Leu Leu Pro Gly Thr Ala Phe Val Glu Leu Ala Val
    930                 935                 940

Arg Val Gly Asp Gln Val Gly His Gly Val Leu Glu Glu Leu Thr Leu
945                 950                 955                 960

Arg Ala Pro Leu Val Leu Pro Glu Gly Gly Gly Val Gln Leu Arg Leu
                965                 970                 975

Thr Val Gly Glu Pro Val Glu Asp Thr Gly Arg Arg Pro Leu Ser Ile
            980                 985                 990

His Ser Leu Ala Glu Asp Ala Asp  Asp Asp Ala Pro Trp  Val Leu His
        995                 1000                1005

Ala Glu  Gly Ala Leu Val Ala  Glu Glu Ser Asn Glu  Ala Thr Ser
    1010                1015                1020

Phe Asp  Leu Ser Arg Trp Pro  Pro Asp Glu Ala Thr  Arg Ile Thr
    1025                1030                1035

Thr Glu  Gly Ala Tyr Glu Arg  Phe Ala Asp Leu Gly  Tyr Val Tyr
    1040                1045                1050

Gly Pro  Ala Phe Gln Ala Leu  Lys Ala Ala Trp Arg  Val Gly Asp
    1055                1060                1065

Glu Thr  Phe Ala Glu Val Ala  Leu Ala Asp Asp Val  Ala Asp Ala
    1070                1075                1080

Glu Arg  Phe Val Leu His Pro  Ala Leu Leu Asp Ser  Ala Leu His
    1085                1090                1095

Ala Val  Ile Leu Gly Ala Gly  Glu Asp Glu Ala Thr  Ser Leu Pro
    1100                1105                1110

Phe Ala  Trp Lys Gly Val Arg  Leu His Ala Phe Gly  Ala Arg Ala
    1115                1120                1125

Ala Arg  Val Arg Phe Thr Pro  Asn Ala Glu Gly Gly  Thr Thr Ile
    1130                1135                1140

Arg Val  Ala Asp Pro Gln Gly  Arg Pro Val Ala Tyr  Val Glu Ser
    1145                1150                1155
```

-continued

Leu Ile Ser Arg Glu Val Ser Ala Glu Gln Leu Ala Pro Ala Pro
1160 1165 1170

Ala Gly Pro Gly Asp Ser Leu Phe His Leu Ala Trp Thr Pro Ala
1175 1180 1185

Ala Thr Ala Thr Ala Ala Glu Ala Asp Trp Thr Thr Val Thr Glu
1190 1195 1200

Leu Ala Glu Leu Ser Gly Pro Val Pro Ser Thr Val Ala Trp Thr
1205 1210 1215

Pro Pro Ala Gly Thr Gly Arg Ile Ala Asp Asp Val Arg Thr Val
1220 1225 1230

Thr Ala Gln Thr Leu Arg Thr Leu Gln Thr Trp Leu Thr Asp Glu
1235 1240 1245

Arg Phe Ala Gly Ser Arg Leu Leu Val Val Thr Arg Gly Asp Asp
1250 1255 1260

Leu Ala His Ala Ser Ala Trp Gly Leu Val Arg Ala Ala Arg Ser
1265 1270 1275

Glu Asp Pro Glu Arg Phe Ala Leu Leu Asp Thr Asp Gly Asp Asp
1280 1285 1290

Pro Glu Thr Ile Gly Arg Ala Val Ala Ser Gly Glu Pro Asp Leu
1295 1300 1305

Arg Val Arg Gly Gln Glu Ile Leu Val Pro Arg Leu Ala Arg Val
1310 1315 1320

Pro Ala Ala Pro Glu Glu Asp Ala Pro Ser Arg Ser Pro Trp Asp
1325 1330 1335

Arg Pro Gly Ala Val Leu Ile Thr Gly Gly Thr Gly Gly Leu Gly
1340 1345 1350

Ala Leu Val Ala Arg His Leu Val Ala Glu Arg Gly Val Arg Asp
1355 1360 1365

Leu Leu Leu Thr Ser Arg Arg Gly Ile Asp Ala Gln Gly Ala Ala
1370 1375 1380

Asp Leu His Gln Glu Leu Thr Ala Leu Gly Ala Thr Val Glu Ile
1385 1390 1395

Ala Ala Cys Asp Val Ala Asp Arg Asp Ala Val Glu Ala Leu Leu
1400 1405 1410

Ala Gly Arg Ser Leu Gly Ser Val Val His Thr Ala Gly Val Leu
1415 1420 1425

Ala Asp Ser Met Ile Ala Asn Leu Thr Ala His Gly Leu Asp Gln
1430 1435 1440

Val Leu Arg Pro Lys Val Asp Gly Ala Leu Asn Leu His Asp Leu
1445 1450 1455

Thr Arg Asp Gln Glu Leu Gly Ala Phe Val Leu Phe Ser Ser Ala
1460 1465 1470

Ala Gly Val Leu Gly Ser Pro Gly Gln Gly Asn Tyr Ala Ala Ala
1475 1480 1485

Asn Thr Phe Leu Asp Ala Leu Ala Ala Arg Arg His Ala Glu Gly
1490 1495 1500

Leu Pro Ala Gln Ser Leu Ala Trp Gly Leu Trp Ala Asp Thr Gly
1505 1510 1515

Gly Met Ala Gly His Leu Ser Glu Ala Asp Leu Arg Arg Leu Arg
1520 1525 1530

Arg Gln Gly Met Pro Ala Leu Ser Ser Gln Asp Gly Leu Ala Leu
1535 1540 1545

```
Phe Asp  Ala Ala Ser Val Arg  Pro Glu Pro Ala Leu  Val Pro Met
    1550                 1555                 1560

Ser Leu  Asp Leu Arg Ala Leu  Arg Asn Gly Ala Gly  Gly Glu Leu
    1565                 1570                 1575

Pro Val  Val Leu Arg Gly Leu  Val Pro Ala Val Arg  Arg Arg Ser
    1580                 1585                 1590

Ala Thr  Thr Asp Pro Ser Ala  Leu Arg Arg Glu Leu  Ala Ala Met
    1595                 1600                 1605

Pro Ala  Gln Gln Arg Glu Arg  Ala Leu Ser Asp Leu  Val Leu Ser
    1610                 1615                 1620

Leu Ala  Ala Ser Val Leu Gly  His Ala Asp Ala Glu  Ala Val Asp
    1625                 1630                 1635

Pro Ser  Arg Asp Phe Leu Glu  Ser Gly Phe Asp Ser  Leu Thr Ala
    1640                 1645                 1650

Met Glu  Leu Arg Thr Ala Leu  Ile Ala Ala Thr Gly  Ala Lys Leu
    1655                 1660                 1665

Pro Thr  Met Ala Val Phe Asp  Ser Lys Thr Pro Ala  Asn Leu Ala
    1670                 1675                 1680

Arg Leu  Leu Ala Asp Glu Met  Glu Ser Gly Thr Ala  Ala Ala Gly
    1685                 1690                 1695

Ala Glu  Ser Ala Ala Glu Pro  Ser Glu Glu Asp Asp  Glu Thr Val
    1700                 1705                 1710

Thr Glu  Met Phe Arg Arg Ala  Val Arg Ala Gly Asp  Thr Thr Gly
    1715                 1720                 1725

Ala Leu  Gly Leu Met Ser Ala  Val Ala Ala Leu Arg  Pro Arg Phe
    1730                 1735                 1740

Val Thr  Pro Ala Asp Leu Ala  Arg Thr Pro Lys Thr  Val Arg Leu
    1745                 1750                 1755

Ala Asp  Gly Pro Gly Arg Pro  Arg Leu Ile Cys Leu  Ala Thr Pro
    1760                 1765                 1770

Met Ala  Gly Gly Gly Val His  Gln His Ala Arg Leu  Gly Ser Glu
    1775                 1780                 1785

Phe Arg  Asp Val Arg His Val  Ser Ala Val Ala Leu  Pro Gly Phe
    1790                 1795                 1800

His Arg  Asp Glu Pro Leu Pro  Asp Ser Val Glu Val  Leu Thr Gln
    1805                 1810                 1815

Val Leu  Gly Asp Ala Val Leu  Ala Ala Ala Asp Gly  Glu Pro Phe
    1820                 1825                 1830

Val Leu  Leu Gly Tyr Ser Ser  Gly Gly Ile Ile Gly  His Ile Ile
    1835                 1840                 1845

Ala Arg  His Leu Lys Glu Thr  Leu Lys Val Pro Pro  Ala Gly Leu
    1850                 1855                 1860

Val Leu  Ile Asp Thr Phe Arg  Val Glu Asp Thr Ala  Met Asn Val
    1865                 1870                 1875

Gly Phe  Asp His Leu Met Gly  Glu Leu Leu Thr Val  Glu Thr Thr
    1880                 1885                 1890

Leu Gly  Asn Tyr Asp Ala Ala  Arg Leu Ser Ala Met  Pro His Tyr
    1895                 1900                 1905

Phe Gln  Val Leu Ala Gly Phe  Asp Pro Val Arg Leu  Asp Thr Pro
    1910                 1915                 1920

Thr Leu  Phe Val Gln Ala Ser  Glu Pro Phe Val Gln  Pro Pro Glu
    1925                 1930                 1935

Gly Val  Asp Val Ala Glu Met  Arg Ala Arg Pro Trp  Asp Ser Glu
```

```
    1940                1945                1950

His Thr  Leu Arg Thr Val Glu  Gly Asn His Phe Ser  Leu Gly Gln
    1955                1960                1965

Asp His  Ala Pro Ala Thr Ala  Arg Val Ile Glu Glu  Trp Leu Glu
    1970                1975                1980

Thr Leu  Asp
    1985


<210> SEQ ID NO 34
<211> LENGTH: 10134
<212> TYPE: DNA
<213> ORGANISM: Streptomyces sp. MP28-13

<400> SEQUENCE: 34

atgtcgaagg actccaacga cgaacggctt cgcgagtatc tgcggcttgc caccggtgag     60

ttgcagcaga ctcggcgccg tctgcgtgag gcggaggatc gggagcggga gccgatcgcg    120

atcgtgggaa tggcatgccg cttccccggt ggcgcgtcct cgccggaagg actctgggac    180

ctcgtcgccg acggtctgga aacggtgggc gagttcccca ccgaccgggg ctggaacctg    240

gactcgctgt acgaccctga cgggacgggc gagaacacca gctacgtcaa caagggcagc    300

ttcctggacg gcgcgggcga cttcgacccc gagttcttcg gcatcagccc ccttgaggcg    360

atggcgatgg acccgcagca gcggctgctg ctggaaacct cctgggaggc cgtggagcgg    420

gccgggatcg acccgccgtc gctgaagggc accgccaccg gagtcttcgc cgggctcgtg    480

taccacgact atccgagcag cagtgtgacc ggtgcgctgg tttccggccg ggtggcctac    540

acgctggggc tggagggtcc ggcggtgacc gtcgacaccg cctgctcgtc ctcgctggtc    600

gcactggaca tggcggtcaa ggccctgcgc agtggggaat gttccctcgc cctggccggc    660

ggcgtgacga tcatgtcgac gccggtcacc ttcgtggagt tcagccggca gcggggtctg    720

tcgacggacg gccgctgcaa ggcgttcgcc tcggcggccg acggcaccgg gtggggtgag    780

ggtgtcggca tgctggtggt ggagcggctg tcggacgccc gccgcaacgg ccacccgatt    840

ctggcggtcg tgcgcggcag cgccgtcaac caggacggcg ccagcaacgg catcaccgcc    900

ccgaacggcc cgtcccagcg ccgggtgatc cagcaggccc tggccaacgc gggcctggtg    960

gggtccgatg tggacgtcgt ggaggcccac ggtaccggga ccaccctggg cgacccgatc   1020

gaggcgcagg cgctgctggc cacctacggg caggaccgcc ccgaggaccg cccgctctgg   1080

ctcgggtcgg tcaagtcgaa catcgggcac acacaggccg ccgccggtgt ggcgggcatc   1140

atcaagatgg tccaggcgat acgccacggc tccctgccca agacactgca cgtggacgaa   1200

ccgtccccgc aggtggactg gacggcggga agcgtccggc tgctcaccga ggcccgcgcc   1260

tggccggagg gcggcccgcg ccgcgccgcc gtgtcctcgt tcggggccag cgggaccaac   1320

gcccacatcg tcctggagga ggctccgcag gccgaggacg taccggccga agagtcgccg   1380

gagtcgccgg agccgcgtga gcaccgggaa cttccggtgg tgccctggct gatctccggg   1440

aagaccgagg ccgccgtacg cgcctacgcg gagcggctcc aggccgtcgc cacgcacgac   1500

ctacggccgg tggacgtggg atggtccctg gccacgcggc gggcgtcgta cgactaccgg   1560

gccgccgtac tggccgccga cgaagagggc ttctcccagg ggctcgccgc tctggtgcag   1620

ggggaagcac cggtgacagc ggcccggccc ggcgccggcg cggtcatggt gttccccgga   1680

cagggctccc agtgggtggg catggcgacc gagctgatgg cgtcgtccgc cgtgttcacg   1740

gagcagatgt ccgcgtgcga ggaggcactg gcgccgttcg tggactggtc gttgagcgag   1800
```

-continued gcgctcggtg acgaggccct gctggaacgt gtagacgtcg tgcagcccgt cctgtgggcg 1860
gtcatggtgt cactggccgg tctgtggcgg cactacggag tcgagcccgt cggcgtggtg 1920
ggccactccc agggcgagat cgccgcggcg agcgtggccg gagcgctgtc gttgcaggac 1980
ggcgcccggg tggtcgccct gcgcagcaag gcgctgctgg ccctctccgg ccagggcggg 2040
atggtgtcgg tcgccctccc ccgggaggag accgagcggc tgatcgagcg ctggggcacc 2100
cggacgggca tcgcggtggt caacggcaac gccgccaccg tggtctcggg cgaggtcgac 2160
gcgctggacg aactgatggc ctcctgcgag gccgacggcg tacgggcgcg ccggatccag 2220
gtggactacg cctcgcactc ggcacaggtg gagcgcatag agcgggaact gctcgacgtg 2280
ctggcgccca tcaagccccg cgccgcgcgg atccccttct actccaccgt gaccggcggg 2340
ctgctggaca ccaccgctct cgacgccggc tactggtacc ggaatctgcg ccagaccgtg 2400
gagttcgacc ggaccatccg ccggctgacc gagcagggcg tgggggtgtt catcgaggcc 2460
agcccgcacc cggtgctggc gccgagcatg gaacagacca cgatcggcac gctgcgccgc 2520
aacgacggcg gcctcgaccg tttcctgagc gtgctggccc aggcacacac ccgcggcgtg 2580
gacgtcgact gggagaaggt gtacgacgcg accggggcgg ggcagacgga actgcccacg 2640
tacgccttcc agcacaaccg ctactggctg aacgacgaga cggcgaacgc cgacgcggcc 2700
tccatgggcc tgggctcgct gggccacccg ctgctcgggg cgatggtcat gctcgcgggc 2760
tcggaggagg tcgtgctcac cggacggctg tcgaccggga cgctgccctg gctcaccgac 2820
catgtcatcg gcggctcgat cctcttcccc ggcaccggat tcgtggagct ggtgatccgg 2880
gccggcgacg aggtcggctg cggccgtgtc gaggagctga cgatcgaggc gccgctggtc 2940
ctcgccgaac gcggcggggt cgccgtccag gtcgtcgtcg gagcggcgga cgaagagggc 3000
cgccgcgagg tccaggtgta ctcccgcgac caggacgcga ccgacctgcc ctggaaccgg 3060
cacgccaccg gtctgctcgc caccgccacc tccgccgggg gaggggaact ggccgagtgg 3120
cccccgcccg gcgccgagcc gctggacctc gatgtcgaca ccctctacga ggagttggtc 3180
ggcacgggtt tggcgtacgg gccgaccttc cgggggcttc gggccgcctg gcgggccggc 3240
gacgaggtgt tcgccgagat cgccctgccg gacaacgcgg tggcggacgc ctttggtctg 3300
cacccggccc tcttcgacgc gggcctgcac gccatcggac tctccccggc gggaaccggc 3360
gatgtggcga tgctgccgtt cgcctggtcg ggagtggaac tgcacgcctc cggcgcgggc 3420
gcgctgcggg tgcgcgtcac gcccgtacag gacggcgtgg cggccctgac catcgccgac 3480
gcgaccggcc ggcccgtcgc cacggtcgac tcgttggtcc tgcggcccct cacggacatg 3540
gcgaccaagg cccgtacgga gccgctgtac cacgtcgccc tggccccggt cgccgccggt 3600
accgcctcca ccggggggca gccgcccaac gacgaggagg tgttccgcct ccccggcgga 3660
ctggacgtac gcgcggcggt gaacctggcg ctggaggcac tgcagtccgc cggctcccgt 3720
ctggtggtcg tcacgcgcgg cgcggtctcg gtgaacggcg gggacgtcga cgacctggcc 3780
gcggcggccg tctggggtct ggtgcgtacc gcccagaccg aagaccccgg ccggttcttc 3840
ctgatcgacc tggacggtga caccgacgag gcgccgagcg cggacaacgc cgacctcgcg 3900
cctgcgctgt cgaccggtga gccccgggtg gtggtacgcg acggtgtcgc ccacgtgccc 3960
cggctggccc gcgtgtccgc ggtgccggag acgacggacg acctggcgcc ggcgttcggc 4020
gacgaggtgc tgatcaccgg tggagtgggt gtcctgggtg ctctgctggc ccggcatctc 4080
gtcaccgagt acggggtgtc acggctcctg ctgaccggtc gccggggcgt ggacacgccc 4140
ggcgcggcgg agttggtgga ggagttgagc gggctggggg ccgaggtcga ggtcgccgcc 4200

-continued

```
tgcgacgtcg gcgaccgtga ggcgctcgcg gcgctgctgg ccgggcgttc gctcaccggt   4260
gtggtgcacg cggcgggtgt cctggacgac ggtgtgatcg ggtccctgac gcccgagcgg   4320
gtggacctgg tgatgcgccc caaggtggac gccgccctgt atctgcacga gctgacacgc   4380
gacatggacc tgaccgcgtt cgtactcttc tcctccgcgg ccggcgtgat cggctcgccg   4440
gggcagggca actacgcggc ggccaacgcc tatctggacg ccctggccga gcgccgccgt   4500
gcgggtggcc tgcccgccca gtccctggcg tggggcctgt ggcggaccag caccggtatg   4560
gccagtgaac tgacggacac cgaccggtcc cgtatggaac gcggcggcat cctgtcgctg   4620
tcccacagcg aggggctggc gctcttcgac gctgcgacgg cggcggacgg acccgccgta   4680
ctcgtccccg tcaagctcga cctcccggcc gtccgcgccg gcggcgcggt gccggagctg   4740
ctgcgcggcc tggtcccggt cgtcacccgt ggcaccgccc gcacccgcgc cgacgcggac   4800
gggctccgcg agcggctcgt gggcatgtcc gacgaccagc gcttcgacat gctgctgaac   4860
ctggtccgcg cgcaggccgc caccacgctc ggctacgccg gaccgggggc cgtcgacccg   4920
gagcgcgcgt tccgcgatct gggtgtcgac tcgctggcgg cgatggaact gcgcaacggt   4980
ctcggcggcg cgaccggcct gcggcttccg gccacgctgg tgttcgacta cccgaacccc   5040
accgttctcg cgcgtcatct gctggacgag gtctcgggaa cggtgcacga gggccgtctc   5100
acccccgtcg cggccccggt cggcgacgac ccgatcgcga tcgtcgcgat ggcgtgccgc   5160
tacccgggag gcgtgtcctc gccggaggac ctgtggcggc tggtcgacag cggcacggac   5220
gccatctcac acttccccac cgaccgcggc tgggacctgg agcggatcta cgaccccacg   5280
gccacccgcc cccgcaccag ctacgtcgac aagggcggat tcctttacga cgcggcccag   5340
ttcgatcccg gcttcttcgg gatcgcgccg aacgaggcgc tggtgatgga ccctcagcag   5400
cggctgctgc tggaggcgtc gtgggaggtt cttgagcgcg cgggcatcga cccgacgact   5460
ctcaagggca gcctgaccgg tgtcttcgcc gggatgatgt accacgacta cacccacaac   5520
agcagcacgg gcgccatcgc ctccggccgc gtctcctaca ccctggggct cgaaggcccc   5580
gcggtgaccg tcgacaccgc ctgctcgtcc tcgctggtcg ccctgcacct ggcggcgcag   5640
gccctgcggt cgggggagtg ctcgctcgcc ctggccggcg gcgtcaccgt gatggccgcg   5700
gcggacaact tcatcgagtt cagcgagcag cggggtctgg cgaccgacgg ccgctgcaag   5760
tccttcgcgg ccgccgccga cggcgccggc tggagtgagg gtgtcggcat gctcctggtg   5820
gagcggctgt cggacgcccg ccgcaacggc cacccggtgc tggccctcgt acggggcacg   5880
gcgaccaacc aggacggcgc gagcaacggc ctgaccgccc ccaacgggcc gtcccagcag   5940
cgggtgatca agcaggcgct ggccaacgcg ggcctggcgg gcgccgatgt ggacgcggtc   6000
gaggcgcacg gcacgggcac caccctgggt gatccgatcg aggcgcaggc gctgctggcc   6060
acctacggcc agggccgccc cgaggaccga ccgctgtggc tggggtcgat caagtcgaac   6120
atcggtcaca cccaggccgc cgcgggtgtg gcgggcatca tcaagatggt cgaggcgatg   6180
cggcagggca cgctgccacg gacgctgcac gtggacgcgc ccacacccca ggtggactgg   6240
gaggccggcc aggtccagct gctcaccgag acgagggagt ggccgaacga cggccgcccg   6300
cgccgcgcgg gcgtgtcctc cttcggcatc agcggcacca acgcccacgt catcatcgag   6360
gaggccgtcc cggtcgagga agcgccggtg gagcggcggg agttgcccgt cgtcccccctg  6420
gtgctgtcgg cccggacccg taccgcgctc caggcccagc tcgaccggat cacctccgtc   6480
gacgcggacg agctggacgt ggcgtactcg gccgcgaccg gccgggccgc cctggaacac   6540
```

-continued cgcgcggtgc ggatcggctc cgagaccgtg atcgactcgg tcaccgaggg cgggctggcg 6600
ttcctgttca ccggacaggg cagtcagtgg gccgggatgg gccaggagct gtacgagacg 6660
ttccccgctt tcgccacggc gttcgacgag gtgtgcgccg tgctcgaccc cgcgctgcgc 6720
gaggtgatgt ggggcgacga ggaggccctg ggccgcaccg agttcaccca gcccgcgatc 6780
ttcgctctcc aggtcgccct gttccggctg gtggagtcgt gggggatcaa gccggacctc 6840
atgaccggcc actccatcgg ggaactcgcc gccgcccata cggccggggt gttcgatctg 6900
gctgatgccg cccggctgat cacggcgcgc ggacggctga tccaggaact cccgcccggc 6960
ggggcgatgg tggcgatccg ggccaccgag gaggaggtca cgccgcacct caccgagcag 7020
gtgagcgtcg cggcggtcaa cacccccggc tcggtggtga tctcgggcgc cgaggaggcc 7080
gtcaccgcgg tcgccgagcg gttcgccgac cgcaagacga ctcggctgaa ggtgtcgcac 7140
gcgttccact cgccgctgat ggacccgatg ctcgaagagt tccggaaggt cgccgagagc 7200
gtcacctacc gcgagccggt catccagctg accaaggacg tggcgtcggc ggagtactgg 7260
gtacggcacg tgcgcgacgc ggtgcggttc gccgacgacg tacgccacct gcaggaccgg 7320
ggcatcaccc ggttcatgga ggtcggaccg gacagtgtgc tcaccgcgat ggtgcggcag 7380
accgccgacg ggacggtcgc ggccacccag cgaaacgacc gtccgggcgt ggaaaccctc 7440
ttcaccggcg tcggccggct gttcgccgcc ggtgtgcggg tcgactggaa cgccgtgttc 7500
gacgggcgcg gggcgcggcg ggtcgagctg ccgacgtacc ccttccagcg gcagccgttc 7560
tggatcgagt cggggcgcgg cgcggacgcg tccgaccacc cgctgctgga ccagacggtc 7620
gctgtcgcgg gggcggaccg gaccgtgctg accgggcgtc tgtcgctcgg tacccagccc 7680
tggctcgccg aacacgcggt cgccggcacc ctgctcttcc ccggtacggg cttcgtcgaa 7740
ctggccgtcc gcgcgggcga cgaggtcggc tgcggccgga tcgaggaact gacgatcgag 7800
gcaccgctgg tccttgccga acacaccgcc acggccgtac aggtcgtggt cggggtggac 7860
gacggagcgg gccaccgggc tgtcgaggtg tacgcccgag gcgcggacga tccccatctg 7920
ccctggaccc gccacgccgc cggaaccctg gccccggcca ccggcggccc cgcggccgag 7980
gcgatgaccc agtggccacc gcccggtgca gagcccgtgg aactggcggg gctgtacgag 8040
agcctggcgg aagccggagt cgagtacggg ccggcgttcc agggactcaa gtccgcctgg 8100
cgcgaagagg ggacggtcta cgccgacgtc gtcctgtccg ggcggcggga ccgcttcggg 8160
atccacccgg cactcctgga cgcggccctg cacacggtcc cgttgctgtc gggcgacgac 8220
cgcgtcgtcc tgccgttctc ctgggcggga gtggaactgc acgcctccgg cgccaccgcg 8280
ctccgtgtcc ggatgacgct ccgcggccag gaccgggtgg ccctccacgc cgtcgacggc 8340
gccgggcagc cggtcgtctc cgtggacgcc ctgaccctgc gtccgatggc cgccggtgcg 8400
ctcacgcgcg tcgactcgct cttccaggtc gagtggacgc ccgtcgccgt acgcgacgac 8460
gcggccggtg acgcgaaggt gtggcggacc gagggcgacg acgtgctctc cacactgcat 8520
ccgctgctca aggcgatcca ggcggagacc gagaccctcg cggtcgtcac gcgcggcgcg 8580
gtgtccgtgg ccggtgagcg ggtgagcgac ctggccggcg cctcggcgtg gggactggtg 8640
cgcagcgccc agtcggagga tccgggccgg ttcgtcctgg tcgacgtggc cggtgaggac 8700
gagaaggcgg acatcgccct ggcgctggcg gcgggagagc cccaggtggc cgtccgggac 8760
gggaaggtct acgtaccgag gctgagggcg gcctcggtcg cggagtccga gccgtcctcg 8820
gtcttcggcg acgaggtact gatcacgggc gcgtccggcg ccctgggcgg actggtcgcg 8880
cgccatctcg tcaccgggca cggcgtacgg cgactgctgc tgaccagccg ccggggcctg 8940

-continued gcggcgcccg gcgcggcgga gttggtggag gagctggccg ggctgggggc cgaggtcgag 9000
gtcgccgcct gcgacgtcgg cgaccgtgag gcgctcgcgg cgctgctggc cgggcgttcg 9060
ctcaccggtg tggtgcacgc ggcgggcgtt ctggacgacg gcgtgatcgc gtcgctgacc 9120
cccgaacgcc tggacaaggt cgtcacaccc aaggcggtgg ccgccctgca tctgcacgag 9180
ctgacacgcg acatggacct gaccgcgttc gtactcttct cctcggtggc cggcgtgatc 9240
ggcacaccgg ggcagggcaa ctacgccgcg gccaacgcgc ttctggacgc actggccgcg 9300
caccggcgcg ccgacggcct gcccgcccag tccctggcct ggggcctgtg gacgaccgac 9360
gccggcatgg ccggtgacct ggcggacacc gaccggcagc ggatcgaccg cgcgggcctc 9420
gtgggactct cgcccgagca gggtctcgaa ctcctcgacg tggcgggcgc gctggccaca 9480
ccggcgctgg tgcccatgaa cctggacacc aggacgctga acgcggccga cgtgcctttg 9540
atgctgcgcg gactggtacg cggctcctcg cggcgtgccg tgtcggcgca atccacgggc 9600
ggcggggccg cgctgcgcaa gcgcctggcg gcactgcccg ccgacgatcg gtacgacgaa 9660
gtcctcgacc tcgtccgtac ccacgcggcg gcggtactgg gtcacgcggg tcccgaggcc 9720
gtcgaaccgg agcgggcctt cggcgatctg ggcttcgact cgctgggcgc tgtcgagttc 9780
cgcaacaccc tcaacgccgc ggccgggctg cgactgtccg ccaccatgat cttcgaccat 9840
ccgaccgccc gggtgctcgc cgagcacatc ggcgcggagc tggcacccga cggtgacgcc 9900
ggcgccgccg ccgacgagga gacggtccgc cgcctgctcg ggtcgattcc gctcacccgg 9960
ctgcacgacg cggggctgat ggaggccctg ctcgaactcg ccggatccgg cgccgcctcc 10020
ggcatggcgg cagccgtgcc cgaggaggac tcgatcgacg cgatggacgc cgaagccctg 10080
atcagcatgg ccctgcagga caccgatccg gacgaagcga cgcgggaagt ctga 10134

<210> SEQ ID NO 35
<211> LENGTH: 3377
<212> TYPE: PRT
<213> ORGANISM: Streptomyces sp. MP28-13

<400> SEQUENCE: 35

Met Ser Lys Asp Ser Asn Asp Glu Arg Leu Arg Glu Tyr Leu Arg Leu
1 5 10 15

Ala Thr Gly Glu Leu Gln Gln Thr Arg Arg Arg Leu Arg Glu Ala Glu
20 25 30

Asp Arg Glu Arg Glu Pro Ile Ala Ile Val Gly Met Ala Cys Arg Phe
35 40 45

Pro Gly Gly Ala Ser Ser Pro Glu Gly Leu Trp Asp Leu Val Ala Asp
50 55 60

Gly Leu Glu Thr Val Gly Glu Phe Pro Thr Asp Arg Gly Trp Asn Leu
65 70 75 80

Asp Ser Leu Tyr Asp Pro Asp Gly Thr Gly Glu Asn Thr Ser Tyr Val
85 90 95

Asn Lys Gly Ser Phe Leu Asp Gly Ala Gly Asp Phe Asp Pro Glu Phe
100 105 110

Phe Gly Ile Ser Pro Leu Glu Ala Met Ala Met Asp Pro Gln Gln Arg
115 120 125

Leu Leu Leu Glu Thr Ser Trp Glu Ala Val Glu Arg Ala Gly Ile Asp
130 135 140

Pro Pro Ser Leu Lys Gly Thr Ala Thr Gly Val Phe Ala Gly Leu Val
145 150 155 160

-continued

```
Tyr His Asp Tyr Pro Ser Ser Ser Val Thr Gly Ala Leu Val Ser Gly
                165                 170                 175

Arg Val Ala Tyr Thr Leu Gly Leu Glu Gly Pro Ala Val Thr Val Asp
            180                 185                 190

Thr Ala Cys Ser Ser Ser Leu Val Ala Leu Asp Met Ala Val Lys Ala
        195                 200                 205

Leu Arg Ser Gly Glu Cys Ser Leu Ala Leu Ala Gly Gly Val Thr Ile
    210                 215                 220

Met Ser Thr Pro Val Thr Phe Val Glu Phe Ser Arg Gln Arg Gly Leu
225                 230                 235                 240

Ser Thr Asp Gly Arg Cys Lys Ala Phe Ala Ser Ala Ala Asp Gly Thr
                245                 250                 255

Gly Trp Gly Glu Gly Val Gly Met Leu Val Val Glu Arg Leu Ser Asp
            260                 265                 270

Ala Arg Arg Asn Gly His Pro Ile Leu Ala Val Val Arg Gly Ser Ala
        275                 280                 285

Val Asn Gln Asp Gly Ala Ser Asn Gly Ile Thr Ala Pro Asn Gly Pro
    290                 295                 300

Ser Gln Arg Arg Val Ile Gln Gln Ala Leu Ala Asn Ala Gly Leu Val
305                 310                 315                 320

Gly Ser Asp Val Asp Val Val Glu Ala His Gly Thr Gly Thr Thr Leu
                325                 330                 335

Gly Asp Pro Ile Glu Ala Gln Ala Leu Leu Ala Thr Tyr Gly Gln Asp
            340                 345                 350

Arg Pro Glu Asp Arg Pro Leu Trp Leu Gly Ser Val Lys Ser Asn Ile
        355                 360                 365

Gly His Thr Gln Ala Ala Ala Gly Val Ala Gly Ile Ile Lys Met Val
    370                 375                 380

Gln Ala Ile Arg His Gly Ser Leu Pro Lys Thr Leu His Val Asp Glu
385                 390                 395                 400

Pro Ser Pro Gln Val Asp Trp Thr Ala Gly Ser Val Arg Leu Leu Thr
                405                 410                 415

Glu Ala Arg Ala Trp Pro Glu Gly Gly Pro Arg Arg Ala Ala Val Ser
            420                 425                 430

Ser Phe Gly Ala Ser Gly Thr Asn Ala His Ile Val Leu Glu Glu Ala
        435                 440                 445

Pro Gln Ala Glu Asp Val Pro Ala Glu Glu Ser Pro Glu Ser Pro Glu
    450                 455                 460

Pro Arg Glu His Arg Glu Leu Pro Val Val Pro Trp Leu Ile Ser Gly
465                 470                 475                 480

Lys Thr Glu Ala Ala Val Arg Ala Tyr Ala Glu Arg Leu Gln Ala Val
                485                 490                 495

Ala Thr His Asp Leu Arg Pro Val Asp Val Gly Trp Ser Leu Ala Thr
            500                 505                 510

Arg Arg Ala Ser Tyr Asp Tyr Arg Ala Ala Val Leu Ala Ala Asp Glu
        515                 520                 525

Glu Gly Phe Ser Gln Gly Leu Ala Ala Leu Val Gln Gly Glu Ala Pro
    530                 535                 540

Val Thr Ala Ala Arg Pro Gly Ala Gly Ala Val Met Val Phe Pro Gly
545                 550                 555                 560

Gln Gly Ser Gln Trp Val Gly Met Ala Thr Glu Leu Met Ala Ser Ser
                565                 570                 575

Ala Val Phe Thr Glu Gln Met Ser Ala Cys Glu Glu Ala Leu Ala Pro
```

-continued

```
            580                 585                 590

Phe Val Asp Trp Ser Leu Ser Glu Ala Leu Gly Asp Glu Ala Leu Leu
        595                 600                 605

Glu Arg Val Asp Val Val Gln Pro Val Leu Trp Ala Val Met Val Ser
    610                 615                 620

Leu Ala Gly Leu Trp Arg His Tyr Gly Val Glu Pro Val Gly Val Val
625                 630                 635                 640

Gly His Ser Gln Gly Glu Ile Ala Ala Ala Ser Val Ala Gly Ala Leu
                645                 650                 655

Ser Leu Gln Asp Gly Ala Arg Val Val Ala Leu Arg Ser Lys Ala Leu
            660                 665                 670

Leu Ala Leu Ser Gly Gln Gly Gly Met Val Ser Val Ala Leu Pro Arg
        675                 680                 685

Glu Glu Thr Glu Arg Leu Ile Glu Arg Trp Gly Thr Arg Thr Gly Ile
    690                 695                 700

Ala Val Val Asn Gly Asn Ala Ala Thr Val Val Ser Gly Glu Val Asp
705                 710                 715                 720

Ala Leu Asp Glu Leu Met Ala Ser Cys Glu Ala Asp Gly Val Arg Ala
                725                 730                 735

Arg Arg Ile Gln Val Asp Tyr Ala Ser His Ser Ala Gln Val Glu Arg
            740                 745                 750

Ile Glu Arg Glu Leu Leu Asp Val Leu Ala Pro Ile Lys Pro Arg Ala
        755                 760                 765

Ala Arg Ile Pro Phe Tyr Ser Thr Val Thr Gly Gly Leu Leu Asp Thr
    770                 775                 780

Thr Ala Leu Asp Ala Gly Tyr Trp Tyr Arg Asn Leu Arg Gln Thr Val
785                 790                 795                 800

Glu Phe Asp Arg Thr Ile Arg Arg Leu Thr Glu Gln Gly Val Gly Val
                805                 810                 815

Phe Ile Glu Ala Ser Pro His Pro Val Leu Ala Pro Ser Met Glu Gln
            820                 825                 830

Thr Thr Ile Gly Thr Leu Arg Arg Asn Asp Gly Gly Leu Asp Arg Phe
        835                 840                 845

Leu Ser Val Leu Ala Gln Ala His Thr Arg Gly Val Asp Val Asp Trp
    850                 855                 860

Glu Lys Val Tyr Asp Ala Thr Gly Ala Gly Gln Thr Glu Leu Pro Thr
865                 870                 875                 880

Tyr Ala Phe Gln His Asn Arg Tyr Trp Leu Asn Asp Glu Thr Ala Asn
                885                 890                 895

Ala Asp Ala Ala Ser Met Gly Leu Gly Ser Leu Gly His Pro Leu Leu
            900                 905                 910

Gly Ala Met Val Met Leu Ala Gly Ser Glu Glu Val Val Leu Thr Gly
        915                 920                 925

Arg Leu Ser Thr Gly Thr Leu Pro Trp Leu Thr Asp His Val Ile Gly
    930                 935                 940

Gly Ser Ile Leu Phe Pro Gly Thr Gly Phe Val Glu Leu Val Ile Arg
945                 950                 955                 960

Ala Gly Asp Glu Val Gly Cys Gly Arg Val Glu Glu Leu Thr Ile Glu
                965                 970                 975

Ala Pro Leu Val Leu Ala Glu Arg Gly Gly Val Ala Val Gln Val Val
            980                 985                 990

Val Gly Ala Ala Asp Glu Glu Gly  Arg Arg Glu Val Gln  Val Tyr Ser
        995                 1000                1005
```

```
Arg Asp  Gln Asp Ala Thr Asp  Leu Pro Trp Asn Arg  His Ala Thr
    1010                 1015                 1020

Gly Leu  Leu Ala Thr Ala Thr  Ser Ala Gly Gly Gly  Glu Leu Ala
    1025                 1030                 1035

Glu Trp  Pro Pro Pro Gly Ala  Glu Pro Leu Asp Leu  Asp Val Asp
    1040                 1045                 1050

Thr Leu  Tyr Glu Glu Leu Val  Gly Thr Gly Leu Ala  Tyr Gly Pro
    1055                 1060                 1065

Thr Phe  Arg Gly Leu Arg Ala  Ala Trp Arg Ala Gly  Asp Glu Val
    1070                 1075                 1080

Phe Ala  Glu Ile Ala Leu Pro  Asp Asn Ala Val Ala  Asp Ala Phe
    1085                 1090                 1095

Gly Leu  His Pro Ala Leu Phe  Asp Ala Gly Leu His  Ala Ile Gly
    1100                 1105                 1110

Leu Ser  Pro Ala Gly Thr Gly  Asp Val Ala Met Leu  Pro Phe Ala
    1115                 1120                 1125

Trp Ser  Gly Val Glu Leu His  Ala Ser Gly Ala Gly  Ala Leu Arg
    1130                 1135                 1140

Val Arg  Val Thr Pro Val Gln  Asp Gly Val Ala Ala  Leu Thr Ile
    1145                 1150                 1155

Ala Asp  Ala Thr Gly Arg Pro  Val Ala Thr Val Asp  Ser Leu Val
    1160                 1165                 1170

Leu Arg  Pro Leu Thr Asp Met  Ala Thr Lys Ala Arg  Thr Glu Pro
    1175                 1180                 1185

Leu Tyr  His Val Ala Leu Ala  Pro Val Ala Ala Gly  Thr Ala Ser
    1190                 1195                 1200

Thr Gly  Gly Gln Pro Pro Asn  Asp Glu Glu Val Phe  Arg Leu Pro
    1205                 1210                 1215

Gly Gly  Leu Asp Val Arg Ala  Ala Val Asn Leu Ala  Leu Glu Ala
    1220                 1225                 1230

Leu Gln  Ser Ala Gly Ser Arg  Leu Val Val Val Thr  Arg Gly Ala
    1235                 1240                 1245

Val Ser  Val Asn Gly Gly Asp  Val Asp Asp Leu Ala  Ala Ala Ala
    1250                 1255                 1260

Val Trp  Gly Leu Val Arg Thr  Ala Gln Thr Glu Asp  Pro Gly Arg
    1265                 1270                 1275

Phe Phe  Leu Ile Asp Leu Asp  Gly Asp Thr Asp Glu  Ala Pro Ser
    1280                 1285                 1290

Ala Asp  Asn Ala Asp Leu Ala  Pro Ala Leu Ser Thr  Gly Glu Pro
    1295                 1300                 1305

Arg Val  Val Val Arg Asp Gly  Val Ala His Val Pro  Arg Leu Ala
    1310                 1315                 1320

Arg Val  Ser Ala Val Pro Glu  Thr Thr Asp Asp Leu  Ala Pro Ala
    1325                 1330                 1335

Phe Gly  Asp Glu Val Leu Ile  Thr Gly Gly Val Gly  Val Leu Gly
    1340                 1345                 1350

Ala Leu  Leu Ala Arg His Leu  Val Thr Glu Tyr Gly  Val Ser Arg
    1355                 1360                 1365

Leu Leu  Leu Thr Gly Arg Arg  Gly Val Asp Thr Pro  Gly Ala Ala
    1370                 1375                 1380

Glu Leu  Val Glu Glu Leu Ser  Gly Leu Gly Ala Glu  Val Glu Val
    1385                 1390                 1395
```

```
Ala Ala  Cys Asp Val Gly Asp  Arg Glu Ala Leu Ala  Ala Leu Leu
    1400                 1405                 1410

Ala Gly  Arg Ser Leu Thr Gly  Val Val His Ala Ala  Gly Val Leu
    1415                 1420                 1425

Asp Asp  Gly Val Ile Gly Ser  Leu Thr Pro Glu Arg  Val Asp Leu
    1430                 1435                 1440

Val Met  Arg Pro Lys Val Asp  Ala Ala Leu Tyr Leu  His Glu Leu
    1445                 1450                 1455

Thr Arg  Asp Met Asp Leu Thr  Ala Phe Val Leu Phe  Ser Ser Ala
    1460                 1465                 1470

Ala Gly  Val Ile Gly Ser Pro  Gly Gln Gly Asn Tyr  Ala Ala Ala
    1475                 1480                 1485

Asn Ala  Tyr Leu Asp Ala Leu  Ala Glu Arg Arg Arg  Ala Gly Gly
    1490                 1495                 1500

Leu Pro  Ala Gln Ser Leu Ala  Trp Gly Leu Trp Arg  Thr Ser Thr
    1505                 1510                 1515

Gly Met  Ala Ser Glu Leu Thr  Asp Thr Asp Arg Ser  Arg Met Glu
    1520                 1525                 1530

Arg Gly  Gly Ile Leu Ser Leu  Ser His Ser Glu Gly  Leu Ala Leu
    1535                 1540                 1545

Phe Asp  Ala Ala Thr Ala Ala  Asp Gly Pro Ala Val  Leu Val Pro
    1550                 1555                 1560

Val Lys  Leu Asp Leu Pro Ala  Val Arg Ala Gly Gly  Ala Val Pro
    1565                 1570                 1575

Glu Leu  Leu Arg Gly Leu Val  Pro Val Val Thr Arg  Gly Thr Ala
    1580                 1585                 1590

Arg Thr  Arg Ala Asp Ala Asp  Gly Leu Arg Glu Arg  Leu Val Gly
    1595                 1600                 1605

Met Ser  Asp Asp Gln Arg Phe  Asp Met Leu Leu Asn  Leu Val Arg
    1610                 1615                 1620

Ala Gln  Ala Ala Thr Thr Leu  Gly Tyr Ala Gly Pro  Gly Ala Val
    1625                 1630                 1635

Asp Pro  Glu Arg Ala Phe Arg  Asp Leu Gly Val Asp  Ser Leu Ala
    1640                 1645                 1650

Ala Met  Glu Leu Arg Asn Gly  Leu Gly Gly Ala Thr  Gly Leu Arg
    1655                 1660                 1665

Leu Pro  Ala Thr Leu Val Phe  Asp Tyr Pro Asn Pro  Thr Val Leu
    1670                 1675                 1680

Ala Arg  His Leu Leu Asp Glu  Val Ser Gly Thr Val  His Glu Gly
    1685                 1690                 1695

Arg Leu  Thr Pro Val Ala Ala  Pro Val Gly Asp Asp  Pro Ile Ala
    1700                 1705                 1710

Ile Val  Ala Met Ala Cys Arg  Tyr Pro Gly Gly Val  Ser Ser Pro
    1715                 1720                 1725

Glu Asp  Leu Trp Arg Leu Val  Asp Ser Gly Thr Asp  Ala Ile Ser
    1730                 1735                 1740

His Phe  Pro Thr Asp Arg Gly  Trp Asp Leu Glu Arg  Ile Tyr Asp
    1745                 1750                 1755

Pro Thr  Ala Thr Arg Pro Arg  Thr Ser Tyr Val Asp  Lys Gly Gly
    1760                 1765                 1770

Phe Leu  Tyr Asp Ala Ala Gln  Phe Asp Pro Gly Phe  Phe Gly Ile
    1775                 1780                 1785

Ala Pro  Asn Glu Ala Leu Val  Met Asp Pro Gln Gln  Arg Leu Leu
```

-continued

```
    1790                1795                1800

Leu Glu  Ala Ser Trp Glu Val  Leu Glu Arg Ala Gly  Ile Asp Pro
    1805                1810                1815

Thr Thr  Leu Lys Gly Ser Leu  Thr Gly Val Phe Ala  Gly Met Met
    1820                1825                1830

Tyr His  Asp Tyr Thr His Asn  Ser Ser Thr Gly Ala  Ile Ala Ser
    1835                1840                1845

Gly Arg  Val Ser Tyr Thr Leu  Gly Leu Glu Gly Pro  Ala Val Thr
    1850                1855                1860

Val Asp  Thr Ala Cys Ser Ser  Ser Leu Val Ala Leu  His Leu Ala
    1865                1870                1875

Ala Gln  Ala Leu Arg Ser Gly  Glu Cys Ser Leu Ala  Leu Ala Gly
    1880                1885                1890

Gly Val  Thr Val Met Ala Ala  Ala Asp Asn Phe Ile  Glu Phe Ser
    1895                1900                1905

Glu Gln  Arg Gly Leu Ala Thr  Asp Gly Arg Cys Lys  Ser Phe Ala
    1910                1915                1920

Ala Ala  Ala Asp Gly Ala Gly  Trp Ser Glu Gly Val  Gly Met Leu
    1925                1930                1935

Leu Val  Glu Arg Leu Ser Asp  Ala Arg Arg Asn Gly  His Pro Val
    1940                1945                1950

Leu Ala  Leu Val Arg Gly Thr  Ala Thr Asn Gln Asp  Gly Ala Ser
    1955                1960                1965

Asn Gly  Leu Thr Ala Pro Asn  Gly Pro Ser Gln Gln  Arg Val Ile
    1970                1975                1980

Lys Gln  Ala Leu Ala Asn Ala  Gly Leu Ala Gly Ala  Asp Val Asp
    1985                1990                1995

Ala Val  Glu Ala His Gly Thr  Gly Thr Thr Leu Gly  Asp Pro Ile
    2000                2005                2010

Glu Ala  Gln Ala Leu Leu Ala  Thr Tyr Gly Gln Gly  Arg Pro Glu
    2015                2020                2025

Asp Arg  Pro Leu Trp Leu Gly  Ser Ile Lys Ser Asn  Ile Gly His
    2030                2035                2040

Thr Gln  Ala Ala Ala Gly Val  Ala Gly Ile Ile Lys  Met Val Glu
    2045                2050                2055

Ala Met  Arg Gln Gly Thr Leu  Pro Arg Thr Leu His  Val Asp Ala
    2060                2065                2070

Pro Thr  Pro Gln Val Asp Trp  Glu Ala Gly Gln Val  Gln Leu Leu
    2075                2080                2085

Thr Glu  Thr Arg Glu Trp Pro  Asn Asp Gly Arg Pro  Arg Arg Ala
    2090                2095                2100

Gly Val  Ser Ser Phe Gly Ile  Ser Gly Thr Asn Ala  His Val Ile
    2105                2110                2115

Ile Glu  Glu Ala Val Pro Val  Glu Glu Ala Pro Val  Glu Arg Arg
    2120                2125                2130

Glu Leu  Pro Val Val Pro Leu  Val Leu Ser Ala Arg  Thr Arg Thr
    2135                2140                2145

Ala Leu  Gln Ala Gln Leu Asp  Arg Ile Thr Ser Val  Asp Ala Asp
    2150                2155                2160

Glu Leu  Asp Val Ala Tyr Ser  Ala Ala Thr Gly Arg  Ala Ala Leu
    2165                2170                2175

Glu His  Arg Ala Val Arg Ile  Gly Ser Glu Thr Val  Ile Asp Ser
    2180                2185                2190
```

Val Thr Glu Gly Gly Leu Ala Phe Leu Phe Thr Gly Gln Gly Ser
2195 2200 2205

Gln Trp Ala Gly Met Gly Gln Glu Leu Tyr Glu Thr Phe Pro Ala
2210 2215 2220

Phe Ala Thr Ala Phe Asp Glu Val Cys Ala Val Leu Asp Pro Ala
2225 2230 2235

Leu Arg Glu Val Met Trp Gly Asp Glu Glu Ala Leu Gly Arg Thr
2240 2245 2250

Glu Phe Thr Gln Pro Ala Ile Phe Ala Leu Gln Val Ala Leu Phe
2255 2260 2265

Arg Leu Val Glu Ser Trp Gly Ile Lys Pro Asp Leu Met Thr Gly
2270 2275 2280

His Ser Ile Gly Glu Leu Ala Ala Ala His Thr Ala Gly Val Phe
2285 2290 2295

Asp Leu Ala Asp Ala Ala Arg Leu Ile Thr Ala Arg Gly Arg Leu
2300 2305 2310

Ile Gln Glu Leu Pro Pro Gly Gly Ala Met Val Ala Ile Arg Ala
2315 2320 2325

Thr Glu Glu Glu Val Thr Pro His Leu Thr Glu Gln Val Ser Val
2330 2335 2340

Ala Ala Val Asn Thr Pro Gly Ser Val Val Ile Ser Gly Ala Glu
2345 2350 2355

Glu Ala Val Thr Ala Val Ala Glu Arg Phe Ala Asp Arg Lys Thr
2360 2365 2370

Thr Arg Leu Lys Val Ser His Ala Phe His Ser Pro Leu Met Asp
2375 2380 2385

Pro Met Leu Glu Glu Phe Arg Lys Val Ala Glu Ser Val Thr Tyr
2390 2395 2400

Arg Glu Pro Val Ile Gln Leu Thr Lys Asp Val Ala Ser Ala Glu
2405 2410 2415

Tyr Trp Val Arg His Val Arg Asp Ala Val Arg Phe Ala Asp Asp
2420 2425 2430

Val Arg His Leu Gln Asp Arg Gly Ile Thr Arg Phe Met Glu Val
2435 2440 2445

Gly Pro Asp Ser Val Leu Thr Ala Met Val Arg Gln Thr Ala Asp
2450 2455 2460

Gly Thr Val Ala Ala Thr Gln Arg Asn Asp Arg Pro Gly Val Glu
2465 2470 2475

Thr Leu Phe Thr Gly Val Gly Arg Leu Phe Ala Ala Gly Val Arg
2480 2485 2490

Val Asp Trp Asn Ala Val Phe Asp Gly Arg Gly Ala Arg Arg Val
2495 2500 2505

Glu Leu Pro Thr Tyr Pro Phe Gln Arg Gln Pro Phe Trp Ile Glu
2510 2515 2520

Ser Gly Arg Gly Ala Asp Ala Ser Asp His Pro Leu Leu Asp Gln
2525 2530 2535

Thr Val Ala Val Ala Gly Ala Asp Arg Thr Val Leu Thr Gly Arg
2540 2545 2550

Leu Ser Leu Gly Thr Gln Pro Trp Leu Ala Glu His Ala Val Ala
2555 2560 2565

Gly Thr Leu Leu Phe Pro Gly Thr Gly Phe Val Glu Leu Ala Val
2570 2575 2580

```
Arg Ala Gly Asp Glu Val Gly Cys Gly Arg Ile Glu Glu Leu Thr
    2585                2590                2595

Ile Glu Ala Pro Leu Val Leu Ala Glu His Thr Ala Thr Ala Val
    2600                2605                2610

Gln Val Val Val Gly Val Asp Asp Gly Ala Gly His Arg Ala Val
    2615                2620                2625

Glu Val Tyr Ala Arg Gly Ala Asp Asp Pro His Leu Pro Trp Thr
    2630                2635                2640

Arg His Ala Ala Gly Thr Leu Ala Pro Ala Thr Gly Gly Pro Ala
    2645                2650                2655

Ala Glu Ala Met Thr Gln Trp Pro Pro Pro Gly Ala Glu Pro Val
    2660                2665                2670

Glu Leu Ala Gly Leu Tyr Glu Ser Leu Ala Glu Ala Gly Val Glu
    2675                2680                2685

Tyr Gly Pro Ala Phe Gln Gly Leu Lys Ser Ala Trp Arg Glu Glu
    2690                2695                2700

Gly Thr Val Tyr Ala Asp Val Val Leu Ser Gly Ala Ala Asp Arg
    2705                2710                2715

Phe Gly Ile His Pro Ala Leu Leu Asp Ala Ala Leu His Thr Val
    2720                2725                2730

Pro Leu Leu Ser Gly Asp Asp Arg Val Val Leu Pro Phe Ser Trp
    2735                2740                2745

Ala Gly Val Glu Leu His Ala Ser Gly Ala Thr Ala Leu Arg Val
    2750                2755                2760

Arg Met Thr Leu Arg Gly Gln Asp Arg Val Ala Leu His Ala Val
    2765                2770                2775

Asp Gly Ala Gly Gln Pro Val Val Ser Val Asp Ala Leu Thr Leu
    2780                2785                2790

Arg Pro Met Ala Ala Gly Ala Leu Thr Arg Val Asp Ser Leu Phe
    2795                2800                2805

Gln Val Glu Trp Thr Pro Val Ala Val Arg Asp Asp Ala Ala Gly
    2810                2815                2820

Asp Ala Lys Val Trp Arg Thr Glu Gly Asp Asp Val Leu Ser Thr
    2825                2830                2835

Leu His Pro Leu Leu Lys Ala Ile Gln Ala Glu Thr Glu Thr Leu
    2840                2845                2850

Ala Val Val Thr Arg Gly Ala Val Ser Val Ala Gly Glu Arg Val
    2855                2860                2865

Ser Asp Leu Ala Gly Ala Ser Ala Trp Gly Leu Val Arg Ser Ala
    2870                2875                2880

Gln Ser Glu Asp Pro Gly Arg Phe Val Leu Val Asp Val Ala Gly
    2885                2890                2895

Glu Asp Glu Lys Ala Asp Ile Ala Leu Ala Leu Ala Ala Gly Glu
    2900                2905                2910

Pro Gln Val Ala Val Arg Asp Gly Lys Val Tyr Val Pro Arg Leu
    2915                2920                2925

Arg Ala Ala Ser Val Ala Glu Ser Glu Pro Ser Ser Val Phe Gly
    2930                2935                2940

Asp Glu Val Leu Ile Thr Gly Ala Ser Gly Ala Leu Gly Gly Leu
    2945                2950                2955

Val Ala Arg His Leu Val Thr Gly His Gly Val Arg Arg Leu Leu
    2960                2965                2970

Leu Thr Ser Arg Arg Gly Leu Ala Ala Pro Gly Ala Ala Glu Leu
```

```
    2975                2980                2985

Val Glu  Glu Leu Ala Gly Leu  Gly Ala Glu Val Glu  Val Ala Ala
    2990                2995                3000

Cys Asp  Val Gly Asp Arg Glu  Ala Leu Ala Ala Leu  Leu Ala Gly
    3005                3010                3015

Arg Ser  Leu Thr Gly Val Val  His Ala Ala Gly Val  Leu Asp Asp
    3020                3025                3030

Gly Val  Ile Ala Ser Leu Thr  Pro Glu Arg Leu Asp  Lys Val Val
    3035                3040                3045

Thr Pro  Lys Ala Val Ala Ala  Leu His Leu His Glu  Leu Thr Arg
    3050                3055                3060

Asp Met  Asp Leu Thr Ala Phe  Val Leu Phe Ser Ser  Val Ala Gly
    3065                3070                3075

Val Ile  Gly Thr Pro Gly Gln  Gly Asn Tyr Ala Ala  Ala Asn Ala
    3080                3085                3090

Leu Leu  Asp Ala Leu Ala Ala  His Arg Arg Ala Asp  Gly Leu Pro
    3095                3100                3105

Ala Gln  Ser Leu Ala Trp Gly  Leu Trp Thr Thr Asp  Ala Gly Met
    3110                3115                3120

Ala Gly  Asp Leu Ala Asp Thr  Asp Arg Gln Arg Ile  Asp Arg Ala
    3125                3130                3135

Gly Leu  Val Gly Leu Ser Pro  Glu Gln Gly Leu Glu  Leu Leu Asp
    3140                3145                3150

Val Ala  Gly Ala Leu Ala Thr  Pro Ala Leu Val Pro  Met Asn Leu
    3155                3160                3165

Asp Thr  Arg Thr Leu Asn Ala  Ala Asp Val Pro Leu  Met Leu Arg
    3170                3175                3180

Gly Leu  Val Arg Gly Ser Ser  Arg Arg Ala Val Ser  Ala Gln Ser
    3185                3190                3195

Thr Gly  Gly Gly Ala Ala Leu  Arg Lys Arg Leu Ala  Ala Leu Pro
    3200                3205                3210

Ala Asp  Asp Arg Tyr Asp Glu  Val Leu Asp Leu Val  Arg Thr His
    3215                3220                3225

Ala Ala  Ala Val Leu Gly His  Ala Gly Pro Glu Ala  Val Glu Pro
    3230                3235                3240

Glu Arg  Ala Phe Gly Asp Leu  Gly Phe Asp Ser Leu  Gly Ala Val
    3245                3250                3255

Glu Phe  Arg Asn Thr Leu Asn  Ala Ala Ala Gly Leu  Arg Leu Ser
    3260                3265                3270

Ala Thr  Met Ile Phe Asp His  Pro Thr Ala Arg Val  Leu Ala Glu
    3275                3280                3285

His Ile  Gly Ala Glu Leu Ala  Pro Asp Gly Asp Ala  Gly Ala Ala
    3290                3295                3300

Ala Asp  Glu Glu Thr Val Arg  Arg Leu Leu Gly Ser  Ile Pro Leu
    3305                3310                3315

Thr Arg  Leu His Asp Ala Gly  Leu Met Glu Ala Leu  Leu Glu Leu
    3320                3325                3330

Ala Gly  Ser Gly Ala Ala Ser  Gly Met Ala Ala Ala  Val Pro Glu
    3335                3340                3345

Glu Asp  Ser Ile Asp Ala Met  Asp Ala Glu Ala Leu  Ile Ser Met
    3350                3355                3360

Ala Leu  Gln Asp Thr Asp Pro  Asp Glu Ala Thr Arg  Glu Val
    3365                3370                3375
```

<210> SEQ ID NO 36
<211> LENGTH: 4896
<212> TYPE: DNA
<213> ORGANISM: Streptomyces sp. MP28-13

<400> SEQUENCE: 36
gtgagcgacc aggagaagct tcttgactac ctcaagcgcg cgaccacgga tctgcgcaca 60
gcgcgcagac gcgtcgccga gcttgagcag cgtgaccagg agccgatcgc cattgtctcg 120
atggcgtgcc gctacccggg cggtgtgaac tcgcccgagg acttgtggcg gctcgtcgac 180
gagggcgtcg acgcgatctc cgagttcccg gcagaccgcg gctggggagt ggaggacatc 240
tacgaccccg aggtcggcaa gcccggaaag acaacgtccc gcgagggcgg attcctgcac 300
gacgcagcgg agttcgacgc cgagttcttc ggtatcagtc cgcgcgaggc cctggagacc 360
gacccgcagc agcggctgct gctggaggcg tcctgggagg tgctggagcg cgccgggatc 420
gaccccgcct cgctgaaggg cagcccgacc ggtgtgttcg ccggggtgat gtaccacgac 480
tacgccggcg gcagcagcgg cggcagcatc gtctccgggc gcgtcgccta cacgttgggc 540
ctggtgggtc ccgcggtcac catggacacc gcgtgctcgt cctcgctggt cgcgctgcac 600
acggcgatcc agtcgctgcg ttccggtgag tgctcgctcg ctctcgcggg tggtgtgacg 660
gtgatgtcca cgcccgagat gttcctctac ttcagcgagc agcgcggcct gtcgatcgac 720
ggccgctgca agtcgttcag cgacgccgcc aacggcatga gctgctccga aggtgtcgga 780
gtactccttc tggagcggct gtcggacgcg cgtcgcctgg ggcatccggt gctggcggtg 840
gtgcgcggga gcgcgctgaa ccaggacggg gccagcaacg gtctgaccgc cccaacggc 900 ccggcgcagc gccgggtgat caagcaggcg ctggcgaagg cgggtctgtc gacggcggat 960
gtggacgcgg tcgaggcaca cggcacgggt acgacgctgg gtgacccgat cgaggcgcag 1020
gcgctgctgg agacgtacgg tcagggccgt ccggaggggc ggccgttgtg gctgggttcg 1080
atcaagtcga acatcggtca tacgcaggcg gcggcgggtg tggcggggat catcaagatg 1140
gtcgaggcga tgcgccacgg caggctgccc aagacgctgc atgtggatga gccgacgaag 1200
caggtggact gggacgcggg tgaggtgcgg ctgctgacgg aggcgcgtga gtggccgagc 1260
gaaggccgtc cgcgccgcgc gggagtgtcg tcgttcgggc tcagcggaac caacgcccac 1320
gtcatcgtcg aagaggccgt ccccgtcgag gaagtggtgg tggagcggcg ggagttgccg 1380
gtggcgccgg tggtggtgtc ggggaagacc ccggcggcgc tggaggcgca gatcggccgc 1440
ttcggcgaac tggccgcgaa cgggaacgcg ctcgacgtgg cgtactcggc cgcgacaggg 1500
cgcgctgttc tggagcaccg ggcggtgctg gtgggccccg agaccgtgac cggctcggtc 1560
gccgagggca aggtggcgtt cctgttcacc gggcagggga gtcaacgcct gggtatggga 1620
cgggagttgt acgagacgtt ccccgccttc gcgtcggcgt tcgacgaggt gtgtgcggtg 1680
ctcgaccccg ctgtgcgtga ggtgatgtgg ggcgacgaag aagtactgag ccgtacggag 1740
ttcacccagc ctgcgatctt cgctcttgag gtggcgttgt tccggttggt ggagtcgtgg 1800
ggggtcaagc cggacttcct ggtggggcat tcgatcggtg agctggcggc ggcgcatgtg 1860
gcgggggtgt tcggtctgga ggatgcgggc cggttgatct cggcgcgtgg gcggttgatg 1920
caggcgttgc cggcgggtgg ggcgatggtc gcgatccagg ccaccgaaga agaagtactc 1980
ccgctgctca cggacgaggt gagtgtcgcg gcggtcaaca gcccgtcctc ggtggtgatt 2040
tcgggcgagg agaaggcggt gacggcggtc gcggagcggt tcaccgaccg caagcgcaac 2100

-continued

```
cgtctgacgg tctcgcacgc cttccactca ccgctgatgg acccgatgct ggacgacttc   2160
cgcgagatcg ccgagagcgt cacgtacagc gaaccggcca tccggctgac caaggacgtc   2220
ggttcggcgg agtactgggt cgggcacgta cgcgacgcgg tgcggttcgc cgatgatgtc   2280
cggcatttgc aggacgaggg tgtgacgcgg ttcctggaga tcggtccgga tggtgtgctg   2340
acggcgatgg cgggacagag tgccgacggc accctggcgc ccacgctgcg acgcgaccgc   2400
cccgaggtgg agagtgtgtt cgccggggtg ggccggttgt tcgcggccgg tgttccggtc   2460
gactgggacg cggtgttcga cgggcgtggt gcgcggcggg tggatctgcc cacgtacgcc   2520
ttccagcgca agcgttactg gctgatcgag cagtccaagt ccacggccgg cgcggacgcc   2580
gtcgaccacc ccctgctgac ctccggcatg gtgctcccgg acaccggcgg tgtggtgttc   2640
accggacgtc tctccctcga cacccacccc tggctcgccg accacgacgc cttcggcgcc   2700
gtggtcgtgc ccggggaagt gttcctggaa ctcgccctga cggcagcgga gcagacgggt   2760
cgcgggcgcg tcgaagcgct cgacctccac gcgccgctgg tcatggccgg caccgaggac   2820
gacacgacac tgcgcgcgat ggtcgacgag gccggggcgt tcagcgtgta cgcgcgccgt   2880
ggcgaccgga cggcggcctg ggtcaagcac gccaccggcg tcctgacctc cgaggccacc   2940
gagtcctcgt ggacacgtga cgacgagacg tacgccacgg tgctcgaagc cgccgcgcac   3000
accgccggac tccaccccga cggcgagccg acgctcgccc atgtgtggcg cggcgcctcg   3060
gtgagcgtcg gccaggacgg acagcccgtt ctgtcggtgg cctcggtcga gacccgctcg   3120
atcaccacgg acgaggtacg ggcacacacc ggcggccgtg aatcgctgtt ccacgtcgac   3180
tgggtcgcag cccccgcacc cgtcggctcc gagaccggtg ctcatgtcgt ctacgagtgc   3240
ccgccactgg acgagcccgc gcccgaaggc ttccggacga tcacccatca ggtgctcccc   3300
gtcatccagc ggtggctgga cgacgagcag gcggcatccg ccaagctcgt cgtcgtcacg   3360
cgcggcgcga ccgacggaag cgacctcggg cacgcggcgg tctggggcct ggtgcgttcg   3420
gcggagtcgg agcacccggg ccggttcgtc ctggtggacc tggacgccga agccgaactc   3480
cccgacgagg tgctgcgcct cgccgagccc gagatcgccg tacgggacgg cgagatccgg   3540
gtggcgaggc tggcccgcgt ccccgcggtc gaaggccgcg tccagtcgtg gggcacgcac   3600
ggcacgatcc tgatcaccgg tggcctgaac gggctcggcg ccctggccgc ccggcacctg   3660
gccgcggagc acggcgcgaa gagcctgctg ctgaccagcc gccggggcat ggacacgccg   3720
ggcgcggccg aactggtggc ggagctgacc ggatcgggcg ccgaggtgga ggtcgtcgtc   3780
tgcgacgtca ccgaccggga cgcgctggcc gccctgctgg ccgagcggcc cctgacgggc   3840
ctcgtgcact cggccggtgt gctggacgac ggactcatgg gagcgttgac gcccgagcgg   3900
ctggacacgg tcatgaggcc gaaggtcgac gccgcctggc atctgcacga actcaccctg   3960
gaccacgatc tctcgtcgtt cgtgatcttc tcctccgtcg ccggcacgct cggcggcgcg   4020
ggacagggca actacgccgc cgcgaacgcc tggctggacg cgctcgccag gcatcgcgcg   4080
accaagggc tgcccgcgct gaccctcggc tggggaccct ggaccgaggt cgggggcatg   4140
gccgaccgtc tggacgacgc cgagctggcg cggctcaggc gctcgggaat gccgccgctg   4200
tccccggacg aggggctggc gctgatggat gccgcgaccc tgcgcggccg gccgccgatg   4260
acgctgccgg tccggttcga cctggcggtg atgcggtccc tcgccgagac ggggacactg   4320
cccgcgatat tcggcggact ggtacgcggc cagaaccgtc gcgcgccggc aggccgggcg   4380
tcgtgggagc ggctgtccgg actgaccgtg ccggaacgcg agaagttcct cctggagttg   4440
gtacggggcc acgtcgccca ggtgctcgga cacggcggcg ccgacgaggt gcccccggac   4500
```

```
cgcgctttca acgaactcgg cctcacctcg ctgggcgcgg tggaactgcg caacgccctc   4560

aacaccgaga cagggctgtc actgcccccg accctggcct tcgactaccc gacccccctg   4620

gccatcgccg agctcgtgca cgacgggctg cgcccggagg aggccgacgg ggcggccgcg   4680

ctgctggccg aactgaaccg gctggaagcc gtgctgaccg agctggcatc gggcgaccgc   4740

gaagcccacg ccaaggtcac ggcccgcctc gaaaccatgt cgcgacgggc gcgagacgcc   4800

gggagcggcg tgacggacga gcccgtcggc ggcctcgtga ccgaatccga tgacgagttg   4860

ttcgcggtgc tgaacaagga actcggactg tcctga                             4896


<210> SEQ ID NO 37
<211> LENGTH: 1631
<212> TYPE: PRT
<213> ORGANISM: Streptomyces sp. MP28-13

<400> SEQUENCE: 37

Met Ser Asp Gln Glu Lys Leu Leu Asp Tyr Leu Lys Arg Ala Thr Thr
1               5                   10                  15

Asp Leu Arg Thr Ala Arg Arg Arg Val Ala Glu Leu Glu Gln Arg Asp
            20                  25                  30

Gln Glu Pro Ile Ala Ile Val Ser Met Ala Cys Arg Tyr Pro Gly Gly
        35                  40                  45

Val Asn Ser Pro Glu Asp Leu Trp Arg Leu Val Asp Glu Gly Val Asp
    50                  55                  60

Ala Ile Ser Glu Phe Pro Ala Asp Arg Gly Trp Gly Val Glu Asp Ile
65                  70                  75                  80

Tyr Asp Pro Glu Val Gly Lys Pro Gly Lys Thr Thr Ser Arg Glu Gly
                85                  90                  95

Gly Phe Leu His Asp Ala Ala Glu Phe Asp Ala Glu Phe Phe Gly Ile
            100                 105                 110

Ser Pro Arg Glu Ala Leu Glu Thr Asp Pro Gln Gln Arg Leu Leu Leu
        115                 120                 125

Glu Ala Ser Trp Glu Val Leu Glu Arg Ala Gly Ile Asp Pro Ala Ser
    130                 135                 140

Leu Lys Gly Ser Pro Thr Gly Val Phe Ala Gly Val Met Tyr His Asp
145                 150                 155                 160

Tyr Ala Gly Gly Ser Ser Gly Gly Ser Ile Val Ser Gly Arg Val Ala
                165                 170                 175

Tyr Thr Leu Gly Leu Val Gly Pro Ala Val Thr Met Asp Thr Ala Cys
            180                 185                 190

Ser Ser Ser Leu Val Ala Leu His Thr Ala Ile Gln Ser Leu Arg Ser
        195                 200                 205

Gly Glu Cys Ser Leu Ala Leu Ala Gly Gly Val Thr Val Met Ser Thr
    210                 215                 220

Pro Glu Met Phe Leu Tyr Phe Ser Glu Gln Arg Gly Leu Ser Ile Asp
225                 230                 235                 240

Gly Arg Cys Lys Ser Phe Ser Asp Ala Ala Asn Gly Met Ser Cys Ser
                245                 250                 255

Glu Gly Val Gly Val Leu Leu Leu Glu Arg Leu Ser Asp Ala Arg Arg
            260                 265                 270

Leu Gly His Pro Val Leu Ala Val Val Arg Gly Ser Ala Leu Asn Gln
        275                 280                 285

Asp Gly Ala Ser Asn Gly Leu Thr Ala Pro Asn Gly Pro Ala Gln Arg
    290                 295                 300
```

```
Arg Val Ile Lys Gln Ala Leu Ala Lys Ala Gly Leu Ser Thr Ala Asp
305                 310                 315                 320

Val Asp Ala Val Glu Ala His Gly Thr Gly Thr Thr Leu Gly Asp Pro
                325                 330                 335

Ile Glu Ala Gln Ala Leu Leu Glu Thr Tyr Gly Gln Gly Arg Pro Glu
            340                 345                 350

Gly Arg Pro Leu Trp Leu Gly Ser Ile Lys Ser Asn Ile Gly His Thr
        355                 360                 365

Gln Ala Ala Ala Gly Val Ala Gly Ile Ile Lys Met Val Glu Ala Met
    370                 375                 380

Arg His Gly Arg Leu Pro Lys Thr Leu His Val Asp Glu Pro Thr Lys
385                 390                 395                 400

Gln Val Asp Trp Asp Ala Gly Glu Val Arg Leu Leu Thr Glu Ala Arg
                405                 410                 415

Glu Trp Pro Ser Glu Gly Arg Pro Arg Arg Ala Gly Val Ser Ser Phe
            420                 425                 430

Gly Leu Ser Gly Thr Asn Ala His Val Ile Val Glu Glu Ala Val Pro
        435                 440                 445

Val Glu Glu Val Val Val Glu Arg Arg Glu Leu Pro Val Ala Pro Val
    450                 455                 460

Val Val Ser Gly Lys Thr Pro Ala Ala Leu Glu Ala Gln Ile Gly Arg
465                 470                 475                 480

Phe Gly Glu Leu Ala Ala Asn Gly Asn Ala Leu Asp Val Ala Tyr Ser
                485                 490                 495

Ala Ala Thr Gly Arg Ala Val Leu Glu His Arg Ala Val Leu Val Gly
            500                 505                 510

Pro Glu Thr Val Thr Gly Ser Val Ala Glu Gly Lys Val Ala Phe Leu
        515                 520                 525

Phe Thr Gly Gln Gly Ser Gln Arg Leu Gly Met Gly Arg Glu Leu Tyr
    530                 535                 540

Glu Thr Phe Pro Ala Phe Ala Ser Ala Phe Asp Glu Val Cys Ala Val
545                 550                 555                 560

Leu Asp Pro Ala Val Arg Glu Val Met Trp Gly Asp Glu Glu Val Leu
                565                 570                 575

Ser Arg Thr Glu Phe Thr Gln Pro Ala Ile Phe Ala Leu Glu Val Ala
            580                 585                 590

Leu Phe Arg Leu Val Glu Ser Trp Gly Val Lys Pro Asp Phe Leu Val
        595                 600                 605

Gly His Ser Ile Gly Glu Leu Ala Ala Ala His Val Ala Gly Val Phe
    610                 615                 620

Gly Leu Glu Asp Ala Gly Arg Leu Ile Ser Ala Arg Gly Arg Leu Met
625                 630                 635                 640

Gln Ala Leu Pro Ala Gly Gly Ala Met Val Ala Ile Gln Ala Thr Glu
                645                 650                 655

Glu Glu Val Leu Pro Leu Leu Thr Asp Glu Val Ser Val Ala Ala Val
            660                 665                 670

Asn Ser Pro Ser Ser Val Val Ile Ser Gly Glu Glu Lys Ala Val Thr
        675                 680                 685

Ala Val Ala Glu Arg Phe Thr Asp Arg Lys Arg Asn Arg Leu Thr Val
    690                 695                 700

Ser His Ala Phe His Ser Pro Leu Met Asp Pro Met Leu Asp Asp Phe
705                 710                 715                 720
```

```
Arg Glu Ile Ala Glu Ser Val Thr Tyr Ser Glu Pro Ala Ile Arg Leu
                725                 730                 735

Thr Lys Asp Val Gly Ser Ala Glu Tyr Trp Val Gly His Val Arg Asp
            740                 745                 750

Ala Val Arg Phe Ala Asp Asp Val Arg His Leu Gln Asp Glu Gly Val
        755                 760                 765

Thr Arg Phe Leu Glu Ile Gly Pro Asp Gly Val Leu Thr Ala Met Ala
    770                 775                 780

Gly Gln Ser Ala Asp Gly Thr Leu Ala Pro Thr Leu Arg Arg Asp Arg
785                 790                 795                 800

Pro Glu Val Glu Ser Val Phe Ala Gly Val Gly Arg Leu Phe Ala Ala
                805                 810                 815

Gly Val Pro Val Asp Trp Asp Ala Val Phe Asp Gly Arg Gly Ala Arg
            820                 825                 830

Arg Val Asp Leu Pro Thr Tyr Ala Phe Gln Arg Lys Arg Tyr Trp Leu
        835                 840                 845

Ile Glu Gln Ser Lys Ser Thr Ala Gly Ala Asp Ala Val Asp His Pro
    850                 855                 860

Leu Leu Thr Ser Gly Met Val Leu Pro Asp Thr Gly Gly Val Val Phe
865                 870                 875                 880

Thr Gly Arg Leu Ser Leu Asp Thr His Pro Trp Leu Ala Asp His Asp
                885                 890                 895

Ala Phe Gly Ala Val Val Val Pro Gly Glu Val Phe Leu Glu Leu Ala
            900                 905                 910

Leu Thr Ala Ala Glu Gln Thr Gly Arg Gly Arg Val Glu Ala Leu Asp
        915                 920                 925

Leu His Ala Pro Leu Val Met Ala Gly Thr Glu Asp Asp Thr Thr Leu
    930                 935                 940

Arg Ala Met Val Asp Glu Ala Gly Ala Phe Ser Val Tyr Ala Arg Arg
945                 950                 955                 960

Gly Asp Arg Thr Ala Ala Trp Val Lys His Ala Thr Gly Val Leu Thr
                965                 970                 975

Ser Glu Ala Thr Glu Ser Ser Trp Thr Arg Asp Asp Glu Thr Tyr Ala
            980                 985                 990

Thr Val Leu Glu Ala Ala Ala His  Thr Ala Gly Leu His  Pro Asp Gly
        995                 1000                1005

Glu Pro  Thr Leu Ala His Val  Trp Arg Gly Ala Ser  Val Ser Val
    1010                1015                1020

Gly Gln  Asp Gly Gln Pro Val  Leu Ser Val Ala Ser  Val Glu Thr
    1025                1030                1035

Arg Ser  Ile Thr Thr Asp Glu  Val Arg Ala His Thr  Gly Gly Arg
    1040                1045                1050

Glu Ser  Leu Phe His Val Asp  Trp Val Ala Ala Pro  Ala Pro Val
    1055                1060                1065

Gly Ser  Glu Thr Gly Ala His  Val Val Tyr Glu Cys  Pro Pro Leu
    1070                1075                1080

Asp Glu  Pro Ala Pro Glu Gly  Phe Arg Thr Ile Thr  His Gln Val
    1085                1090                1095

Leu Pro  Val Ile Gln Arg Trp  Leu Asp Asp Glu Gln  Ala Ala Ser
    1100                1105                1110

Ala Lys  Leu Val Val Val Thr  Arg Gly Ala Thr Asp  Gly Ser Asp
    1115                1120                1125

Leu Gly  His Ala Ala Val Trp  Gly Leu Val Arg Ser  Ala Glu Ser
```

```
    1130                1135                1140

Glu His  Pro Gly Arg Phe Val  Leu Val Asp Leu Asp  Ala Glu Ala
    1145                1150                1155

Glu Leu  Pro Asp Glu Val Leu  Arg Leu Ala Glu Pro  Glu Ile Ala
    1160                1165                1170

Val Arg  Asp Gly Glu Ile Arg  Val Ala Arg Leu Ala  Arg Val Pro
    1175                1180                1185

Ala Val  Glu Gly Arg Val Gln  Ser Trp Gly Thr His  Gly Thr Ile
    1190                1195                1200

Leu Ile  Thr Gly Gly Leu Asn  Gly Leu Gly Ala Leu  Ala Ala Arg
    1205                1210                1215

His Leu  Ala Ala Glu His Gly  Ala Lys Ser Leu Leu  Leu Thr Ser
    1220                1225                1230

Arg Arg  Gly Met Asp Thr Pro  Gly Ala Ala Glu Leu  Val Ala Glu
    1235                1240                1245

Leu Thr  Gly Ser Gly Ala Glu  Val Glu Val Val Val  Cys Asp Val
    1250                1255                1260

Thr Asp  Arg Asp Ala Leu Ala  Ala Leu Leu Ala Glu  Arg Pro Leu
    1265                1270                1275

Thr Gly  Leu Val His Ser Ala  Gly Val Leu Asp Asp  Gly Leu Met
    1280                1285                1290

Gly Ala  Leu Thr Pro Glu Arg  Leu Asp Thr Val Met  Arg Pro Lys
    1295                1300                1305

Val Asp  Ala Ala Trp His Leu  His Glu Leu Thr Leu  Asp His Asp
    1310                1315                1320

Leu Ser  Ser Phe Val Ile Phe  Ser Ser Val Ala Gly  Thr Leu Gly
    1325                1330                1335

Gly Ala  Gly Gln Gly Asn Tyr  Ala Ala Ala Asn Ala  Trp Leu Asp
    1340                1345                1350

Ala Leu  Ala Arg His Arg Ala  Thr Lys Gly Leu Pro  Ala Leu Thr
    1355                1360                1365

Leu Gly  Trp Gly Pro Trp Thr  Glu Val Gly Gly Met  Ala Asp Arg
    1370                1375                1380

Leu Asp  Asp Ala Glu Leu Ala  Arg Leu Arg Arg Ser  Gly Met Pro
    1385                1390                1395

Pro Leu  Ser Pro Asp Glu Gly  Leu Ala Leu Met Asp  Ala Ala Thr
    1400                1405                1410

Leu Arg  Gly Arg Pro Pro Met  Thr Leu Pro Val Arg  Phe Asp Leu
    1415                1420                1425

Ala Val  Met Arg Ser Leu Ala  Glu Thr Gly Thr Leu  Pro Ala Ile
    1430                1435                1440

Phe Gly  Gly Leu Val Arg Gly  Gln Asn Arg Arg Ala  Pro Ala Gly
    1445                1450                1455

Arg Ala  Ser Trp Glu Arg Leu  Ser Gly Leu Thr Val  Pro Glu Arg
    1460                1465                1470

Glu Lys  Phe Leu Leu Glu Leu  Val Arg Gly His Val  Ala Gln Val
    1475                1480                1485

Leu Gly  His Gly Gly Ala Asp  Glu Val Pro Pro Asp  Arg Ala Phe
    1490                1495                1500

Asn Glu  Leu Gly Leu Thr Ser  Leu Gly Ala Val Glu  Leu Arg Asn
    1505                1510                1515

Ala Leu  Asn Thr Glu Thr Gly  Leu Ser Leu Pro Pro  Thr Leu Ala
    1520                1525                1530
```

```
Phe Asp  Tyr Pro Thr Pro Leu  Ala Ile Ala Glu Leu  Val His Asp
    1535                 1540                 1545

Gly Leu  Arg Pro Glu Glu Ala  Asp Gly Ala Ala Ala  Leu Leu Ala
    1550                 1555                 1560

Glu Leu  Asn Arg Leu Glu Ala  Val Leu Thr Glu Leu  Ala Ser Gly
    1565                 1570                 1575

Asp Arg  Glu Ala His Ala Lys  Val Thr Ala Arg Leu  Glu Thr Met
    1580                 1585                 1590

Ser Arg  Arg Ala Arg Asp Ala  Gly Ser Gly Val Thr  Asp Glu Pro
    1595                 1600                 1605

Val Gly  Gly Leu Val Thr Glu  Ser Asp Asp Glu Leu  Phe Ala Val
    1610                 1615                 1620

Leu Asn  Lys Glu Leu Gly Leu  Ser
    1625                 1630


<210> SEQ ID NO 38
<211> LENGTH: 288
<212> TYPE: DNA
<213> ORGANISM: Streptomyces sp. MP28-13

<400> SEQUENCE: 38

atgcaccctg actacgtggc cggcccgcga acacgggaac ccgtcgccgt cacacctgcc      60

gagcacctcg tgcgcgtcgt caggggcgct ccgggagaga tggaactggc ggcgctgctc     120

gcggtgttga gcgccctgac cggtacccgg gagcaggccg tcgcgtcctc cgcggcccga     180

cagcggcgca actccgcctg ggcgcggtc cgttacgcct cacccggtgc ctggtacaca      240

ccgccgggcg cctggacggg cggccaggac agagagtggc ggcactga                  288


<210> SEQ ID NO 39
<211> LENGTH: 95
<212> TYPE: PRT
<213> ORGANISM: Streptomyces sp. MP28-13

<400> SEQUENCE: 39

Met His Pro Asp Tyr Val Ala Gly Pro Arg Thr Arg Glu Pro Val Ala
1               5                   10                  15

Val Thr Pro Ala Glu His Leu Val Arg Val Val Arg Gly Ala Pro Gly
            20                  25                  30

Glu Met Glu Leu Ala Ala Leu Leu Ala Val Leu Ser Ala Leu Thr Gly
        35                  40                  45

Thr Arg Glu Gln Ala Val Ala Ser Ser Ala Ala Arg Gln Arg Arg Asn
    50                  55                  60

Ser Ala Trp Gly Ala Val Arg Tyr Ala Ser Pro Gly Ala Trp Tyr Thr
65                  70                  75                  80

Pro Pro Gly Ala Trp Thr Gly Gly Gln Asp Arg Glu Trp Arg His
                85                  90                  95


<210> SEQ ID NO 40
<211> LENGTH: 774
<212> TYPE: DNA
<213> ORGANISM: Streptomyces sp. MP28-13

<400> SEQUENCE: 40

atgaccgcca tatcgagcga caacgcgtcc aattggattc gagaatttca tccggcggac      60

cggacatccc cgaggatgat ctgcttcccc cacgcgggcg gtgcggcgag ctactacttc     120

cccgtctccc gggcgctggc cgggaagatc gaagtcctcg ccatccagta cccggggcgc     180
```

```
caggaccgtt acacggaacc ggccatcggc aacgtcgagg ccctcgccgc cgcggtcttc    240

cgtgagcttc cgacggagga cctggaccgg acctggctct tcgggcacag catgggggcc    300

gccgtcgcct tcgaggtggc ccggctgatg gaacgggagt tgaaccagtc gcctgtcggg    360

atcatcctct ccggccggcg cgcaccgtcc cggttccgtc ccgagaccct ccacctgcag    420

ggcgacgcgg cgatcatcgc caacgtgcag tcgctcagcg gtaccgacgc gatcctcttc    480

gaggaccccg acacccagcg gctgatcatg ccggcgctgc gagccgacta ccgggccatc    540

gagacctacc ggccgcccgg cactccacgc gtcgcgtgcc cgatccacac cttcgtgggc    600

gacgccgacc cgttggccac gctggacgag gtcggcagct ggcgcgacca cacctcggcc    660

gagtacaccc tgcgcgtttt cccgggtgac cacttctatc tgacggcgcg tgccgtcgag    720

gtcatctccg cgatctccca gctgatcgtg gagcccaccc agacccgcgg ctga          774


<210> SEQ ID NO 41
<211> LENGTH: 257
<212> TYPE: PRT
<213> ORGANISM: Streptomyces sp. MP28-13

<400> SEQUENCE: 41

Met Thr Ala Ile Ser Ser Asp Asn Ala Ser Asn Trp Ile Arg Glu Phe
1               5                   10                  15

His Pro Ala Asp Arg Thr Ser Pro Arg Met Ile Cys Phe Pro His Ala
            20                  25                  30

Gly Gly Ala Ala Ser Tyr Tyr Phe Pro Val Ser Arg Ala Leu Ala Gly
        35                  40                  45

Lys Ile Glu Val Leu Ala Ile Gln Tyr Pro Gly Arg Gln Asp Arg Tyr
    50                  55                  60

Thr Glu Pro Ala Ile Gly Asn Val Glu Ala Leu Ala Ala Ala Val Phe
65                  70                  75                  80

Arg Glu Leu Pro Thr Glu Asp Leu Asp Arg Thr Trp Leu Phe Gly His
                85                  90                  95

Ser Met Gly Ala Ala Val Ala Phe Glu Val Ala Arg Leu Met Glu Arg
            100                 105                 110

Glu Leu Asn Gln Ser Pro Val Gly Ile Ile Leu Ser Gly Arg Arg Ala
        115                 120                 125

Pro Ser Arg Phe Arg Pro Glu Thr Leu His Leu Gln Gly Asp Ala Ala
    130                 135                 140

Ile Ile Ala Asn Val Gln Ser Leu Ser Gly Thr Asp Ala Ile Leu Phe
145                 150                 155                 160

Glu Asp Pro Asp Thr Gln Arg Leu Ile Met Pro Ala Leu Arg Ala Asp
                165                 170                 175

Tyr Arg Ala Ile Glu Thr Tyr Arg Pro Pro Gly Thr Pro Arg Val Ala
            180                 185                 190

Cys Pro Ile His Thr Phe Val Gly Asp Ala Asp Pro Leu Ala Thr Leu
        195                 200                 205

Asp Glu Val Gly Ser Trp Arg Asp His Thr Ser Ala Glu Tyr Thr Leu
    210                 215                 220

Arg Val Phe Pro Gly Asp His Phe Tyr Leu Thr Ala Arg Ala Val Glu
225                 230                 235                 240

Val Ile Ser Ala Ile Ser Gln Leu Ile Val Glu Pro Thr Gln Thr Arg
                245                 250                 255

Gly
```

<210> SEQ ID NO 42
<211> LENGTH: 714
<212> TYPE: DNA
<213> ORGANISM: Streptomyces sp. MP28-13

<400> SEQUENCE: 42

```
gtgttctact acgtactgaa gtacgtgctg ttggggcccg tgctgcggtt gctcttccgg      60

ccccggatcg aggggctcga acacatcccg gcggacggcg ccgcgatcgt cgcgggcaat     120

catctctcct tctccgacca cttcctgatg cccgcgatca tccggcggcg gatcacgttt     180

ctcgcgaagg ccgagtactt caccggtccc ggcgtcaagg gacgcctcac cgcctccttc     240

ttccgcggcg tcggccagat cccggtcgac cggtccggca aggaggccgg gaaggccgcg     300

atccgggaag ggctcggggt gctcggcaag ggtgagttgc tggggatcta cccggagggc     360

acgcgctcgc acgacggacg gctctacaag ggcaaggtcg gggtggcggt gatggccatc     420

agggcgcagg tcccggtggt gccgtgcgcg atggtgggta cgttcgagat ccagccgccc     480

ggtcagaaga tcccgaacat ccggcgggtc acgatccggt tcggtgagcc gctggacttc     540

tcgcgctacg cgggtctgga gaaccagaag gcggcggtcc gcgcggtcac cgacgagatc     600

atgtacgcga tcctcggtct gtccgggcag gagtacgtgg accggtacgc cgccgaggtg     660

aaggccgagg aggcgcagca ggcgccgaag aagttcccgc gcctgcgacg ctga           714
```

<210> SEQ ID NO 43
<211> LENGTH: 237
<212> TYPE: PRT
<213> ORGANISM: Streptomyces sp. MP28-13

<400> SEQUENCE: 43

```
Met Phe Tyr Tyr Val Leu Lys Tyr Val Leu Leu Gly Pro Val Leu Arg
1               5                   10                  15

Leu Leu Phe Arg Pro Arg Ile Glu Gly Leu Glu His Ile Pro Ala Asp
            20                  25                  30

Gly Ala Ala Ile Val Ala Gly Asn His Leu Ser Phe Ser Asp His Phe
        35                  40                  45

Leu Met Pro Ala Ile Ile Arg Arg Arg Ile Thr Phe Leu Ala Lys Ala
    50                  55                  60

Glu Tyr Phe Thr Gly Pro Gly Val Lys Gly Arg Leu Thr Ala Ser Phe
65                  70                  75                  80

Phe Arg Gly Val Gly Gln Ile Pro Val Asp Arg Ser Gly Lys Glu Ala
                85                  90                  95

Gly Lys Ala Ala Ile Arg Glu Gly Leu Gly Val Leu Gly Lys Gly Glu
            100                 105                 110

Leu Leu Gly Ile Tyr Pro Glu Gly Thr Arg Ser His Asp Gly Arg Leu
        115                 120                 125

Tyr Lys Gly Lys Val Gly Val Ala Val Met Ala Ile Arg Ala Gln Val
    130                 135                 140

Pro Val Val Pro Cys Ala Met Val Gly Thr Phe Glu Ile Gln Pro Pro
145                 150                 155                 160

Gly Gln Lys Ile Pro Asn Ile Arg Arg Val Thr Ile Arg Phe Gly Glu
                165                 170                 175

Pro Leu Asp Phe Ser Arg Tyr Ala Gly Leu Glu Asn Gln Lys Ala Ala
            180                 185                 190

Val Arg Ala Val Thr Asp Glu Ile Met Tyr Ala Ile Leu Gly Leu Ser
        195                 200                 205
```

-continued

```
Gly Gln Glu Tyr Val Asp Arg Tyr Ala Ala Glu Val Lys Ala Glu Glu
    210                 215                 220

Ala Gln Gln Ala Pro Lys Lys Phe Pro Arg Leu Arg Arg
225                 230                 235


<210> SEQ ID NO 44
<211> LENGTH: 1611
<212> TYPE: DNA
<213> ORGANISM: Streptomyces sp. MP28-13

<400> SEQUENCE: 44

ttgagacgca cagcagtgct tggctcggcc ggcactctgc tcgcgggcac gctcatagcg     60

accacgctcg ccgcctcgtc ggcgagcgcc gacggccgcg ccgacagtgg cccggccgcg    120

tcgggcaagg aacagaagac gctgaacgcc caggcggccg gcgccgagat cgccgccgag    180

cgggccgcga agaagggcat cgactgggcg gactgcccgg ccgactgggc cctggagaag    240

ccgatccagt gcggctacat cagtgtcccg ctcgactacg cccgtccgaa cggcaagcag    300

atcaagatag ccgtcgaccg gatcggcaac accgggacgg cgggtgagcg tcagggctcc    360

ctcgtctaca accccggtgg ccccggcgcg tccggcatgg cgttcccgcg ccgcgtcgtg    420

accaagaacg ccatctgggc ggacgccgcc aaggcgtacg acttcgtcgg cttcgacccg    480

cgcggcgtcg ggcgctcgac gcccatctcc tgcgtcgacc cgcaggagtt cgtcaaggct    540

cccaaggccg accccgtccc cgacaccgag gccgacaagc gcgcccagcg caagctcgcg    600

gccgagtacg cggacggctg caaggagcgc agcggctgga tgctgccgca catgacgacg    660

cccaacagcg cgcgcgacct ggacgtcctg cgggccgcgc tcggcgacaa gaagctcaac    720

tacgtgggtg tctcctacgg cacctacctg ggcgccgtct acggcacgct cttcccgtcc    780

catgtacggc gcatggtgct ggacagcgtg gtcaacccgt cgaaggagaa gatctggtac    840

caggccaacc tggaccagga cgtcgccttc gagacacgct tcgacgactg gaagaagtgg    900

gtcgccgaga acgacgcggc gttccacatc ggcgacaccg tcgccaaggt cgagaagcag    960

tgggacaagc tccgcgccac cgccaagaag aacccgatcg gcggcgtcgt gggaccggcc   1020

gaactcatcg ggctgttcca gagcgcgccc tactacgact ccagctgggt gccggtcgcc   1080

gacacctgga gcaagtacct ggccggagac acccaggcgc tcgtcgacgc cgccgcgccg   1140

gacctgtccg acacggtggg caacacccgc gccgagaaca gcaacgcggt ctacaccgcc   1200

gtcgagtgcg ccgacgccaa gtggcccacg agctggcgca cctgggaccg ggacaacacc   1260

cggctccacc gcgaccaccc gttcctcacc tgggccaacg cctggatgaa cctgccctgt   1320

tcgacctggg gcgtagagca gcagacaccg atcgaggtcg gtacgggccg cggcctgccg   1380

cccgtactga tcgcgcagtc cacgcgtgac gccgccaccc cgtacggggg cgccgtcgag   1440

ctgcacaagc gcttcaaggg ctcacgcctg atcaccgagc gggacgccgg ttcgcacggc   1500

atcaccaatg tcgcgaacgc gtgcatcaac gaccgggtcg agtcgtatct gctcagcggc   1560

gagctggacc gccgcgacgt gacgtgcgca ccgcacgcca cacccaagcc g            1611


<210> SEQ ID NO 45
<211> LENGTH: 537
<212> TYPE: PRT
<213> ORGANISM: Streptomyces sp. MP28-13

<400> SEQUENCE: 45

Met Arg Arg Thr Ala Val Leu Gly Ser Ala Gly Thr Leu Leu Ala Gly
1               5                   10                  15
```

-continued

```
Thr Leu Ile Ala Thr Thr Leu Ala Ala Ser Ser Ala Ser Ala Asp Gly
            20                  25                  30

Arg Ala Asp Ser Gly Pro Ala Ala Ser Gly Lys Glu Gln Lys Thr Leu
        35                  40                  45

Asn Ala Gln Ala Ala Gly Ala Glu Ile Ala Ala Glu Arg Ala Ala Lys
    50                  55                  60

Lys Gly Ile Asp Trp Ala Asp Cys Pro Ala Asp Trp Ala Leu Glu Lys
65                  70                  75                  80

Pro Ile Gln Cys Gly Tyr Ile Ser Val Pro Leu Asp Tyr Ala Arg Pro
                85                  90                  95

Asn Gly Lys Gln Ile Lys Ile Ala Val Asp Arg Ile Gly Asn Thr Gly
            100                 105                 110

Thr Ala Gly Glu Arg Gln Gly Ser Leu Val Tyr Asn Pro Gly Gly Pro
        115                 120                 125

Gly Ala Ser Gly Met Ala Phe Pro Arg Arg Val Val Thr Lys Asn Ala
    130                 135                 140

Ile Trp Ala Asp Ala Ala Lys Ala Tyr Asp Phe Val Gly Phe Asp Pro
145                 150                 155                 160

Arg Gly Val Gly Arg Ser Thr Pro Ile Ser Cys Val Asp Pro Gln Glu
                165                 170                 175

Phe Val Lys Ala Pro Lys Ala Asp Pro Val Pro Asp Thr Glu Ala Asp
            180                 185                 190

Lys Arg Ala Gln Arg Lys Leu Ala Ala Glu Tyr Ala Asp Gly Cys Lys
        195                 200                 205

Glu Arg Ser Gly Trp Met Leu Pro His Met Thr Thr Pro Asn Ser Ala
    210                 215                 220

Arg Asp Leu Asp Val Leu Arg Ala Ala Leu Gly Asp Lys Lys Leu Asn
225                 230                 235                 240

Tyr Val Gly Val Ser Tyr Gly Thr Tyr Leu Gly Ala Val Tyr Gly Thr
                245                 250                 255

Leu Phe Pro Ser His Val Arg Arg Met Val Leu Asp Ser Val Val Asn
            260                 265                 270

Pro Ser Lys Glu Lys Ile Trp Tyr Gln Ala Asn Leu Asp Gln Asp Val
        275                 280                 285

Ala Phe Glu Thr Arg Phe Asp Asp Trp Lys Lys Trp Val Ala Glu Asn
    290                 295                 300

Asp Ala Ala Phe His Ile Gly Asp Thr Val Ala Lys Val Glu Lys Gln
305                 310                 315                 320

Trp Asp Lys Leu Arg Ala Thr Ala Lys Lys Asn Pro Ile Gly Gly Val
                325                 330                 335

Val Gly Pro Ala Glu Leu Ile Gly Leu Phe Gln Ser Ala Pro Tyr Tyr
            340                 345                 350

Asp Ser Ser Trp Val Pro Val Ala Asp Thr Trp Ser Lys Tyr Leu Ala
        355                 360                 365

Gly Asp Thr Gln Ala Leu Val Asp Ala Ala Ala Pro Asp Leu Ser Asp
    370                 375                 380

Thr Val Gly Asn Thr Arg Ala Glu Asn Ser Asn Ala Val Tyr Thr Ala
385                 390                 395                 400

Val Glu Cys Ala Asp Ala Lys Trp Pro Thr Ser Trp Arg Thr Trp Asp
                405                 410                 415

Arg Asp Asn Thr Arg Leu His Arg Asp His Pro Phe Leu Thr Trp Ala
            420                 425                 430

Asn Ala Trp Met Asn Leu Pro Cys Ser Thr Trp Gly Val Glu Gln Gln
```

```
        435                 440                 445

Thr Pro Ile Glu Val Gly Thr Gly Arg Gly Leu Pro Pro Val Leu Ile
    450                 455                 460

Ala Gln Ser Thr Arg Asp Ala Ala Thr Pro Tyr Gly Gly Ala Val Glu
465                 470                 475                 480

Leu His Lys Arg Phe Lys Gly Ser Arg Leu Ile Thr Glu Arg Asp Ala
                485                 490                 495

Gly Ser His Gly Ile Thr Asn Val Ala Asn Ala Cys Ile Asn Asp Arg
            500                 505                 510

Val Glu Ser Tyr Leu Leu Ser Gly Glu Leu Asp Arg Arg Asp Val Thr
        515                 520                 525

Cys Ala Pro His Ala Thr Pro Lys Pro
    530                 535


<210> SEQ ID NO 46
<211> LENGTH: 1490
<212> TYPE: DNA
<213> ORGANISM: Streptomyces sp. MP28-13

<400> SEQUENCE: 46

tagagtttga tcatggctca ggacgaacgc tggcggcgtg cttaacacat gcaagtcgaa     60

cgatgaagcc ttcgggtgga ttagtggcga acgggtgagt aacacgtggg caatctgccc    120

tgcactctgg gacaagccct ggaaacgggg tctaataccg gatatactg tgcccctcat    180

gggggacggt tgaaagctcc ggcggtgcag gatgagcccg cggcctatca gcttgttggt    240

ggggtaatgg cctaccaagg cgacgacggg tagccggcct gagagggcga ccggccacac    300

tgggactgag acacggccca gactcctacg ggaggcagca gtggggaata ttgcacaatg    360

ggcgaaagcc tgatgcagcg acgccgcgtg agggatgacg gccttcgggt tgtaaacctc    420

tttcagcagg gaagaagcga aagtgacggt acctgcagaa gaagcgccgg ctaactacgt    480

gccagcagcc gcggtaatac gtagggcgca agcgttgtcc ggaattattg ggcgtaaaga    540

gctcgtaggc ggtctgtcac gtcgggtgtg aaagcccggg gcttaacccc gggtctgcat    600

tcgatacggg cagactagag tgtggtaggg gagatcggaa ttcctggtgt agcggtgaaa    660

tgcgcagata tcaggaggaa caccggtggc gaaggcggat ctctgggcca ttactgacgc    720

tgaggagcga aagcgtgggg agcgaacagg attagatacc ctggtagtcc acgccgtaaa    780

cgttgggaac taggtgttgg cgacattcca cgtcgtcggt gccgcagcta acgcattaag    840

ttccccgcct ggggagtacg gccgcaaggc taaaactcaa aggaattgac gggggcccgc    900

acaagcagcg gagcatgtgg cttaattcga cgcaacgcga agaaccttac caaggcttga    960

catacaccgg aaagcatcag agatggtgcc ccccttgtgg tcggtgtaca ggtggtgcat   1020

ggctgtcgtc agctcgtgtc gtgagatgtt gggttaagtc ccgcaacgag cgcaaccctt   1080

gttctgtgtt gccagcatgc ccttcggggt gatggggact cacaggagac cgccggggtc   1140

aactcggagg aaggtgggga cgacgtcaag tcatcatgcc ccttatgtct tgggctgcac   1200

acgtgctaca atggccggta caatgagctg cgataccgca aggtggagcg aatctcaaaa   1260

agccggtctc agttcggatt ggggtctgca actcgacccc atgaagtcgg agttgctagt   1320

aatcgcagat cagcattgct gcggtgaata cgttcccggg ccttgtacac accgcccgtc   1380

acgtcacgaa agtcggtaac acccgaagcc ggtggcccaa ccccttgtgg gagggagctg   1440

tcgaaggtgg gactggcgat tgggacgaag tcgtaacaag gtagccgtaa               1490
```

<210> SEQ ID NO 47
<211> LENGTH: 20
<212> TYPE: DNA
<213> ORGANISM: Artificial sequence
<220> FEATURE:
<223> OTHER INFORMATION: KSMA-F degenerate primer

<400> SEQUENCE: 47
tsgcsatgga cccscagcag 20

<210> SEQ ID NO 48
<211> LENGTH: 20
<212> TYPE: DNA
<213> ORGANISM: Artificial sequence
<220> FEATURE:
<223> OTHER INFORMATION: KSMB-R degenerate primer

<400> SEQUENCE: 48
ccsgtsccgt gsgcctcsac 20

<210> SEQ ID NO 49
<211> LENGTH: 17
<212> TYPE: DNA
<213> ORGANISM: Artificial sequence
<220> FEATURE:
<223> OTHER INFORMATION: M13 forward (-20) primer

<400> SEQUENCE: 49
gtaaaacgac ggccagt 17

<210> SEQ ID NO 50
<211> LENGTH: 16
<212> TYPE: DNA
<213> ORGANISM: Artificial sequence
<220> FEATURE:
<223> OTHER INFORMATION: M13 reverse primer

<400> SEQUENCE: 50
aacagctatg accatg 16

<210> SEQ ID NO 51
<211> LENGTH: 725
<212> TYPE: DNA
<213> ORGANISM: Streptomyces sp. MP28-13
<220> FEATURE:
<221> NAME/KEY: misc_feature
<222> LOCATION: (633)..(633)
<223> OTHER INFORMATION: n is a, c, g, or t

<400> SEQUENCE: 51
tccggtcccg tgcgcctcga ccgcgtccac atccgccgtc gacagacccg ccttcgccag 60
cgcctgcttg atcacgcgac gctgggaggg gccgttcggc gcggtgatgc cgttgctggc 120
gccgtcctgg ttgagcgcgc tcccgcgcac caccgcgagc accggatgcc ccagccgacg 180
cgcctccgac agacgctcca ccaccaggac gcccgcgccc tcgccccacc cggtgccgtc 240
ggtggaggac gagaaggact tgcagcggcc gtccgcggcc aggccgcgct gctcgctgaa 300
gtcgatgaac gaccgcggtg ttcccatgac ggtcacgccg cccacgaggg cgagcgagca 360
ctcgccggaa cgcagtgcct gcgccgccca gtgcagggcc accagggacg acgagcatgc 420
cgtgtccacg ctcaccgcgg ggccttcgag accgagggtg taggccaccc ggcccgacac 480
gaggctgccg ccgccggtgc cgccggggta gtcgtggtac atcaccccgg cgaacacacc 540
ggtcgggctg cccttcagcg tggtgggtgc gatcccggca cgctccagcg cctcccacga 600

-continued

```
ggtctccagc agcaaccgct gctgcgggtc canggccgaa atcacgaatt ctggatccga    660

tacgtaacgc gtctgcagca tgcgtggtac cgagctttcc ctatagtgag tcgtattaga    720

gcttg                                                                725


<210> SEQ ID NO 52
<211> LENGTH: 19
<212> TYPE: DNA
<213> ORGANISM: Artificial sequence
<220> FEATURE:
<223> OTHER INFORMATION: SuperCos forward primer

<400> SEQUENCE: 52

ggccgcaatt aaccctcac                                                  19


<210> SEQ ID NO 53
<211> LENGTH: 20
<212> TYPE: DNA
<213> ORGANISM: Artificial sequence
<220> FEATURE:
<223> OTHER INFORMATION: SuperCos Reverse primer

<400> SEQUENCE: 53

ggccgcataa tacgactcac                                                 20
```